United States Patent
Mackall et al.

(10) Patent No.: US 11,400,117 B2
(45) Date of Patent: Aug. 2, 2022

(54) COMPOSITIONS AND METHODS FOR INHIBITING T CELL EXHAUSTION

(71) Applicant: The Board of Trustees of the Leland Stanford Junior University, Stanford, CA (US)

(72) Inventors: Crystal Mackall, Stanford, CA (US); Rachel Lynn, Stanford, CA (US); Evan Weber, Stanford, CA (US); Elena Sotillo, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 16/221,155

(22) Filed: Dec. 14, 2018

(65) Prior Publication Data
US 2019/0183932 A1    Jun. 20, 2019

Related U.S. Application Data

(60) Provisional application No. 62/738,687, filed on Sep. 28, 2018, provisional application No. 62/599,299, filed on Dec. 15, 2017.

(51) Int. Cl.
| | |
|---|---|
| *A61K 35/17* | (2015.01) |
| *A61P 35/00* | (2006.01) |
| *C07K 14/725* | (2006.01) |
| *C07K 16/28* | (2006.01) |
| *C07K 16/30* | (2006.01) |
| *A61K 39/00* | (2006.01) |
| *C07K 16/32* | (2006.01) |
| *C07K 14/47* | (2006.01) |
| *A61K 38/17* | (2006.01) |

(52) U.S. Cl.
CPC .......... *A61K 35/17* (2013.01); *A61K 39/0011* (2013.01); *A61P 35/00* (2018.01); *C07K 14/4702* (2013.01); *C07K 14/7051* (2013.01); *C07K 16/2803* (2013.01); *C07K 16/3084* (2013.01); *C07K 16/32* (2013.01); *A61K 38/1709* (2013.01); *A61K 2039/5156* (2013.01); *C07K 16/2812* (2013.01); *C07K 16/2815* (2013.01); *C07K 2317/524* (2013.01); *C07K 2317/526* (2013.01); *C07K 2317/622* (2013.01); *C07K 2317/70* (2013.01); *C07K 2319/03* (2013.01); *C07K 2319/33* (2013.01)

(58) Field of Classification Search
None
See application file for complete search history.

(56) References Cited

U.S. PATENT DOCUMENTS

| 5,958,671 A * | 9/1999 | Glimcher ............. G01N 33/505 435/4 |
| 2014/0241983 A1 | 8/2014 | Hu et al. |
| 2016/0317654 A1 | 11/2016 | Noelle |

FOREIGN PATENT DOCUMENTS

| WO | WO-2013063019 A1 * | 5/2013 | ........... C12N 15/113 |
| WO | WO-2015092024 A2 * | 6/2015 | ............. C07K 16/30 |
| WO | WO 2015164594 | 10/2015 | |
| WO | WO 2016179283 | 11/2016 | |
| WO | WO 2017/165412 | 9/2017 | |

OTHER PUBLICATIONS

Accession No. NM_002228.3, 2015, pp. 1-7.*
Atsaves et al., 2019, Cancers, vol. 11: 1-21.*
Valdez et al., 2012, Immunity, vol. 36: 668-679.*
Parra et al., 1998, J. Immunol. vol. 160: 5374-5381.*
Ghosh et al., 2012, J. Biol. Chem. vol. 287: 11833-11841.*
Bannister, A. J., et al. Stimulation of c-Jun activity by CBP: c-Jun residues Ser63/73 are required for CBP induced stimulation in vivo and CBP binding in vitro. Oncogene. Dec. 21, 1995;11(12):2509-14.
Behrens, A. et al. Jun N-terminal kinase 2 modulates thymocyte apoptosis and T cell activation through c-Jun and nuclear factor of activated T cell (NF-AT). Proc Natl Acad Sci U S A. Feb. 13, 2001;98(4):1769-74.
Behrens, A., et al. Oncogenic transformation by ras and fos is mediated by c-Jun N-terminal phosphorylation. Oncogene. May 18, 2000;19(22):2657-63.
Bengsch, B. et al. Epigenomic-Guided Mass Cytometry Profiling Reveals Disease-Specific Features of Exhausted CD8 T Cells. vol. 48, Issue 5, May 15, 2018, pp. 1029-1045.e5.
Bohmann, D. et al. Human proto-oncogene c-jun encodes a DNA binding protein with structural and functional properties of transcription factor AP-1. Science Dec. 4, 1987: vol. 238, Issue 4832, pp. 1386-1392.
Buenrostro, J. D., et al.Transposition of native chromatin for fast and sensitive epigenomic profiling of open chromatin, DNA-binding proteins and nucleosome position. Nat Methods 10, 1213-1218, doi:10.1038/nmeth.2688 (2013).
Chiu, R., Angel, P. & Karin, M. Jun-B differs in its biological properties from, and is a negative regulator of, c-Jun. Cell 59, 979-986 (1989).

(Continued)

*Primary Examiner* — Amy E Juedes
(74) *Attorney, Agent, or Firm* — Brian E. Davy; Bozicevic, Field & Francis LLP

(57) ABSTRACT

The present invention relates to T cell compositions and methods of using the same in the context of therapy and treatment. In particular, the invention provides T cells that are modified (e.g., genetically and/or functionally) to maintain functionality under conditions in which unmodified T cells display exhaustion. Compositions and methods disclosed herein find use in preventing exhaustion of engineered (e.g., chimeric antigen receptor (CAR) T cells) as well as non-engineered T cells thereby enhancing T cell function (e.g., activity against cancer or infectious disease).

12 Claims, 62 Drawing Sheets

(56) References Cited

OTHER PUBLICATIONS

Corces, M. R. et al. An improved ATAC-seq protocol reduces background and enables interrogation of frozen tissues. Nat Methods 14, 959-962, doi:10.1038/nmeth.4396 (2017).

D'Angelo, S.P. et al. Antitumor Activity Associated with Prolonged Persistence of Adoptively Transferred NY-ESO-1(c259)T Cells in Synovial Sarcoma. Cancer Discov. Aug. 2018;8(8):944-957.

Davila, M. L. et al. Efficacy and toxicity management of 19-28z CAR T cell therapy in B cell acute lymphoblastic leukemia. Sci Transl Med 6, 224ra225, doi:10.1126/scitranslmed.3008226 (2014).

Derijard, B. et al. JNK1: a protein kinase stimulated by UV light and Ha-Ras that binds and phosphorylates the c-Jun activation domain. Cell. Mar. 25, 1994;76(6):1025-37.

Di Stasi, A. et al. Inducible apoptosis as a safety switch for adoptive cell therapy. N Engl J Med. Nov. 3, 2011;365(18):1673-83.

Echlin, D. R., et al. B-ATF functions as a negative regulator of AP-1 mediated transcription and blocks cellular transformation by Ras and Fos. Oncogene 19, 1752-1763.

Eyquem, J. et al. Targeting a CAR to the TRAC locus with CRISPR/Cas9 enhances tumour rejection. Nature. Mar. 2, 2017;543(7643):113-117.

Fahmy, TM et al. Increased TCR Avidity after T Cell Activation: A Mechanism for Sensing Low-Density Antigen. Immunity. Feb. 2001, vo. 14, No. 2, pp. 135-143.

Finch, S. et al. JunB negatively regulates AP-1 activity and cell proliferation of malignant mouse keratinocytes. Journal of Cancer Research and Clinical Oncology. Jan. 2002, Epub Nov. 6, 2001, vol. 128, No. 1, pp. 3-10.

Foletta, VC et al. Transcriptional regulation in the immune system: all roads lead to AP-1. Journal of Leukocyte Biology. Feb. 1998, vol. 63, No. 2, pp. 139-152.

Fraietta, J. A. et al. Determinants of response and resistance to CD19 chimeric antigen receptor (CAR) T cell therapy of chronic lymphocytic leukemia. Nat Med. May 2018;24(5):563-571.

Fraietta, J. A. et al. Disruption of TET2 promotes the therapeutic efficacy of CD19-targeted T cells. Nature. Jun. 2018;558(7709):307-312.

Fry, T. J. et al. CD22-targeted CAR T cells induce remission in B-ALL that is naive or resistant to CD19-targeted CAR immunotherapy. Nat Med. Jan. 2018;24(1):20-28.

Heczey, A. et al. CAR T Cells Administered in Combination with Lymphodepletion and PD-1 Inhibition to Patients with Neuroblastoma. Mol Then Sep. 6, 2017;25(9):2214-2224.

Hegde, M., et al. Cellular immunotherapy for pediatric solid tumors. Cytotherapy. Jan. 2015;17(1):3-17.

Horwacik, I. et al. Structural Basis of GD2 Ganglioside and Mimetic Peptide Recognition by 14G2a Antibody. Mol Cell Proteomics. Oct. 2015;14(10):2577-90.

Hu, G. et al. A Genome-wide Regulatory Network Identifies Key Transcription Factors for Memory CD8+ T Cell Development. Nature Communications. Dec. 2013, vol. 4, No. 2830, pp. 1-31.

Hudecek, M. et al. The nonsignaling extracellular spacer domain of chimeric antigen receptors is decisive for in vivo antitumor activity. Cancer Immunol Res. Feb. 2015;3(2):125-35.

International Search Report and Written Opinion, International Patent Application No. PCT/US2018/065801, dated May 30, 2019, 23 pages.

Iwamoto, M., et al. A general chemical method to regulate protein stability in the mammalian central nervous system. Chem Biol. Sep. 24, 2010;17(9):981-8.

Jena, B. et al. Chimeric antigen receptor (CAR)-specific monoclonal antibody to detect CD19-specific T cells in clinical trials. PLoS One. 2013;8(3):e57838.

June, C. H., et al. CAR T cell immunotherapy for human cancer. Science. Mar. 23, 2018;359(6382):1361-1365.

Jurado, J. et al. Alternative splicing of c-fos pre-mRNA: contribution of the rates of synthesis and degradation to the copy number of each transcript isoform and detection of a truncated c-Fos immunoreactive species. BMC Molecular Biology. Sep. 21, 2007, vol. 8, No. 83; pp. 1-14.

Li, P. et al. BATF-JUN is critical for IRF4-mediated transcription in T cells. Nature. Oct. 25, 2012;490(7421):543-6.

Liang, G. et al. Characterization of Human Activiating Transcription Factor 4, a Transcriptional Activator that Interacts with Multiple Domains . . . Journal of Biological Chemistry. Sep. 19, 1997, vol. 272, No. 38, pp. 24088-24095.

Long, A. H. et al. 4-1BB costimulation ameliorates T cell exhaustion induced by tonic signaling of chimeric antigen receptors. Nat Med. Jun. 2015;21(6):581-90.

Long, A. H. et al. Reduction of MDSCs with All-trans Retinoic Acid Improves CAR Therapy Efficacy for Sarcomas. Cancer Immunol Res. Oct. 2016;4(10):869-880.

Majzner, R. G. et al. Tumor Antigen Escape from CAR T-cell Therapy. Cancer Discov. Oct. 2018;8(10):1219-1226.

Man, K. et al. Transcription Factor IRF4 Promotes CD8(+) T Cell Exhaustion and Limits the Development of Memory-like T Cells during Chronic Infection. Immunity. Dec. 19, 2017;47(6):1129-1141.e5.

Mariani, O. et al. JUN oncogene amplification and overexpression block adipocytic differentiation in highly aggressive sarcomas. Cancer Cell. Apr. 2007;11(4):361-74.

Martinez, G. J. et al. The transcription factor NFAT promotes exhaustion of activated CD8(+) T cells. Immunity. Feb. 17, 2015;42(2):265-278.

Maude, S. L. et al. Tisagenlecleucel in Children and Young Adults with B-Cell Lymphoblastic Leukemia. N Engl J Med. Feb. 1, 2018;378(5):439-448.

Meixner, A., et al. JunD regulates lymphocyte proliferation and T helper cell cytokine expression. EMBO J. Mar. 24, 2004;23(6):1325-35.

Milone, M. C. et al. Chimeric receptors containing CD137 signal transduction domains mediate enhanced survival of T cells and increased antileukemic efficacy in vivo. Mol Ther. Aug. 2009;17(8):1453-64.

Mootha, V. K. et al. PGC-1 alpha-responsive genes involved in oxidative phosphorylation are coordinately downregulated in human diabetes. Nat Genet. Jul. 2003;34(3):267-73.

Murphy, T. L., et al. Specificity through cooperation: BATF-IRF interactions control immune-regulatory networks. Nat Rev Immunol. Jul. 2013;13(7):499-509.

Neelapu, S. S. et al. Axicabtagene Ciloleucel CAR T-Cell Therapy in Refractory Large B-Cell Lymphoma. N Engl J Med. Dec. 28, 2017;377(26):2531-2544.

Pauken, K. E. et al. Epigenetic stability of exhausted T cells limits durability of reinvigoration by PD-1 blockade. Science. Dec. 2, 2016;354(6316):1160-1165.

Philip, M. et al. Chromatin states define tumour-specific T cell dysfunction and reprogramming. Nature. May 25, 2017;545(7655):452-456.

Porter, D. L. et al. Chimeric antigen receptor T cells persist and induce sustained remissions in relapsed refractory chronic lymphocytic leukemia. Sci Transl Med. Sep. 2, 2015;7(303):303ra139.

Quigley, M. et al. Transcriptional analysis of HIV-specific CD8+ T cells shows that PD-1 inhibits T cell function by upregulating BATF. Nat Med. Oct. 2010;16(10):1147-51.

Roychoudhuri, R. et al. BACH2 regulates CD8(+) T cell differentiation by controlling access of AP-1 factors to enhancers. Nat Immunol. Jul. 2016;17(7):851-860.

Schep, A. N., et al. chromVAR: inferring transcription-factor-associated accessibility from single-cell epigenomic data. Nat Methods. Oct. 2017;14(10):975-978.

(56) References Cited

OTHER PUBLICATIONS

Sen, D. R. et al. The epigenetic landscape of T cell exhaustion. Science. Dec. 2, 2016;354(6316):1165-1169.

Shaulian, E. AP-1—The Jun proteins: Oncogenes or tumor suppressors in disguise? Cell Signal. Jun. 2010;22(6):894-9.

Singh, N., et al. Early memory phenotypes drive T cell proliferation in patients with pediatric malignancies. Sci Transl Med. Jan. 6, 2016;8(320):320ra3.

Subramanian, A. et al. Gene set enrichment analysis: a knowledge-based approach for interpreting genome-wide expression profiles. Proc Natl Acad Sci U S A. Oct. 25, 2005;102(43):15545-50.

Walker, A. J. et al. Tumor Antigen and Receptor Densities Regulate Efficacy of a Chimeric Antigen Receptor Targeting Anaplastic Lymphoma Kinase. Mol Ther. Sep. 6, 2017;25(9):2189-2201.

Weiss, C. et al. JNK phosphorylation relieves HDAC3-dependent suppression of the transcriptional activity of c-Jun. EMBO J. Jul. 15, 2003;22(14):3686-95.

Wherry, E. J. et al. Molecular and cellular insights into T cell exhaustion. Nat Rev Immunol. Aug. 2015;15(8):486-99.

Wherry, E. J. et al. Molecular signature of CD8+ T cell exhaustion during chronic viral infection. Immunity. Oct. 2007;27(4):670-84.

Wickham, H. Ggplot2 : elegant graphics for data analysis. (Springer, 2009).

Zheng, G. X. et al. Massively parallel digital transcriptional profiling of single cells. Nat Commun. Jan. 16, 2017;8:14049.

Lynn et al., Abstract LB-112: Engineering AP1 to combat CAR T cell exhaustion. Proceedings: AACR Annual Meeting 2018; Apr. 14-18, 2018; Chicago, IL. 2 pages.

Kawasaki et al., Increased c-Fos/activator protein-1 confers resistance against anergy induction on antigen-specific T cell. Int Immunol. Dec. 1999;11(12):1873-80.

Sundstedt et al., In vivo anergized CD4+ T cells have defective expression and function of the activating protein-1 transcription factor. J Immunol. Dec. 1, 1998;161(11):5930-6.

Macian et al., Transcriptional mechanisms underlying lymphocyte tolerance. Cell. Jun. 14, 2002;109(6):719-31.

Lynn et al., c-Jun overexpression in CAR T cells induces exhaustion resistance. Nature. Dec. 2019;576(7786):293-300.

Papavassiliou et al., The Multifaceted Output of c-Jun Biological Activity: Focus at the Junction of CD8 T Cell Activation and Exhaustion. Cells. Nov. 13, 2020;9(11):2470.

Stephen et al., Transforming growth factor β-mediated suppression of antitumor T cells requires FoxP1 transcription factor expression. Immunity. Sep. 18, 2014;41(3):427-439.

Extended EP Search Report for EP18889872.0, dated Aug. 6, 2021, 8 pages.

* cited by examiner

FIG. 1A
FIG. 1B
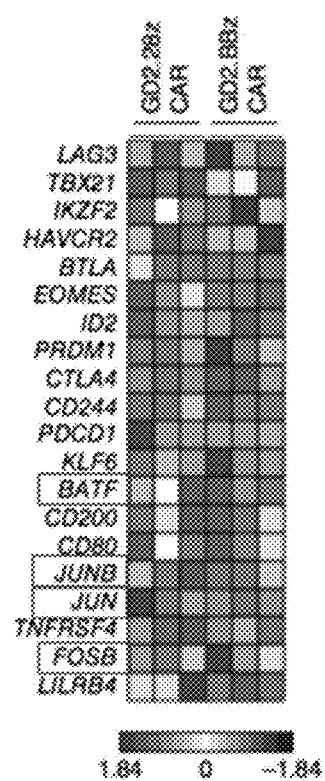
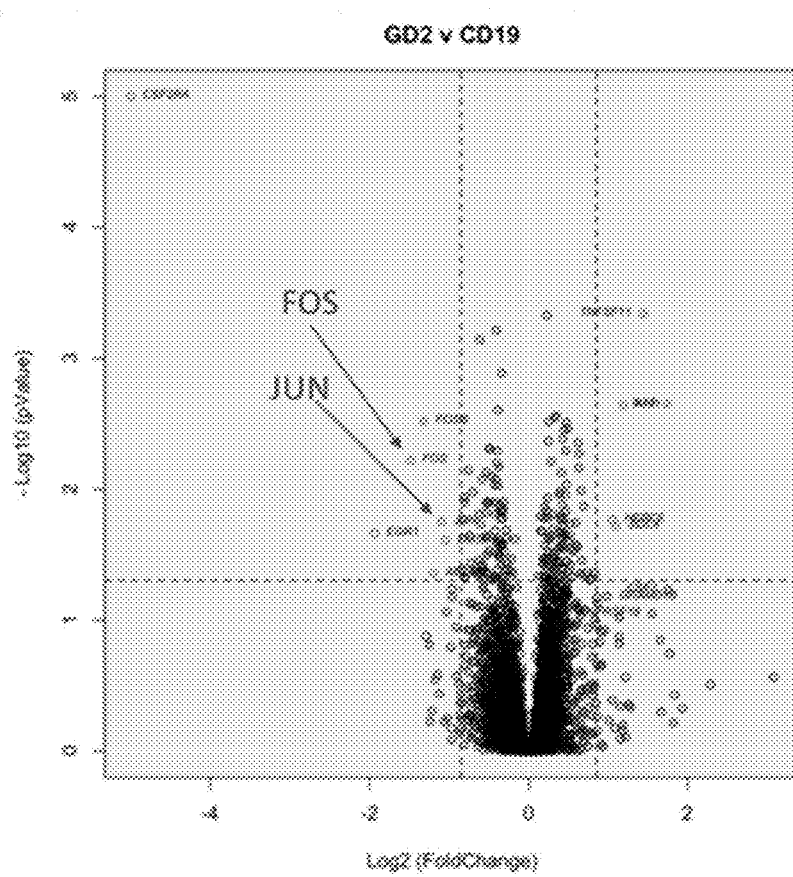

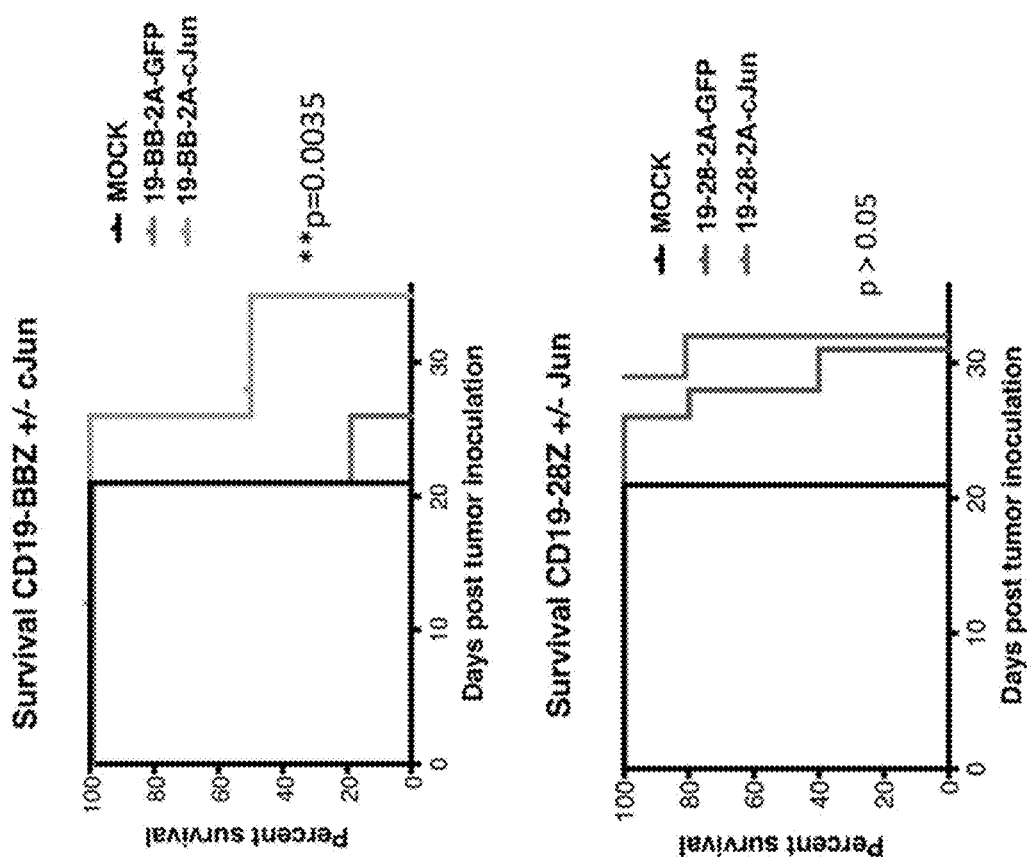
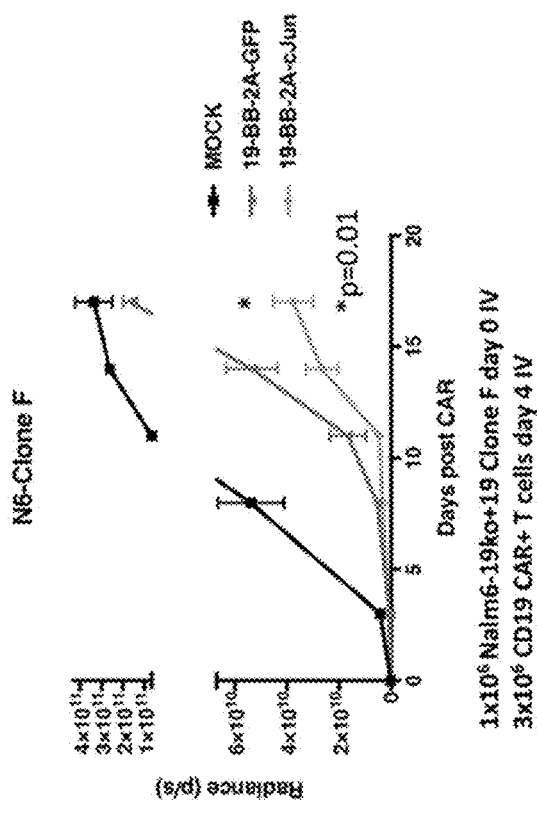
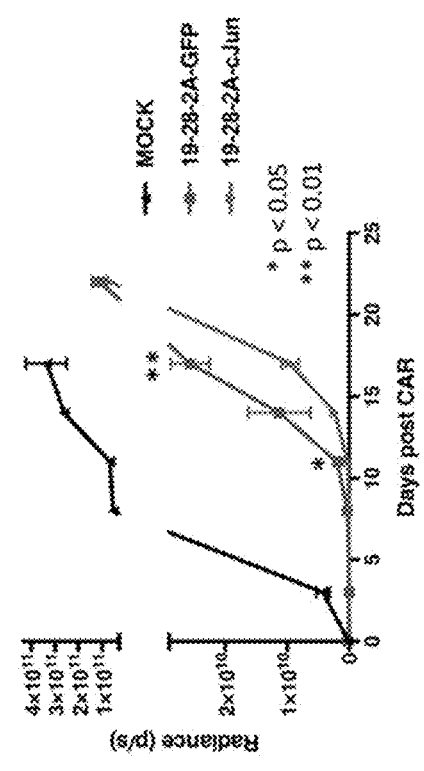
FIG. 11A  FIG. 11B  FIG. 11C  FIG. 11D

FIG. 12A
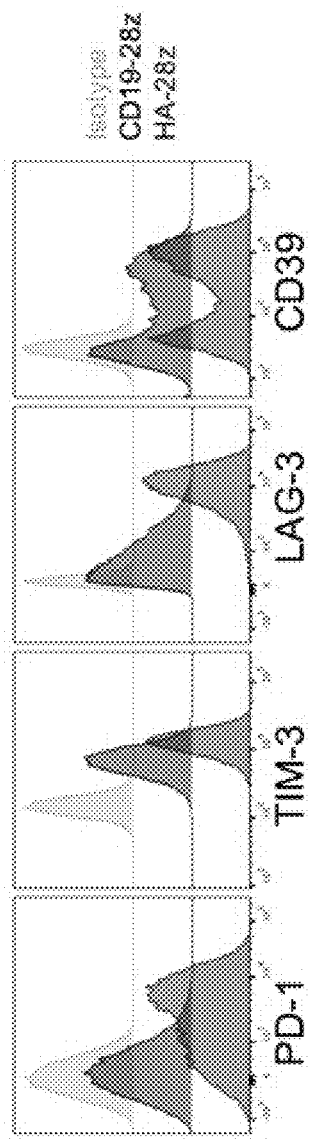
FIG. 12B
FIG. 12C
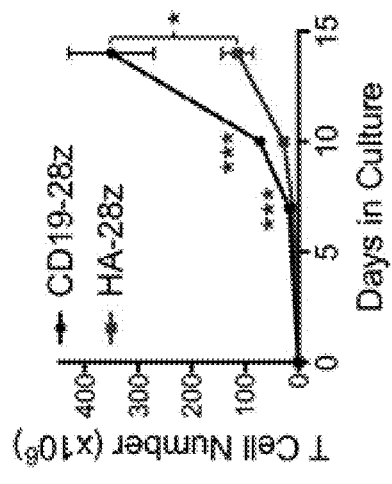
FIG. 12D
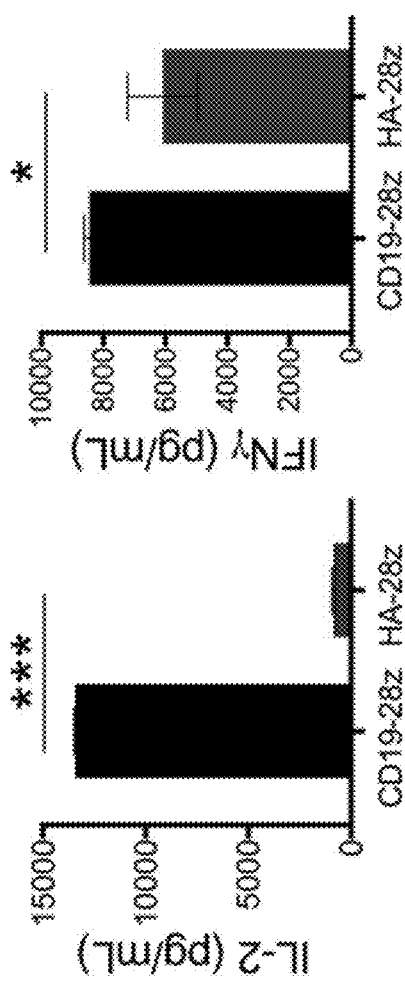

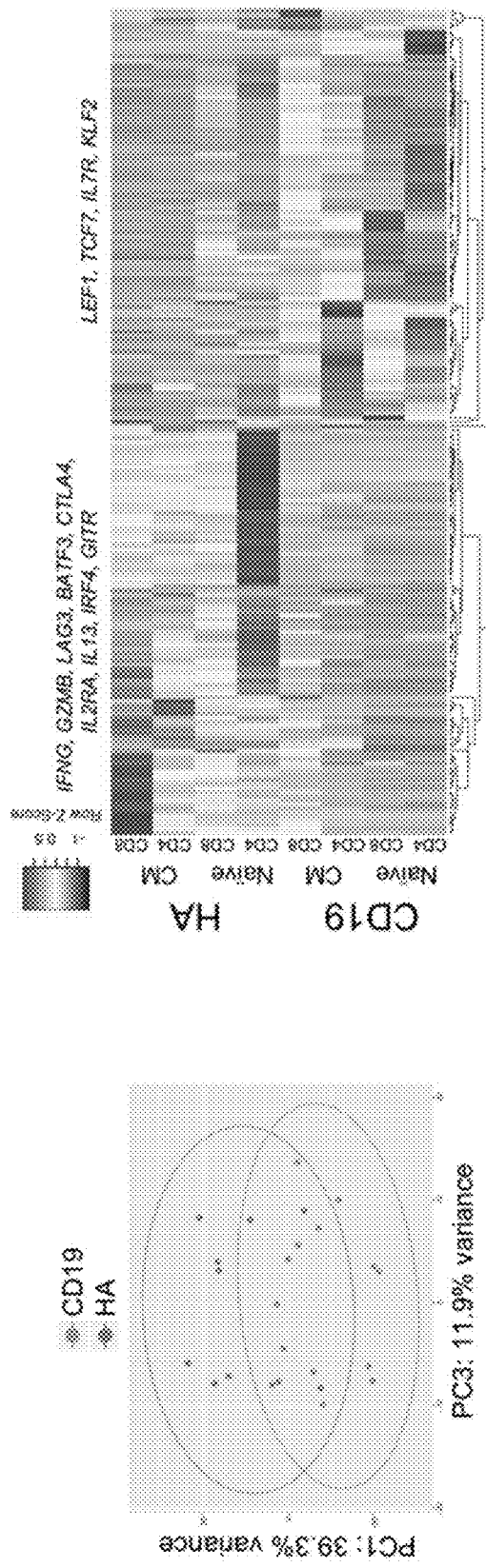
FIG. 12E
FIG. 12F
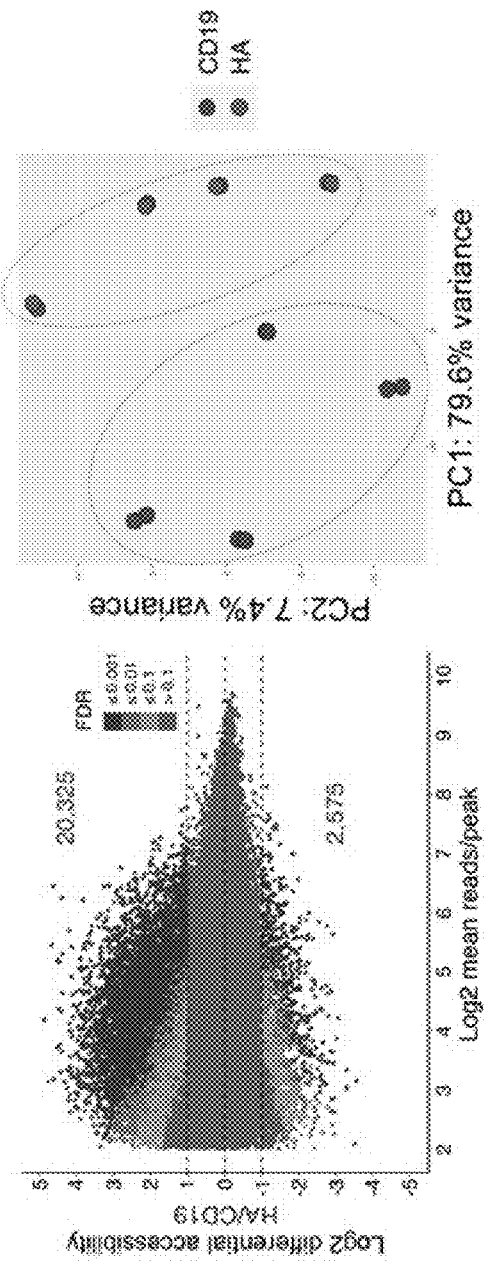
FIG. 12G
FIG. 12H

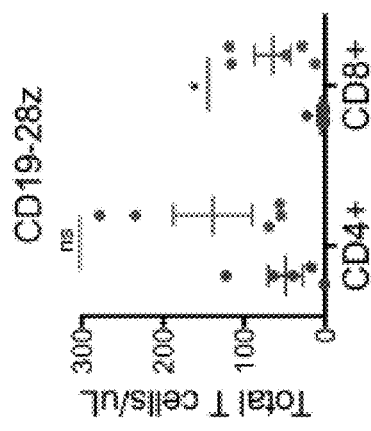
FIG. 14H
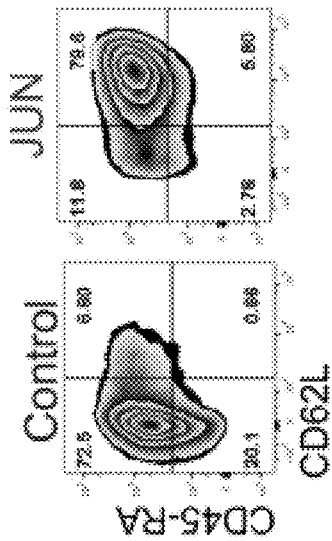
FIG. 14I
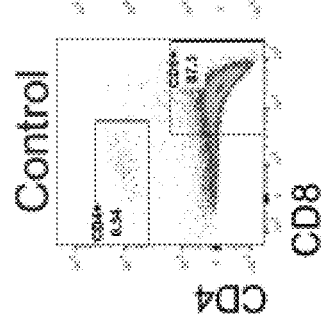
FIG. 14J
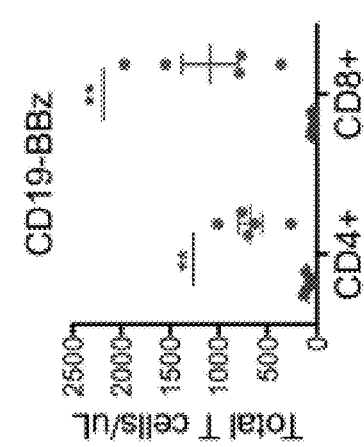
FIG. 14K
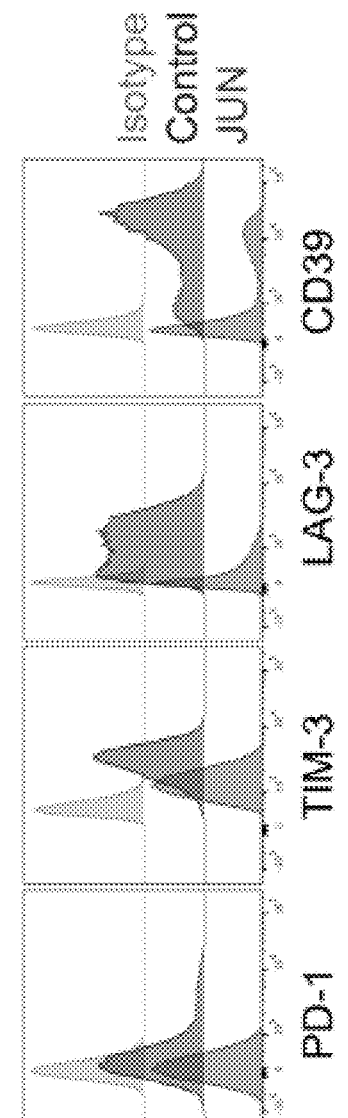

FIG. 15B  FIG. 15C

FIG. 15H
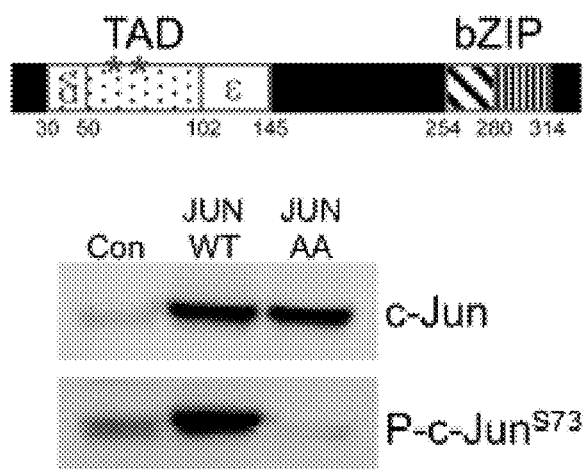
FIG. 15I
FIG. 15J
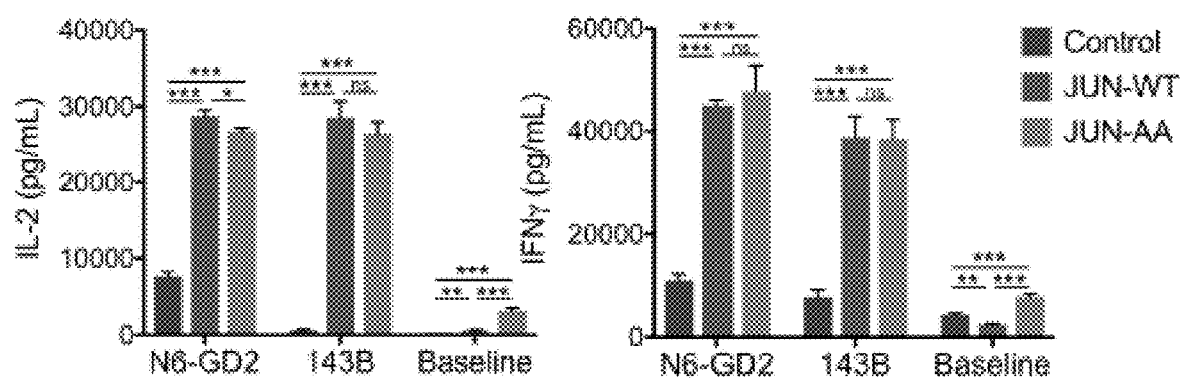

FIG. 16A  FIG. 16B
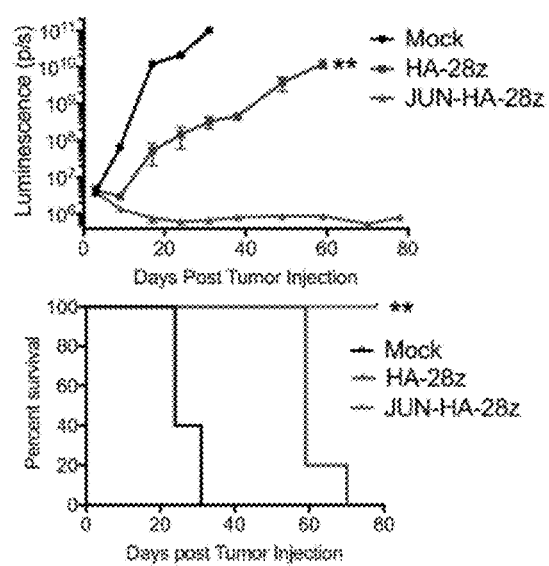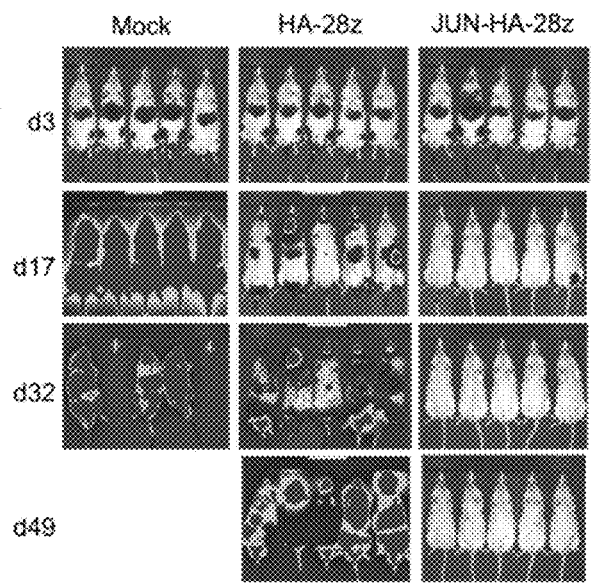
FIG. 16C
FIG. 16D
FIG. 16E
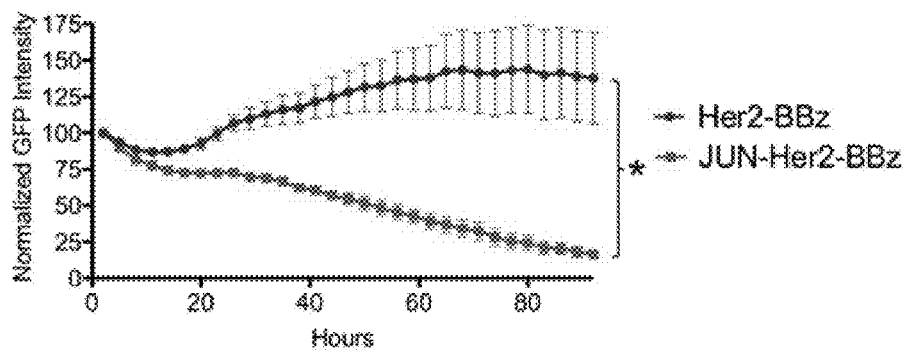

FIG. 16F
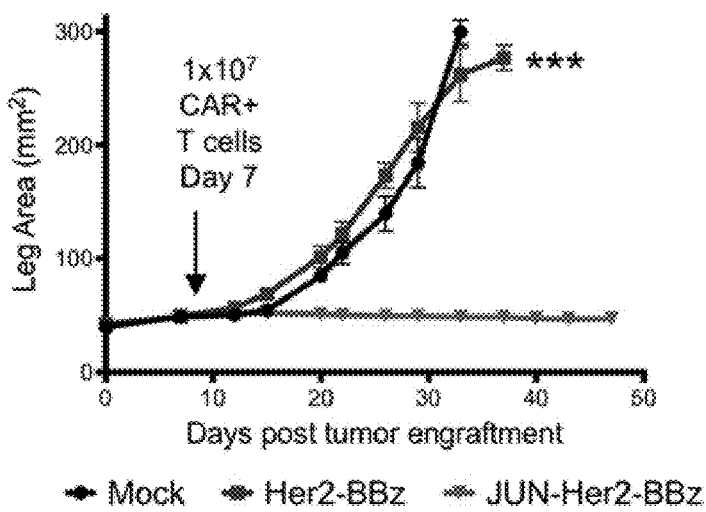
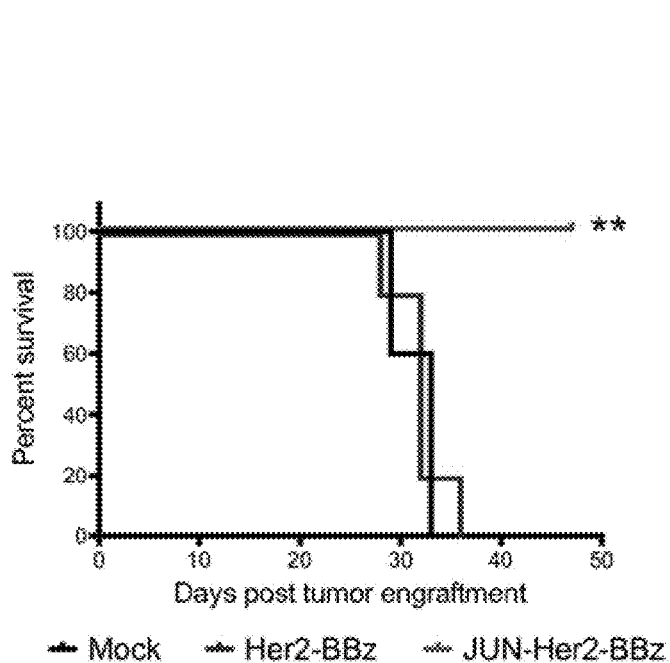
FIG. 16G
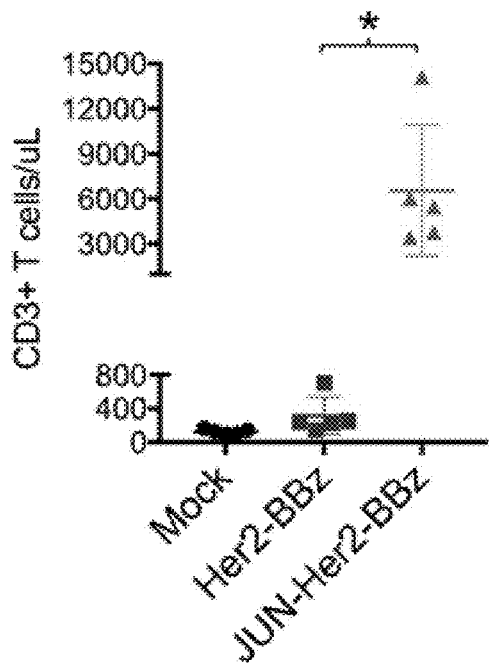
FIG. 16H

FIG. 17A
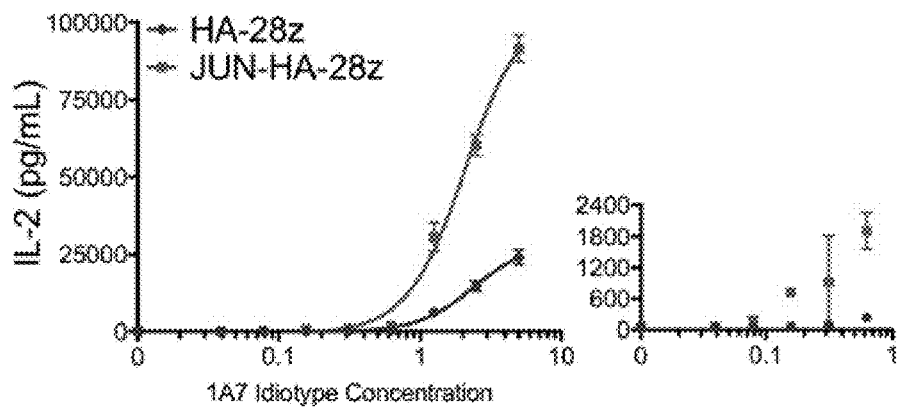
FIG. 17B
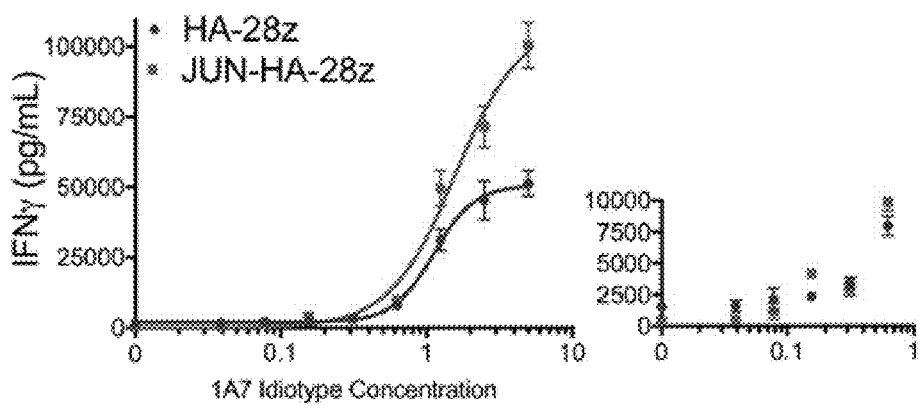
FIG. 17C
FIG. 17D
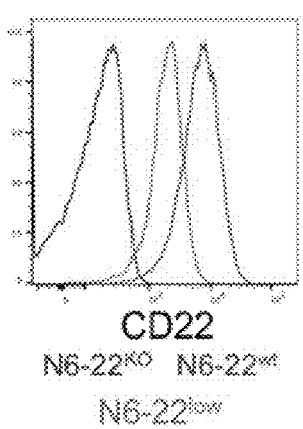
FIG. 17E
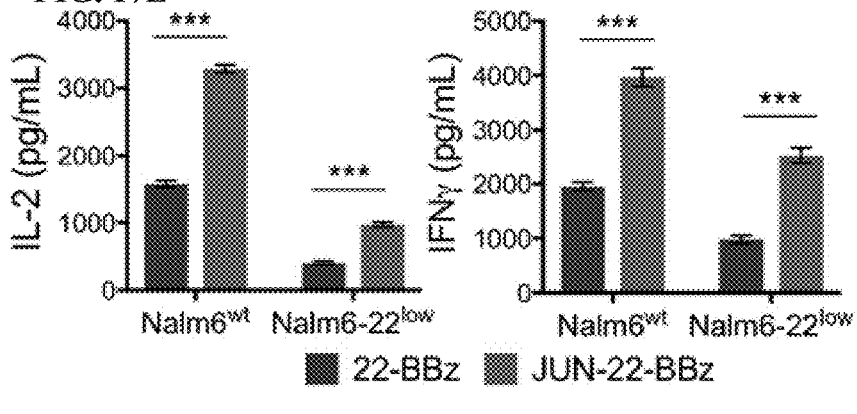

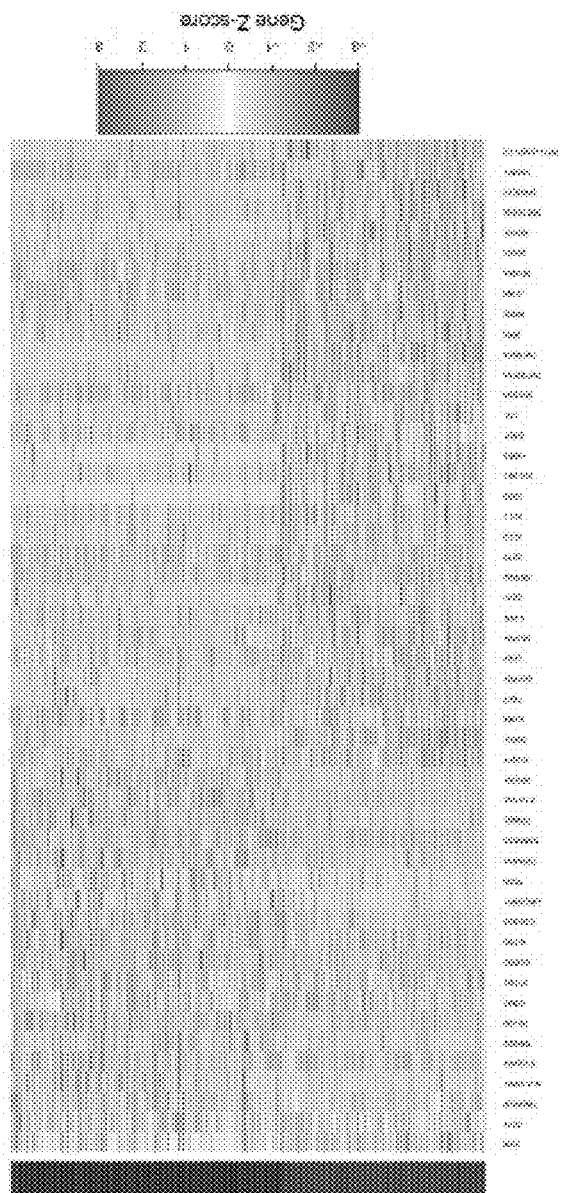
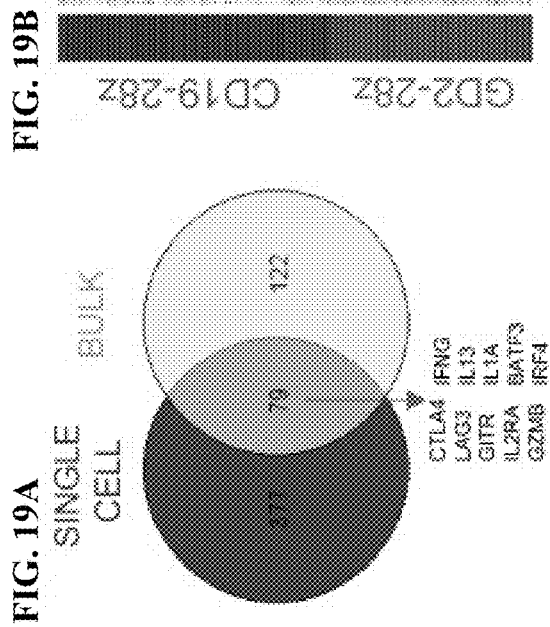
FIG. 19A
FIG. 19B

FIG. 22A 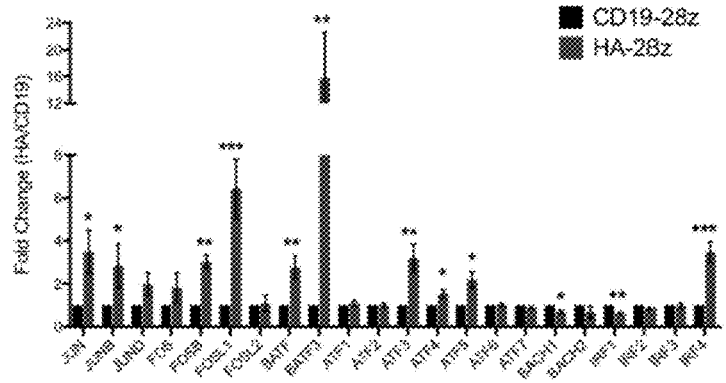 FIG. 22B 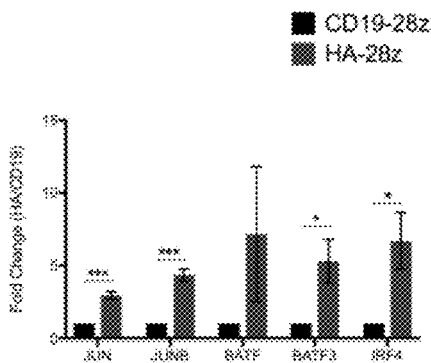
FIG. 22C

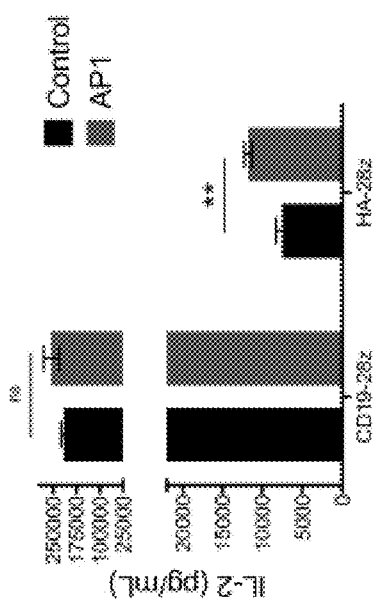
FIG. 23A
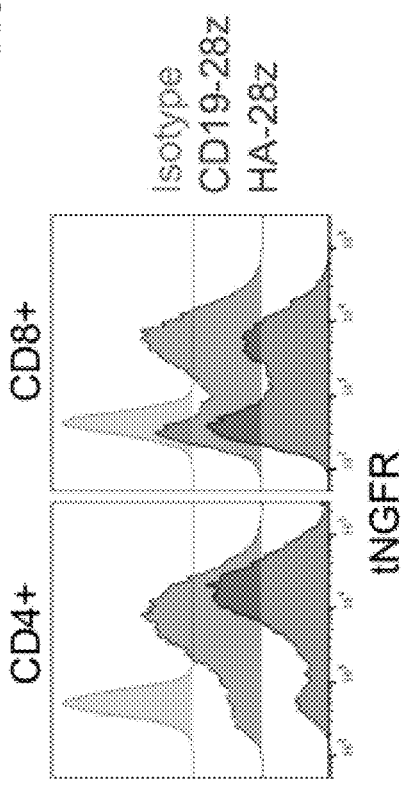
FIG. 23B
FIG. 23C
FIG. 23D
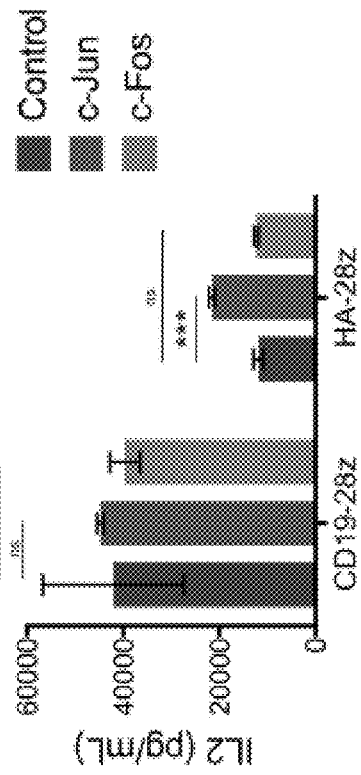
FIG. 23E FIG. 25A
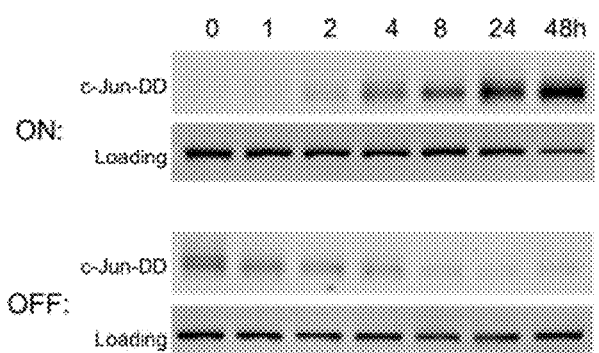
FIG. 25B
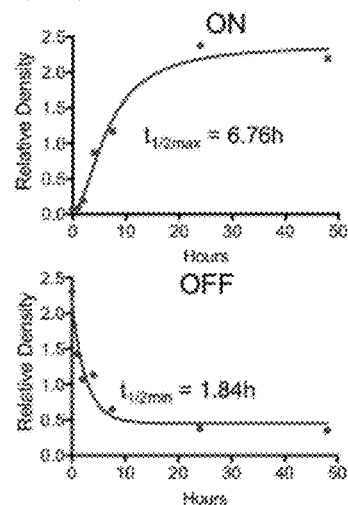
FIG. 25C
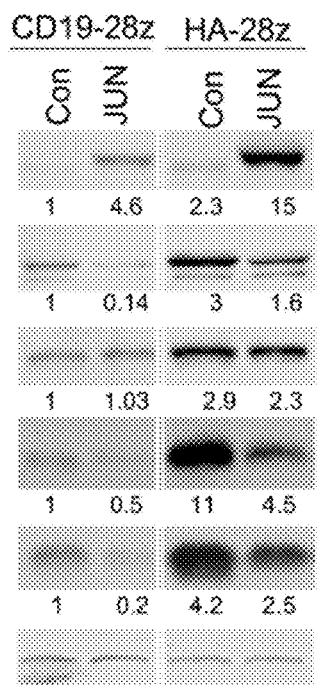
FIG. 25E
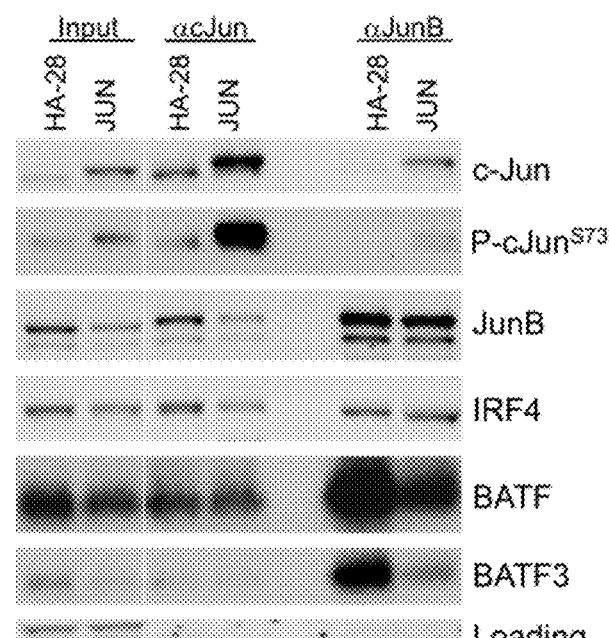
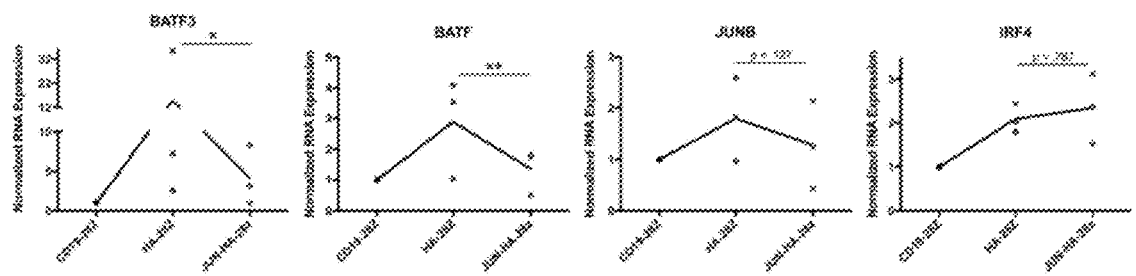
FIG. 25D FIG. 31A
FIG. 31B
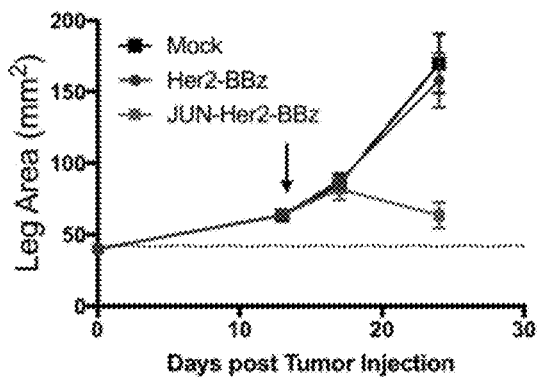
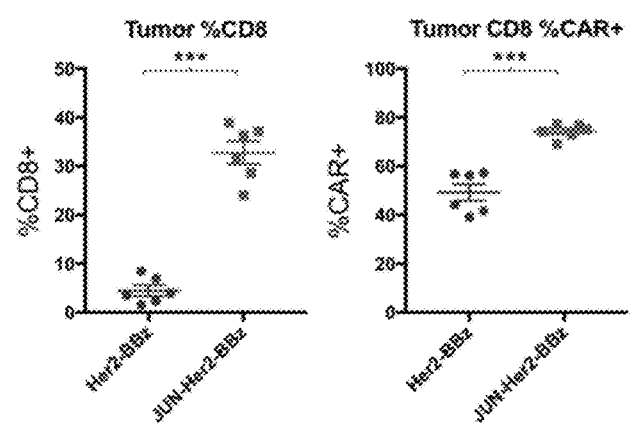
FIG. 31C
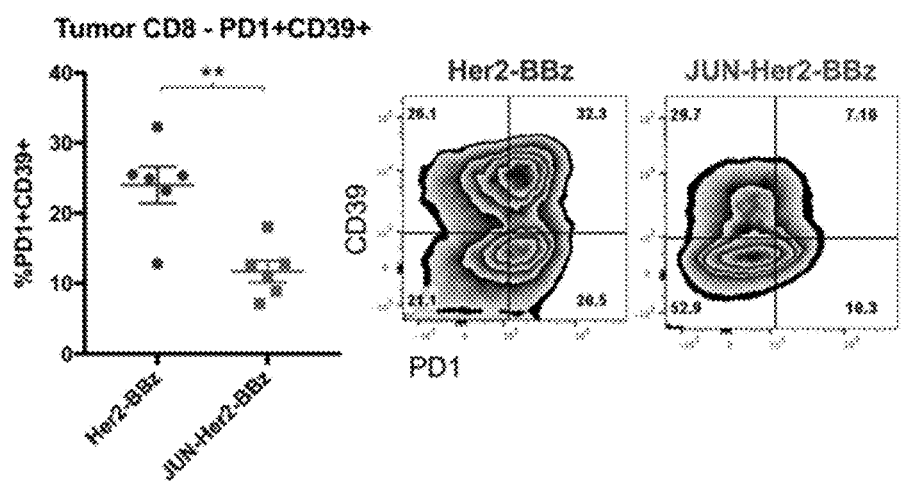
FIG. 31D
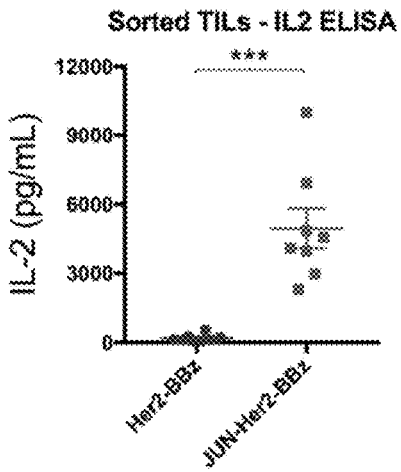

COMPOSITIONS AND METHODS FOR INHIBITING T CELL EXHAUSTION

CROSS REFERENCE TO RELATED APPLICATIONS

This application claims priority to and the benefit of U.S. Provisional Application No. 62/738,687, filed Sep. 28, 2018 and U.S. Provisional Application No. 62/599,299, filed Dec. 15, 2017, which are hereby incorporated by reference in their entireties.

FIELD OF THE INVENTION

The present invention relates to T cell compositions and methods of using the same in the context of therapy and treatment. In particular, the invention provides T cells that are modified (e.g., genetically and/or functionally) to maintain functionality under conditions in which unmodified T cells display exhaustion. Compositions and methods disclosed herein find use in preventing exhaustion of engineered (e.g., chimeric antigen receptor (CAR) T cells) as well as non-engineered T cells thereby enhancing T cell function (e.g., activity against cancer or infectious disease). Compositions and methods of the invention find use in both clinical and research settings, for example, within the fields of biology, immunology, medicine, and oncology.

BACKGROUND

T cells are immune cells that become activated via T cell receptor (TCR) signaling and co-stimulation following engagement with antigen. Physiologic activation through the T cell receptor renders T cells capable of mediating potent antitumor and/or anti-infective effects. During resolution of an acute inflammatory response, a subset of activated effector T cells differentiate into long-lived memory cells. By contrast, in patients with chronic infections or cancer, T cells not infrequently undergo pathologic differentiation toward a state of dysfunction, which has been termed T cell exhaustion. T cell exhaustion is characterized by marked changes in metabolic function, transcriptional programming, loss of effector function (ex. cytokine secretion, killing capacity), and co-expression of multiple surface inhibitory receptors. The root cause of T cell exhaustion is persistent antigen exposure leading to continuous TCR signaling. Prevention or reversal of T cell exhaustion has been long sought as a means to enhance T cell effectiveness (e.g., in patients with cancer or chronic infections).

Chimeric antigen receptor (CAR) T cells demonstrate impressive response rates in B cell malignancies, but long-term disease control occurs in only approximately 50% of patients with B-ALL1 and large B cell lymphoma (Ref 2; herein incorporated by reference in its entirety), and is even less frequent in CLL (Ref 3; herein incorporated by reference in its entirety). Moreover, despite numerous trials, CAR T cells have not mediated sustained antitumor effects in solid tumors (Ref 4; herein incorporated by reference in its entirety). Numerous factors limit the efficacy of CAR T cells, including heterogeneous antigen expression and a requirement for high antigen density for optimal CAR function enabling rapid selection of antigen loss variants (Refs. 5-7; herein incorporated by reference in their entireties), the suppressive tumor microenvironment (Ref 8; herein incorporated by reference in its entirety) and intrinsic T cell dysfunction as a result of T cell exhaustion (Refs. 3,9,10; herein incorporated by reference in their entireties).

T cell exhaustion has been increasingly incriminated as a cause of T cell dysfunction in CAR T cells. Tonic antigen-independent signaling, due to scFv aggregation, commonly occurs in T cells expressing CARs and can induce rapid exhaustion (Ref 9; herein incorporated by reference in its entirety). Integration of the CD28 endodomain into second generation CART cell receptors enhances expansion, but also predisposes CAR T cells to exhaustion, both in the setting of tonically signaling receptors and in CD19-28z CAR T cells exposed to high tumor burdens (Ref 9; herein incorporated by reference in its entirety). Increased frequency of T cells bearing exhaustion characteristics contained within CD19-BBz CAR grafts were recently demonstrated to distinguish non-responding from responding patients treated for CLL3. A broad base of data from diverse studies implicates intrinsic T cell dysfunction due to T cell exhaustion as a major factor limiting the efficacy of CART cell therapeutics and raises the prospect that engineering exhaustion-resistant CAR T cells could substantially improve clinical outcomes.

SUMMARY

The present invention relates to compositions and methods for use in preventing exhaustion of engineered (e.g., T cells engineered to express a synthetic receptor such as an engineered T cell receptor or a chimeric antigen receptor (CAR)) as well as non-engineered (e.g., native) T cells. T cells modified (e.g., to prevent T cell exhaustion) according to the invention, compositions containing same, and methods of using same enhance T cell functionality (e.g., activity against cancer or infectious disease).

CAR T cells mediate antitumor effects in a small subset of cancer patients, but dysfunction due to T cell exhaustion is an important barrier to progress. To investigate the biology of exhaustion in human T cells expressing CAR receptors, experiments were conducted during development of embodiments herein using a model system employing a tonically signaling CAR, which induces hallmarks of exhaustion described in other settings. Results demonstrate that exhaustion was associated with a profound defect in IL-2 production alongside increased chromatin accessibility of AP-1 transcription factor motifs, and overexpression of numerous bZIP and IRF transcription factors that have been implicated in inhibitory activity. Engineering CAR T cells to overexpress an AP-1 factor (e.g., c-Jun) enhanced expansion potential, increased functional capacity, diminished terminal differentiation, and improved antitumor potency in numerous in vivo tumor models.

Experiments conducted during development of embodiments herein additionally demonstrate that functional deficiency in an AP-1 factor (e.g., c-Jun) mediates dysfunction in exhausted human T cells and that engineering CAR T cells to overexpress an AP-1 factor (e.g., c-Jun) renders them exhaustion-resistant, thereby addressing a major barrier to progress for this emerging class of therapeutics.

Experiments conducted during development of embodiments herein additionally demonstrate that knockdown of IRF4 dramatically increases functional activity of exhausted HA-28z CAR T cells, that the enhanced in vivo function of c-Jun modified HA-28z CAR T cells can not be replicated by ex vivo provision of IL-2, that c-Jun enhanced Her2-BBz CAR T cell activity within a suppressive solid tumor microenvironment, that c-Jun overexpression increases resistance to TGFβ-mediated suppression of exhausted HA-28z CAR T cells, and that transcriptional changes in c-Jun modified cells are consistent with reduced exhaustion and increased memory formation.

As described herein, engineered T cells (e.g., T cells engineered to express a synthetic receptor such as an engineered T cell receptor or a CAR), as well as non-engineered (e.g., native, natural) T cells are provided that are modified to overexpress and/or contain elevated levels (e.g., are made to have physiologically elevated levels) of one or more activator protein 1 (AP-1) transcription factors (e.g., c-Fos, c-Jun, Activating transcription factor (ATF) and Jun dimerization protein (JDP) families) and/or modified (e.g., genetically) for reduced expression and/or activity of one or more AP-1 inhibitory complex members (e.g., JunB and BATF3 and other BATF family members, IRF4, and ATF family members).

Accordingly, in one aspect, the invention provides T cells modified to overexpress and/or contain elevated levels of one or more AP-1 transcription factors. For example, in one embodiment, c-Jun is expressed in T cells that are engineered to express a synthetic receptor such as an engineered T cell receptor or a chimeric antigen receptor (CAR). In another embodiment, c-Jun is expressed in T cells with a native, natural T cell receptor. The invention is not limited by the means of expressing one or more AP-1 transcription factors. In one embodiment, when co-expressed with an engineered TCR or CAR, c-Jun (and/or other AP-1 transcription factor) and the engineered receptor are co-expressed from distinct viral vectors. In another embodiment, they are expressed from a single vector construct using a bicistronic vector. C-Jun (and/or other AP-1 transcription factor) may be expressed constitutively or in a regulated fashion (e.g., using a system to regulate expression remotely via a small molecule or using an endogenously regulated system). c-Jun and/or other AP-1 transcription factor genes may, in another embodiment, be genetically integrated into the cellular DNA using a retroviral, lentiviral or other viral vector or via CRISPR/Cas9 based system. In yet another embodiment, c-Jun and/or other AP-1 transcription factors is/are expressed via RNA or an oncolytic virus or other transient expression system known in the art. C-Jun and/or other AP-1 transcription factors can be delivered ex vivo into T cells for adoptive transfer, or delivered via in vivo genetic transfer.

Similarly, the invention is not limited by the type of T cell modified to overexpress and/or contain elevated levels of one or more AP-1 transcription factors and/or modified (e.g., genetically) for reduced expression and/or activity of one or more AP-1 inhibitory complex members (e.g., JunB and BATF3 and other BATF family members, IRF4, and ATF family members). In some embodiments, the T cells are CD3+ T cells (e.g., a combination of CD4+ and CD8+ T cells). In certain embodiments, the T cells are CD8+ T cells. In other embodiments, the T cells are CD4+ T cells. In some embodiments, the T cells are natural killer (NK) T cells. In some embodiments, the T cells are alpha beta T cells. In some embodiments, the T cells are gamma delta T cells. In some embodiments, the T cells are a combination of CD4+ and CD8 T+ cells (e.g., that are CD3+). In certain embodiments, the T cells are memory T cells. In certain embodiments, the memory T cells are central memory T cells. In certain embodiments, the memory T cells are effector memory T cells. In some embodiments, the T cells are tumor infiltrating lymphocytes. In certain embodiments, the T cells are a combination of CD8+ T cells, CD4+ T cells, NK T cells, memory T cells, and/or gamma delta T cells. In some embodiments, the T cells are cytokine-induced killer cells.

In some embodiments, the T cell is an anti-tumor T cell (e.g., a T cell with activity against a tumor (e.g., an autologous tumor) that becomes activated and expands in response to antigen). Anti-tumor T cells (e.g., useful for adoptive T cell transfer) include, in one embodiment, peripheral blood derived T cells genetically modified with receptors that recognize and respond to tumor antigens. Such receptors are generally composed of extracellular domains comprising a single-chain antibody (scFv) specific for tumor antigen, linked to intracellular T cell signaling motifs (See, e.g., Westwood, J. A. et al, 2005, Proc. Natl. Acad. Sci., USA, 102(52):19051-19056). Other anti-tumor T cells include T cells obtained from resected tumors or tumor biopsies (e.g., tumor infiltrating lymphocytes (TILs). In another embodiment, the T cell is a polyclonal or monoclonal tumor-reactive T cell (e.g., obtained by apheresis, expanded ex vivo against tumor antigens presented by autologous or artificial antigen-presenting cells). In another embodiment, the T cell is engineered to express a T cell receptor of human or murine origin that recognizes a tumor antigen. The invention is not limited by the type of tumor antigen so recognized. Indeed, any T cell containing a receptor that recognizes a tumor antigen finds use in the compositions and methods of the invention. Examples include, but are not limited to, T cells expressing a receptor (e.g., a native or naturally occurring receptor, or a receptor engineered to express a synthetic receptor such as an engineered T cell receptor or a CAR) that recognize an antigen selected from CD19, CD20, CD22, receptor tyrosine kinase-like orphan receptor 1 (ROR1), disialoganglioside 2 (GD2), Epstein-Barr Virus (EBV) protein or antigen, folate receptor, mesothelin, human carcinoembryonic antigen (CEA), CD33/IL3Rα, tyrosine protein kinase Met (c-Met) or hepatocyte growth factor receptor (HGFR), prostate-specific membrane antigen (PSMA), Glycolipid F77, epidermal growth factor receptor variant III (EGFRvIII), NY-ESO-1, melanoma antigen gene (MAGE) Family Member A3 (MAGE-A3), melanoma antigen recognized by T cells 1 (MART-1), GP1000, p53, or other tumor antigen described herein.

In some embodiments, the T cell is engineered to express a CAR. The invention is not limited by the type CAR. Indeed, any CAR that binds with specificity to a desired antigen (e.g., tumor antigen) may be modified as disclosed and described herein to overexpress and/or contain elevated levels (e.g., are made to have physiologically elevated levels) of one or more AP-1 transcription factors (e.g., c-Jun). In certain embodiments, the CAR comprises an antigen-binding domain. In certain embodiments, the antigen-binding domain is a single-chain variable fragment (scFv) containing heavy and light chain variable regions that bind with specificity to the desired antigen. In some embodiments, the CAR further comprises a transmembrane domain (e.g., a T cell transmembrane domain (e.g., a CD28 transmembrane domain)) and a signaling domain comprising one or more immunoreceptor tyrosine-based activation motifs (ITAMs)(e.g., a T cell receptor signaling domain (e.g., TCR zeta chain). In some embodiments, the CAR comprises one or more co-stimulatory domains (e.g., domains that provide a second signal to stimulate T cell activation). The invention is not limited by the type of co-stimulatory domain. Indeed, any co-stimulatory domain known in the art may be used including, but not limited to, CD28, OX40/CD134, 4-1BB/CD137/TNFRSF9, the high affinity immunoglobulin E receptor-gamma subunit (FcERIγ, ICOS/CD278, interleukin 2 subunit beta (ILRβ) or CD122, cytokine receptor common subunit gamma (IL-2Rγ) or CD132, and CD40. In one embodiment, the co-stimulatory domain is 4-1BB.

In one aspect, the invention provides a method of treating a disease or condition in a subject comprising administering to the subject (e.g., a patient) having a disease or condition an effective amount of T cells modified to express and/or contain elevated levels of one or more AP-1 transcription factors and/or modified (e.g., genetically) for reduced expression and/or activity of one or more AP-1 inhibitory complex members (e.g., JunB and BATF3 and other BATF family members, IRF4, and ATF family members). The invention is not limited by the type of disease or condition treated. Indeed, any disease or condition that is treatable (e.g., for which signs or symptoms of the disease are ameliorated upon treatment) via administration of T cells can be treated in an improved and more effective manner using compositions and methods of the invention (e.g., containing and/or using T cells modified to express and/or contain elevated levels of one or more AP-1 transcription factors). In one embodiment, the disease or condition is cancer. In another embodiment, the disease or condition is an infectious disease. The invention is not limited by the type of cancer or by the type of infectious disease. Indeed, any cancer known in the art for which T cell therapy is used for treatment may be treated with the compositions and methods of the invention. In like manner, any infectious disease known in the art for which T cell therapy is used for treatment may be treated with the compositions and methods of the invention. In one embodiment, administration to a subject (e.g., a patient) having a disease or condition of an effective amount of T cells modified to express and/or contain elevated levels of one or more AP-1 transcription factors and/or reduced expression and/or activity of one or more AP-1 inhibitory complex members inhibits T cell exhaustion (e.g., compared to a subject receiving the same amount of engineered T cells (e.g., CART cells or T cells comprising a recombinant TCR) not modified to express and/or contain elevated levels of one or more AP-1 transcription factors or to have reduced expression and/or activity of one or more AP-1 inhibitory complex members).

Thus, the invention provides, in one embodiment, a method of inhibiting T cell exhaustion (e.g. maintaining functionality of T cells exposed to excessive antigen (e.g., in the context of treating a disease or condition)) via modification of T cells to express and/or contain elevated levels of one or more AP-1 transcription factors and/or reduced expression and/or activity of one or more AP-1 inhibitory complex members (e.g., compared to control T cells not so modified). In one embodiment, T cells modified to express and/or contain elevated levels of one or more AP-1 transcription factors (e.g., c-Jun) display increased functionality and/or activity (e.g., increased antigen induced cytokine production, enhanced killing capacity (e.g., increased recognition of tumor targets with low surface antigen), increased memory cell formation, and/or enhanced proliferation in response to antigen) and/or reduced features of exhaustion (e.g., lower levels of markers indicative of exhaustion (e.g., PD-1, TIM-3, LAG-3) and/or lower levels of programmed cell death). In some embodiments, T cells modified to express and/or contain elevated levels of one or more AP-1 transcription factors and/or reduced expression and/or activity of one or more AP-1 inhibitory complex members described herein significantly enhance clinical efficacy (e.g., of engineered T cells (e.g., CAR T cells) and/or non-engineered natural T cells).

In certain embodiments, the present invention demonstrates that treatment of a subject having cancer with a therapeutically effective amount of a composition comprising T cells modified to express and/or contain elevated levels of one or more AP-1 transcription factors is superior to treatment of a subject having cancer with T cells expressing normal amounts of one or more AP-1 transcription factors. In some embodiments, treatment of animals (e.g., humans) suffering from cancer with therapeutically effective amounts of immunotherapeutic compositions comprising T cells modified to express and/or contain elevated levels of one or more AP-1 transcription factors inhibits the development or growth of cancer cells or and/or renders the cancer cells as a population more susceptible to other treatments (e.g., the cell death-inducing activity of cancer therapeutic drugs or radiation therapies). Accordingly, compositions and methods of the invention may be used as a monotherapy (e.g., to kill cancer cells, and/or reduce or inhibit cancer cell growth, induce apoptosis and/or cell cycle arrest in cancer cells), or when administered in combination with one or more additional agent(s), such as other anti-cancer agents (e.g., cell death-inducing or cell cycle-disrupting cancer therapeutic drugs or radiation therapies) to render a greater proportion of the cancer cells susceptible to killing, inhibited cancer cell growth, induced apoptosis and/or cell cycle arrest compared to the corresponding proportion of cells in an animal treated only with the cancer therapeutic drug or radiation therapy alone.

Accordingly, in certain embodiments, the invention provides methods of treating or delaying the progression of cancer in a patient comprising administering to the patient a therapeutically effective amount of a composition comprising T cells modified (e.g., genetically) to express and/or contain elevated levels of one or more AP-1 transcription factors (e.g., c-Jun) and/or modified (e.g., genetically) for reduced expression and/or activity of one or more AP-1 inhibitory complex members (e.g., JunB and BATF3 and other BATF family members, IRF4, and ATF family members). In certain embodiments, the therapeutically effective amount of the modified T cell composition reduces the number of cancer cells in the patient following such treatment. In certain embodiments, the therapeutically effective amount of the modified T cell composition reduces and/or eliminates the tumor burden in the patient following such treatment. In certain embodiments, the method further comprises administering radiation therapy to the patient. In certain embodiments, the radiation therapy is administered before, at the same time as, and/or after the patient receives the therapeutically effective amount of the modified T cell composition. In certain embodiments, the method further comprises administering to the patient one or more anticancer agents and/or one or more chemotherapeutic agents. In certain embodiments, the one or more anticancer agents and/or one or more chemotherapeutic agents are administered before, at the same time as, and/or after the patient receives the therapeutically effective amount of the modified T cell composition. In certain embodiments, combination treatment of a patient with a therapeutically effective amount of modified T cells and a course of an anticancer agent produces a greater tumor response and clinical benefit in such patient compared to those treated with the modified T cells or anticancer drugs/radiation alone. Since the doses for all approved anticancer drugs and radiation treatments are known, the present invention contemplates the various combinations of them with the modified T cells.

In certain embodiments, the invention provides a therapeutically effective amount of a composition (e.g., an immunotherapeutic composition) comprising T cells modified according to the present disclosure (e.g., for use in treating or delaying the progression of cancer in a subject). As described herein, the composition may further comprise one or more anticancer agents, for example one or more chemotherapeutic agents. The invention also provides the use of the composition to induce cell cycle arrest and/or apoptosis. The invention also relates to the use of the compositions for sensitizing cells to additional agent(s), such as inducers of apoptosis and/or cell cycle arrest, and chemoprotection of normal cells through the induction of cell cycle arrest prior to treatment with chemotherapeutic agents. Compositions of the invention are useful for the treatment, amelioration, or prevention of disorders, such as any type of cancer or infectious disease and additionally any cells responsive to induction of apoptotic cell death (e.g., disorders characterized by dysregulation of apoptosis, including hyperproliferative diseases such as cancer). In certain embodiments, the compositions can be used to treat, ameliorate, or prevent a cancer that additionally is characterized by resistance to cancer therapies (e.g., those cancer cells which are chemoresistant, radiation resistant, hormone resistant, and the like). The invention also provides pharmaceutical compositions comprising the composition (e.g., immunotherapeutic compositions) comprising modified T cells of the invention in a pharmaceutically acceptable carrier.

In another embodiment, the invention provides a method of treating or delaying the progression of cancer in a patient comprising administering to the patient a therapeutically effective amount of a composition comprising T cells modified (e.g., genetically) to express and/or contain elevated levels of one or more AP-1 transcription factors (e.g., c-Jun) in combination with a therapeutically effective amount of an inhibitor of TCR signaling (e.g., in order to prevent T cell exhaustion). In certain embodiments, the inhibitor of TCR signaling is a tyrosine kinase inhibitor. In another embodiment, the tyrosine kinase inhibitor inhibits Lck kinase. An inhibitor of TCR signaling may be administered by any suitable mode of administration, but is typically administered orally. Multiple cycles of treatment may be administered to a subject. In certain embodiments, the inhibitor of TCR signaling is administered according to a standard dosing regimen (e.g., daily or intermittently). In another embodiment, the inhibitor of TCR signaling is administered for a period of time sufficient to restore at least partial T cell function, then discontinued.

These and other embodiments of the subject invention will readily occur to those of skill in the art in view of the disclosure herein.

DESCRIPTION OF THE DRAWINGS

FIG. 1A-B shows AP-1 transcription factors c-Fos and c-Jun are downregulated in GD2-28Z exhausted CAR T cells.

FIG. 11A-D shows that c-Jun modified CD19 CAR T cells show enhanced in vivo activity against $CD19^{low}$ Nalm6 leukemia. $3\times10^6$ CAR+ T cells were delivered IV to mice bearing CD19-low Clone F Nalm6 leukemia tumor. (A-B) Tumor growth (A) and survival (B) of mice treated with CD19-BBZ CART cells+/−c-Jun. c-Jun-modified CD19-BBZ CAR T cells show reduced tumor growth and significantly enhanced survival. (C-D) Tumor growth (C) and survival (D) of mice treated with CD19-28Z CART cells+/−c-Jun. c-Jun-modified CD19-28Z CAR T cells show reduced tumor growth early, but CD19-negative disease eventually grows out in both groups and no survival benefit (p>0.05).

FIG. 12A-J shows that HA-28z CAR T cells manifest phenotypic, functional, transcriptional and epigenetic hallmarks of T cell exhaustion. a) Decreased expansion of HA-28z vs CD19-28z CAR T cells during primary expansion culture. D0=bead activation, D2=transduction. Error bars represent mean±SEM from n=10 donors. b) Surface expression of exhaustion associated markers (D10). c) CD19-28z primarily comprise T stem cell memory (CD45RA+CD62L+) and central memory (CD45RA−

Figure 2A:
FIG. 2A-E shows that enforced AP-1 expression reduces features of exhaustion in CAR T cells.
Figure 2B:
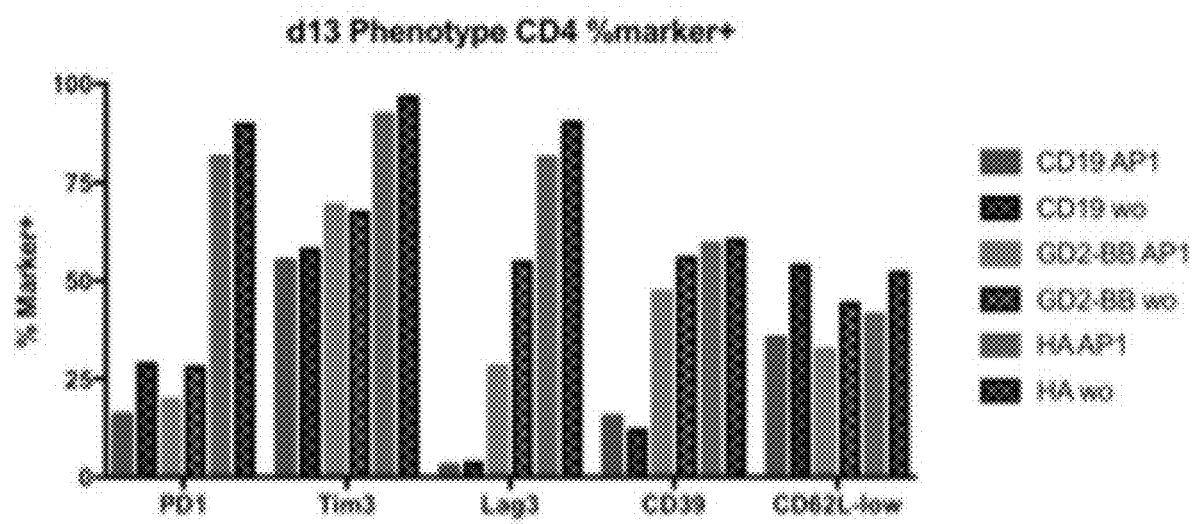
Figure 2C:
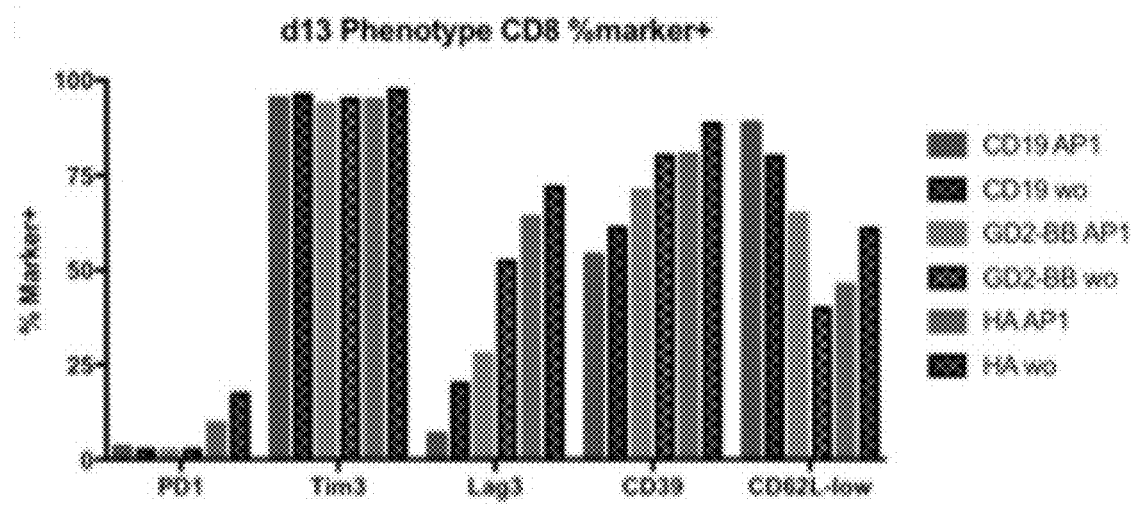
Figure 2D:
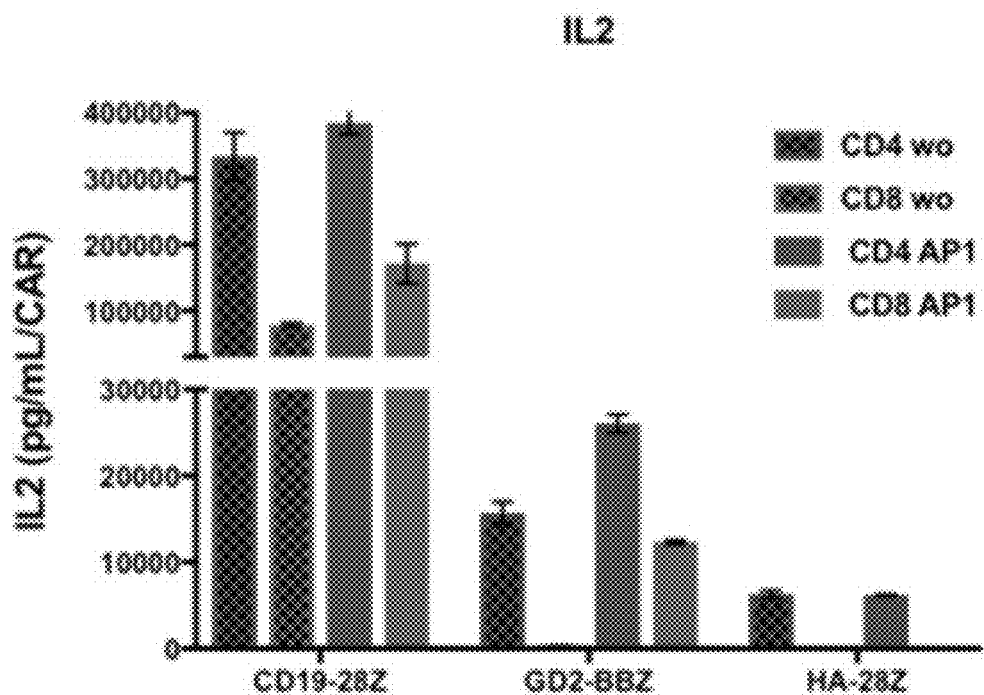
Figure 2E:
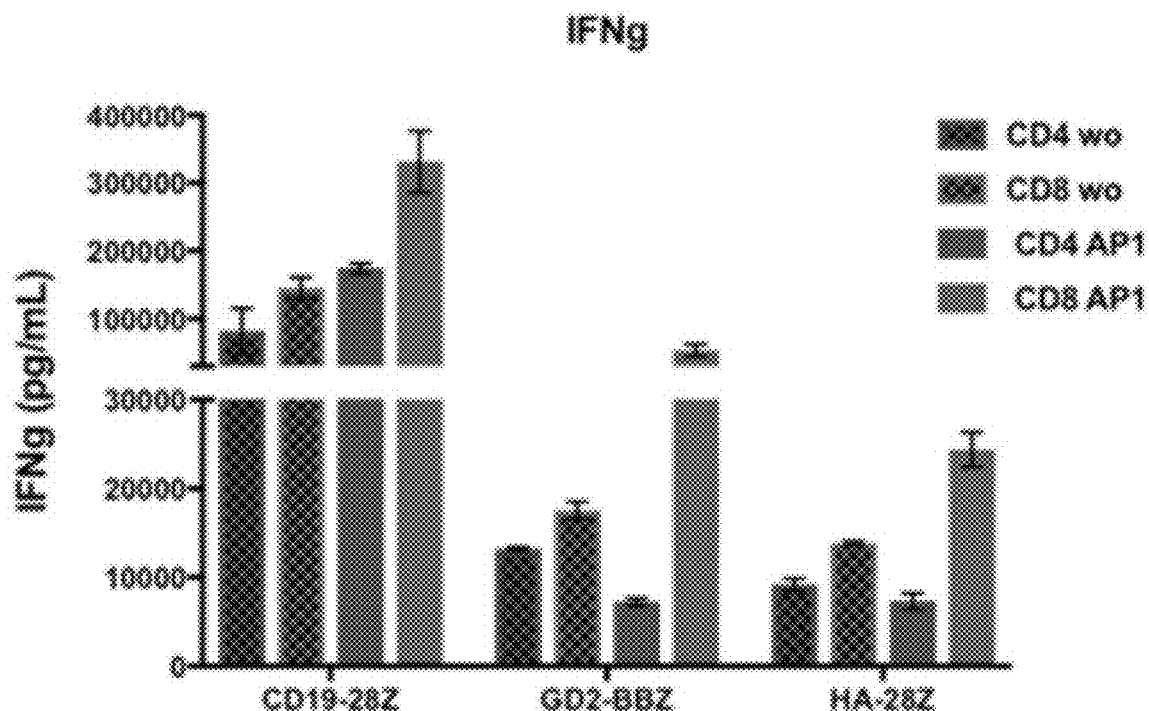

CD62L+, whereas HA-28z primarily comprise CD45RA– CD62L– effector memory cells (D10). d) IL-2 (left) and IFNg (right) release following 24-hour co-culture with CD19+GD2+ Nalm6– GD2 leukemia cells. Error bars represent mean±SD from triplicate wells. One representative donor shown for each assay. e) Principle component analysis (PCA) of global transcriptional profiles of Naïve- and CM-derived CD19 or HA CART cells at days 7, 10, and 14 in culture. PC1 (39.3% variance) separates CD19 from HA CART cells. f) Gene expression of the top 200 genes driving PC1. Genes of interest in each cluster are listed above. g) Differentially accessible chromatin regions in CD8+ CD19 and HA-28z CART cells (D10). Both N and CM subsets are incorporated for each CAR. h) PCA of ATAC-seq chromatin accessibility in CD19 or HA-28z CART cells (D10). PC1 (76.9% variance) separates CD19 from HA CAR samples. i) Global chromatin accessibility profile of subset-derived CD19 and HA-28z CAR T cells (D10). Top 5000 differentially accessible regions (peaks). j) Differentially accessible enhancer regions in CD19 and HA CART cells in the CTLA4 (top) or IL7R (bottom) loci. N—naïve, CM—central memory. * $p<0.05$,  $p<0.01$, * $p<0.001$. ns $p>0.05$.

FIG. 13A-E shows that AP-1 family signature in exhausted CART cells. a) Top 25 transcription factor motif deviation scores in Day 10 HA vs CD19-CAR expressing T cells by chromVAR analysis reveal numerous AP-1 (bZIP) family members in CD4+ and CD8+ T cells derived from N or CM subsets (D10). b) TF motif enrichment analysis in N CD8+ HA-28z CAR T cells demonstrates AP-1 (bZIP) family motifs as the most significantly enriched. c) Bulk RNA-seq expression (FPKM) of indicated AP-1 (bZIP) and IRF family members in CD19 and HA-28z CART cells. Error bars represent mean±SEM from n=6 samples across 3 donors showing paired CD19 vs HA expression for each gene. p-values were generated using the Wilcoxon matched-pairs signed rank test. d) CD19-28z and HA-28z CAR T cells were lysed and expression of the indicated AP-1 family proteins was assessed by western blot. Increased protein expression of JunB, BATF3, and IRF4 in HA-28z CART cells compared to CD19 CART cells was confirmed at days 7, 10, and 14 of culture. e) Correlation network of exhaustion-related transcription factors in N-derived CD8+ (left) and CD4+ (right) GD2-28z CAR T cells using single cell RNA-seq analysis. Transcription factor genes identified as differentially expressed (p<0.05) by DESeq2 form the nodes of the network. Colors represent log 2 fold-change (FC) (GD2 vs CD19 CAR). Edge thickness represents the magnitude of correlation in expression between the relevant pair of genes across cells. A correlation score >0.1 was used to construct networks. * $p<0.05$,  $p<0.01$, * $p<0.001$. ns $p>0.05$.

FIG. 14A-K shows that c-Jun overexpression enhances the function of exhausted CAR T cells. a) Schematic of the JUN-P2A-CAR expression vector. b) Intracellular flow cytometry demonstrating total c-Jun expression in control and JUN-modified CAR T cells (D10). c) Western blot for total c-Jun and phospho-c-JunSer73 in control and JUN-modified CD19 and HA CART cells (D10). (d) IL-2 and (e) IFNg production following 24 hr co-culture of control (blue) or JUN-modified (red) CD19 and HA CART cells in response to antigen+ tumor cells. Error bars represent mean±SD of triplicate wells. Data from one representative donor shown. Fold increases in IL-2 or IFNg production in JUN vs control CAR T cells across multiple donors can be found in FIG. 24. f) Left: Flow cytometry plots showing representative CD45RA/CD62L expression in Control vs JUN-CART cells (D10). Right: Relative frequency of effector (E, RA+62L–), stem cell memory (SCM, RA+62L+), central memory (RA–62L+), and effector memory (RA–62L–) in CD4+ (upper) or CD8+ (lower) Control or JUN-HA-28z CAR T cells. n=6 donors from independent experiments. Lines indicate paired samples from the same donor. Paired, two-tailed t-tests were performed. g) On day 39 of culture, $1\times10^6$ viable T cells from FIG. 24c were re-plated and cultured for 7 days with or without IL-2. h-j) Cell surface phenotype of control or JUN-CD19-28z CAR T cells from (g) on day 46. h) CD4 vs CD8 expression. i) Late expanding CD8+ JUN-modified CD19-28z CART cells have a stem cell memory phenotype (CD45RA+CD62L+). j) Late expanding CD8+ JUN-modified CD19-28z CAR T cells have reduced exhaustion marker expression compared to controls. k) T cells from g were cryopreserved on D10, thawed and rested overnight in IL-2. Healthy NSG mice were infused with 5×106 control or JUN-modified CD19-28z or CD19-BBz CART cells via IV injection. On day 25 post infusion, peripheral blood T cell numbers were quantified by flow cytometry. Error bars represent mean±SEM of n=5 mice per group. * $p<0.05$,  $p<0.01$, * $p<0.001$. ns $p>0.05$. HTM—hinge/transmembrane. ICD—intracellular domain.

FIG. 15A-J shows that functional rescue of exhausted HA-28z CAR T cells requires the presence of c-Jun during both chronic and acute T cell stimulation and is independent of JNP. a) Proposed mechanisms of c-Jun-mediated rescue of T cell exhaustion. AP-1-i indicates an inhibitory AP-1 complex. b) Schematic of the DD regulated JUN expression vector. c) Schematic of drug-induced stabilization of JUN-DD expression. Yellow diamond—TMP stabilizing molecule. d) Total c-Jun expression in control, JUN-WT, and JUN-DD HA-28z CAR T cells (D10) by intracellular flow cytometry (left) and western blot (right). e) IL-2 (left) and IFNg (right) production in Control, JUN-WT, or JUN-DD (OFF, ON) modified HA-28z CAR T cells 24 hr following stimulation with Nalm6-GD2 or 143B target cells, or media alone (baseline) (D10). In d-e) OFF indicates without TMP, ON indicates T cells cultured in the presence of 10 uM TMP from D4 and during co-culture. In f-g) TMP was added either during T cell expansion (starting at D4) or only during co-culture with tumor cells as indicated in f. For ON-OFF and OFF-ON conditions, TMP was removed/added 18 hr prior to co-culture to ensure complete c-Jun degradation/stabilization, respectively, prior to antigen exposure. g) IL-2 expression in one representative donor (left, SD across triplicate wells) and fold increase in IL-2 (SEM of n=6 independent experiments representing 3 different donors, relative to OFF-OFF condition). h-j) Increased functional activity of JUN-CAR T cells is independent of Jun N-terminal phosphorylation (JNP). h) Schematic of c-Jun protein showing N-terminal transactivation domain (TAD). Asterisks represent the JNP sites at Ser63 and Ser73 which are mutated to alanine in the JUN-AA mutant. i) Western blot of total c-Jun and c-Jun-PSer73 in control, JUN-WT, and JUN-AA HA-28z CART cells. j) IL-2 (left) and IFNg (right) release in control, JUN-WT, and JUN-AA HA-28z CAR T cells following 24 hr stimulation with Nalm6-GD2 or 143B target cells or media alone (Baseline). Error bars represent mean±SD of triplicate wells. Representative of 3 independent experiments. * $p<0.05$,  $p<0.01$, * $p<0.001$. ns $p>0.05$. HTM—hinge/transmembrane, ICD—intracellular domain, DD—destabilizing domain from *E. coli* DHFR, TMP—trimethoprim, WT—wildtype.

FIG. 16A-H shows that JUN-modified CART cells increase in vivo activity against leukemia and solid tumors.

In a-c, NSG mice were inoculated with 1×Nalm6-GD2 leukemia cells via IV injection. 3×10$^6$ Mock, HA-28z, or JUN-HA-28z CAR+ T cells were given IV on d3. Tumor progression was monitored using bioluminescent imaging (a-b). Scales are normalized for all time points. c) JUN-HA-28z CAR T cells induced long term tumor-free survival. Error bars represent mean±SEM of n=5 mice/group. This finding was reproducible in >3 independent experiments, however, in some experiments long term survival was diminished due to outgrowth of GD2(−) Nalm6 clones. d) Schematic of JUN-Her2-BBz retroviral vector construct. e) Her2-BBz CAR T cell lysis of GFP+ Nalm6-Her2 target cells at 1:8 E:T ratio. Error bars represent mean±SD of triplicate wells. Representative of 2 independent experiments. In f-h, NSG mice were inoculated with 1×10$^6$ 143 b-19 osteosarcoma cells via intramuscular injection. 1×10$^7$ Mock, Her2-BBz, or JUN-Her2-BBz CAR T cells were given IV on d7. f) Tumor growth was monitored by caliper measurements. g) JUN-Her2-BBz CAR T cell treated mice maintained long term, tumor-free survival. h) On d20 following tumor cell implantation, peripheral blood T cells were quantified in mice treated as in f Error bars represent mean±SEM of n=5 mice/group. Representative of 2 independent experiments with similar results. * $p<0.05$,  $p<0.01$, * $p<0.001$. HTM—hinge/transmembrane. ICD—intracellular domain.

FIG. 17A-I shows that JUN-CAR T cells enhance T cell function under suboptimal stimulation. a) IL-2 and b) IFNg production following 24 hr stimulation of control or JUN-modified HA-28z CAR T cells with immobilized 1A7 anti-CAR idiotype antibody. Each curve was fit with non-linear dose response kinetics to determine EC50. Smaller graphs to the right visualize curve where antibody concentration is 0-1 ug/mL. c) Vector schematic of JUN-CD22-BBz retroviral vector construct. d) CD22 surface expression on parental Nalm6, Nalm6-22KO, and Nalm6-22KO+CD22low. e) IL-2 (left) and IFNg (right) release following co-culture of control or JUN CD22-BBz CAR T cells exposed to Nalm6 and Nalm6-22low. Error bars represent mean±SD of triplicate wells. Representative of 3 independent experiments. In f-i), NSG mice were inoculated with 1×10$^6$ Nalm6-22low leukemia cells on day 0. On day 4, 3×10$^6$ control or JUN-CD22-BBz CAR+ T cells or 3×10$^6$ Mock transduced T cells were transferred IV. Tumor growth was monitored by bioluminescent imaging (f) with images (i). g) Mice receiving JUN-22BBz CAR T cells display increased peripheral blood T cells on day 23. h) JUN expression significantly improved long term survival of CAR treated mice. In f-g, error bars represent mean±SEM of n=5 mice per group. Representative of 2 independent experiments with similar results. * $p<0.05$,  $p<0.01$, * $p<0.001$. HTM—hinge/transmembrane. ICD—intracellular domain.

FIG. 18A-G shows that high Affinity (HA) 14g2a-GD2E101K CART cells manifest an exaggerated exhaustion signature compared to the original 14g2a-GD2 CAR. a) Surface inhibitory receptor expression in CD19, GD2, and HA-GD2E101K CART cells at day 10 of culture. High affinity E101K mutation results in increased inhibitory receptor expression in CD4+ and CD8+ CAR T cells, compared to parental GD2 CAR. b) IL-2 secretion following 24 h co-culture of HA-GD2E101K or original GD2-28z CART cells with GD2+ target cells. The increased exhaustion profile of HA-GD2E101K CART cells corresponds to decreased functional activity, as measured by the ability to produce IL-2 upon stimulation. Error bars represent mean±SD of triplicate wells. Representative of at least 4 independent experiments with similar results. c) PCA of bulk RNA-seq demonstrates larger variance between HA-GD2E101K and CD19 CAR T cells, whereas GD2-28z (sh) CAR T cells are intermediary. Left—CD4+ T cells. Right—CD8+ CART cells, Naïve-derived. d-e) HA-GD2E101K CAR expression causes enhanced inhibitory receptor expression (d) and decreased memory formation (e) in CD4+ CAR T cells. (CD8+ data in FIG. 12). f) RNA-seq PCA from FIG. 12e showing PC2 separation is driven by CM vs N and PC3 separation driven by CD4 vs CD8. g) GSEA: gene sets upregulated in day 10 HA-28z CART cells vs CD19-28z CAR T cells showed significant overlap with genes upregulated in Exhausted vs Memory CD8+ (left), Exhausted vs Effector CD8+ (middle), and Exhausted vs Naïve CD8+ (right) in a mouse model of chronic viral infection (Wherry et al. Immunity, 2007). * $p<0.05$,  $p<0.01$, * $p<0.001$. PCA—principle component analysis, NES—normalized enrichment score.

Figure 19C:
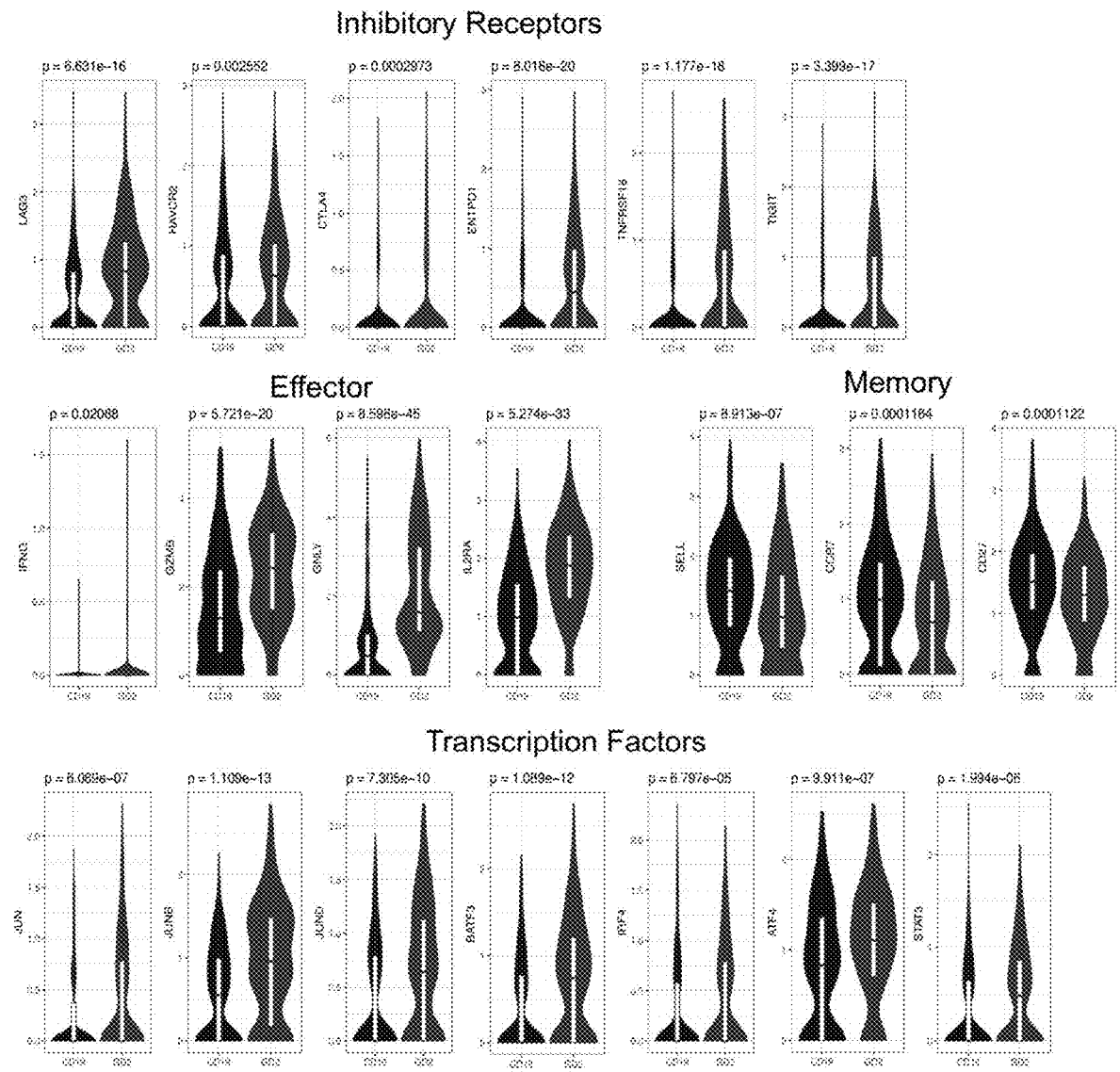
Figure 20A:
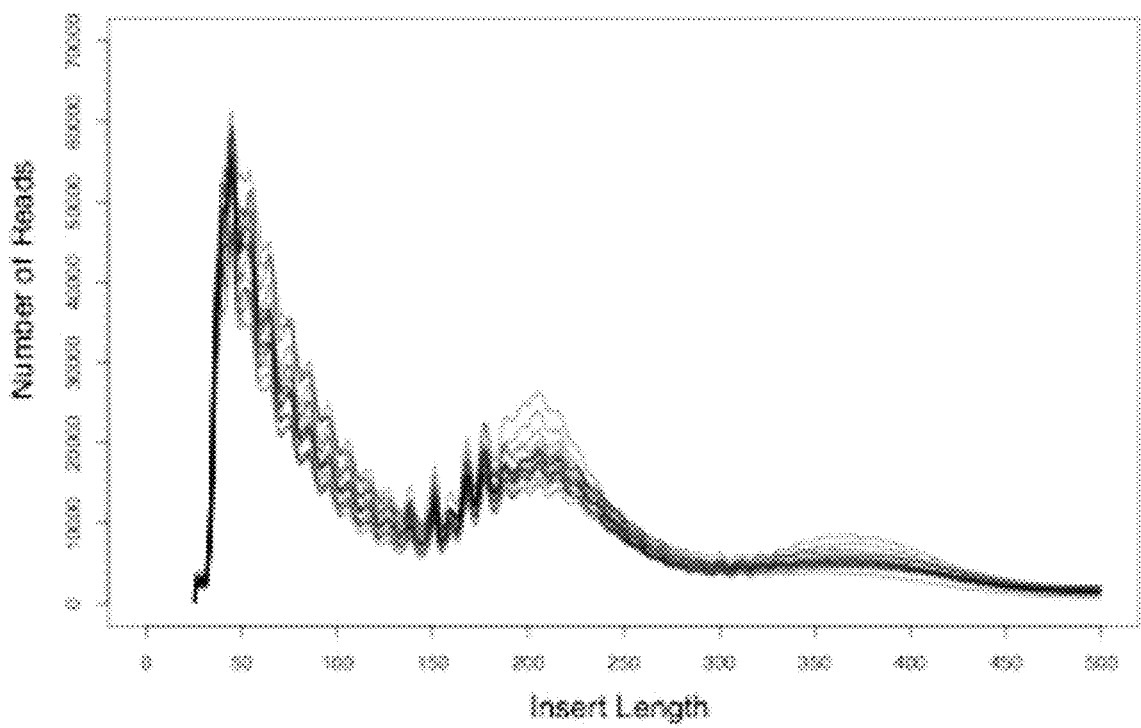
Figure 20B:
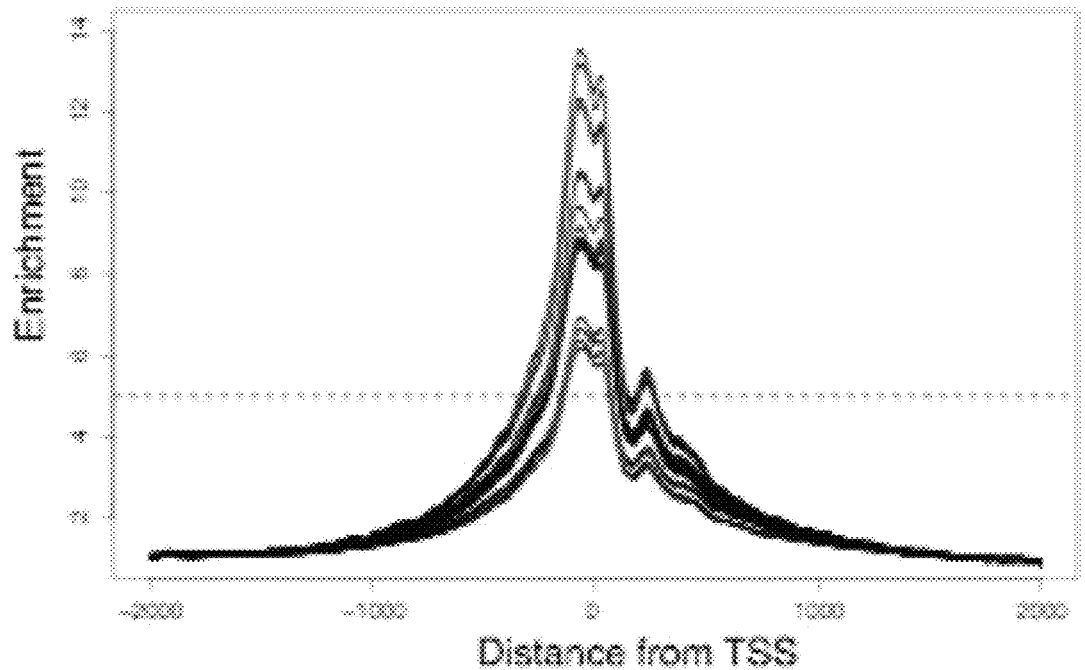
Figure 20C:
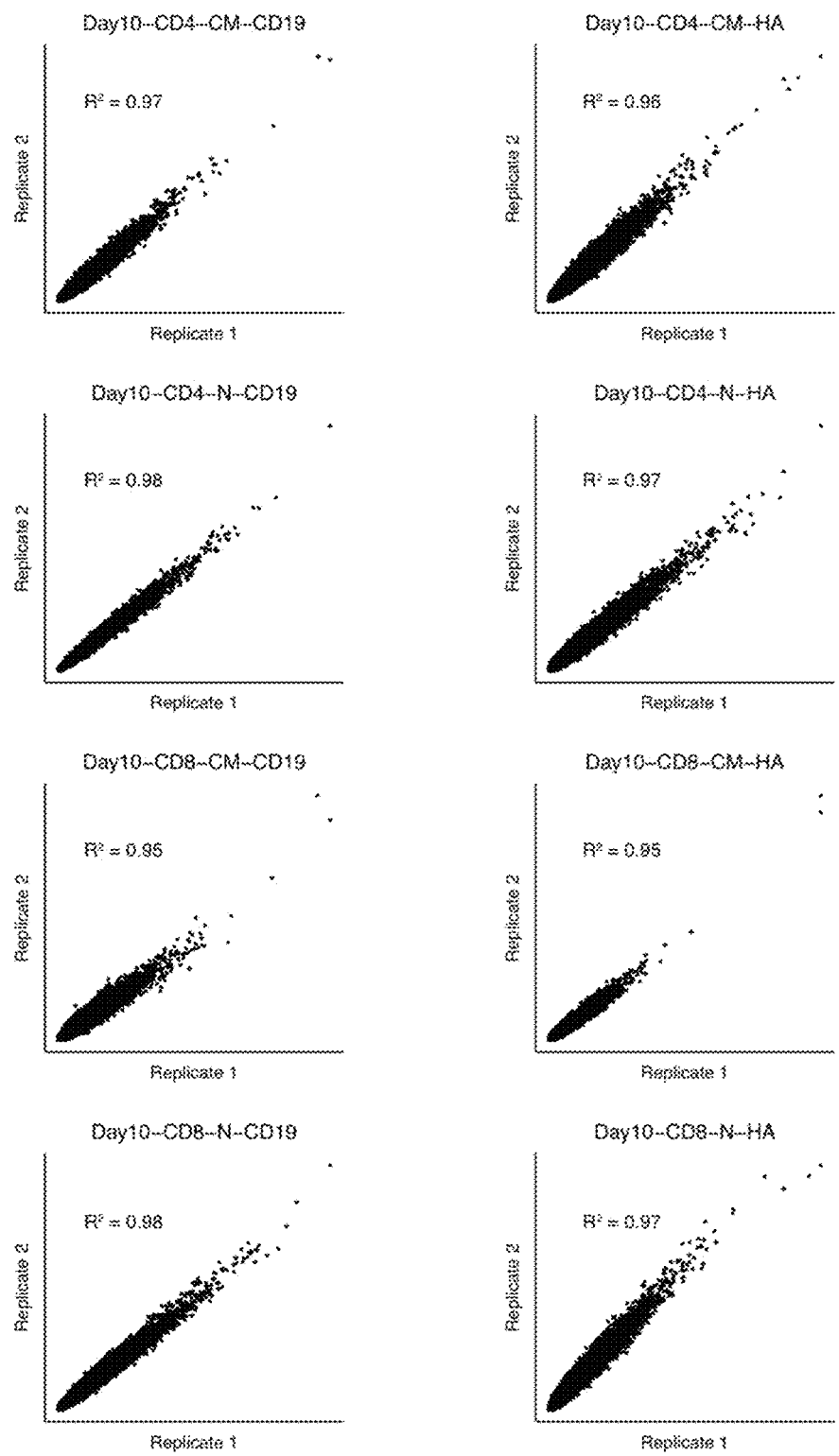
Figure 20D:
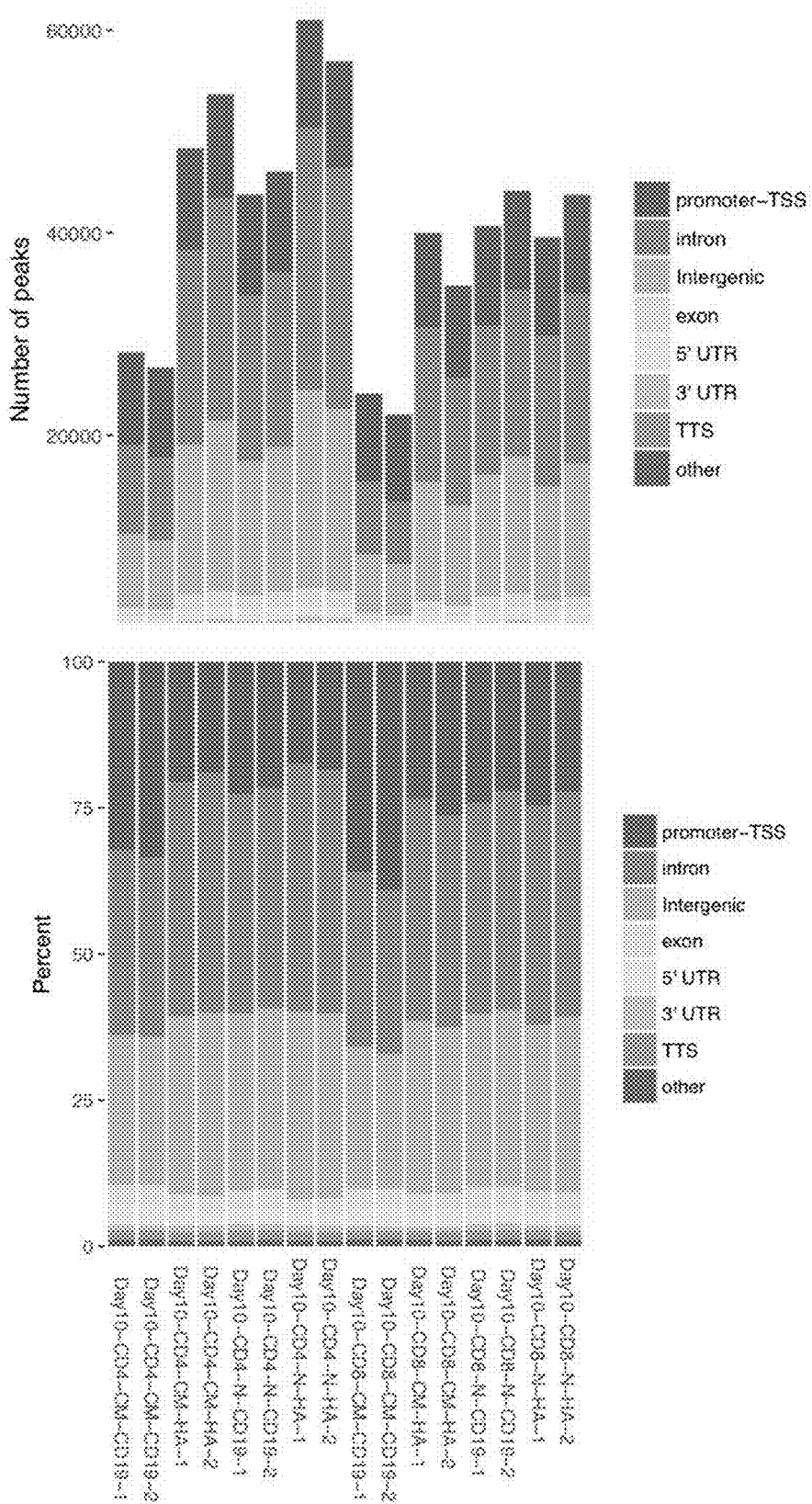

FIG. 19A-C shows that GD2-28z CART cells display an exhaustion signature at the single cell level. a) Venn diagram showing overlapping genes in differential expression analysis of single cell data (red) and the top 200 genes driving the separation of CD19 and HA-28z CART cells in bulk RNA-seq. 79 out of the top 200 genes from bulk RNA-seq are differentially expressed by DESeq2 analysis in GD2-28z vs CD19-28z single cells. Highlighted genes from the intersection include inhibitory receptors (CTLA4, LAG3, GITR, effector molecules CD25, IFNG, GZMB, and cytokines IL13 and IL1A and AP-1/bZIP family transcription factors BATF3 and IRF4. b) Heatmap clustering the top 50 differentially expressed genes in GD2-28z vs CD19-28z single cell transcriptome analysis. Each row represents one cell. c) Violin plots depicting individual gene expression in CD8+ GD2-28z and CD19-28z single CAR T cells. Genes upregulated in GD2 CART cells include inhibitory receptors, effector molecules, and AP-1 family transcription factors, while CD19 CAR T cells have increased expression of memory-associated genes. P-values that are displayed for each gene above the individual plots were calculated using unpaired two-tailed Wilcoxon-Mann-Whitney U test.

FIG. 20A-D shows ATAC-seq data quality control. a) Insert length b) insert distance from transcriptional start site (TSS) for combined (top) and individual samples (below). c) Correlation between replicate samples. d) Location of mapped peaks in each sample by total number of peaks (upper) and frequency of total (lower).

FIG. 21A-D shows AP-1 family comprise the most significantly enriched transcription factor motifs in HA-28z exhausted CAR T cells. a) Differentially accessible chromatin regions in CD4+CD19 and HA CART cells (D10). Both N and CM subsets are incorporated for each CAR. b) PCA from FIG. 1h showing PC2 separation is driven by CM vs N and PC3 separation driven by CD4 vs CD8. c) Top transcription factor motifs enriched in chromatin regions differentially accessible in HA-28z CAR T cells comprise AP-1/bZIP family factors in all starting T cell subsets. CD8+Naïve subset is shown in FIG. 2. d) Peak clustering by shared regulatory motif (left) and enrichment heat map of transcription factor motifs (right) in each cluster. 10 different clusters including clusters associated with exhausted (EX1-EX4) or healthy (HLT1-HLT2) CAR T cells, CM (CM) or N (Naive) starting subset, and CD4 or CD8 T cell subset. Genes of interest in each cluster are highlighted to the right. (N—naïve, CM—central memory).

FIG. 22A-C shows AP-1/bZIP family transcription factors are upregulated in HA-28z CAR T cells and form immunoregulatory complexes. a) Fold change in the gene expression (HA/CD19) for the indicated AP-1/bZIP and IRF family genes from RNA sequencing data from FIG. 2. Error bars represent mean±SEM of n=6 samples across 3 independent donors. b) Fold change in the protein expression (HA/CD19) for the indicated AP-1/bZIP and IRF family proteins was determined by densitometry analysis of western blots. Error bars represent mean±SEM of n=4 experiments across 3 independent donors. * p<0.05,  p<0.01, * p<0.001. c) Western blot analysis for the indicated AP-1/bZIP and IRF family member proteins at input (left columns) or after immunoprecipitation for c-Jun (middle columns) or JunB (right columns) in CD19 and HA-28z CART cells. Numbers below represent the fold increase in protein expression for HA vs CD19 at each condition and colored shapes represent the complexes identified sized to scale. IP-western blots demonstrate the increased presence of c-Jun/JunB, c-Jun/IRF4, c-Jun/BATF, and c-Jun/BATF3 complexes in HA-28z CART cells. IRF4 is also bound at a similar ratio to JunB, while BATF and BATF3 show a preferential complexing with JunB.

FIG. 23A-E shows enhanced activity of AP1-modified CAR T cells is dependent on c-Jun but not c-Fos. a-c) CAR T cells were co-transduced with (AP1) or without (Control) a lentiviral vector encoding both AP1 transcription factors Fos and Jun and a truncated NGFR (tNGFR) surface selection marker. a) Schematic of the lentiviral construct. b) Representative transduction efficiency of AP1 modified CAR T cells as measured by NGFR surface expression in indicated CD4+ and CD8+ CAR T cells. c) IL-2 production in control or AP1-modified CART cells following 24 hr stimulation with 143B-19 target cells. AP1-modified HA-28z CAR T cells show increased IL-2 production compared to control CAR T cells. Representative experiment of 2 independent experiments with similar results. d-e) CAR T cells were co-transduced with lentiviral vectors encoding either AP1 transcription factor Fos or Jun and a truncated NGFR (tNGFR) surface selection marker. d) Schematics of the Fos and Jun lentiviral constructs. e) IL-2 production in control, Fos, or Jun modified CAR T cells following 24 hr stimulation with Nalm6-GD2 target cells. Error bars represent mean±SD of triplicate wells. Representative experiment of 2 independent experiments with similar results. In a and d, * denotes a stop codon. * p<0.05,  p<0.01, * p<0.001, ns p>0.05.

Figure 24A:
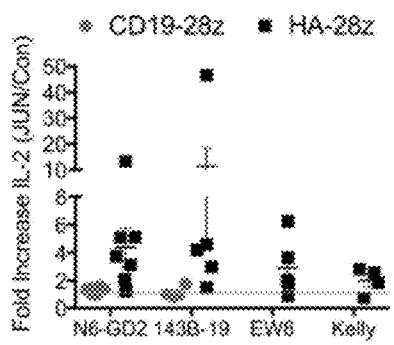
Figure 24B:
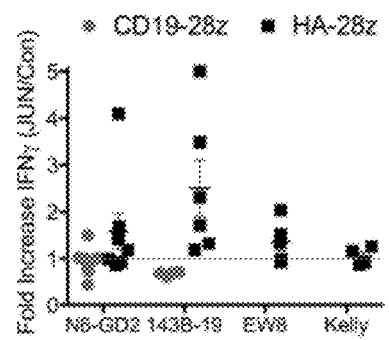
Figure 24C:
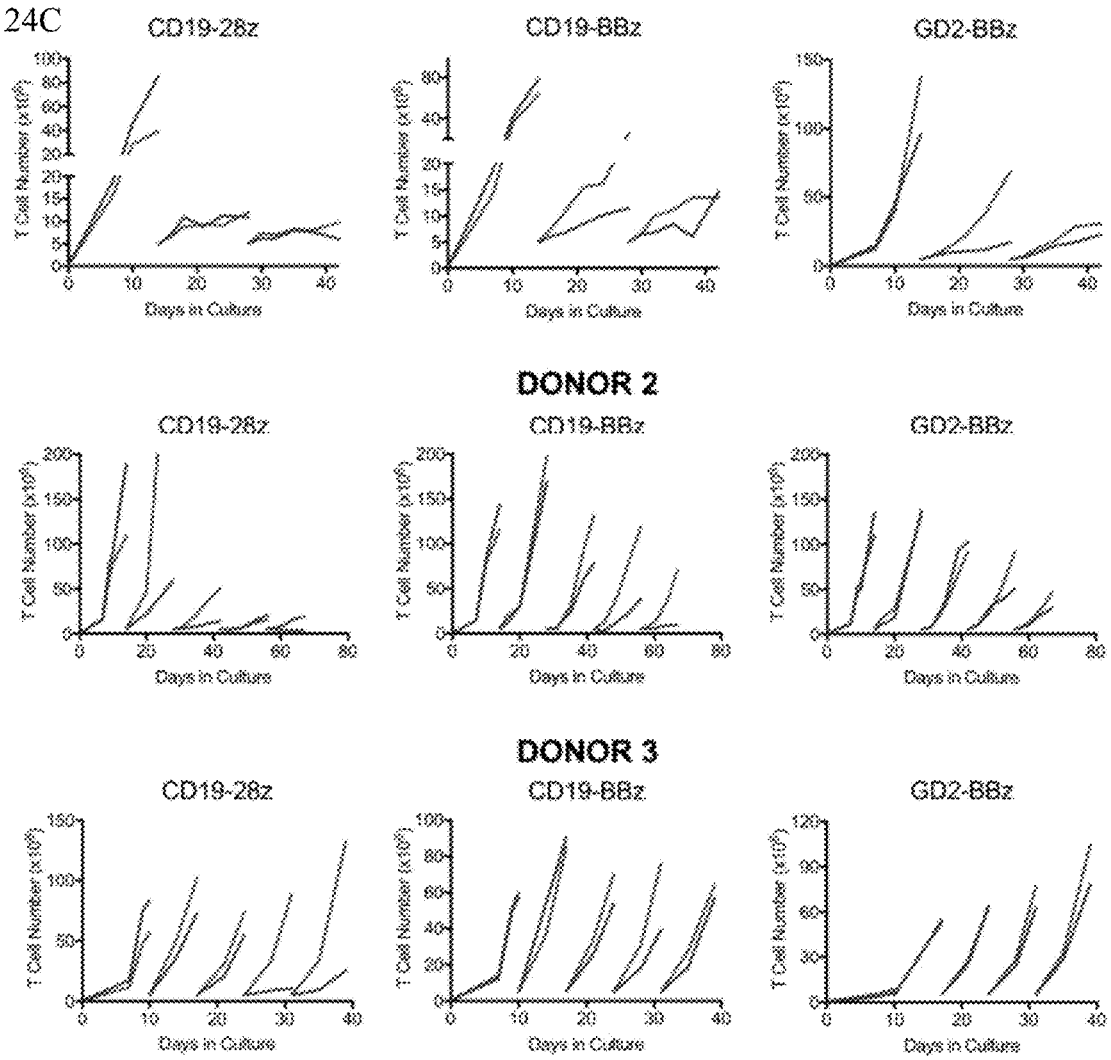
Figure 26A:
Figure 26B:
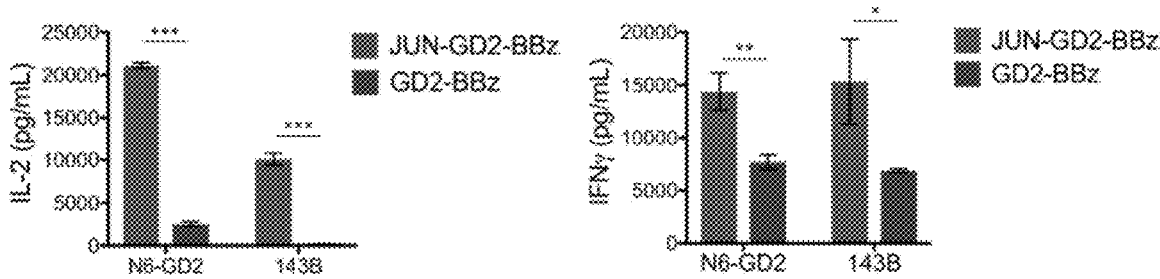
Figure 26C:
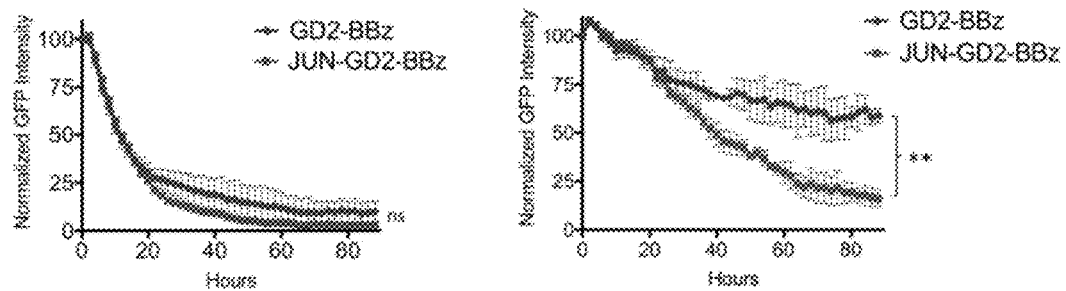
Figure 26D:
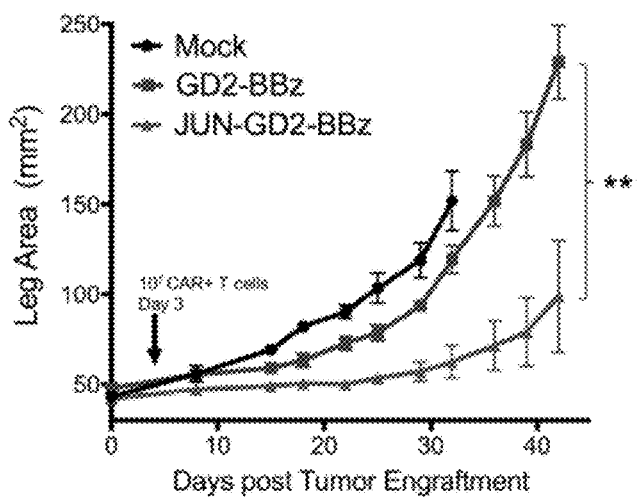
Figure 26E:
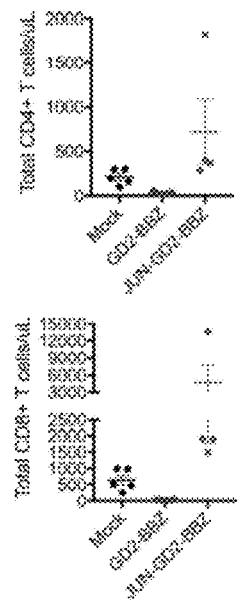

FIG. 24A-C shows extended functional assessment of JUN-modified CAR T cells. a-b) Fold increase in IL-2 (a) and IFNg (b) release following 24 hr co-culture with the indicated target cells in JUN vs Control CD19 and HA-28z CART cells. Each dot represents one independent experiment from different donors. c) Extended expansion of control or JUN-modified CAR T cells in vitro in 3 independent experiments with 3 different healthy donors. At the indicated time points, T cells were re-plated in fresh T cell media+100 IU/mL IL2. T cells were counted and fed to keep cells at 0.5×106/mL every 2-3 days. For DONOR-1, 5×106 viable T cells were re-plated on days 14 and 28. For DONOR-2, 5×106 viable T cells were re-plated on days 14, 28, 42, and 56. For DONOR-3, 5×106 viable T cells were re-plated on days 10, 17, 24, and 31.

FIG. 25A-E shows c-Jun overexpression decreases the prevalence and complexing of inhibitory AP-1 family members JunB, BATF, and BATF3. a) Kinetics of drug-induced c-Jun stability in JUN-DD CAR T cells as assessed by western blot. At time 0, 10 uM TMP was either added to untreated cells (ON) or washed out of previously treated cells (OFF). Cells were removed from each condition at 1, 2, 4, 8, 24, and 48 hr and prepared for western blot analysis of c-Jun expression. The observed band corresponds to the size of JUN-DD. b) Densitometry analysis was performed on the blots from (a) and normalized to a loading control. Expression was plotted vs time and first order kinetics curves fit to the data to determine t½ for OFF and ON kinetics. c) Western blot analysis for the indicated AP-1/bZIP and IRF family member proteins in control and JUN-CAR T cells (D10). Numbers below represent the fold change in protein expression compared to CD19. d) Corresponding decrease in mRNA expression of BATF, BATF3, and JUNB in JUN-HA-28z CART cells compared to HA-28z. n=3 donors, normalized to CD19 mRNA. e) c-Jun overexpression decreases inhibitory JunB/BATF and JunB/BATF3 complexes by IP-western blot analysis. Input (left columns), immunoprecipitation for c-Jun (middle columns), or JunB (right columns) in Control or JUN-HA-28z CAR T cells. IRF4 protein, mRNA, and complexing with c-Jun is unchanged.

FIG. 26A-E shows JUN-CAR T cells enhance GD2-BBz CAR T cell function in solid tumors. a) Vector schematic of JUN-GD2-BBz retroviral vector construct. b) IL-2 (left) and IFNg (right) production in JUN-modified (red) or control (blue) GD2-BBz CAR T cells following 24 hr stimulation with Nalm6-GD2 or 143B target cells. c) GD2-BBz CAR T cell lysis of GFP+ Nalm6-GD2 target cells at 1:1 (left) or 1:4 (right) E:T ratio. In a-c, error bars represent mean±SD of triplicate wells. Representative of at least 3 independent experiments. In d-e, NSG mice were inoculated with 0.5× 106 143B-19 osteosarcoma cells via intramuscular injection. 1×107 Mock, GD2-BBz, or JUN-GD2-BBz CAR T cells were given IV on day 3. d) Tumor growth was monitored by caliper measurements. e) Peripheral blood CD4+ (upper) or CD8+ (lower) T cell counts at day 14 post tumor engraftment. Error bars represent mean±SEM of n=5 mice per group. Representative of 2 independent experiments although early deaths (unrelated to tumor size) precluded survival curves in both models. * p<0.05,  p<0.01, * p<0.001. HTM—hinge/transmembrane. ICD—intracellular domain.

FIG. 27A-E shows N-terminal mutations of c-Jun are capable of rescuing exhausted HA-28z CAR T cells. a) Different c-Jun mutations cloned into the HA-28z CAR T cell vector. b) IL-2 (upper) and IFNg (lower) secretion following 24 hr co-culture with GD2+ 143B osteosarcoma target cells. c) in vitro lysis of GFP+ Nalm6-GD2 or 143B target cells was measured over 5 days at 1:1, 1:2, or 1:4 effector:target (E:T) ratios. At low E:T ratios and late time points, JUN-WT, JUN-AA, JUN-Dd, and JUN-DTAD demonstrate improved control of tumor growth compared to JUN-De, JUN-Dbasic, JUN-DLeu, and JUN-DbZIP CAR T cells. d) Increased cytokine production was confirmed in both CD4+ and CD8+ HA-28z CAR T cells by intracellular cytokine staining and flow cytometry following 5 hr stimulation with Nalm6-GD2. e) Quantification of peripheral T cell counts 12 days following T cell infusion into NSG mice bearing Nalm6-GD2 leukemia.

Figure 28:
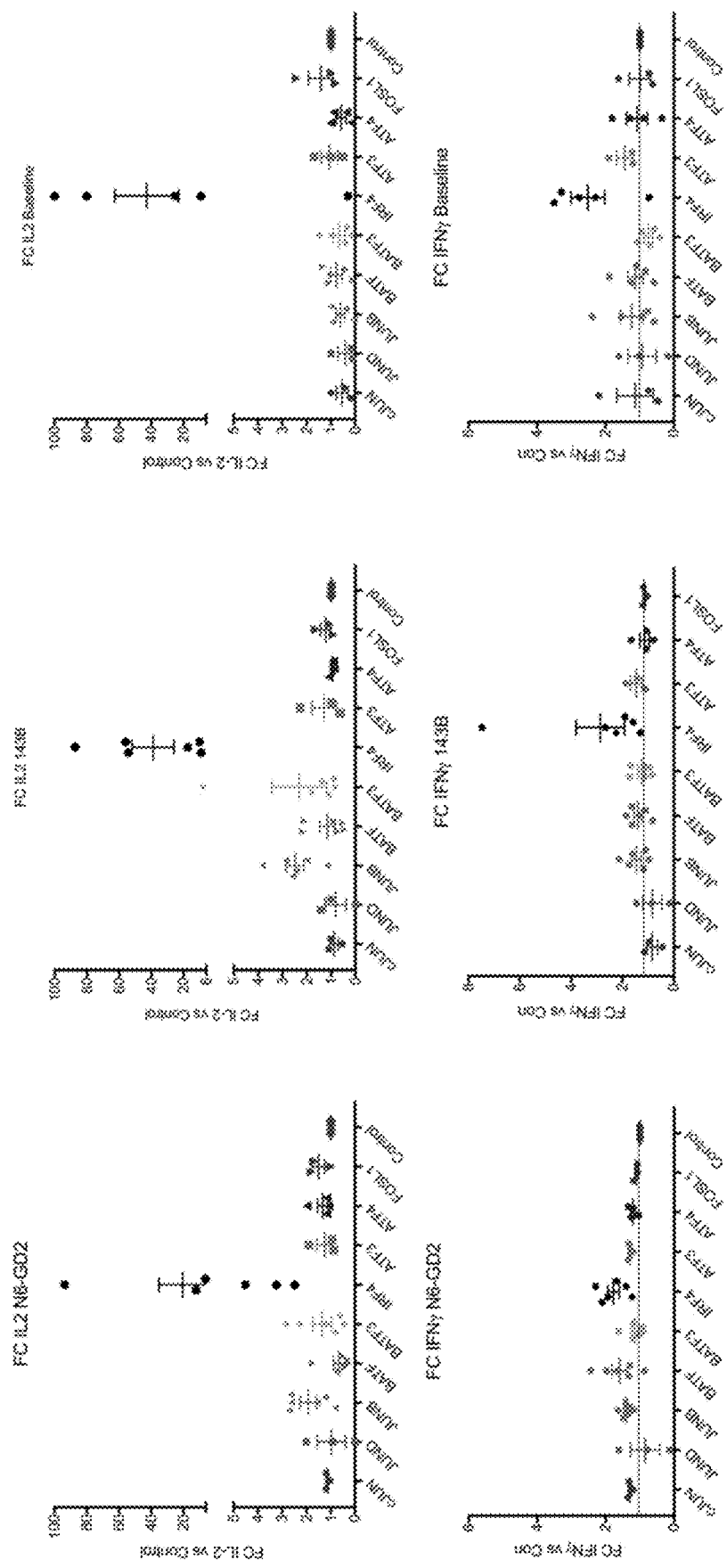

FIG. 28 shows that knockdown of IRF4 dramatically increases functional activity of exhausted HA-28z CAR T cells.

Figure 29A:
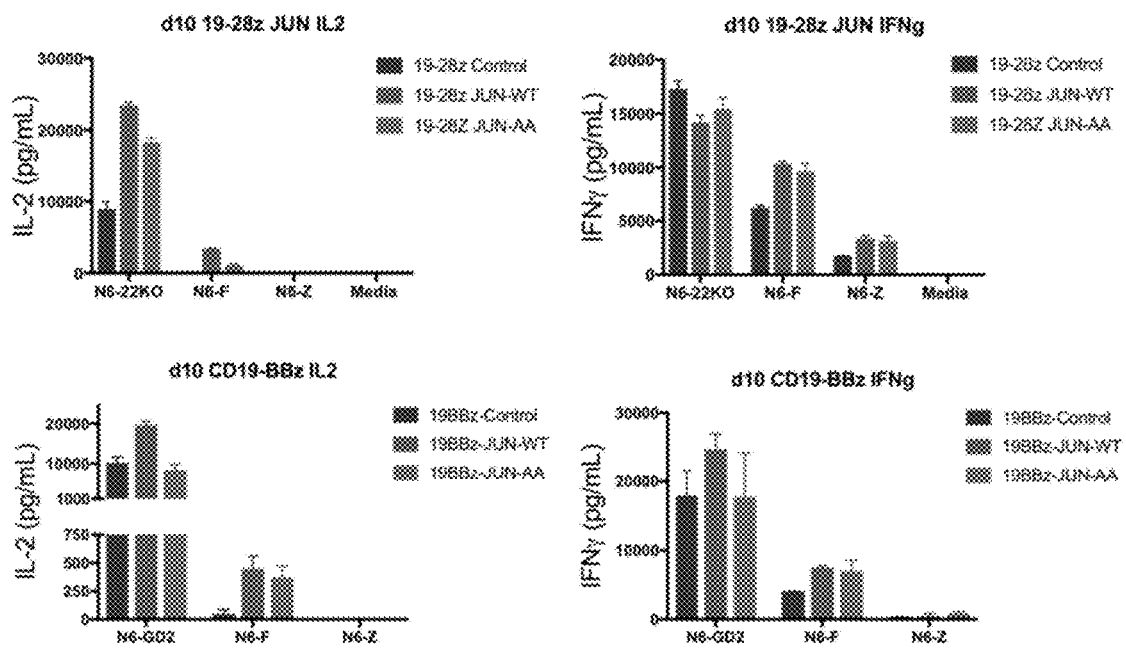
Figure 29B:
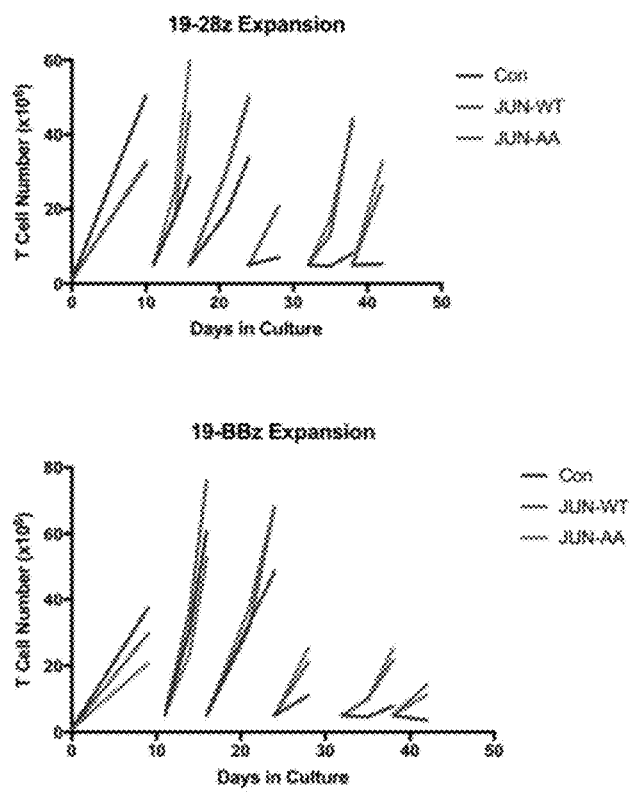
Figure 29C:
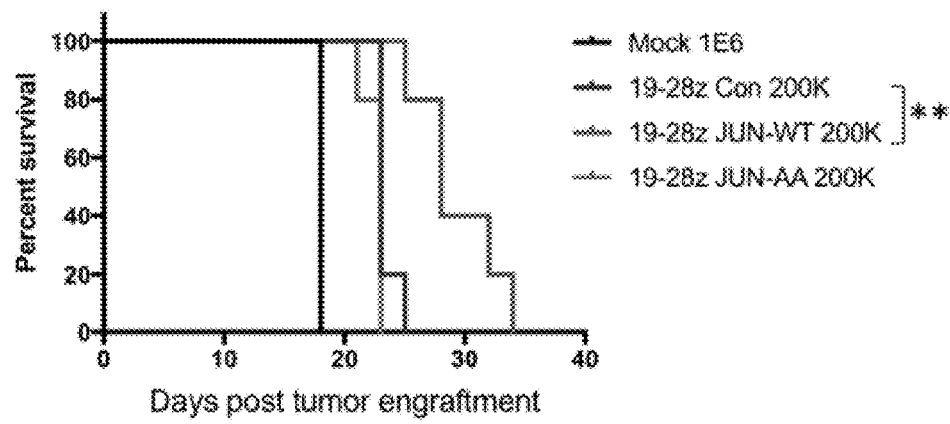
Figure 29C:
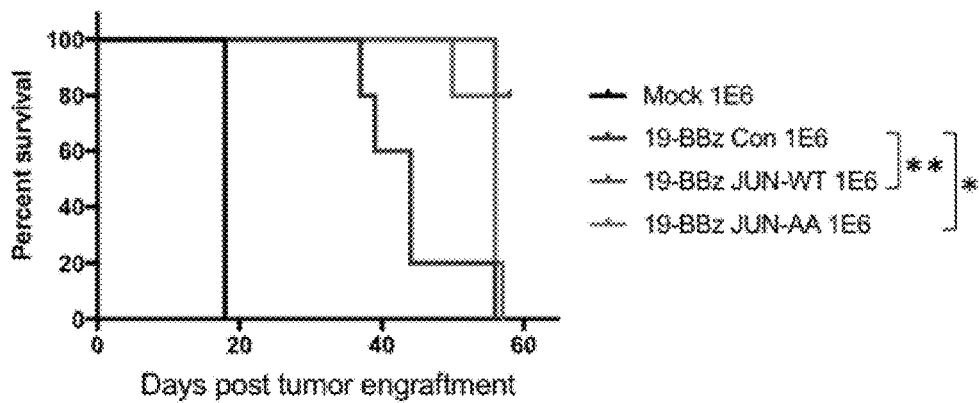

FIG. 29A-C shows that the transcriptional mutant (JUN-AA) also rescues functional activity and proliferative capacity in CD19 CART cells.

Figure 30:
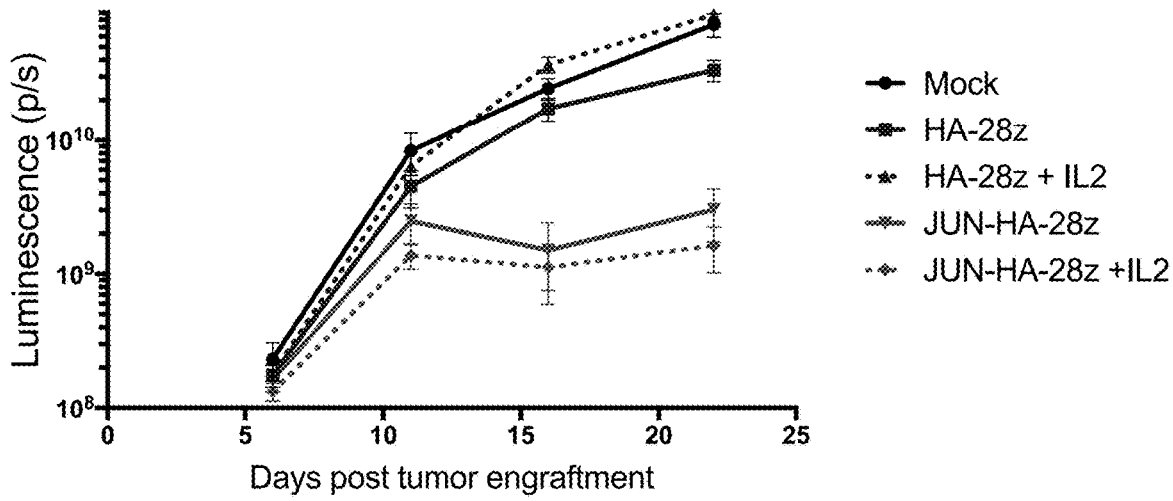

FIG. 30 shows that the enhanced in vivo function of c-Jun modified HA-28z CAR T cells can not be replicated by ex vivo provision of IL-2.

FIG. 31A-E shows that c-Jun enhanced Her2-BBz CAR T cell activity within a suppressive solid tumor microenvironment.

Figure 32:
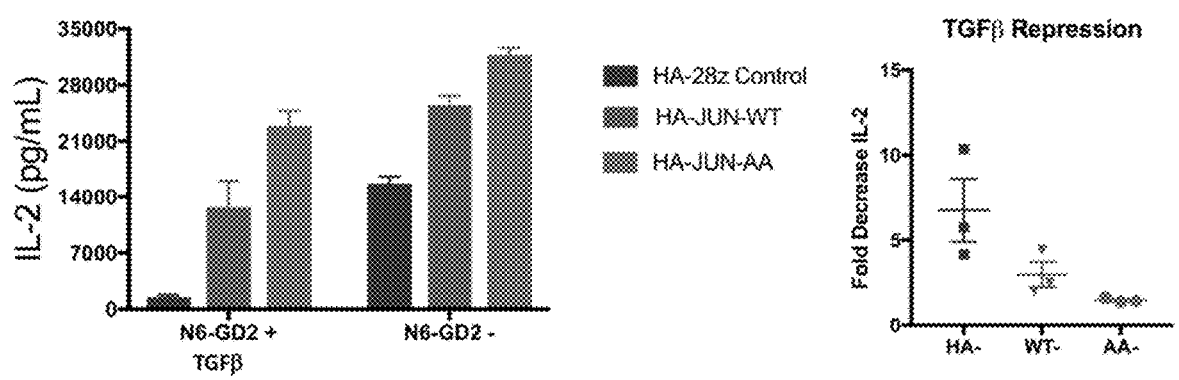

FIG. 32 shows that c-Jun overexpression increases resistance to TGFβ-mediated suppression of exhausted HA-28z CAR T cells.

FIG. 33A-D shows transcriptional changes in c-Jun modified cells are consistent with reduced exhaustion and increased memory formation.

DEFINITIONS

For purposes of interpreting this specification, the following definitions will apply and whenever appropriate, terms used in the singular will also include the plural and vice versa. In the event that any definition set forth below conflicts with any document incorporated herein by reference, the definition set forth below shall control.

As used herein the terms "disease" and "pathologic condition" are used interchangeably, unless indicated otherwise herein, to describe a deviation from the condition regarded as normal or average for members of a species or group (e.g., humans), and which is detrimental to an affected individual under conditions that are not inimical to the majority of individuals of that species or group. Such a deviation can manifest as a state, signs, and/or symptoms (e.g., diarrhea, nausea, fever, pain, blisters, boils, rash, immune suppression, inflammation, etc.) that are associated with any impairment of the normal state of a subject or of any of its organs or tissues that interrupts or modifies the performance of normal functions. A disease or pathological condition may be caused by or result from contact with a microorganism (e.g., a pathogen or other infective agent (e.g., a virus or bacteria)), may be responsive to environmental factors (e.g., malnutrition, industrial hazards, and/or climate), may be responsive to an inherent or latent defect in the organism (e.g., genetic anomalies) or to combinations of these and other factors.

The terms "host," "subject," or "patient" are used interchangeably herein to refer to an individual to be treated by (e.g., administered) the compositions and methods of the present invention. Subjects include, but are not limited to, mammals (e.g., humans, mice, rats, monkeys, horses, cows, pigs, dogs, cats, and the like). In the context of the invention, the term "subject" generally refers to an individual who will be administered or who has been administered one or more compositions of the present invention (e.g., modified or engineered (e.g., genetically) T cells described herein).

"T cell exhaustion" refers to loss of T cell function, which may occur as a result of an infection (e.g., a chronic infection) or a disease. T cell exhaustion is associated with increased expression of PD-1, TIM-3, and LAG-3, apoptosis, and reduced cytokine secretion. Accordingly, the terms "ameliorate T cell exhaustion," "inhibit T cell exhaustion," "reduce T cell exhaustion" and the like refer to a condition of restored functionality of T cells characterized by one or more of the following: decreased expression and/or level of one or more of PD-1, TIM-3, and LAG-3; increased memory cell formation and/or maintenance of memory markers (e.g., CD62L); prevention of apoptosis; increased antigen-induced cytokine (e.g., IL-2) production and/or secretion; enhanced killing capacity; increased recognition of tumor targets with low surface antigen; enhanced proliferation in response to antigen.

The terms "buffer" or "buffering agents" refer to materials that when added to a solution cause the solution to resist changes in pH.

As used herein, the terms "cancer" and "tumor" refer to a tissue or growth comprising cells that have lost the ability to control growth and proliferation. Cancer and tumor cells generally are characterized by a loss of contact inhibition, may be invasive, and may display the ability to metastasize (e.g., they have lost the ability to adhere to other cells/tissues). The present invention is not limited by the type of cancer or the type of treatment (e.g., prophylactically and/or therapeutically treated). Indeed, a variety of cancers may be treated with compositions and methods described herein including, but not limited to, brain cancer or other cancers of the central nervous system, melanomas, lymphomas, bone cancer, epithelial cancer, breast cancer, ovarian cancer, endometrial cancer, colorectal cancer, lung cancer, renal cancer, melanoma, kidney cancer, prostate cancer, sarcomas, carcinomas, and/or a combination thereof.

"Metastasis" as used herein refers to the process by which a cancer spreads or transfers from the site of origin to other regions of the body with the development of a similar cancerous lesion at the new location. A "metastatic" or "metastasizing" cell is one that loses adhesive contacts with neighboring cells and migrates via the bloodstream or lymph from the primary site of disease to invade tissues elsewhere in the body.

The term "anticancer agent" as used herein, refer to any therapeutic agent (e.g., chemotherapeutic compounds and/or molecular therapeutic compounds), antisense therapies, radiation therapies, and the like used in the treatment of hyperproliferative diseases such as cancer (e.g., in mammals, e.g., in humans).

An "effective amount" refers to an amount of a pharmaceutical composition, anticancer agent, or other drug effective, at dosages and for periods of time necessary, to achieve a desired therapeutic or prophylactic result (e.g., relief of some or all symptoms of the disease being treated).

The term "therapeutically effective amount," as used herein, refers to that amount of the therapeutic agent sufficient to result in amelioration of one or more symptoms of a disorder, or prevent advancement of a disorder, or cause regression of the disorder. For example, with respect to the treatment of cancer, in one embodiment, a therapeutically effective amount will refer to the amount of a therapeutic agent that decreases the rate of tumor growth (e.g., reduces and/or eliminates the tumor burden in the patient), decreases tumor mass, decreases the number of metastases, decreases tumor progression, or increases survival time by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

The terms "sensitize" and "sensitizing," as used herein, refer to making, through the administration of a first agent, an animal or a cell within an animal more susceptible, or more responsive, to the biological effects (e.g., promotion or retardation of an aspect of cellular function including, but not limited to, cell division, cell growth, proliferation, invasion, angiogenesis, necrosis, or apoptosis) of a second agent. The sensitizing effect of a first agent on a target cell can be measured as the difference in the intended biological effect (e.g., promotion or retardation of an aspect of cellular function including, but not limited to, cell growth, proliferation, invasion, angiogenesis, or apoptosis) observed upon the administration of a second agent with and without administration of the first agent. The response of the sensitized cell can be increased by at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least 300%, at least about 350%, at least about 400%, at least about 450%, or at least about 500% over the response in the absence of the first agent.

As used herein, the terms "purified" or "to purify" refer to the removal of contaminants or undesired compounds from a sample or composition. As used herein, the term "substantially purified" refers to the removal of from about 70 to 90%, up to 100%, of the contaminants or undesired compounds from a sample or composition.

As used herein, the terms "administration" and "administering" refer to the act of giving a composition to a subject. Exemplary routes of administration to the human body include, but are not limited to, through the eyes (ophthalmic), mouth (oral), skin (transdermal), nose (nasal), lungs (inhalant), oral mucosa (buccal), ear, rectal, by injection (e.g., intravenously, subcutaneously, intraperitoneally, intratumorally, etc.), topically, and the like. In one embodiment, administration of T cells of the invention is via intravenous infusion.

As used herein, the terms "co-administration" and "co-administering" refer to the administration of at least two agent(s) (e.g., genetically modified immune cells and one or more other agents—e.g., anti-cancer agents) or therapies to a subject. In some embodiments, the co-administration of two or more agents or therapies is concurrent. In other embodiments, a first agent/therapy is administered prior to a second agent/therapy. In some embodiments, co-administration can be via the same or different route of administration. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

The terms "pharmaceutically acceptable" or "pharmacologically acceptable," as used herein, refer to compositions that do not substantially produce adverse reactions (e.g., toxic, allergic or other immunologic reactions) when administered to a subject.

As used herein, the term "pharmaceutically acceptable carrier" refers to any of the standard pharmaceutical carriers including, but not limited to, phosphate buffered saline solution, water, and various types of wetting agents (e.g., sodium lauryl sulfate), any and all solvents, dispersion media, coatings, sodium lauryl sulfate, isotonic and absorption delaying agents, disintegrants (e.g., potato starch or sodium starch glycolate), polyethylene glycol, and the like. The compositions also can include stabilizers and preservatives. Examples of carriers, stabilizers and adjuvants have been described and are known in the art (see, e.g., Martin, Remington's Pharmaceutical Sciences, 15th Ed., Mack Publ. Co., Easton, Pa. (1975), incorporated herein by reference).

As used herein, the term "pharmaceutically acceptable salt" refers to any salt (e.g., obtained by reaction with an acid or a base) of a composition of the present invention that is physiologically tolerated in the target subject. "Salts" of the compositions of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compositions of the invention and their pharmaceutically acceptable acid addition salts. Examples of bases include, but are not limited to, alkali metal (e.g., sodium) hydroxides, alkaline earth metal (e.g., magnesium) hydroxides, ammonia, and compounds of formula NW4+, wherein W is C1-4 alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as Na+, NH$_4$+, and NW$_4$+ (wherein W is a C1-4 alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

For therapeutic use, salts of the compositions of the present invention are contemplated as being pharmaceutically acceptable. However, salts of acids and bases that are non-pharmaceutically acceptable may also find use, for example, in the preparation or purification of a pharmaceutically acceptable composition.

As used herein, the term "at risk for disease" refers to a subject that is predisposed to experiencing a particular disease (e.g., infectious disease). This predisposition may be genetic (e.g., a particular genetic tendency to experience the disease, such as heritable disorders), or due to other factors (e.g., environmental conditions, exposures to detrimental compounds present in the environment, etc.). Thus, it is not intended that the present invention be limited to any particular risk (e.g., a subject may be "at risk for disease" simply by being exposed to and interacting with other people), nor is it intended that the present invention be limited to any particular disease (e.g., cancer).

As used herein, the term "kit" refers to any delivery system for delivering materials. In the context of immunotherapeutic agents, such delivery systems include systems that allow for the storage, transport, or delivery of immunogenic agents and/or supporting materials (e.g., written instructions for using the materials, etc.) from one location to another. For example, kits include one or more enclosures (e.g., boxes) containing the relevant immunotherapeutic agents (e.g., modified T cells and/or supporting materials). As used herein, the term "fragmented kit" refers to delivery systems comprising two or more separate containers that each contain a subportion of the total kit components. The containers may be delivered to the intended recipient together or separately. For example, a first container may contain a composition comprising an immunotherapeutic composition for a particular use, while a second container contains a second agent (e.g., a chemotherapeutic agent). Indeed, any delivery system comprising two or more separate containers that each contains a subportion of the total kit components are included in the term "fragmented kit." In contrast, a "combined kit" refers to a delivery system containing all of the components needed for a particular use in a single container (e.g., in a single box housing each of the desired components). The term "kit" includes both fragmented and combined kits.

As used herein, the term "immunoglobulin" or "antibody" refer to proteins that bind one or more epitopes on a specific antigen. Immunoglobulins include, but are not limited to, polyclonal, monoclonal, chimeric, and humanized antibodies, as well as Fab fragments and F(ab')2 fragments of the following classes: IgG, IgA, IgM, IgD, IgE, and secreted immunoglobulins (sIg). Immunoglobulins generally comprise two identical heavy chains and two light chains. However, the terms "antibody" and "immunoglobulin" also encompass single chain antibodies and two chain antibodies.

The "variable region" or "variable domain" of an antibody refers to the amino-terminal domains of the heavy or light chain of the antibody. The variable domain of the heavy chain may be referred to as "VH." The variable domain of the light chain may be referred to as "VL." These domains are generally the most variable parts of an antibody and contain the antigen-binding sites.

"Single-chain Fv" or "scFv" antibody fragments comprise the VH and VL domains of an antibody, wherein these domains are present in a single polypeptide chain. Generally, the scFv polypeptide further comprises a polypeptide linker between the VH and VL domains which enables the scFv to form a structure for antigen binding. For a review of scFv, see, e.g., Pluckthun, in The Pharmacology of Monoclonal Antibodies, vol. 113, Rosenburg and Moore eds., (Springer-Verlag, New York, 1994), pp. 269-315.

As used herein, the term "antigen-binding protein" refers to proteins that bind to a specific antigen. "Antigen-binding proteins" include, but are not limited to, immunoglobulins, including polyclonal, monoclonal, chimeric, and humanized antibodies; Fab fragments, F(ab')2 fragments, and Fab expression libraries; and single chain antibodies.

The term "epitope" as used herein refers to that portion of an antigen that makes contact with a particular immunoglobulin.

The terms "specific binding" or "specifically binding" when used in reference to the interaction of an antibody (or a portion thereof (e.g., scFv) and a protein or peptide means that the interaction is dependent upon the presence of a particular sequence or structure (e.g., the antigenic determinant or epitope) on the protein; in other words the antibody (or a portion thereof (e.g., scFv) is recognizing and binding to a specific protein sequence or structure rather than to proteins in general. For example, if an antibody is specific for epitope "A," the presence of a protein containing epitope A (or free, unlabeled A) in a reaction containing labeled "A" and the antibody will reduce the amount of labeled A bound to the antibody.

As used herein, the terms "non-specific binding" and "background binding" when used in reference to the interaction of an antibody and a protein or peptide refer to an interaction that is not dependent on the presence of a particular structure (i.e., the antibody is binding to proteins in general rather that a particular structure such as an epitope).

As used herein, the term "subject suspected of having cancer" refers to a subject that presents one or more symptoms indicative of a cancer (e.g., a noticeable lump or mass) or is being screened for a cancer (e.g., during a routine physical). A subject suspected of having cancer may also have one or more risk factors for developing cancer. A subject suspected of having cancer has generally not been tested for cancer. However, a "subject suspected of having cancer" encompasses an individual who has received a preliminary diagnosis (e.g., a CT scan showing a mass) but for whom a confirmatory test (e.g., biopsy and/or histology) has not been done or for whom the type and/or stage of cancer is not known. The term further includes people who previously had cancer (e.g., an individual in remission). A "subject suspected of having cancer" is sometimes diagnosed with cancer and is sometimes found to not have cancer.

As used herein, the term "subject diagnosed with a cancer" refers to a subject who has been tested and found to have cancerous cells. The cancer may be diagnosed using any suitable method, including but not limited to, biopsy, x-ray, blood test, etc.

As used herein, the term "post-surgical tumor tissue" refers to cancerous tissue (e.g., organ tissue) that has been removed from a subject (e.g., during surgery).

As used herein, the term "subject at risk for cancer" refers to a subject with one or more risk factors for developing a specific cancer. Risk factors include, but are not limited to, gender, age, genetic predisposition, environmental exposure, and previous incidents of cancer, preexisting non-cancer diseases, and lifestyle.

As used herein, the term "characterizing cancer in a subject" refers to the identification of one or more properties of a cancer sample in a subject, including but not limited to, the presence of benign, pre-cancerous or cancerous tissue and the stage of the cancer.

As used herein, the term "characterizing tissue in a subject" refers to the identification of one or more properties of a tissue sample (e.g., including but not limited to, the presence of cancerous tissue, the presence of pre-cancerous tissue that is likely to become cancerous, and the presence of cancerous tissue that is likely to metastasize).

As used herein, the term "stage of cancer" refers to a qualitative or quantitative assessment of the level of advancement of a cancer. Criteria used to determine the stage of a cancer include, but are not limited to, the size of the tumor, whether the tumor has spread to other parts of the body and where the cancer has spread (e.g., within the same organ or region of the body or to another organ).

As used herein, the term "primary tumor cell" refers to a cancer cell that is isolated from a tumor in a mammal and has not been extensively cultured in vitro.

As used herein, the terms "treatment", "therapeutic use", or "medicinal use" refer to any and all uses of compositions and methods of the invention that remedy a disease state or symptoms, or otherwise prevent, hinder, retard, or reverse the progression of disease or other undesirable symptoms in any way whatsoever. For example, the terms "treatment of cancer" or "treatment of tumor" or grammatical equivalents herein are meant the suppression, regression, or partial or complete disappearance of a pre-existing cancer or tumor. The definition is meant to include any diminution in the size, aggressiveness, or growth rate of a pre-existing cancer or tumor.

As used herein, the terms "improved therapeutic outcome" and "enhanced therapeutic efficacy," relative to cancer refers to a slowing or diminution of the growth of cancer cells or a solid tumor, or a reduction in the total number of cancer cells or total tumor burden. An "improved therapeutic outcome" or "enhanced therapeutic efficacy" means there is an improvement in the condition of the individual according to any clinically acceptable criteria, including reversal of an established tumor, an increase in life expectancy or an improvement in quality of life.

As used herein, the term "gene transfer system" refers to any means of delivering a composition comprising a nucleic acid sequence to a cell or tissue. For example, gene transfer systems include, but are not limited to, vectors (e.g., retroviral, adenoviral, lentiviral, adeno-associated viral, and other nucleic acid-based delivery systems), microinjection of naked nucleic acid, polymer-based delivery systems (e.g., liposome-based and metallic particle-based systems), biolistic injection, transduction with transposase-based systems for gene integration, Crispr/Cas9-mediated gene integration, non-integrating vectors such as RNA or adeno-associated viruses and the like.

As used herein, the term "viral gene transfer system" refers to gene transfer systems comprising viral elements (e.g., intact viruses, modified viruses and viral components such as nucleic acids or proteins) to facilitate delivery of the sample to a desired cell or tissue. Non-limiting examples of viral gene transfer systems useful in the compositions and methods of the invention are lentiviral- and retroviral-gene transfer systems.

As used herein, the term "site-specific recombination target sequences" refers to nucleic acid sequences that provide recognition sequences for recombination factors and the location where recombination takes place.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl)-uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2 thiocytosine, 5-methyl-2 thiouracil, 2-thiouracil, 4-thiouracil, 5-methyluracil, N-uracil-5-oxyacetic acid methylester, and 2,6-diaminopurine.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc.). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed). Cells that contain a heterologous gene are described herein as being "modified" or "engineered" cells. For example, T cells that contain a heterologous AP-1 transcription factor gene (e.g., heterologous AP-1 transcription factor gene expression construct (e.g., used to overexpress AP-1 transcription factor in the T cells)), and/or heterologous receptor gene (e.g., heterologous T cell receptor gene expression construct, or, heterologous chimeric antigen receptor gene expression construct) are described herein as modified and/or engineered T cells.

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Upregulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the terms "an oligonucleotide having a nucleotide sequence encoding a gene" and "polynucleotide having a nucleotide sequence encoding a gene," means a nucleic acid sequence comprising the coding region of a gene or in other words the nucleic acid sequence that encodes a gene product. The coding region may be present in a cDNA, genomic DNA or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

The term "native protein" as used herein to indicate that a protein does not contain amino acid residues encoded by vector sequences; that is, the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

The term "vector," as used herein, is intended to refer to a nucleic acid molecule capable of transporting another nucleic acid to which it has been linked. One type of vector is a "plasmid," which refers to a circular double stranded DNA into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Lentiviral vectors or retroviral vectors may be used (e.g., to introduce DNA encoding one or more AP-1 transcription factors and/or a CAR construct into cells (e.g., T cells)). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors," or simply, "expression vectors." In general, expression vectors of utility in recombinant DNA techniques are often in the form of plasmids. In the present specification, "plasmid" and "vector" may be used interchangeably as the plasmid is the most commonly used form of vector.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell that has stably integrated foreign DNA into the genomic DNA. The term "transient transfection" or "transiently transfected" refers to the introduction of foreign DNA into a cell where the foreign DNA fails to integrate into the genome of the transfected cell. The foreign DNA persists in the nucleus of the transfected cell (e.g., for several days). During this time the foreign DNA is subject to the regulatory controls that govern the expression of endogenous genes in the chromosomes. The term "transient transfectant" refers to cells that have taken up foreign DNA but have failed to integrate this DNA.

As used herein, the term "selectable marker" refers to the use of a gene that encodes an enzymatic activity that confers the ability to grow in medium lacking what would otherwise be an essential nutrient; in addition, a selectable marker may confer resistance to an antibiotic or drug upon the cell in which the selectable marker is expressed. Selectable markers may be "dominant"; a dominant selectable marker encodes an enzymatic activity that can be detected in any eukaryotic cell line. Examples of dominant selectable markers include the bacterial aminoglycoside-3'-phosphotransferase gene (also referred to as the neo gene) that confers resistance to the drug G418 in mammalian cells, the bacterial hygromycin G phosphotransferase (hyg) gene that confers resistance to the antibiotic hygromycin and the bacterial xanthine-guanine phosphoribosyl transferase gene (also referred to as the gpt gene) that confers the ability to grow in the presence of mycophenolic acid. Other selectable markers are not dominant in that their use must be in conjunction with a cell line that lacks the relevant enzyme activity. Examples of non-dominant selectable markers include the thymidine kinase (tk) gene that is used in conjunction with tk-negative (tk⁻) cell lines, the CAD gene that is used in conjunction with CAD-deficient cells and the mammalian hypoxanthine-guanine phosphoribosyl transferase (hprt) gene that is used in conjunction with hprt-negative (hprt⁻) cell lines. A review of the use of selectable markers in mammalian cell lines is provided in Sambrook, J. et al., Molecular Cloning: A Laboratory Manual, 2nd ed., Cold Spring Harbor Laboratory Press, New York (1989) pp. 16.9-16.15.

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Such examples are not however to be construed as limiting the sample types applicable to the present invention.

DETAILED DESCRIPTION OF EMBODIMENTS

The invention is based on the discovery that T cells modified (e.g., genetically) to overexpress and/or contain elevated (e.g., supraphysiologic) levels of one or more AP-1 transcription factors (e.g., c-Jun) display reduced levels of T cell exhaustion (e.g., compared to unmodified T cells expressing normal levels of AP-1 transcription factors). As described in detail herein, expression of AP-1 transcription factors fos and c-Jun is lower/downregulated in exhausted T cells, and T cells modified to overexpress and/or harbor elevated levels of c-Jun or other AP-1 transcription factor display reduced levels of T cell exhaustion. For example, overexpression of the AP-1 transcription factors (in particular, c-Jun) prevented the development of T cell exhaustion and maintained functionality of T cells (e.g., even after exposure to high levels of antigen)(See Examples 1-6). GD2 CART cells expressing increased levels of AP-1 transcription factors (particularly c-Jun) display reduced features of exhaustion (including lower exhaustion markers, increased memory formation, and increased cytokine production) indicating that T cells modified to overexpress and/or contain elevated (e.g., supraphysiologic) levels of one or more AP-1 transcription factors display enhanced clinical efficacy across multiple malignancies (see, e.g., Examples 1-6). Furthermore, CD19 CART cells modified to overexpress c-Jun and CD22 CART cells modified to overexpress c-Jun both displayed increased CART cell recognition of leukemia target cells with low levels of surface antigen (See, e.g., Example 6). CART cells modified to overexpress AP-1 transcription factors displayed reduced T cell exhaustion and enhanced functionality in three separate in vivo tumor models using cJUN-modified CAR T cells (See Example 8). Thus, overexpression of the AP-1 transcription factors (in particular, c-Jun) prevented the development of T cell exhaustion and maintained functionality of T cells. Collectively, these findings show that the compositions and methods of the invention are broadly applicable and address many of the existing barriers to successful CAR T cell therapy.

Accordingly, the invention provides modified T cells (e.g., genetically and/or functionally modified (e.g., to overexpress and/or contain elevated levels of one or more AP-1 transcription factors and/or reduced expression and/or activity of one or more AP-1 inhibitory complex members)) that maintain functionality under conditions in which unmodified T cells display T cell exhaustion. In this way, compositions and methods of the invention can be used to prevent exhaustion of engineered T cells (e.g., engineered to express a specific T cell receptor, or engineered to express a chimeric antigen receptor (CAR)) and to prevent exhaustion of non-engineered T cells (e.g., native or natural T cells (e.g., isolated from a subject) thereby enhancing the functionality (e.g., activity against cancer or infectious disease) of the engineered as well as non-engineered T cells.

Modification of T cells to overexpress and/or contain elevated levels of one or more AP-1 transcription factors can prevent depletion of the AP-1 transcription factors in the T cell (e.g., that occurs as the T cells become exhausted (See, e.g., Example 1) and/or result in elevated (e.g., supraphysiologic) levels of the AP-1 transcription factors. AP-1 transcription factors (e.g., c-Jun) are factors that are induced following T cell activation and participate in the production and secretion of cytokines (e.g., interleukin-2) by T cells. T cells that express CARs undergo tonic, antigen-independent signaling due to receptor clustering and replicate the fundamental biology of T cell exhaustion, as shown by high levels of PD-1, TIM-3, and LAG-3 expression, diminished antigen-induced cytokine production and excessive programmed cell death. AP-1 transcription factors were identified and characterized as being reduced in exhausted T cells (See, e.g., Example 1). Modification of T cells to overexpress and/or contain elevated levels of one or more AP-1 transcription factors significantly enhanced functionality of T cells exposed to conditions that induce T cell exhaustion (See, e.g., Examples 2-5). While an understanding of a mechanism is not needed to practice the present invention, and while the present invention is not limited to any particular mechanism of action, the maintenance and/or elevation of AP-1 transcription factor levels (e.g., the level of c-Jun) within T cells prevents dysfunction of the T cells associated with T cell exhaustion (e.g., a minimal effect of AP-1 transcription factor overexpression was observed in non-exhausted T cells indicating that a relative or absolute deficiency of c-Jun is an important factor in the dysfunction associated with T cell exhaustion).

In some embodiments, T cells are modified to overexpress and/or contain elevated levels of one or more mutated and/or truncated AP-1 transcription factors to prevent depletion of the AP-1 transcription factors in the T cell. Experiments conducted during development of embodiments herein demonstrate that portions of AP-1 family proteins (e.g., c-Jun) can be mutated and/or truncated without impacting the capacity for the mutated/truncated AP-1 factors from mediating the rescue of dysfunctional T cells. For example, c-Jun polypeptides with N-terminal deletions and mutations (e.g., in the transactivation domain) maintain their ability to rescue the function of HA-28z exhausted CAR T cells and retain equivalent increases in cytokine production compared to c-Jun. In some embodiments, an AP-1 (e.g., c-Jun) polypeptide comprises mutations or deletions in the transactivation and/or delta domains. In some embodiments, an AP-1 (e.g., c-Jun) polypeptide comprises mutations or deletions that render the transactivation and/or delta domains inactive or not present. In some embodiments, a mutated/truncated AP-1 (e.g., c-Jun) polypeptide comprises 70% (e.g., 70%, 75%, 80%, 85%, 90%, 95%, 99%, 100%, or ranges therebetween) or greater sequence identity with the C-terminal amino acid residues (e.g., 50 residues, 75 residues, 100 residues, 150 residues, 200 residues 250 residues, or ranges therebetween), C-terminal portion (e.g., quarter, third, half) or C-terminal domains (e.g., epsilon, bZIP, and amino acids C-terminal thereof) of a wild-type AP-1 transcription factor (e.g., c-Jun). In some embodiments, the N-terminal amino acid residues (e.g., 50 residues, 75 residues, 100 residues, 150 residues, or ranges therebetween), N-terminal portion (e.g., quarter, third, half) or N-terminal domains (e.g., delta, transactivation domain, and amino acids N-terminal thereof) of a wild-type AP-1 transcription factor (e.g., c-Jun) are deleted, mutated, or otherwise inactivated. Any embodiments described herein with reference to an AP-1 transcription factor may comprise a mutated/truncated AP-1 (e.g., c-Jun) polypeptide, consistent with, for example the above.

While enhanced expression of AP-1 transcription factors like c-Fos and c-Jun increased functionality of modified T cells, there are other inhibitory AP-1 family members expressed in exhausted activated T cells. Inhibition/knockdown of inhibitory AP-1 complex members (e.g., to increase availability of canonical AP-1 factors) also reduced T cell exhaustion (e.g., See Example 7). In particular, inhibition/knockdown of inhibitory AP-1 complex members resulted in significant enhancement of T cell function (e.g., enhancement of cytokine production and/or expression) of exhausted T cells but not in healthy T cells (e.g., See FIG. 8A-D). Thus, in some embodiments the invention provides compositions and methods of inhibiting T cell exhaustion via the inhibition of expression and/or activity of inhibitory AP-1 complex members (e.g., BATF3, and other BATF family members (BATF 1 and 2), IRF4, IRF8, and other IRF family members (IRF 1, 2, 3, 5, 6, 7, or 9), and ATF family members (ATF 1, 2, 3, 4, 5, 6, or 7)). The invention is not limited by the means of inhibiting expression and/or activity of AP-1 inhibitory complex members (e.g., genes). For example, in some embodiments, expression and/or activity of AP-1 inhibitory complex members occurs at the genomic level (e.g., via disrupting gene expression). In other embodiments, inhibiting expression and/or activity of AP-1 inhibitory complex members occurs at the protein expression and/or activity level (e.g., via disrupting protein expression and/or activity). Exemplary compositions and methods for inhibiting expression and/or activity of AP-1 inhibitory complex members include, but are not limited to, nuclease disruption, CRISPR-Cas9 systems, zinc finger nuclease targeting, TALEN genome editing, shRNA, siRNA, miRNA targeting, degron regulatable promoters, protein inhibitors (e.g., chemical inhibitors, small molecule inhibitors, antibodies, etc.), expression of dominant negatives, and the like. Exemplary compositions for inhibiting expression and/or activity of AP-1 inhibitory complex members are provided in Table 1 below. CAS stands for Chemical Abstracts Service and is a unique numerical identifier assigned to every chemical substance.

TABLE 1

| Protein | Inhibitor Type | Manufacturer | Catalogue # or CAS # |
|---------|----------------|--------------|----------------------|
| IRF4    | CRISPR gRNA    | ABM          | K1098601 |
|         |                |              | K1098602 |
|         |                |              | K1098603 |
|         |                |              | K1098604 |
|         |                |              | K1098605 |
|         | siRNA          | Dharmacon    | E-019668-01 |
|         |                |              | EQ-019668-01 |
|         |                |              | A-019668-15 |
|         |                |              | A-019668-17 |
|         |                |              | A-019668-18 |
|         |                |              | A-019668-23 |
|         |                |              | EU-019668-01 |
|         |                |              | R-019668-00 |
|         |                |              | N-019668-19 |
|         |                |              | N-019668-20 |
|         |                |              | N-019668-21 |
|         |                |              | N-019668-22 |
|         | shRNA          | Dharmacon    | RHS4531-EG3662 |
|         |                |              | RHS5086-EG3662 |
|         |                |              | RHS11851-EG3662 |
|         |                |              | VGH5526-EG3662 |
|         |                |              | V3SH11255-01EG3662 |
|         |                |              | V3SH11252-225869326 |
|         |                |              | V3SH11252-226190350 |
|         |                |              | RHS4533-EG3662 |
|         | Small molecule CPI-0610 |     | 1380087-89-7 (CAS #) |
| IRF8    | CRISPR gRNA    | Dharmacon    | CM-011699-01 |
|         |                |              | CM-011699-02 |
|         |                |              | CM-011699-03 |
|         |                |              | CM-011699-04 |
|         |                |              | CM-011699-05 |
|         | siRNA          | Dharmacon    | E-011699-00 |
|         |                |              | E-011699-13 |
|         |                |              | E-011699-14 |
|         |                |              | E-011699-15 |
|         |                |              | E-011699-16 |
|         |                |              | L-011699-00 |
|         |                |              | L-011699-05 |
|         |                |              | L-011699-06 |
|         | shRNA          | Dharmacon    | VGH5526-EG3394 |
|         |                |              | VGH5518-200160140 |
|         |                |              | VGH5518-200269164 |
|         |                |              | VGH5518-200272765 |
|         |                |              | VGH5518-200274319 |
|         |                |              | VGH5518-200274390 |
|         |                |              | VGH5518-200274390 |

TABLE 1-continued

| Protein | Inhibitor Type | Manufacturer | Catalogue # or CAS # |
|---|---|---|---|
| JUNB | CRISPR gRNA | Dharmacon | GSGH11938-15EG3726 |
| | | | GSGH11935-247584627 |
| | | | GSGH11935-247584627 |
| | | | GSGH11935-247584627 |
| | | | GSGH11935-247584627 |
| | siRNA | Dharmacon | E-003269-00 |
| | | | A-003269-17 |
| | | | A-003269-18 |
| | | | A-003269-19 |
| | | | A-003269-20 |
| | | | L-003269-00 |
| | | | J-003269-09 |
| | shRNA | Dharmacon | RHS4531-EG3726 |
| | | | V3SH11255-01EG3726 |
| | | | V3SH11243-00EG3726 |
| | | | RHS4533-EG3726 |
| | | | RHS5087-EG3726 |
| BATF | CRISPR gRNA | Dharmacon | GSGH11938-15EG10538 |
| | | | GSGH11938-15EG10538 |
| | | | GSGH11935-247503927 |
| | | | CM-008563-01 |
| | | | CM-008563-02 |
| | | | CM-008563-03 |
| | | | CM-008563-04 |
| | siRNA | Dharmacon | E-008563-00 |
| | | | A-008563-15 |
| | | | A-008563-16 |
| | | | A-008563-17 |
| | | | A-008563-18 |
| | | | L-008563-00 |
| | | | J-008563-07 |
| | | | J-008563-08 |
| | shRNA | Dharmacon | RHS4531-EG10538 |
| | | | RHS4531-EG10538 |
| | | | RHS5086-EG10538 |
| | | | V3SH11255-01EG10538 |
| | | | V3SH11243-00EG10538 |
| | | | RHS4533-EG10538 |
| BATF3 | CRISPR gRNA | Dharmacon | RHS4740-EG10379 |
| | | | GSGH11935-247492763 |
| | | | CM-010056-01 |
| | | | CM-010056-02 |
| | | | GSGH11841-EG55509 |
| | | | GSGH11838-246566243 |
| | siRNA | Dharmacon | E-010056-00 |
| | | | EQ-010056-00 |
| | | | L-010056-00 |
| | | | LQ-010056-00 |
| | | | M-010056-01 |
| | | | MQ-010056-01 |
| | shRNA | Dharmacon | RHS4531-EG55509 |
| | | | RHS4531-EG55509 |
| | | | V3SH11243-00EG55509 |
| | | | RHS4533-EG55509 |
| | | | RHS5087-EG55509 |
| IRF1 | CRISPR gRNA | Dharmacon | GSGH11938-15EG3659 |
| | | | GSGH11935-247504821 |
| | | | GSGH11935-247504821 |
| | | | CM-011704-01 |
| | | | CM-011704-02 |
| | | | GSGH11841-EG3659 |
| | | | GSGH11838-246472244 |
| | siRNA | Dharmacon | E-011704-00 |
| | | | L-011704-00 |
| | | | LQ-011704-00 |
| | | | J-011704-06 |
| | | | EU-011704-00 |
| | | | A-011704-17 |
| | | | M-011704-01 |
| | | | MQ-011704-01 |
| | shRNA | Dharmacon | RHS4531-EG3659 |
| | | | RHS5086-EG3659 |
| | | | V3SH11255-01EG3659 |
| | | | V3SH11252-225202363 |
| | | | RHS4533-EG3659 |
| | | | RHS3979-201746248 |
| | | | RHS3979-201746250 |

TABLE 1-continued

| Protein | Inhibitor Type | Manufacturer | Catalogue # or CAS # |
| --- | --- | --- | --- |
| IRF2 | CRISPR gRNA | Dharmacon | GSGH11938-15EG3660<br>GSGH11935-247502225<br>CM-011705-01-0002<br>CM-011705-02<br>GSGH11841-EG3660<br>GSGH11838-246562609 |
|  | siRNA | Dharmacon | E-011705-00<br>EQ-011705-00<br>L-011705-02<br>LQ-011705-02<br>M-011705-01<br>MQ-011705-01 |
|  | shRNA | Dharmacon | RHS4531-EG3660<br>RHS11851-EG3660<br>V3SH11255-01EG3660<br>V3SH11252-224896618<br>V3SH11243-00EG3660<br>V3SH11243-00EG3660<br>RHS4533-EG3660<br>RHS3979-201746276<br>RHS5087-EG3660<br>RHS4740-EG3660 |
| IRF3 | CRISPR gRNA | Dharmacon | GSGH11938-15EG3661<br>GSGH11935-247500025<br>CM-006875-01<br>CM-006875-02<br>GSGH11841-EG3661<br>GSGH11838-246484123 |
|  | siRNA | Dharmacon | E-006875-00<br>EQ-006875-00<br>L-006875-00<br>LQ-006875-00<br>M-006875-02<br>MQ-006875-02 |
|  | shRNA | Dharmacon | RHS4531-EG3661<br>RHS5086-EG3661<br>V3SH11255-01EG3661<br>V3SH11243-00EG3661<br>V3SH11243-00EG3661<br>RHS4533-EG3661 |
| IRF5 | CRISPR gRNA | Dharmacon | GSGH11938-15EG3663<br>CM-011706-01<br>CM-011706-02<br>GSGH11841-EG3663<br>GSGH11838-246491831 |
|  | siRNA | Dharmacon | E-011706-00<br>EQ-011706-00<br>L-011706-00<br>LQ-011706-00 |
|  | shRNA | Dharmacon | RHS4531-EG3663<br>V3SH11255-01EG3663<br>V3SH11252-224705020<br>V3SH11243-00EG3663<br>RHS4533-EG3663<br>RHS5087-EG3663<br>RHS11852-EG3663 |
| IRF6 | CRISPR gRNA | Dharmacon | GSGH11938-15EG3664<br>GSGH11935-247494745<br>CM-012227-01<br>CM-012227-02<br>GSGH11841-EG3664<br>GSGH11838-246518949 |
|  | siRNA | Dharmacon | E-012227-00<br>EQ-012227-00<br>L-012227-00<br>LQ-012227-00<br>M-012227-01<br>MQ-012227-01 |
|  | shRNA | Dharmacon | RHS4531-EG3664<br>RHS5086-EG3664<br>V3SH11255-01EG3664<br>V3SH11252-225664792<br>V3SH11243-00EG3664<br>V3SH11240-225664774<br>RHS4533-EG3664<br>RHS3979-201746411<br>RHS5087-EG3664 |

TABLE 1-continued

| Protein | Inhibitor Type | Manufacturer | Catalogue # or CAS # |
|---|---|---|---|
| IRF7 | CRISPR gRNA | Dharmacon | GSGH11938-15EG3665 |
| | | | GSGH11935-247546071 |
| | | | CM-011810-01 |
| | | | CM-011810-02 |
| | | | GSGH11841-EG3665 |
| | | | GSGH11838-246514132 |
| | siRNA | Dharmacon | E-011810-00 |
| | | | EQ-011810-00 |
| | | | L-011810-00 |
| | | | LQ-011810-00 |
| | | | M-011810-02 |
| | | | MQ-011810-02 |
| | shRNA | Dharmacon | RHS4531-EG3665 |
| | | | RHS5086-EG3665 |
| | | | V3SH11255-01EG3665 |
| | | | V3SH11252-225428941 |
| | | | V3SH11243-00EG3665 |
| | | | V3SH11240-225428924 |
| | | | RHS4533-EG3665 |
| | | | RHS5087-EG3665 |
| IRF9 | CRISPR gRNA | Dharmacon | GSGH11938-15EG10379 |
| | | | GSGH11935-247539665 |
| | | | CM-020858-01 |
| | | | CM-020858-02 |
| | | | GSGH11841-EG10379 |
| | | | GSGH11838-246598314 |
| | siRNA | Dharmacon | E-020858-00 |
| | | | EQ-020858-00 |
| | | | L-020858-00 |
| | | | LQ-020858-00 |
| | | | M-020858-02 |
| | | | MQ-020858-02 |
| | shRNA | Dharmacon | RHS4531-EG10379 |
| | | | RHS5086-EG10379 |
| | | | V3SH11255-01EG10379 |
| | | | V3SH11252-225646741 |
| | | | V3SH11243-00EG10379 |
| | | | RHS4533-EG10379 |
| | | | RHS5087-EG10379 |
| | | | RHS4740-EG10379 |
| BATF2 | CRISPR gRNA | Dharmacon | GSGH11938-15EG116071 |
| | | | CM-016830-01 |
| | | | GSGH11841-EG116071 |
| | siRNA | Dharmacon | E-016830-00 |
| | | | L-016830-02 |
| | | | M-016830-00 |
| | | | EQ-016830-00 |
| | | | LQ-016830-02 |
| | | | MQ-016830-00 |
| | shRNA | Dharmacon | RHS4531-EG116071 |
| | | | RHS5086-EG116071 |
| | | | V3SH11255-01EG116071 |
| | | | V3SH11243-00EG116071 |
| | | | RHS4533-EG116071 |
| | | | RHS5087-EG116071 |
| AFT1 | CRISPR gRNA | Dharmacon | GSGH11938-15EG466 |
| | | | CM-010045-01 |
| | | | GSGH11841-EG466 |
| | siRNA | Dharmacon | E-010045-00 |
| | | | L-010045-00 |
| | | | M-010045-00 |
| | shRNA | Dharmacon | RHS4531-EG466 |
| | | | V3SH11255-01EG466 |
| | | | V3SH11243-00EG466 |
| | | | RHS4533-EG466 |
| | | | RHS5087-EG466 |
| ATF2 | CRISPR gRNA | Dharmacon | GSGH11938-15EG1386 |
| | | | CM-009871-01 |
| | | | GSGH11841-EG1386 |
| | siRNA | Dharmacon | E-009871-00 |
| | | | L-009871-00 |
| | | | M-009871-00 |
| | | | EQ-009871-00 |
| | | | LQ-009871-00 |
| | | | MQ-009871-00 |

TABLE 1-continued

| Protein | Inhibitor Type | Manufacturer | Catalogue # or CAS # |
|---|---|---|---|
| | shRNA | Dharmacon | RHS4531-EG1386 |
| | | | V3SH11255-01EG1386 |
| | | | V3SH11243-00EG1386 |
| | | | RHS4533-EG1386 |
| | | | RHS5087-EG1386 |
| ATF3 | CRISPR gRNA | Dharmacon | GSGH11938-15EG467 |
| | | | CM-008663-01 |
| | | | GSGH11841-EG467 |
| | siRNA | Dharmacon | E-008663-00 |
| | | | L-008663-00 |
| | | | M-008663-00 |
| | | | EQ-008663-00 |
| | | | LQ-008663-00 |
| | | | MQ-008663-00 |
| | shRNA | Dharmacon | RHS4531-EG467 |
| | | | V3SH11255-01EG467 |
| | | | V3SH11243-00EG467 |
| | | | RHS4533-EG467 |
| | | | RHS5087-EG467 |
| ATF4 | CRISPR gRNA | Dharmacon | GSGH11938-15EG468 |
| | | | CM-005125-01 |
| | | | GSGH11841-EG468 |
| | siRNA | Dharmacon | E-005125-00 |
| | | | L-005125-00 |
| | | | M-005125-00 |
| | | | EQ-005125-00 |
| | | | LQ-005125-00 |
| | | | MQ-005125-00 |
| | shRNA | Dharmacon | RHS4531-EG468 |
| | | | V3SH11255-01EG468 |
| | | | V3SH11243-00EG468 |
| | | | RHS4533-EG468 |
| | | | RHS5087-EG468 |
| ATF5 | CRISPR gRNA | Dharmacon | GSGH11938-15EG22809 |
| | | | CM-008822-01 |
| | | | GSGH11841-EG22809 |
| | siRNA | Dharmacon | E-008822-00 |
| | | | L-008822-00 |
| | | | M-008822-00 |
| | | | EQ-008822-00 |
| | | | LQ-008822-00 |
| | | | MQ-008822-00 |
| | shRNA | Dharmacon | RHS4531-EG22809 |
| | | | V3SH11255-01EG22809 |
| | | | V3SH11243-00EG22809 |
| | | | RHS4533-EG22809 |
| | | | RHS4533-EG22809 |
| ATF6 | CRISPR gRNA | Dharmacon | GSGH11938-15EG22926 |
| | | | CM-009917-01 |
| | | | GSGH11841-EG22926 |
| | siRNA | Dharmacon | E-009917-00 |
| | | | L-009917-00 |
| | | | M-009917-00 |
| | | | EQ-009917-00 |
| | | | LQ-009917-00 |
| | | | MQ-009917-00 |
| | shRNA | Dharmacon | RHS4531-EG22926 |
| | | | V3SH11255-01EG22926 |
| | | | V3SH11243-00EG22926 |
| | | | RHS4533-EG22926 |
| ATF7 | CRISPR gRNA | Dharmacon | GSGH11938-15EG11016 |
| | | | CM-008865-01 |
| | | | GSGH11841-EG11016 |
| | siRNA | Dharmacon | E-008865-00 |
| | | | L-008865-00 |
| | | | M-008865-00 |
| | | | EQ-008865-00 |
| | | | LQ-008865-00 |
| | | | MQ-008865-00 |
| | shRNA | Dharmacon | RHS4531-EG11016 |
| | | | V3SH11255-01EG11016 |
| | | | V3SH11243-00EG11016 |
| | | | RHS4533-EG11016 |
| | | | RHS5087-EG11016 |

Thus, the invention provides compositions and methods for reducing T cell exhaustion comprising T cells modified to overexpress and/or contain elevated levels of one or more AP-1 transcription factors and/or modified for reduced expression and/or activity of one or more AP-1 inhibitory complex members. The invention is not limited by the disease or condition that can be treated using modified T cells of the invention. Indeed, the compositions and methods provided herein may be useful in the treatment of any disease for which increased activity of T cells may provide a therapeutic benefit.

Accordingly, the invention provides a composition comprising T cells modified to overexpress and/or contain elevated levels of one or more AP-1 transcription factors and/or modified (e.g., genetically) for reduced expression and/or activity of one or more AP-1 inhibitory complex members (e.g., JunB, BATF3 and other BATF family members, IRF4, IRF8 and other IRF family members, and ATF family members). As described in detail herein, the T cells may be engineered or non-engineered T cells (e.g., tumor infiltrating lymphocytes (TILs)). Furthermore, the invention is not limited by the type of T cell modified to overexpress and/or contain elevated levels of one or more AP-1 transcription factors. In some embodiments, the T cells are CD3+ T cells (e.g., a combination of CD4+ and CD8+ T cells). In certain embodiments, the T cells are CD8+ T cells. In other embodiments, the T cells are CD4+ T cells. In some embodiments, the T cells are natural killer (NK) T cells. In some embodiments, the T cells are gamma delta T cells. In some embodiments, the T cells are a combination of CD4+ and CD8 T+ cells (e.g., that are CD3+). In certain embodiments, the T cells are memory T cells. In certain embodiments, the T cells are a combination of CD8+ T cells, CD4+ T cells, NK T cells, memory T cells, and/or gamma delta T cells. In some embodiments, the T cells are cytokine-induced killer cells. In some embodiments, the T cells are engineered to express a chimeric antigen receptor. In another embodiment, the T cells are engineered to express a specific T cell receptor (e.g., with specificity for a tumor antigen or an infectious disease antigen). In some embodiments, the T cells are anti-tumor T cells. The composition may comprise a pharmaceutically acceptable carrier (e.g., buffer). The composition may further comprise one or more other agents (e.g., chemotherapeutic agent (e.g., a chemotherapeutic agent described herein) and/or antimicrobial agent. Exemplary antimicrobial agents include, but are not limited to, antibodies, benzalkonium chloride, benzethonium chloride, benzyl alcohol, cetylpyridinium chloride, chlorobutanol, phenol, phenylethyl alcohol, phenylmercuric nitrate, thimersol, and/or combinations thereof.

The composition may optionally include one or more additional agents, such as other drugs for treating T cell exhaustion (e.g., anti-PD-1 checkpoint inhibitor, such as nivolumab), or other medications used to treat a subject for an infection or disease associated with T cell exhaustion (e.g., antiviral, antibiotic, antimicrobial, or anti-cancer drugs).

Antimicrobial therapeutic agents may be used as therapeutic agents in a composition of the present invention. Any agent that can kill, inhibit, or otherwise attenuate the function of microbial organisms may be used, as well as any agent contemplated to have such activities. Antimicrobial agents include, but are not limited to, natural and synthetic antibiotics, antibodies, inhibitory proteins (e.g., defensins), antisense nucleic acids, membrane disruptive agents and the like, used alone or in combination. Indeed, any type of antibiotic may be used including, but not limited to, antibacterial agents, antiviral agents, antifungal agents, and the like.

Several strategies for targeting tumor antigens are known in the art. For example, GD2-targeting immunotherapies are currently under clinical and preclinical investigation in several diseases, including neuroblastoma, osteosarcoma, and melanoma (see, e.g., Thomas et al., PLoS One, 2016. 11(3): p. e0152196; Long et al., Nature Medicine, 2015. 21(6): p. 581-590; Long et al., Cancer Immunology Research, 2016. 4(10): p. 869-880; Yu et al., N Engl J Med, 2010. 363(14): p. 1324-34; Perez Horta et al., Immunotherapy, 2016. 8(9): p. 1097-117; Heczey et al, Molecular Therapy). Unlike mAbs which do not efficiently cross the blood-brain barrier, activated CAR T cells efficiently infiltrate the CNS following adoptive transfer. Accordingly, in one embodiment, any CAR T cell may be modified according to the compositions and methods of the invention (e.g., modified to overexpress and/or contain elevated levels of one or more AP-1 transcription factors (e.g., thereby enhancing CART cell functionality and/or inhibiting exhaustion of the CART cells)).

For example, as described herein, a modified T cell of the invention (e.g., modified to overexpress and/or contain elevated levels of one or more AP-1 transcription factors and/or modified (e.g., genetically) for reduced expression and/or activity of one or more AP-1 inhibitory complex members (e.g., JunB and BATF3 and other BATF family members, IRF4, and ATF family members)) may also be engineered to contain a CAR that comprises a target-specific binding element otherwise referred to as an antigen binding moiety. The choice of moiety depends upon the type and number of ligands that define the surface of a target cell. For example, the antigen binding domain may be chosen to recognize a ligand that acts as a cell surface marker on target cells associated with a particular disease state. Examples of cell surface markers that may act as ligands for the antigen moiety domain in the CAR of the invention include those associated with viral, bacterial and parasitic infections, autoimmune disease and cancer cells.

For example, the CAR may be engineered to target a tumor antigen of interest by way of engineering a desired antigen binding moiety that specifically binds to an antigen on a tumor cell. As used herein, a "tumor antigen" or "hyperproliferative disorder antigen" or "antigen associated with a hyperproliferative disorder" or "cancer antigen," refers to antigens that are common to specific hyperproliferative disorders such as cancer. Exemplary antigens mentioned herein are included by way of example. The list is not intended to be exclusive and further examples will be readily apparent to those of skill in the art.

Tumor antigens are proteins that are produced by tumor cells that elicit an immune response, particularly T-cell mediated immune responses. Thus, an antigen binding moiety can be selected based on the particular type of cancer to be treated. Tumor antigens are well known in the art and include, for example, a glioma-associated antigen, carcinoembryonic antigen (CEA), beta-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostate-specific antigen (PSA), PAP, NY-ESO-1, LAGE-1a, p53, prostein, PSMA, Her2/neu, survivin and telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor and mesothelin.

A tumor antigen may comprise one or more antigenic cancer antigens/epitopes associated with a malignant tumor. Malignant tumors express a number of proteins that can serve as target antigens for an immune attack. These molecules include but are not limited to tissue-specific antigens such as MART-1, tyrosinase and GP100 in melanoma and prostatic acid phosphatase (PAP) and prostate-specific antigen (PSA) in prostate cancer. Other target molecules belong to the group of transformation-related molecules such as the oncogene HER-2/Neu/ErbB-2. Still another group of target antigens are onco-fetal antigens such as carcinoembryonic antigen (CEA). In B-cell lymphoma the tumor-specific idiotype immunoglobulin constitutes a truly tumor-specific immunoglobulin antigen that is unique to the individual tumor. B-cell differentiation antigens such as CD19, CD20 and CD37 are other candidates for target antigens in B-cell lymphoma.

The tumor antigen may also be a tumor-specific antigen (TSA) or a tumor-associated antigen (TAA). A TSA is unique to tumor cells and does not occur on other cells in the body. A TAA is not unique to a tumor cell and instead is also expressed on some normal cells under conditions that fail to induce a state of immunologic tolerance to the antigen. The expression of the antigen on the tumor may occur under conditions that enable the immune system to respond to the antigen. TAAs may be antigens that are expressed on normal cells during fetal development when the immune system is immature and unable to respond or they may be antigens that are normally present at extremely low levels on normal cells but which are expressed at much higher levels on tumor cells.

Examples of TSA or TAA include, but are not limited to, differentiation antigens such as MART-1/MelanA (MART-1), gp100 (Pmel 17), tyrosinase, TRP-1, TRP-2 and tumor-specific multilineage antigens such as MAGE-1, MAGE-3, BAGE, GAGE-1, GAGE-2, p15; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO-1, p185erbB2, p180erbB-3, c-met, nm-23H1, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.291\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCAS1, SDCCAG16, TA-90\Mac-2 binding protein\cyclophilin C-associated protein, TAAL6, TAG72, TLP, and TPS.

Depending on the desired antigen to be targeted, a CAR can be engineered to include the appropriate antigen binding moiety specific to the desired antigen target. For example, if CD19 is the desired antigen that is to be targeted, an antibody for CD19 can be used as the antigen binding moiety for incorporation into the CAR of the invention.

Methods of Treatment

In another aspect, provided herein are methods of treating a disease or condition in a subject comprising administering to the subject (e.g., a patient) having the disease or condition an effective amount of T cells modified to express and/or contain elevated levels of one or more AP-1 transcription factors. The invention is not limited by the type of disease or condition treated. Indeed, any disease or condition that is treatable (e.g., for which signs or symptoms of the disease are ameliorated upon treatment) via administration of T cells can be treated in an improved and more effective manner using compositions and methods of the invention (e.g. containing and/or using T cells modified to express and/or contain elevated levels of one or more AP-1 transcription factors). In one embodiment, the disease or condition is cancer. In another embodiment, the disease or condition is an infectious disease. The invention is not limited by the type of cancer or by the type of infectious disease. Indeed, any cancer known in the art for which T cell therapy is used for treatment may be treated with the compositions and methods of the invention. Similarly, any infectious disease known in the art for which T cell therapy is used for treatment may be treated with the compositions and methods of the invention. In one embodiment, administrating an effective amount of T cells modified to express and/or contain elevated levels of one or more AP-1 transcription factors to a subject (e.g., a patient) having a disease or condition inhibits T cell exhaustion in the subject (e.g., that would otherwise occur when the same amount of non-modified T cells are administered to the subject). For example, in certain embodiments, the methods comprise methods of treating a subject having a disease or condition responsive to treatment with adoptive cell therapy. In certain embodiments, the methods of treating a subject having a disease or condition responsive to treatment with adoptive cell therapy comprise a step of administering a composition comprising an effective amount of T cells genetically modified to express elevated levels of one or more AP-1 transcription factors, wherein the T cells genetically modified to express elevated levels of one or more AP-1 transcription factors display reduced levels of T cell exhaustion compared to T cells expressing normal levels of one or more AP-1 transcription factors. In certain embodiments, the disease or condition comprises cancer.

In one aspect, the invention provides methods for the treatment of cancers/tumors using T cells modified/engineered to express one or more AP-1 transcription factors. In various aspects of the invention, methods of treating cancer/tumors are provided, the methods comprising administering to a patient having such a cancer or tumor an effective amount of T cells modified/engineered to express one or more AP-1 transcription factors. The invention is not limited by the type of cancer and/or tumor treated. As used herein, the term "cancer" refers to various types of malignant neoplasms, most of which can invade surrounding tissues, and may metastasize to different sites (see, for example, PDR Medical Dictionary, 1st edition (1995), incorporated herein by reference in its entirety for all purposes). The terms "neoplasm" and "tumor" refer to an abnormal tissue that grows by cellular proliferation more rapidly than normal and continues to grow after the stimuli that initiated proliferation is removed. Such abnormal tissue shows partial or complete lack of structural organization and functional coordination with the normal tissue which may be either benign (i.e., benign tumor) or malignant (i.e., malignant tumor). Examples of general categories of cancer include, but are not limited to, carcinomas (e.g., malignant tumors derived from epithelial cells such as, for example, common forms of breast, prostate, lung and colon cancer), sarcomas (e.g., malignant tumors derived from connective tissue or mesenchymal cells), lymphomas (e.g., malignancies derived from hematopoietic cells), leukemias (e.g., malignancies derived from hematopoietic cells), germ cell tumors (e.g., tumors derived from totipotent cells. In adults most often found in the testicle or ovary; in fetuses, babies and young children, most often found on the body midline, particularly at the tip of the tailbone), blastic tumors (e.g., a typically malignant tumor which resembles an immature or embryonic tissue) and the like. Further examples of tumors and/or neoplasms that may be treated using the compositions and methods of the invention include but are not limited to those neoplasms associated with cancers of neural tissue, blood forming tissue, breast, skin, bone, prostate, ovaries, uterus, cervix, liver, lung, brain, larynx, gallbladder, pancreas, rectum, parathyroid, thyroid, adrenal gland, immune system, head and neck, colon, stomach, bronchi, and/or kidneys. In some embodiments, the cancer is an occult cancer, previously diagnosed primary cancer, or a metastatic cancer.

In certain embodiments, the presence of elevated levels of one or more AP-1 transcription factors in the modified T cells (e.g., CAR T cells (e.g., compared to T cells that are not modified)) results in a more effective treatment (e.g., killing and/or inhibition of progression) of cancers/tumors than with treatment using T cells (e.g., CART cells) that are not modified to contain elevated levels of one or more AP-1 transcription factors.

In certain embodiments, the invention provides methods of treating (e.g., inhibiting growth of and/or killing) cancers and/or tumors using T cells (e.g., CD3+ T cells)) genetically engineered to overexpress and/or contain elevated (e.g., supraphysiologic) levels of one or more AP-1 transcription factors and that are engineered to express a receptor that recognizes a tumor surface antigen (e.g., CD19, CD20, CD22, ROR1, GD2, EBV protein or antigen, folate receptor, Mesothelin, human carcinoembryonic antigen, CD33/IL3Ra, c-Met, PSMA, Glycolipid F77, EGFRvIII, NY-ESO-1, MAGE-A3, MART-1, GP1000, and/or p53) and transmit a signal that activates the T cell to induce expansion of the T cell and/or tumor killing. A non-limiting example of a receptor is a chimeric antigen receptor (CAR) that incorporates an scFv derived from a mAb that recognizes GD2, as well as a transmembrane domain, and one or more intracellular signaling domains. The CAR may be further engineered to incorporate other signaling elements that facilitate expansion of the engineered cells following encounter with the tumor cell antigen (e.g., GD2 antigen) as well elements that enable long-term persistence of the engineered cells. The invention further provides compositions comprising the genetically engineered cells (e.g., immunotherapeutic compositions produced and administered in sufficient quantity to reach the cancers and/or tumors).

Construction of Modified T Cells.

As described herein, the invention provides compositions comprising T cells that are modified (e.g., genetically (e.g., transduced)) to express (e.g., heterologously) one or more AP-1 transcription factors. For example, the invention provides transduced T cells. A "transduced cell" is a cell into which has been introduced a nucleic acid molecule using molecular biology techniques. T cells that are modified/transduced to express one or more heterologous AP-1 transcription factors may be transduced by any technique by which a nucleic acid molecule can be introduced into such a cell, including, but not limited to, transfection with viral vectors (e.g., retroviral, lentiviral or other viral vector), via CRISPR/Cas9 based system, transformation with plasmid vectors, and/or introduction of naked DNA by electroporation, lipofection, and particle gun acceleration. Viral and/or plasmid vectors may be used for in vitro, in vivo, and/or ex vivo expression. An AP-1 transcription factor may be co-expressed with an engineered TCR or CAR, with both the transcription factor and the TCR and/or CAR co-expressed from distinct viral vectors. In another embodiment, they are expressed from a single vector construct using a bicistronic vector. C-Jun (and/or other AP-1 transcription factor) may be expressed constitutively or in a regulated fashion (e.g., using a system to regulate expression remotely via a small molecule or using an endogenously regulated system). c-Jun and/or other AP-1 transcription factor genes may, in another embodiment, be genetically integrated into the cellular DNA using a retroviral, lentiviral or other viral vector or via CRISPR/Cas9 based system. In yet another embodiment, c-Jun and/or other AP-1 transcription factor is expressed via RNA or an oncolytic virus or other transient expression system known in the art. C-Jun and/or other AP-1 transcription fact can be delivered ex vivo into T cells (e.g., wherein the T cells are used for adoptive transfer), or delivered via in vivo genetic transfer.

The invention is not limited by the chimeric antigen receptor (CAR) expressed in T cells (e.g., the CAR construct used in methods of the invention). In one embodiment, the CAR comprises a fusion protein of the variable regions of the heavy (VH) and light chains (VL) (e.g., a single chain variable fragment (scFv)) of an immunoglobulin that binds with specificity to a tumor antigen (e.g., GD2). Those of ordinary skill in the art know that scFv is a fusion protein of the variable regions of the heavy (VH) and light chains (VL) of immunoglobulins, connected with a linker peptide (e.g., of about 10 to about 25 amino acids). The invention is not limited by the type of linker. In some embodiments, the linker is rich in glycine (e.g., for flexibility). In some embodiments, the linker comprises serine and/or threonine (e.g., for solubility). In some embodiments, the linker comprises a portion rich in glycine and a portion comprising serine and/or threonine.

Any antibody/immunoglobulin that binds with specificity to a tumor antigen (e.g., GD2) may be used to construct a CAR (e.g., using VH and VL regions to construct a fusion protein, scFv) for expression in immune cells used in therapeutic methods of the invention. Examples of such antibodies/immunoglobulins include, but are not limited to, for GD2: 14G2a, ch14.18, hu14.18K322A, m3F8, hu3F8-IgG1, hu3F8-IgG4, HM3F8, UNITUXIN, DMAb-20 or any other antibody that binds with specificity to GD2 (e.g., known or described in the art, or yet to be identified). A tumor antigen (e.g., GD2) CAR may comprise a receptor incorporating variants within scFv of a tumor antigen (e.g., GD2) antibody generated to enhance affinity and/or diminish tonic signaling. A tumor antigen (e.g., GD2) CAR may incorporate variable lengths of the hinge regions (e.g., between the scFv and the signaling domains) and/or varying transmembrane domains. The invention is not limited by the transmembrane domain used. Indeed, any transmembrane domain may be used including, but not limited to, all or part of the transmembrane domain of TCR Zeta chain (CD3ζ), CD28, OX40/CD134, 4-1BB/CD137/TNFRSF9, FcERIγ, ICOS/CD278, ILRB/CD122, IL-2RG/CD132, or CD40.

A CAR construct of the invention may include an intracellular signaling domain (e.g., CD3 zeta of a native T cell receptor complex and/or other signaling domain (e.g., a MyD88 signaling domain)) that transduces the event of ligand binding to an intracellular signal (e.g., that activates (e.g., partially) the T cell. Absent co-stimulatory signals, receptor-ligand biding is often insufficient for full activation and proliferation of the T cell. Thus, a CAR construct may include one or more co-stimulatory domains (e.g., that provide a second signal to stimulate full T cell activation). In one embodiment, a co-stimulatory domain is used that increases CAR immune T cell cytokine production. In another embodiment, a co-stimulatory domain is used that facilitates T cell replication. In still another embodiment, a co-stimulatory domain is used that prevents CAR T cell exhaustion. In another embodiment, a co-stimulatory domain is used that increases T cell antitumor activity. In still a further embodiment, a co-stimulatory domain is used that enhances survival of CART cells (e.g., post-infusion into patients). Examples of proteins, or domains or portions thereof, that may be used to provide co-stimulatory signals include, but are not limited to, B7-1/CD80; CD28; B7-2/ CD86; CTLA-4; B7-H1/PD-L1; ICOS/CD278; ILRB/ CD122; IL-2RG/CD132; B7-H2; PD-1; B7-H3; PD-L2; B7-H4; PDCD6; BTLA; 4-1BB/TNFSF9/CD137; FcERIγ; CD40 Ligand/TNFSF5; 4-1BB Ligand/TNFSF9; GITR/TN-FRSF18; BAFF/BLyS/TNFSF13B; GITR Ligand/ TNFSF18; BAFF R/TNFRSF13C; HVEM/TNFRSF14; CD27/TNFRSF7; LIGHT/TNFSF14; CD27 Ligand/ TNFSF7; OX40/TNFRSF4; CD30/TNFRSF8; OX40 Ligand/TNFSF4; CD30 Ligand/TNFSF8; TAC1/ TNFRSF13B; CD40/TNFRSF5; 2B4/CD244/SLAMF4; CD84/SLAMF5; BLAME/SLAMF8; CD229/SLAMF3; CD2 CRACC/SLAMF7; CD2F-10/SLAMF9; NTB-A/ SLAMF6; CD48/SLAMF2; SLAM/CD150; CD58/LFA-3; CD2; Ikaros; CD53; Integrin alpha 4/CD49d; CD82/Kai-1; Integrin alpha 4 beta 1; CD90/Thy1; Integrin alpha 4 beta 7/LPAM-1; CD96; LAG-3; CD160; LMIR1/CD300A; CRTAM; TCL1A; DAP12; TIM-1/KIM-1/HAVCR; Dectin-1/CLEC7A; TIM-4; DPPIV/CD26; TSLP; EphB6; TSLP R; and HLA-DR. In one embodiment, a CAR construct expressed in T cells used in compositions and methods of the invention includes a CD28 endodomain, a 4-1BB endodomain, and/or an OX40 endodomain. In certain embodiments, a CAR construct specific for a tumor antigen (e.g., GD2) of the invention comprises an scFv of an antibody that binds with specificity to the tumor antigen (e.g., GD2), a transmembrane domain (e.g., of CD8), T cell receptor intracellular signaling domain (e.g., TCR zeta chain (CD3 zeta)) and at least one co-stimulatory domain (e.g., 4-1BB).

The invention is not limited by the means of genetically expressing TCRs, CARs, and/or one or more AP-1 transcription factors in T cells. Indeed, any means known in the art and/or described herein may be used. Non-limiting examples of methods of genetically engineering T cells include, but are not limited to, retrovirus- or lentivirus-mediated transduction, transduction with transposase-based systems for gene integration, Crispr/Cas9-mediated gene integration, non-integrating vectors such as RNA or adeno-associated viruses, or other methods described herein. Compositions comprising engineered T cells may incorporate non-engineered T cells or other immune cells, or T cell subsets selected for greater expansion or persistence capacity. In order to diminish toxicity, incorporation of elements that allow killing of engineered cells may be incorporated. In order to diminish toxicity and/or enhance efficacy, incorporation of elements that allow regulation of protein expression in engineered cells may be included.

Cancer Therapeutics, Compositions, and Combination Therapy.

In certain embodiments, the invention provides methods for treating or delaying the progression of cancer, or for treating or delaying the progress of infectious disease, in an individual comprising administering to the individual an effective amount of modified T cells of the invention. In some embodiments, the treatment results in a sustained response in the individual after cessation of the treatment. The methods described herein may find use in treating conditions where enhanced immunogenicity is desired such as increasing tumor immunogenicity for the treatment of cancer. Also provided herein are methods of enhancing immune function in an individual having cancer comprising administering to the individual an effective amount of modified T cells of the invention. Any type of T cell genetically modified to express CAR and/or TCR known in the art or described herein may be used in these methods.

In some embodiments, the individual has cancer that is resistant (e.g., has been demonstrated to be resistant) to one or more other forms of anti-cancer treatment (e.g., chemotherapy, immunotherapy, etc.). In some embodiments, resistance includes recurrence of cancer or refractory cancer. Recurrence may refer to the reappearance of cancer, in the original site or a new site, after treatment. In some embodiments, resistance includes progression of the cancer during treatment with chemotherapy. In some embodiments, resistance includes cancer that does not respond to traditional or conventional treatment with a chemotherapeutic agent. The cancer may be resistant at the beginning of treatment or it may become resistant during treatment. In some embodiments, the cancer is at early stage or at late stage.

In certain embodiments, the invention provides that exposure of animals (e.g., humans) suffering from cancers/ tumors to therapeutically effective amounts of immunotherapeutic compositions comprising T cells modified to express and/or contain elevated levels of one or more AP-1 transcription factors inhibits the growth of such cancer cells outright and/or renders such cells as a population more susceptible to cancer therapeutic drugs or radiation therapies (e.g., to the cell death-inducing activity thereof). The immunotherapeutic compositions and methods of the invention can be used for the treatment, amelioration, or prevention of disorders, such as any type of cancer.

In certain embodiments, immunotherapeutic compositions comprising T cells modified to express and/or contain elevated levels of one or more AP-1 transcription factors are used to treat, ameliorate, or prevent a cancer that is characterized by resistance to one or more conventional cancer therapies (e.g., those cancer cells which are chemoresistant, radiation resistant, hormone resistant, and the like). As described herein, any T cell genetically modified to express a tumor specific CAR may be used in the immunotherapeutic compositions and methods of the invention.

Immunotherapeutic compositions (e.g., comprising T cells modified to express and/or contain elevated levels of one or more AP-1 transcription factors) and methods of the invention may be used to induce cytotoxic activities against tumor cells and/or to promote cell survival and function (e.g., survival and function of the modified immune cells). For example, immunotherapeutic compositions and methods of the invention can be used to induce interleukin-2 (IL-2) to promote T cell survival; to induce Fas Ligand (FasL) and/or tumor necrosis factor-related apoptosis inducing ligand (TRAIL) (e.g., to induce tumor cell apoptosis); and/or to induce interferon (IFN)-gamma (e.g., to activate the innate immune response (e.g., against cancer)). In some embodiments, compositions and methods of the invention are used to induce cell cycle arrest and/or apoptosis and also to potentiate the induction of cell cycle arrest and/or apoptosis either alone or in response to additional apoptosis induction signals. In some embodiments, T cells modified to express and/or contain elevated levels of one or more AP-1 transcription factors sensitize cancer cells to induction of cell cycle arrest and/or apoptosis, including cells that are normally resistant to such inducing stimuli.

In some embodiments, the compositions and methods of the present invention are used to treat diseased cells, tissues, organs, or pathological conditions and/or disease states in an animal (e.g., a mammalian patient including, but not limited to, humans and companion animals). In this regard, various diseases and pathologies are amenable to treatment or prophylaxis using the present methods and compositions. In some embodiments, cancer cells being treated are metastatic. In other embodiments, the cancer cells being treated are resistant to anticancer agents.

Some embodiments of the present invention provide methods for administering an effective amount of T cells modified to express and/or contain elevated levels of one or more AP-1 transcription factors and at least one additional therapeutic agent (including, but not limited to, chemotherapeutic antineoplastics, apoptosis-modulating agents, antimicrobials, antivirals, antifungals, and anti-inflammatory agents) and/or therapeutic technique (e.g., surgical intervention, and/or radiotherapies). In a particular embodiment, the additional therapeutic agent(s) is an anticancer agent.

A number of suitable anticancer agents are contemplated for use in the methods of the present invention. Indeed, the present invention contemplates, but is not limited to, administration of numerous anticancer agents such as: agents that induce apoptosis; polynucleotides (e.g., anti-sense, ribozymes, siRNA); polypeptides (e.g., enzymes and antibodies); biological mimetics; alkaloids; alkylating agents; antitumor antibiotics; antimetabolites; hormones; platinum compounds; monoclonal or polyclonal antibodies (e.g., antibodies conjugated with anticancer drugs, toxins, defensins), toxins; radionuclides; biological response modifiers (e.g., interferons (e.g., IFN-α) and interleukins (e.g., IL-2)); adoptive immunotherapy agents; hematopoietic growth factors; agents that induce tumor cell differentiation (e.g., all-trans-retinoic acid); gene therapy reagents (e.g., antisense therapy reagents and nucleotides); tumor vaccines; angiogenesis inhibitors; proteasome inhibitors: NF-KB modulators; anti-CDK compounds; HDAC inhibitors; and the like. Numerous other examples of chemotherapeutic compounds and anticancer therapies suitable for co-administration with the disclosed compounds are known to those skilled in the art.

In certain embodiments, anticancer agents comprise agents that induce or stimulate apoptosis. Agents that induce apoptosis include, but are not limited to, radiation (e.g., X-rays, gamma rays, UV); tumor necrosis factor (TNF)-related factors (e.g., TNF family receptor proteins, TNF family ligands, TRAIL, antibodies to TRAIL-R1 or TRAIL-R2); kinase inhibitors (e.g., epidermal growth factor receptor (EGFR) kinase inhibitor, vascular growth factor receptor (VGFR) kinase inhibitor, fibroblast growth factor receptor (FGFR) kinase inhibitor, platelet-derived growth factor receptor (PDGFR) kinase inhibitor, and Bcr-Abl kinase inhibitors (such as GLEEVEC)); antisense molecules; antibodies (e.g., HERCEPTIN, RITUXAN, ZEVALIN, and AVASTIN); anti-estrogens (e.g., raloxifene and tamoxifen); anti-androgens (e.g., flutamide, bicalutamide, finasteride, aminoglutethamide, ketoconazole, and corticosteroids); cyclooxygenase 2 (COX-2) inhibitors (e.g., celecoxib, meloxicam, NS-398, and non-steroidal anti-inflammatory drugs (NSAIDs)); anti-inflammatory drugs (e.g., butazolidin, DECADRON, DELTASONE, dexamethasone, dexamethasone intensol, DEXONE, HEXADROL, hydroxychloroquine, METICORTEN, ORADEXON, ORASONE, oxyphenbutazone, PEDIAPRED, phenylbutazone, PLAQUENIL, prednisolone, prednisone, PRELONE, and TANDEARIL); and cancer chemotherapeutic drugs (e.g., irinotecan (CAMPTOSAR), CPT-11, fludarabine (FLUDARA), dacarbazine (DTIC), dexamethasone, mitoxantrone, MYLOTARG, VP-16, cisplatin, carboplatin, oxaliplatin, 5-FU, doxorubicin, gemcitabine, bortezomib, gefitinib, bevacizumab, TAXOTERE or TAXOL); cellular signaling molecules; ceramides and cytokines; staurosporine, and the like.

In still other embodiments, the compositions and methods of the present invention are used together with at least one anti-hyperproliferative or antineoplastic agent selected from alkylating agents, antimetabolites, and natural products (e.g., herbs and other plant and/or animal derived compounds).

Alkylating agents suitable for use in the present compositions and methods include, but are not limited to: 1) nitrogen mustards (e.g., mechlorethamine, cyclophosphamide, ifosfamide, melphalan (L-sarcolysin); and chlorambucil); 2) ethylenimines and methylmelamines (e.g., hexamethylmelamine and thiotepa); 3) alkyl sulfonates (e.g., busulfan); 4) nitrosoureas (e.g., carmustine (BCNU); lomustine (CCNU); semustine (methyl-CCNU); and streptozocin (streptozotocin)); and 5) triazenes (e.g., dacarbazine (DTIC; dimethyltriazenoimid-azolecarboxamide).

In some embodiments, antimetabolites suitable for use in the present compositions and methods include, but are not limited to: 1) folic acid analogs (e.g., methotrexate (amethopterin)); 2) pyrimidine analogs (e.g., fluorouracil (5-fluorouracil; 5-FU), floxuridine (fluorode-oxyuridine; FudR), and cytarabine (cytosine arabinoside)); and 3) purine analogs (e.g., mercaptopurine (6-mercaptopurine; 6-MP), thioguanine (6-thioguanine; TG), and pentostatin (2'-deoxycoformycin)).

In still further embodiments, chemotherapeutic agents suitable for use in the compositions and methods of the present invention include, but are not limited to: 1) *vinca* alkaloids (e.g., vinblastine (VBL), vincristine); 2) epipodophyllotoxins (e.g., etoposide and teniposide); 3) antibiotics (e.g., dactinomycin (actinomycin D), daunorubicin (daunomycin; rubidomycin), doxorubicin, bleomycin, plicamycin (mithramycin), and mitomycin (mitomycin C)); 4) enzymes (e.g., L-asparaginase); 5) biological response modifiers (e.g., interferon-alfa); 6) platinum coordinating complexes (e.g., cisplatin (cis-DDP) and carboplatin); 7) anthracenediones (e.g., mitoxantrone); 8) substituted ureas (e.g., hydroxyurea); 9) methylhydrazine derivatives (e.g., procarbazine (N-methylhydrazine; MIH)); 10) adrenocortical suppressants (e.g., mitotane (o,p'-DDD) and aminoglutethimide); 11) adrenocorticosteroids (e.g., prednisone); 12) progestins (e.g., hydroxyprogesterone caproate, medroxyprogesterone acetate, and megestrol acetate); 13) estrogens (e.g., diethylstilbestrol and ethinyl estradiol); 14) antiestrogens (e.g., tamoxifen); 15) androgens (e.g., testosterone propionate and fluoxymesterone); 16) antiandrogens (e.g., flutamide): and 17) gonadotropin-releasing hormone analogs (e.g., leuprolide).

Any oncolytic agent that is routinely used in a cancer therapy context may also be used in the compositions and methods of the present invention. For example, the U.S. Food and Drug Administration maintains a formulary of oncolytic agents approved for use in the United States. International counterpart agencies to the U.S.F.D.A. maintain similar formularies.

Anticancer agents further include compounds which have been identified to have anticancer activity. Examples include, but are not limited to, 3-AP, 12-O-tetradecanoylphorbol-13-acetate, 17AAG, 852A, ABI-007, ABR-217620, ABT-751, ADI-PEG 20, AE-941, AG-013736, AGRO100, alanosine, AMG 706, antibody G250, antineoplastons, AP23573, apaziquone, APC8015, atiprimod, ATN-161, atrasentan, azacitidine, BB-10901, BCX-1777, bevacizumab, BG00001, bicalutamide, BMS 247550, bortezomib, bryostatin-1, buserelin, calcitriol, CCI-779, CDB-2914, cefixime, cetuximab, CG0070, cilengitide, clofarabine, combretastatin A4 phosphate, CP-675,206, CP-724, 714, CpG 7909, curcumin, decitabine, DENSPM, doxercalciferol, E7070, E7389, ecteinascidin 743, efaproxiral, eflornithine, EKB-569, enzastaurin, erlotinib, exisulind, fenretinide, flavopiridol, fludarabine, flutamide, fotemustine, FR901228, G17DT, galiximab, gefitinib, genistein, glufosfamide, GTI-2040, histrelin, HKI-272, homoharringtonine, HSPPC-96, hu14.18-interleukin-2 fusion protein, HuMax-CD4, iloprost, imiquimod, infliximab, interleukin-12, IPI-504, irofulven, ixabepilone, lapatinib, lenalidomide, lestaurtinib, leuprolide, LMB-9 immunotoxin, lonafarnib, luniliximab, mafosfamide, MB07133, MDX-010, MLN2704, monoclonal antibody 3F8, monoclonal antibody J591, motexafin, MS-275, MVA-MUC1-IL2, nilutamide, nitrocamptothecin, nolatrexed dihydrochloride, nolvadex, NS-9, O6-benzylguanine, oblimersen sodium, ONYX-015, oregovomab, OSI-774, panitumumab, paraplatin, PD-0325901, pemetrexed, PHY906, pioglitazone, pirfenidone, pixantrone, PS-341, PSC 833, PXD101, pyrazoloacridine, R115777, RAD001, ranpirnase, rebeccamycin analogue, rhuAngiostatin protein, rhuMab 2C4, rosiglitazone, rubitecan, S-1, S-8184, satraplatin, SB-, 15992, SGN-0010, SGN-40, sorafenib, SR31747A, ST1571, SU011248, suberoylanilide hydroxamic acid, suramin, talabostat, talampanel, tariquidar, temsirolimus, TGFa-PE38 immunotoxin, thalidomide, thymalfasin, tipifarnib, tirapazamine, TLK286, trabectedin, trimetrexate glucuronate, TroVax, UCN-1, valproic acid, vinflunine, VNP40101M, volociximab, vorinostat, VX-680, ZD1839, ZD6474, zileuton, and zosuquidar trihydrochloride.

The present invention provides methods for administering compositions and methods of the invention with (e.g., before, during, or after) radiation therapy. The invention is not limited by the types, amounts, or delivery and administration systems used to deliver the therapeutic dose of radiation to an animal. For example, the animal may receive photon radiotherapy, particle beam radiation therapy, other types of radiotherapies, and combinations thereof. In some embodiments, the radiation is delivered to the animal using a linear accelerator. In still other embodiments, the radiation is delivered using a gamma knife.

The source of radiation can be external or internal to the animal. External radiation therapy is most common and involves directing a beam of high-energy radiation to a tumor site through the skin using, for instance, a linear accelerator. While the beam of radiation is localized to the tumor site, it is nearly impossible to avoid exposure of normal, healthy tissue. However, external radiation is usually well tolerated by animals. Internal radiation therapy involves implanting a radiation-emitting source, such as beads, wires, pellets, capsules, particles, and the like, inside the body at or near the tumor site including the use of delivery systems that specifically target cancer cells (e.g., using particles attached to cancer cell binding ligands). Such implants can be removed following treatment, or left in the body inactive. Types of internal radiation therapy include, but are not limited to, brachytherapy, interstitial irradiation, intracavity irradiation, radioimmunotherapy, and the like.

The animal may optionally receive radiosensitizers (e.g., metronidazole, misonidazole, intra-arterial Budr, intravenous iododeoxyuridine (IudR), nitroimidazole, 5-substituted-4-nitroimidazoles, 2H-isoindolediones, [[(2-bromoethyl)-amino]methyl]-nitro-1H-imidazole-1-ethanol, nitroaniline derivatives, DNA-affinic hypoxia selective cytotoxins, halogenated DNA ligand, 1,2,4 benzotriazine oxides, 2-nitroimidazole derivatives, fluorine-containing nitroazole derivatives, benzamide, nicotinamide, acridine-intercalator, 5-thiotretrazole derivative, 3-nitro-1,2,4-triazole, 4,5-dinitroimidazole derivative, hydroxylated texaphrins, cisplatin, mitomycin, tiripazamine, nitrosourea, mercaptopurine, methotrexate, fluorouracil, bleomycin, vincristine, carboplatin, epirubicin, doxorubicin, cyclophosphamide, vindesine, etoposide, paclitaxel, heat (hyperthermia), and the like), radioprotectors (e.g., cysteamine, aminoalkyl dihydrogen phosphorothioates, amifostine (WR 2721), IL-1, IL-6, and the like). Radiosensitizers enhance the killing of tumor cells. Radioprotectors protect healthy tissue from the harmful effects of radiation.

Any type of radiation can be administered to an animal, so long as the dose of radiation is tolerated by the animal without unacceptable negative side-effects. Suitable types of radiotherapy include, for example, ionizing (electromagnetic) radiotherapy (e.g., X-rays or gamma rays) or particle beam radiation therapy (e.g., high linear energy radiation). Ionizing radiation is defined as radiation comprising particles or photons that have sufficient energy to produce ionization, i.e., gain or loss of electrons (as described in, for example, U.S. Pat. No. 5,770,581 incorporated herein by reference in its entirety). The effects of radiation can be at least partially controlled by the clinician. In one embodiment, the dose of radiation is fractionated for maximal target cell exposure and reduced toxicity.

In one embodiment, the total dose of radiation administered to an animal is about 0.01 Gray (Gy) to about 100 Gy. In another embodiment, about 10 Gy to about 65 Gy (e.g., about 15 Gy, 20 Gy, 25 Gy, 30 Gy, 35 Gy, 40 Gy, 45 Gy, 50 Gy, 55 Gy, or 60 Gy) are administered over the course of treatment. While in some embodiments a complete dose of radiation can be administered over the course of one day, the total dose is ideally fractionated and administered over several days. Desirably, radiotherapy is administered over the course of at least about 3 days, e.g., at least 5, 7, 10, 14, 17, 21, 25, 28, 32, 35, 38, 42, 46, 52, or 56 days (about 1-8 weeks). Accordingly, a daily dose of radiation will comprise approximately 1-5 Gy (e.g., about 1 Gy, 1.5 Gy, 1.8 Gy, 2 Gy, 2.5 Gy, 2.8 Gy, 3 Gy, 3.2 Gy, 3.5 Gy, 3.8 Gy, 4 Gy, 4.2 Gy, or 4.5 Gy), or 1-2 Gy (e.g., 1.5-2 Gy). The daily dose of radiation should be sufficient to induce destruction of the targeted cells. If stretched over a period, in one embodiment, radiation is not administered every day, thereby allowing the animal to rest and the effects of the therapy to be realized. For example, radiation desirably is administered on 5 consecutive days, and not administered on 2 days, for each week of treatment, thereby allowing 2 days of rest per week. However, radiation can be administered 1 day/week, 2 days/week, 3 days/week, 4 days/week, 5 days/week, 6 days/week, or all 7 days/week, depending on the animal's responsiveness and any potential side effects. Radiation therapy can be initiated at any time in the therapeutic period. In one embodiment, radiation is initiated in week 1 or week 2, and is administered for the remaining duration of the therapeutic period. For example, radiation is administered in weeks 1-6 or in weeks 2-6 of a therapeutic period comprising 6 weeks for treating, for instance, a solid tumor. Alternatively, radiation is administered in weeks 1-5 or weeks 2-5 of a therapeutic period comprising 5 weeks. These exemplary radiotherapy administration schedules are not intended, however, to limit the present invention.

In some embodiments of the present invention, T cells modified to express and/or contain elevated levels of one or more AP-1 transcription factors and one or more therapeutic agents or anticancer agents are administered to an animal under one or more of the following conditions: at different periodicities, at different durations, at different concentrations, by different administration routes, etc. In some embodiments, T cells modified to express and/or contain elevated levels of one or more AP-1 transcription factors are administered prior to the therapeutic or anticancer agent, e.g., 0.5, 1, 2, 3, 4, 5, 10, 12, 18 hours or more, 1, 2, 3, 4, 5, 6 or more days, or 1, 2, 3, 4, 5, 6 or more weeks prior to the administration of the therapeutic or anticancer agent. In some embodiments, T cells modified to express and/or contain elevated levels of one or more AP-1 transcription factors are administered after the therapeutic or anticancer agent, e.g., 0.5, 1, 2, 3, 4, 5, 10, 12, 18 or more hours, 1, 2, 3, 4, 5, 6 or more days, or 1, 2, 3, 4, 5, 6, or more weeks after the administration of the anticancer agent. In some embodiments, T cells modified to express and/or contain elevated levels of one or more AP-1 transcription factors and the therapeutic or anticancer agent are administered concurrently but on different schedules, e.g., modified immune cells are administered daily while the therapeutic or anticancer agent is administered once a week, once every two weeks, once every three weeks, once every four weeks, or more. In other embodiments, T cells modified to express and/or contain elevated levels of one or more AP-1 transcription factors are administered once a week while the therapeutic or anticancer agent is administered daily, once a week, once every two weeks, once every three weeks, once every four weeks, or more.

Compositions within the scope of this invention include all compositions wherein the T cells modified to express and/or contain elevated levels of one or more AP-1 transcription factors are contained in an amount which is effective to achieve its intended purpose. While individual needs vary, determination of optimal ranges of effective amounts of each component is within the skill of the art. In one non-limiting example, T cells modified to express and/or contain elevated levels of one or more AP-1 transcription factors may be administered to mammals, e.g. humans, in order to provide the human between 1000 and $10^{10}$ T cells per day (e.g., for treating cancer). In another embodiment, between 1000 and $10^{10}$ modified T cells are administered to treat, ameliorate, or prevent cancer (e.g., prevent metastasis, recurrence, and/or progression of cancer). The unit dose may be administered in one or more administrations one or more times daily (e.g., for 1, 2, 3, 4, 5, 6, or more days or weeks).

T cells may be administered as part of a pharmaceutical preparation containing suitable pharmaceutically acceptable carriers comprising excipients and auxiliaries which facilitate processing and/or administration of the modified cells into preparations which can be used pharmaceutically. T immune cells and/or pharmaceutical preparations containing the same may be administered intravenously, intramuscularly, subcutaneously, intratumorally, intraperitoneally, intrathecally, or intraventricularly. An effective amount of T cells and/or pharmaceutical preparations containing the same may be administered for prevention or treatment of disease. The appropriate dosage may be determined based on the type of disease to be treated, the type of modified T cell, the severity and course of the disease, the clinical condition of the individual, the individual's clinical history and response to the treatment, and the discretion of the attending physician.

The efficacy of any of the methods described herein (e.g., treatment with T cells modified to express and/or contain elevated levels of one or more AP-1 transcription factors alone in in combination with one or more chemotherapeutic agents described herein) may be tested in various models known in the art, such as clinical or pre-clinical models. Suitable pre-clinical models are exemplified herein. For any exemplary model, after developing tumors, mice are randomly recruited into treatment groups receiving treatment or control treatment. Tumor size (e.g., tumor volume) is measured during the course of treatment, and overall survival rate is also monitored.

In some embodiments, a sample is obtained prior to treatment with T cells (e.g., alone or in combination with another therapy described herein) as a baseline for measuring response to treatment. In some embodiments, the sample is a tissue sample (e.g., formalin-fixed and paraffin-embedded (FFPE), archival, fresh or frozen). In some embodiments, the sample is whole blood. In some embodiments, the whole blood comprises immune cells, circulating tumor cells and any combinations thereof.

Responsiveness to treatment may refer to any one or more of: extending survival (including overall survival and progression free survival); resulting in an objective response (including a complete response or a partial response); or improving signs or symptoms of cancer. In some embodiments, responsiveness may refer to improvement of one or more factors according to the published set of RECIST guidelines for determining the status of a tumor in a cancer patient, i.e., responding, stabilizing, or progressing. For a more detailed discussion of these guidelines, see Eisenhauer et al., Eur J Cancer 2009; 45: 228-47; Topalian et al., N Engl J Med 2012; 366:2443-54; Wolchok et al., Clin Can Res 2009; 15:7412-20; and Therasse, P., et al. J. Natl. Cancer Inst. 92:205-16 (2000). A responsive subject may refer to a subject whose cancer(s) show improvement, e.g., according to one or more factors based on RECIST criteria. A non-responsive subject may refer to a subject whose cancer(s) do not show improvement, e.g., according to one or more factors based on RECIST criteria.

Conventional response criteria may not be adequate to characterize the anti-tumor activity of immunotherapeutic agents, which can produce delayed responses that may be preceded by initial apparent radiological progression, including the appearance of new lesions. Therefore, modified response criteria have been developed that account for the possible appearance of new lesions and allow radiological progression to be confirmed at a subsequent assessment. Accordingly, in some embodiments, responsiveness may refer to improvement of one of more factors according to immune-related response criteria2 (irRC). See, e.g., Wolchok et al., Clin Can Res 2009; 15:7412-20. In some embodiments, new lesions are added into the defined tumor burden and followed, e.g., for radiological progression at a subsequent assessment. In some embodiments, presence of non-target lesions are included in assessment of complete response and not included in assessment of radiological progression. In some embodiments, radiological progression may be determined only on the basis of measurable disease and/or may be confirmed by a consecutive assessment >4 weeks from the date first documented.

The specification is considered to be sufficient to enable one skilled in the art to practice the invention. Various modifications of the invention in addition to those shown and described herein will become apparent to those skilled in the art from the foregoing description and fall within the scope of the appended claims. All publications, patents, and patent applications cited herein are hereby incorporated by reference in their entirety for all purposes.

EXAMPLES

The following examples illustrate but do not limit the compounds, compositions, and methods of the present invention. Other suitable modifications and adaptations of the variety of conditions and parameters normally encountered in clinical therapy and which are obvious to those skilled in the art are within the spirit and scope of the invention.

Material and Methods

Viral Vector Construction

MSGV retroviral vectors encoding the following CARs were previously described: CD19-28z, CD19-BBz, GD2-28z, GD2-BBz, Her2-BBz, and CD22-BBz. To create the HA-28z CAR, a point mutation was introduced into the 14G2a scFv of the GD2-28z CAR plasmid to create the E101K mutation. The "4/2NQ" mutations46 were introduced into the CH2CH3 domains of the IgG1 spacer region to diminish Fc receptor recognition for in vivo use of HA-28z CART cells. Codon optimized cDNAs encoding c-Jun (JUN), c-Fos (FOS), and truncated NGFR (tNGFR) were synthesized by IDT and cloned into lentiviral expression vectors to create JUN-P2A-FOS, and JUN and FOS single expression vectors co-expressing tNGFR under the separate PGK promoter. JUN-P2A was then subcloned into the XhoI site of MSGV CAR vectors using the In-Fusion HD cloning kit (Takara) upstream of the CAR leader sequence to create JUN-P2A-CAR retroviral vectors. For JUN-AA, point mutations were introduced to convert Ser63 and Ser73 to Ala. The E. coli DHFR-DD sequence was inserted upstream of Jun to create JUN-DD constructs. In some cases, GFP cDNA was also subcloned upstream of the CAR to create GFP-P2A-CAR vector controls.

Viral Vector Production

Retroviral supernatant was produced in the 293GP packaging cell line as previously described. Briefly, 70% confluent 293GP 20 cm plates were co-transfected with 20 ug MSGV vector plasmid and 10 ug RD114 envelope plasmid DNA using Lipofectamine 2000. Media was replaced at 24 and 48 hours post transfection. The 48 HR and 72 HR viral supernatants were harvested, centrifuged to remove cell debris, and frozen at −80C for future use. Third generation, self-inactivating lentiviral supernatant was produced in the 293T packaging cell line as previously described. Briefly, 70% confluent 293T 20 cm plates were co-transfected with 18 ug pELNS vector plasmid, and 18 ug pRSV-Rev, 18 ug pMDLg/pRRE (Gag/Pol) and 7 ug pMD2.G (VSVG envelope) packaging plasmid DNA using Lipofectamine 2000. Media was replaced at 24 hours post transfection. The 24 HR and 48 HR viral supernatants were harvested, combined, and concentrated by ultracentrifugation at 28,000 RPM for 2.5 hr. Concentrated lentiviral stocks were frozen at −80C for future use.

T Cell Isolation

Primary human T cells were isolated from healthy donors using the RosetteSep Human T cell Enrichment kit (Stem Cell Technologies). Buffy coats were purchased from Stanford Blood Center and processed according to the manufacturer's protocol using Lymphoprep density gradient medium and SepMate-50 tubes. Isolated T cells were cryopreserved at $2 \times 10^7$ T cells per vial in CryoStor CS10 cryopreservation medium (Stem Cell Technologies).

CAR T Cell Production

Cryopreserved T cells were thawed and activated same day with Human T-Expander CD3/CD28 Dynabeads (Gibco) at 3:1 beads:cell ratio in T cell media (AIMV supplemented with 5% FBS, 10 mM HEPES, 2 mM GlutaMAX, 100 U/mL penicillin, and 100 ug/mL streptomycin (Gibco)). Recombinant human IL-2 (Peprotech) was provided at 100 U/mL. T cells were transduced with retroviral vector on days 2 and 3 post activation and maintained at $0.5-1 \times 10^6$ cells per mL in T cell media with IL-2. Unless otherwise indicated, CAR T cells were used for in vitro assays or transferred into mice on day 10-11 post activation.

Retroviral Transduction

Non-tissue culture treated 12-well plates were coated overnight at 4C with 1 mL Retronectin (Takara) at 25 ug/mL in PBS. Plates were washed with PBS and blocked with 2% BSA for 15 min. Thawed retroviral supernatant was added at −1 mL per well and centrifuged for 2 hours at 32C at 3200 RPM before the addition of cells.

Cell Lines

The Kelly neuroblastoma, EW8 Ewing's sarcoma, 143b and TC32 osteosarcoma cell lines were originally obtained from ATCC. Some cell lines were stably transduced with GFP and firefly luciferase (GL). The CD19+CD22+ Nalm6-GL B-ALL cell line was provided by David Barrett. Nalm6-GD2 was created by co-transducing Nalm6-GL with cDNAs for GD2 synthase and GD3 synthase. A single cell clone was then chosen for high GD2 expression. Nalm6-22KO and 22low have been previously described and were kindly provided by Terry Fry. All cell lines were cultured in complete media (RPMI supplemented with 10% FBS, 10 mM HEPES, 2 mM GlutaMAX, 100 U/mL penicillin, and 100 ug/mL streptomycin (Gibco)).

Flow Cytometry

CD22 and Her2 CARs were detected using human CD22-Fc and Her2-Fc recombinant proteins (R&D). The idiotype antibodies and Fc-fusion proteins were conjugated with Dylight488 and/or 650 antibody labeling kits (Thermo Fisher). T cell surface phenotype was assessed using the following antibodies:

From BioLegend: CD4-APC-Cy7 (clone OKT4), CD8-PerCp-Cy5.5 (clone SK1), TIM3-BV510 (clone F38-2E2), CD39-FITC or APC-Cy7 (clone A1), CD95-PE (clone DX2), CD3-PacBlue (clone HIT3a), From eBioscience: PD1-PE-Cy7 (clone eBio J105), LAG3-PE (clone 3DS223H), CD45RO-PE-Cy7 (clone UCHL1), CD45-PerCp-Cy5.5 (clone HI30), From BD: CD45RA-FITC or BV711 (clone HI100), CCR7-BV421 (clone 150503), CD122-BV510 (clone Mik-b3), CD62L-BV605 (clone DREG-56), CD4-BUV395 (clone SK3), CD8-BUV805 (clone SK1).

Cytokine Production $1 \times 10^5$ CAR+ T cells and $1 \times 10^5$ tumor cells were cultured in 200 uL CM in 96-well flat bottom plates for 24 hours. For idiotype stimulation, serial dilutions of 1A7 were crosslinked in 1× Coating Buffer (BioLegend) overnight at 4C on Nunc Maxisorp 96-well ELISA plates (Thermo Scientific). Wells were washed once with PBS and $1 \times 10^5$ CAR+ T cells were plated in 200 uL CM and cultured for 24 h. Triplicate wells were plated for each condition. Culture supernatants were collected and analyzed for IFNg and IL-2 by ELISA (BioLegend).

Lysis Assay $5 \times 10^4$ GFP+ leukemia or $2.5 \times 10^4$ GFP+ adherent tumor cells were co-cultured with CAR T cells in 200 uL CM in 96-well flat bottom plates for up to 96 hours. Triplicate wells were plated for each condition. Plates were imaged every 2-3 hours using the IncuCyte ZOOM Live-Cell analysis system (Essen Bioscience). 4 images per well at 10× zoom were collected at each time point. Total integrated GFP intensity per well was assessed as a quantitative measure of live, GFP+ tumor cells. Values were normalized to the starting measurement and plotted over time. E:T ratios are indicated in the Figure legends.

Western Blotting and Immunoprecipitations

Whole-cell protein lysates were obtained in nondenaturing buffer (150 mmol/L NaCl, 50 mmol/L Tris-pH8, 1%

NP-10, 0.25% sodium deoxycholate). Protein concentrations were estimated by Bio-Rad colorimetric assay. Immunoblotting was performed by loading 20 μg of protein onto 11% PAGE gels followed by transfer to PVF membranes. Signals were detected by enhanced chemiluminescence (Pierce) or with the Odyssey imaging system. Representative blots are shown. The following primary antibodies used were purchased from Cell Signaling: c-Jun (60A8), P-c-JunSer73 (D47G9), JunB(C37F9), BATF(D7C5) and IRF4 (4964). The BATF3 (AF7437) antibody was from R&D. Immunoprecipitations were performed in 100 mg of whole-cell protein lysates in 150 μL of nondenaturing buffer and 7.5 mg of agar-conjugated antibodies c-Jun (G4) or JunB (C11) (Sant Cruz Biotechnology). After overnight incubation at 4° C. Beads were washed 3 times with nondenaturing buffer, and proteins were eluted in Laemmli sample buffer, boiled, and loaded onto PAGE gels. Detection of immuno-precipitated proteins was performed with above-mentioned reagents and antibodies.

Mice

Immunocompromised NOD/SCID/IL2Rg−/− (NSG) mice were purchased from JAX and bred in-house. All mice were bred, housed, and treated under Stanford University IACUC (APLAC) approved protocols. 6-8 week old mice were inoculated with either $1\times10^6$ Nalm6-GL leukemia via intravenous (IV) or $0.5-1\times10^6$ 143B osteosarcoma via intramuscular (IM) injections. All CAR T cells were injected IV. Time and treatment dose are indicated in the Figure legends. Leukemia progression was measured by bioluminescent imaging using the IVIS imaging system. Values were analyzed using Living Image software. Solid tumor progression was followed using caliper measurements of the injected leg area. 5 mice per group were treated in each experiment, and each experiment was repeated 2 or 3 times as indicated. Mice were randomized to ensure equal pre-treatment tumor burden before CAR T cell treatment.

Blood and Tissue Analysis

Peripheral blood sampling was conducted via retro-orbital blood collection under isoflurane anesthesia at the indicated time points. 50 μL blood was labeled with CD45, CD3, CD4, and CD8, lysed using BD FACS Lysing Solution and quantified using CountBright Absolute Counting beads (Thermo Fisher) on a BD Fortessa flow cytometer.

ATAC-seq

ATAC-seq library preparation was carried out as described previously48. Briefly, 100,000 cells from each sample were sorted by FACS into CM, centrifuged at 500 g at 4° C., then resuspended in ATAC-seq Resuspension Buffer (RSB) (10 mM Tris-HCl, 10 mM NaCl, 3 mM MgCl2) supplemented with 0.1% NP-40, 0.1% Tween-20, and 0.01% Digitonin. Samples were split into two replicates each prior to all subsequent steps. Samples were incubated on ice for 3 minutes, then washed out with 1 mL RSB supplemented with 0.1% Tween-20. Nuclei were pelleted at 500 g for 10 minutes at 4° C. The nuclei pellet was resuspended in 50 μL transposition mix (25 μl 2×TD buffer, 2.5 μl transposase (Illumina), 16.5 μl PBS, 0.5 μl 1% digitonin, 0.5 μl 10% Tween-20, 5 μl H2O) and incubated at 37° C. for 30 minutes in a thermomixer with 1000 RPM shaking. The reaction was cleaned up using the Qiagen MinElute PCR Purification Kit. Libraries were PCR-amplified using the NEBNext Hi-Fidelity PCR Master Mix and custom primers (IDT) as described previously20. Libraries were sufficiently amplified following 5 cycles of PCR, as indicated by qPCR fluorescence curves20. Libraries were purified with the Qiagen MinElute PCR Purification Kit and quantified with the KAPA Library Quantification Kit. Libraries were sequenced on the Illumina NextSeq at the Stanford Functional Genomics Facility with paired-end 75 bp reads. Adapter sequences were trimmed using SeqPurge and aligned to hg19 genome using bowtie2. These reads were then filtered for mitochondrial reads, low mapping quality (Q>=20), and PCR duplicates using Picard tools. Then we converted the bam to a bed and got the Tn5 corrected insertion sites ("+" stranded+4 bp, "−" stranded −5 bp). To Identify peaks, we called peaks for each sample using MACS2 "—shift −75—extsize 150—nomodel—call-summits—nolambda keep-dup all −p 0.00001" using the insertion beds. To get a union peak set, we (1) extended all summits to 500 bp, (2) merged all summit bed files and then (3) used bedtools cluster and selected the summit with the highest MACS2 score. This was then filtered by the ENCODE hg19 blacklist (https://www.encodeproject.org/annotations/ENCSR636HFF/), to remove peaks that extend beyond the ends of chromosomes. We then annotated these peaks using HOMER and computed the occurrence of a TF motif using motifmatchr in R with chromVARMotifs HOMER set. To create sequencing tracks, we read the Tn5 corrected insertion sites into R and created a coverage pileup binned every 100 bp using rtracklayer. We then counted all insertions that fell within each peak to get a counts matrix (peak×samples). To determined differential peaks we first used peaks that were annotated as "TSS" as control genes or "Housekeeping Peaks" for DESeq2 and then computed differential peaks with this normalization. All clustering was performed using the regularized log transform values from DESeq2. Transcription factor motif deviation analysis was carried out using chromVAR as described previously21. TF motif enrichment were calculated using a hypergeometric test in R testing the representation of a motif (from motifmatchr above) in a subset of peaks vs all peaks.

Subset RNA-seq

For T cell subset-specific RNA-seq, T cells were isolated from healthy donor buffy coats as described above. Before activation, naïve and central memory CD4+ or CD8+ subsets were isolated using a BD FACSAria cell sorter (Stem Cell FACS Core, Stanford University School of Medicine) using the following markers: Naïve (CD45RA+CD45RO−, CD62L+, CCR7+, CD95−, and CD122−), Central Memory (CD45RA-CD45RO+, CD62L+, CCR7+). Sorted starting populations were activated, transduced, and cultured as described above. On days 7, 10, and 14 of culture, CAR+ CD4+ and CD8+ cells were sorted, and RNA was isolated using Qiagen mRNEasy kit. Samples were library prepped and sequenced via Illumina NextSeq paired end platform by the Stanford Functional Genomics Core.

Bulk RNA-seq

For bulk RNA isolation, healthy donor T cells were prepared as described. On day 10 or 11 of culture, total mRNA was isolated from 2×106 bulk CART cells using Qiagen RNEasy Plus mini isolation kit. Bulk RNA-seq was performed by BGI America (Cambridge, Mass.) using the BGISEQ-500 platform, single end 50 bp-read length, at 30×106 reads per sample. Principal component analysis was performed using stats package and plots with ggplot2 package in R (version 3.5)49. Gene set enrichment analysis was performed using the GSEA software (Broad Institute) as described50,51.

Single Cell RNA-seq

To compare gene expression in single CD19-CAR and GD2-CAR T cells, we sorted naïve T-cell subset on day 0 for subsequent single-cell analysis on day 10 using the Chromium platform (10× Genomics) and the Chromium Single Cell 3' v2 Reagent Kit according to the manufacturer's instructions. cDNA libraries were prepared separately for CD19-CAR and GD2-CAR cells, and the CD4+ cells and CD8+ cells were combined in each run to be separated bioinformatically downstream. Sequencing was performed on the Illumina NextSeq system (paired-end, 26 bp into read 1 and 98 bp into read 2) to a depth >100,000 reads per cell. Single-cell RNA-sequencing reads were aligned to the Genome Reference Consortium Human Build 38 (GRCh38), normalized for batch effects, and filtered for cell events using the Cell Ranger software (10x Genomics). A total of 804 CD19-CAR and 726 GD2-CAR T cells were sequenced to an average of 350,587 post-normalization reads per cell. The cell-gene matrix was further processed using the Cell Ranger R Kit software (10x Genomics) as described52. Briefly, we first selected genes with >1 unique molecular identifier (UMI) counts in any given cell. UMI counts were then normalized to UMI sums for each cell and multiplied by a median UMI count across cells. Next, the data were transformed by taking a natural logarithm of the resulting data matrix.

Statistical Analysis

Unless otherwise noted, statistical analyses for significant differences between groups were conducted using unpaired 2-tailed t-tests without assuming consistent SD using Graph-Pad Prism7. For bulk RNA-seq in FIG. 2C, the nonparametric Wilcoxon matched-pair signed rank test was used. Survival curves were compared using the Log-rank Mantel-Cox test. A table with the full statistical analysis, including exact p values, t ratio, and dof can be found in the supplementary materials.

Example 1

Gene Expression Analysis of T Cell Exhaustion

Antigen-independent tonic signaling by chimeric antigen receptors (CARs) can increase differentiation and exhaustion of T cells, limiting their potency. For example, GD2 specific CARs have been described to self-aggregate in the absence of antigen leading to activation of chronic downstream T cell activation signaling cascade. While GD2-CARs incorporating a CD28 costimulatory domain rapidly develop hallmark features of T cell exhaustion, GD2-CARs incorporating a 4-1BB costimulatory domain show reduced evidence of T cell exhaustion and retain greater functionality, despite similar aggregation and signaling. The most prominent features of T cell exhaustion in GD2-28z expressing T cells include increased surface expression of inhibitory receptors (e.g., PD1, TIM3, LAG3, CD39), reduced expression of memory markers (e.g., CD62L and CCR7), and decreased cytokine production (particularly IL2) upon antigen stimulation.

Experiments were conducted during development of embodiments of the invention in order to assess gene transcription analysis in exhausted versus non-exhausted T cells. Reduced expression of AP-1 family members was discovered in GD2-28Z CART cells compared to GD2-BBZ (nonexhausted CAR) (See FIG. 1a). The classic AP-1 partners FOS and JUN were also among the top downregulated genes in GD2-28Z CAR T cells compared to healthy CD19-28Z CAR T cells by RNA sequencing analysis (See FIG. 1b). The AP-1 family of transcription factors are activated downstream of TCR signaling and regulate a wide and diverse array of key T cell functions including growth, apoptosis, cytokine production, and effector functions. Additional experiments were performed, during development of embodiments of the invention, in order to assess and characterize functional roles of AP-1 family members in CART cells (e.g., whether a lack of AP-1 family members in CAR T cells contributes to their CAR T cell phenotype).

Example 2

Construction of CAR T Cells with Forced Expression of c-Jun and c-Fos

In order to determine if replacement of AP-1 could alleviate the symptoms of exhaustion in GD2-28Z CAR T cells, a lentiviral expression construct was constructed with enforced expression of c-Jun and c-Fos under a constitutive promoter (See FIG. 2a). This construct also encoded a truncated nerve growth factor receptor (NGFR (tNGFR)) expression cassette to serve as a surface marker of T cell transduction. Activated primary human T cells were subsequently transduced with CD19, GD2-BBZ, or high affinity (HA) GD2-28Z CAR with (AP-1) or without (wo) the AP-1 expression vector.

Example 3

Expression of c-Jun and c-Fos in CAR T Cells

On day 8 of T cell culture, AP-1 transduced CD4 or CD8 CART cells were sorted using NGFR. Constitutive expression of AP-1 reduced the frequency of exhaustion-associated inhibitory receptors PD1, TIM3, LAG3, and CD39, and increased memory marker CD62L in both CD4 (See FIG. 2b) and CD8 (See FIG. 2c) CAR T cells. CAR T cells were co-cultured with (AP-1) or without (wo) AP-1 co-transduction with CD19 and GD2 antigen expressing tumor cells in order to assess functional changes in the AP-1 transduced CAR T cells. In most conditions, AP-1 transduced CAR T cells released more IL2 (See FIG. 2d) and IFN☐ (See FIG. 2e) compared to those without.

Example 4

CAR T Cells with Forced Expression of c-Jun or c-Fos

Figure 3A:
FIG. 3A-F shows that the functional benefit of AP-1 is primarily from c-Jun expression.

In order to assess whether the functional benefit of AP-1 expression required both c-Fos and c-Jun expression, individual lentiviral vectors were created encoding c-Jun or c-Fos alone (See FIG. 3a). CAR T cells were transduced with either c-Fos or c-Jun encoding vectors.

Figure 3B:
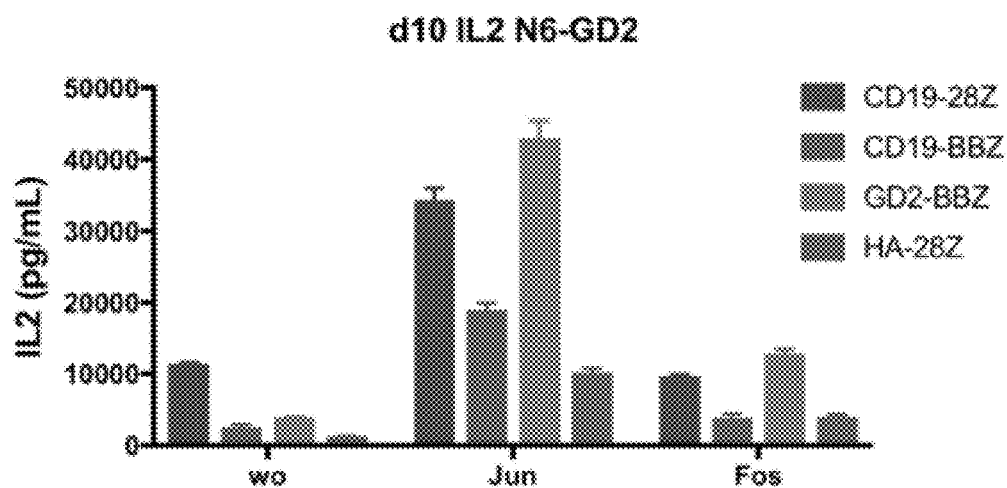
Figure 3C:
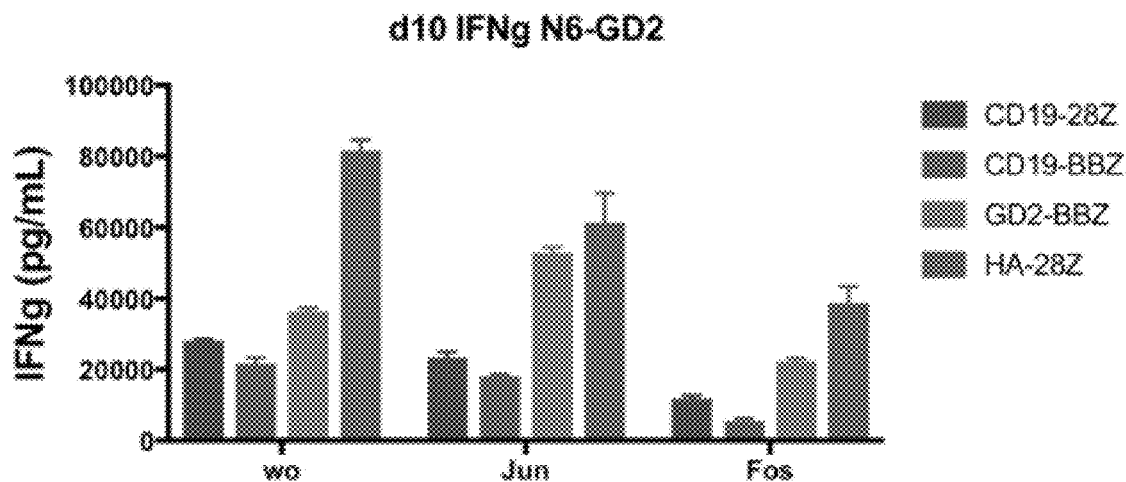
Figure 3D:
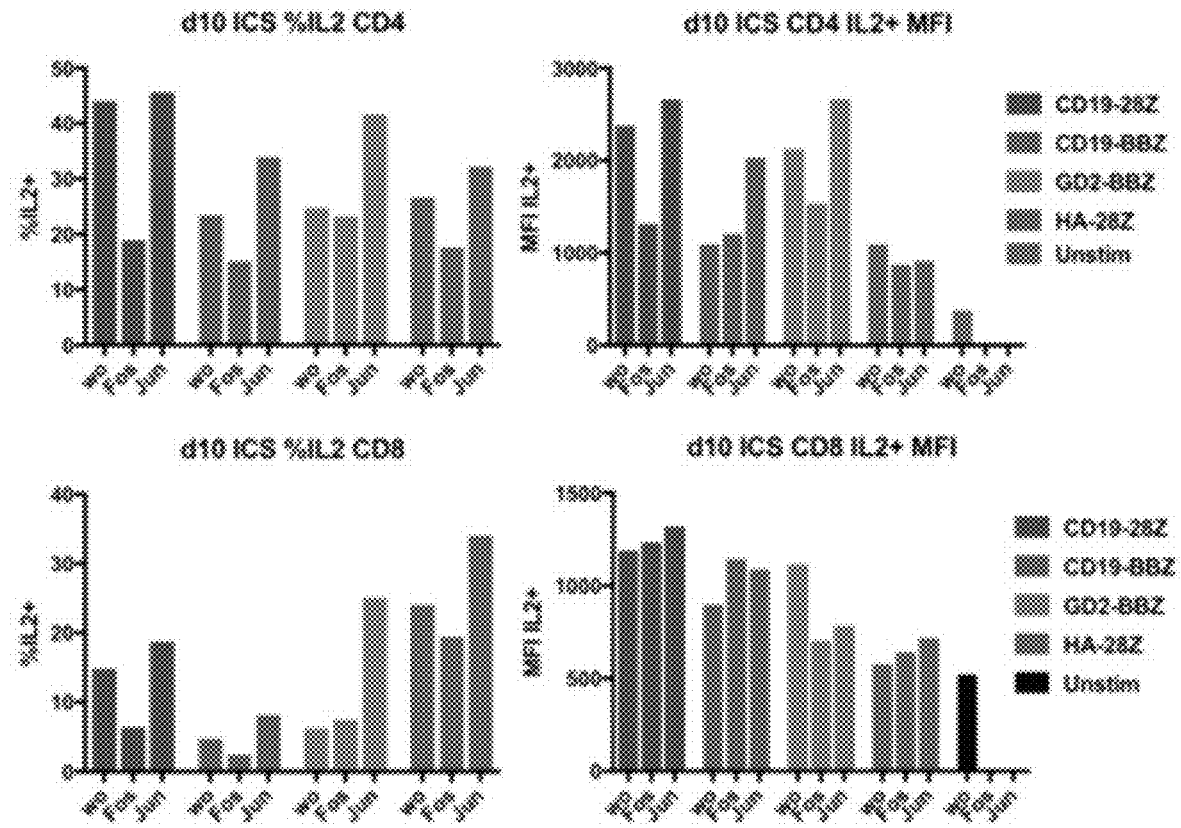
Figure 3E:
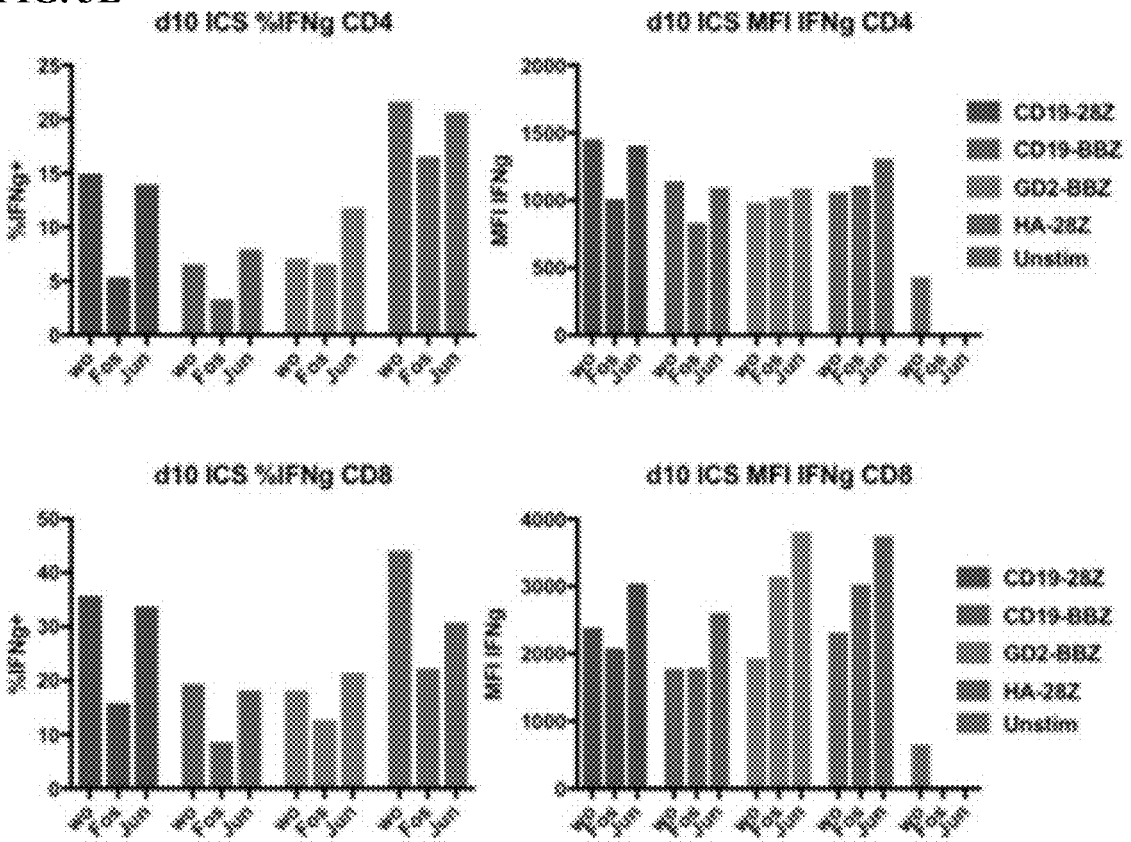
Figure 3F:
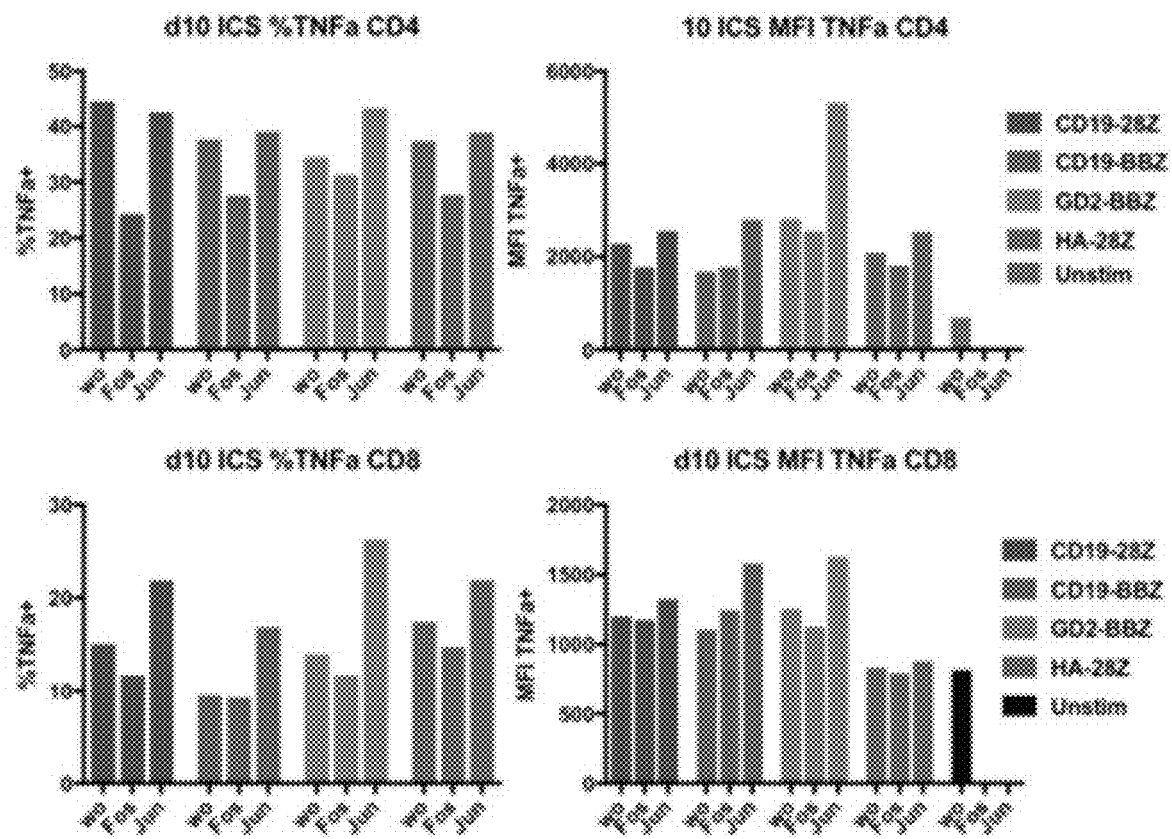

Upon CAR T cell stimulation with antigen positive tumor cells, only CAR T cells expressing c-Jun resulted in increased IL2 while c-Fos expression alone was not sufficient (See FIG. 3b). IFN☐ secretion was similarly but less dramatically impacted by c-Jun overexpression (See FIG. 3c). To confirm increased cytokine expression in c-Jun expressing CAR T cells on an individual cell level, intracellular cytokine staining (ICS) by flow cytometry was performed following 6 hr T cell stimulation with antigen positive tumor cells. In the majority of cases, an increase in the frequency and/or the mean fluorescence intensity (MFI) of IL2 (See FIG. 3d), IFN☐ (See FIG. 3e), and TNFa (See FIG. 3O in c-Jun transduced CAR T cells was found compared to those without (wo) while c-Fos transduction generally led to a decrease in cytokine production compared to controls. These data indicates that c-Jun overexpression can increase both the frequency of CAR T cells responding to antigen stimulation and the level of cytokine produced by an individual CAR T cell upon antigen encounter.

Example 5

Figures 4A, 4B:
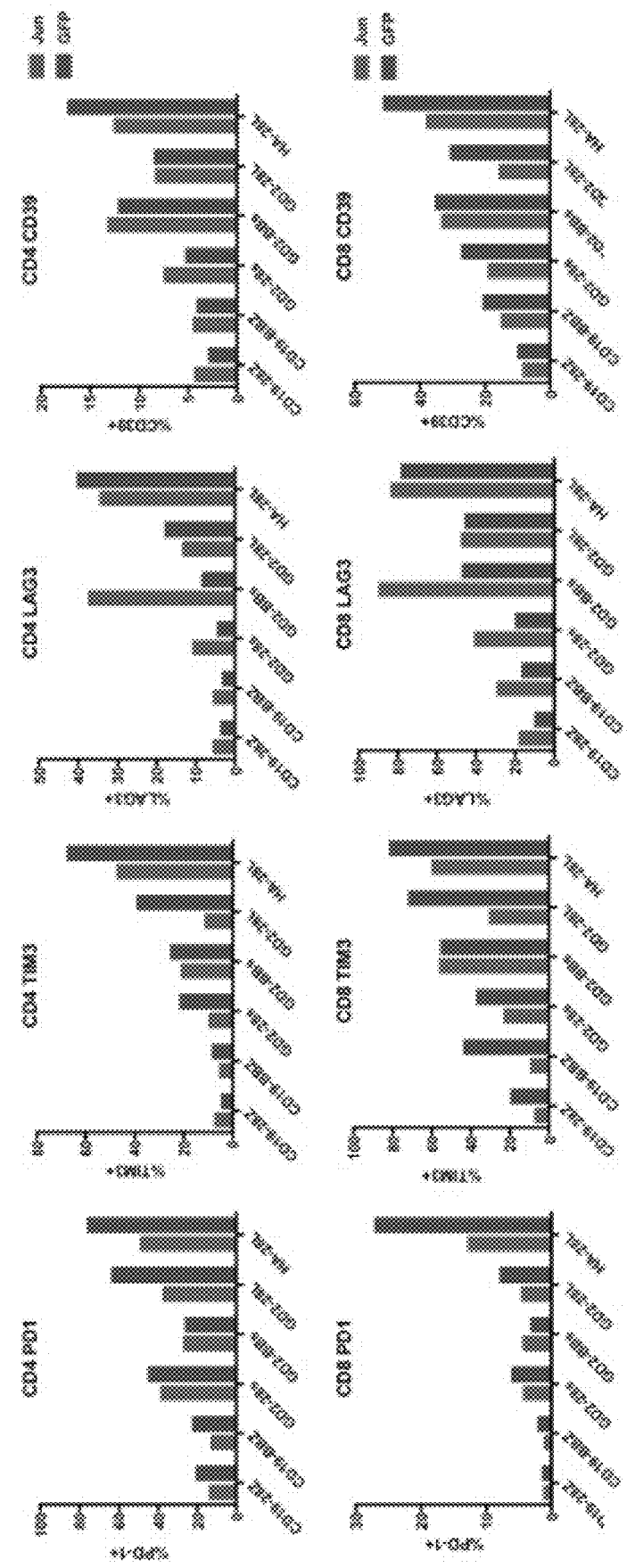
FIG. 4A-E shows that bi-cistronic expression of c-Jun with a CAR enhances CAR T functional activity.
Figure 4C:
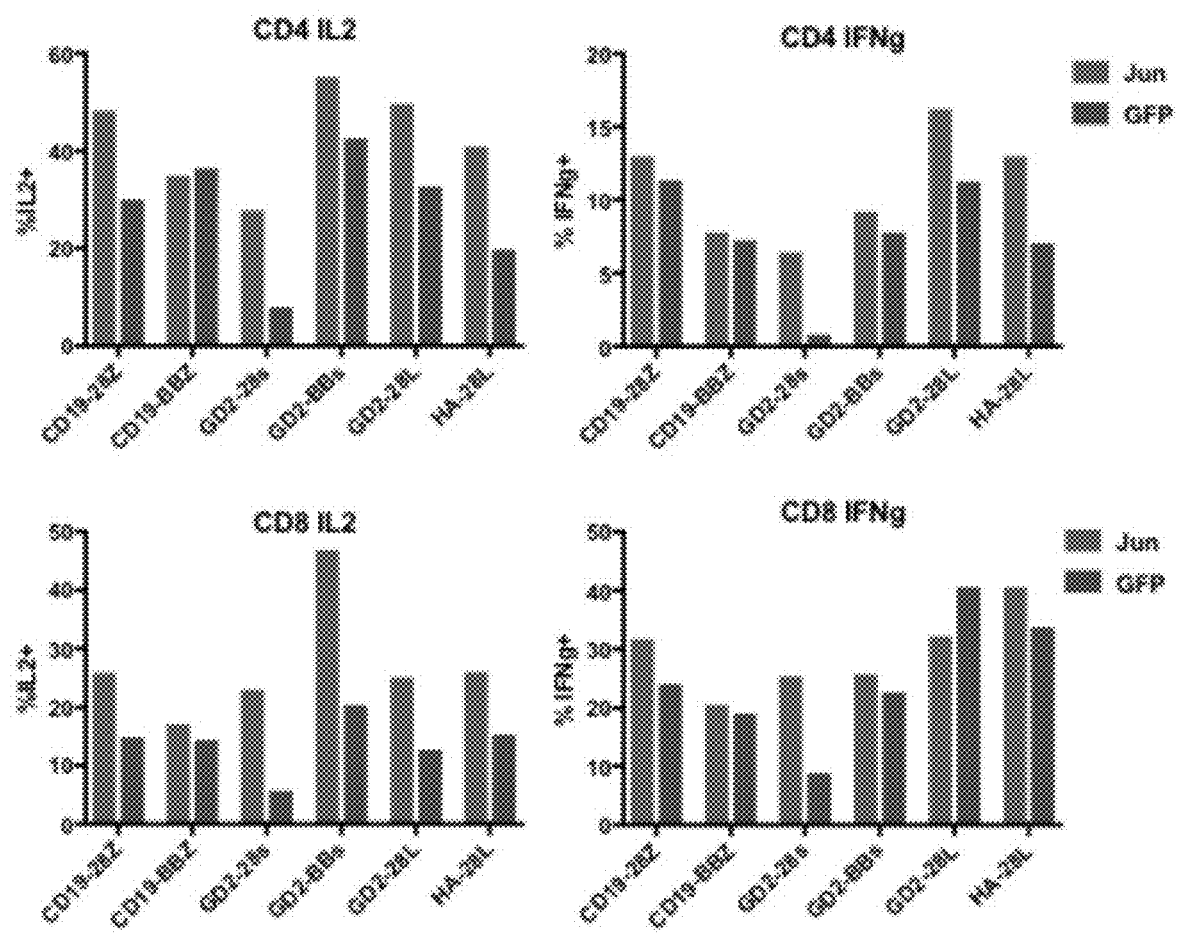
Figure 4D:
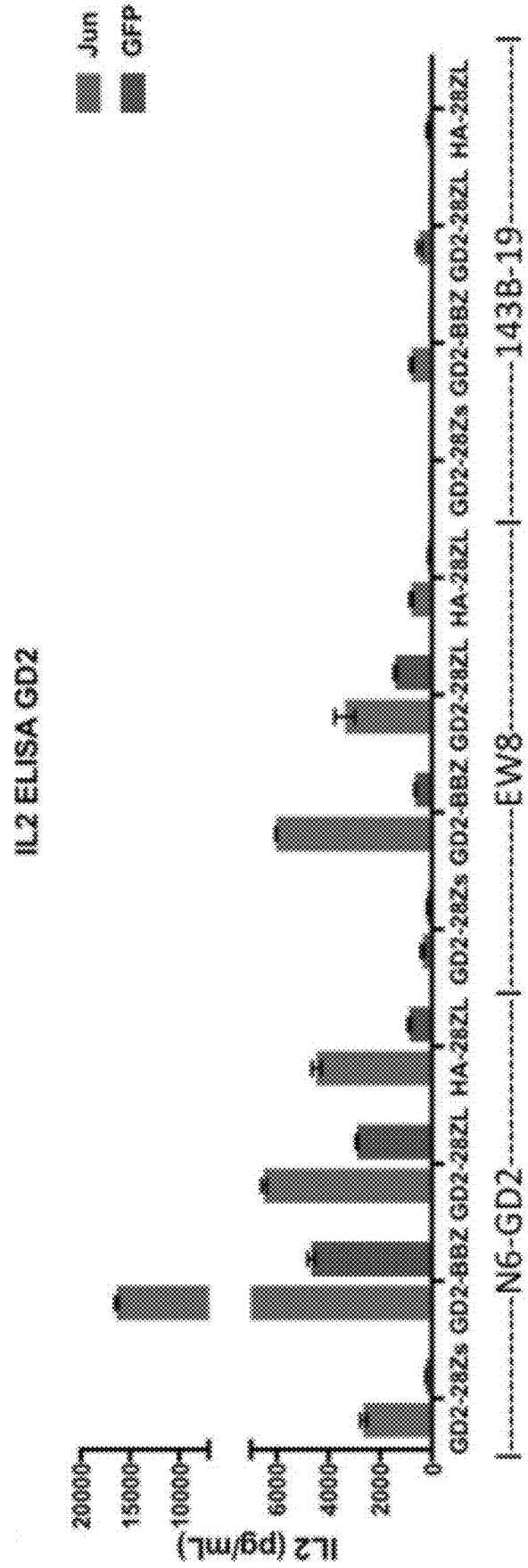
Figure 4E:
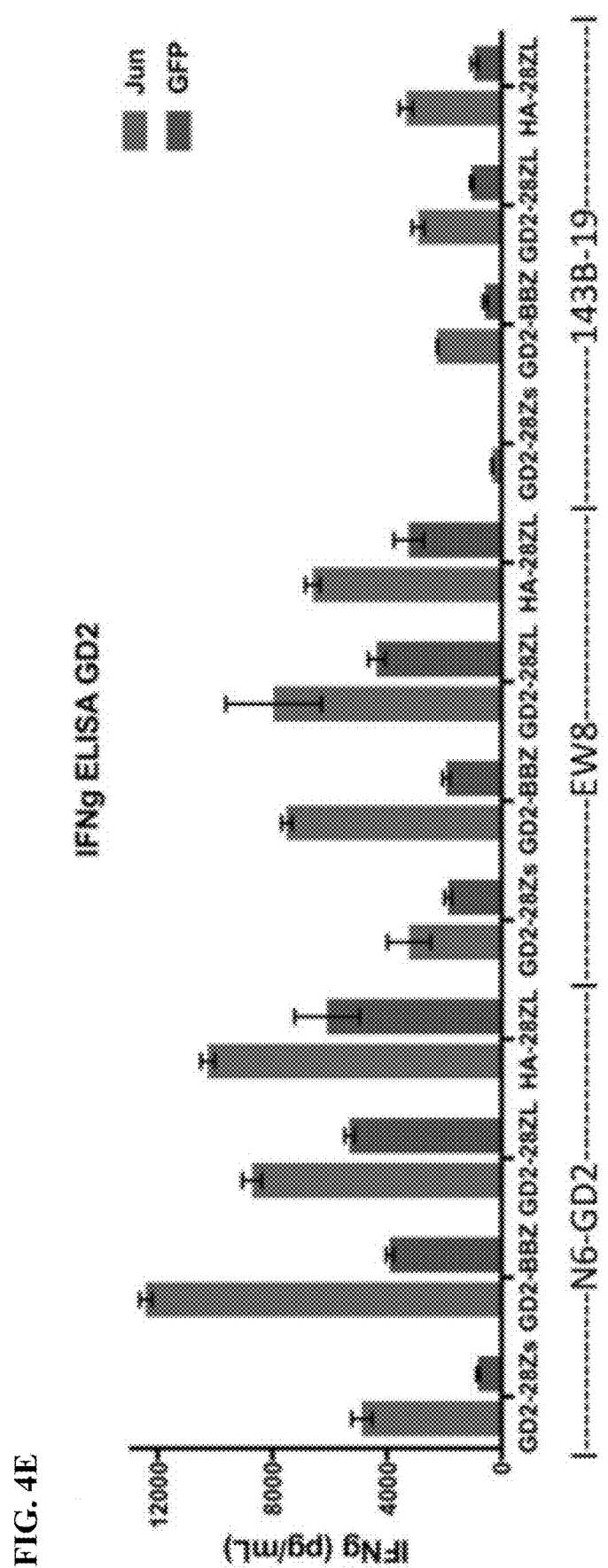
Figure 5A:
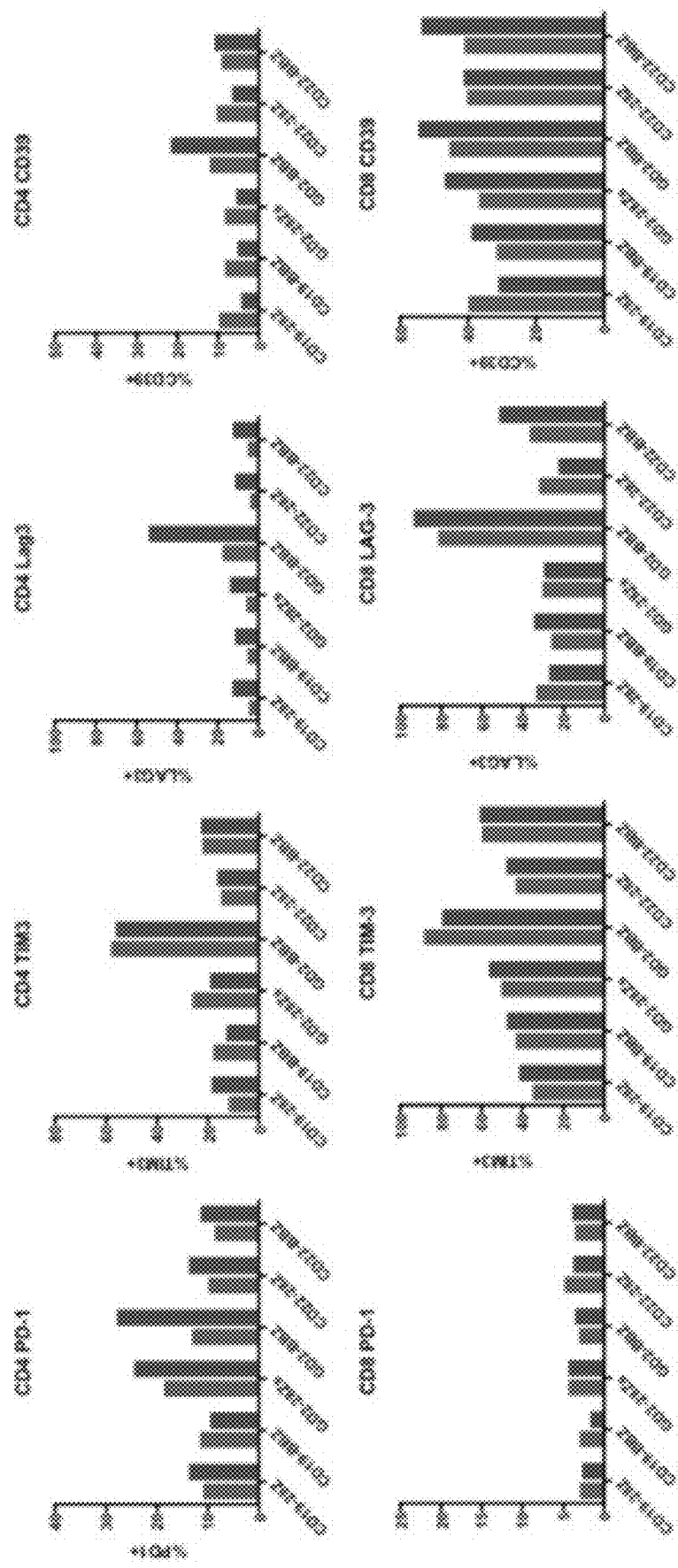
FIG. 5A-C shows that bi-cistronic expression of c-Jun with a CAR enhances CAR T functional activity and central memory phenotype.
Figure 5B:
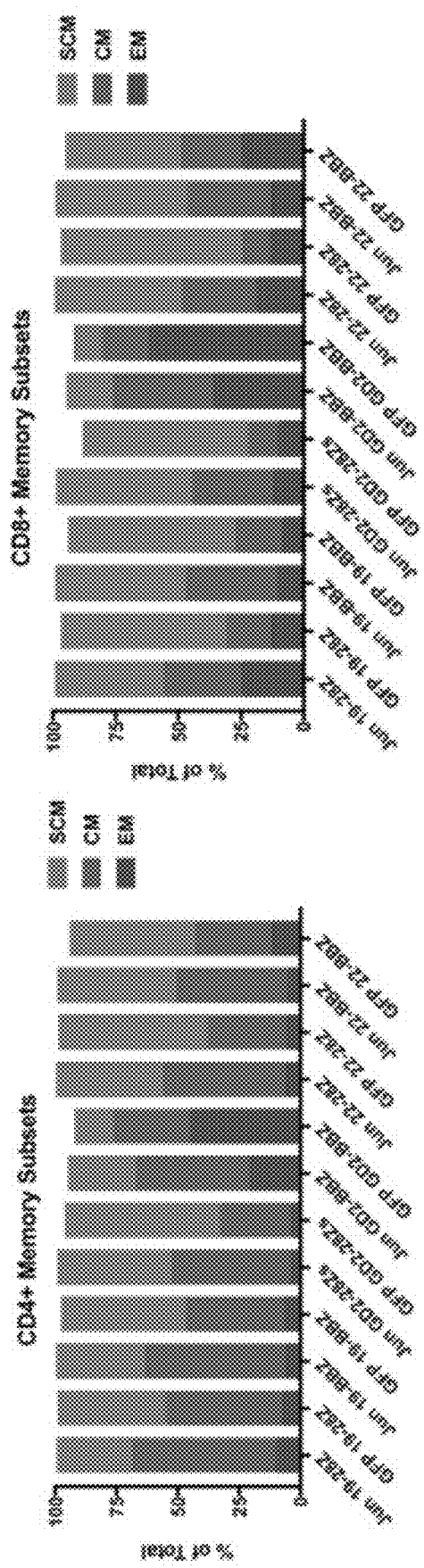
Figure 5C:
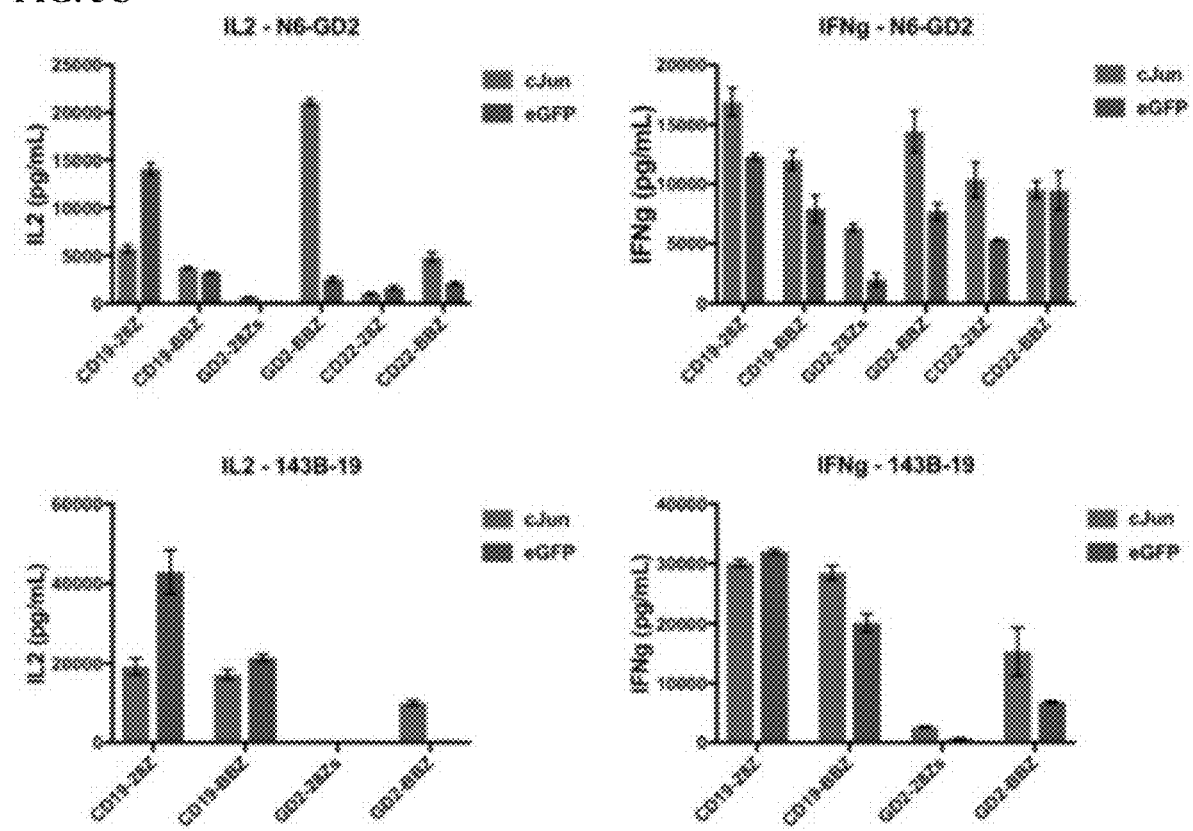
Figure 6A:
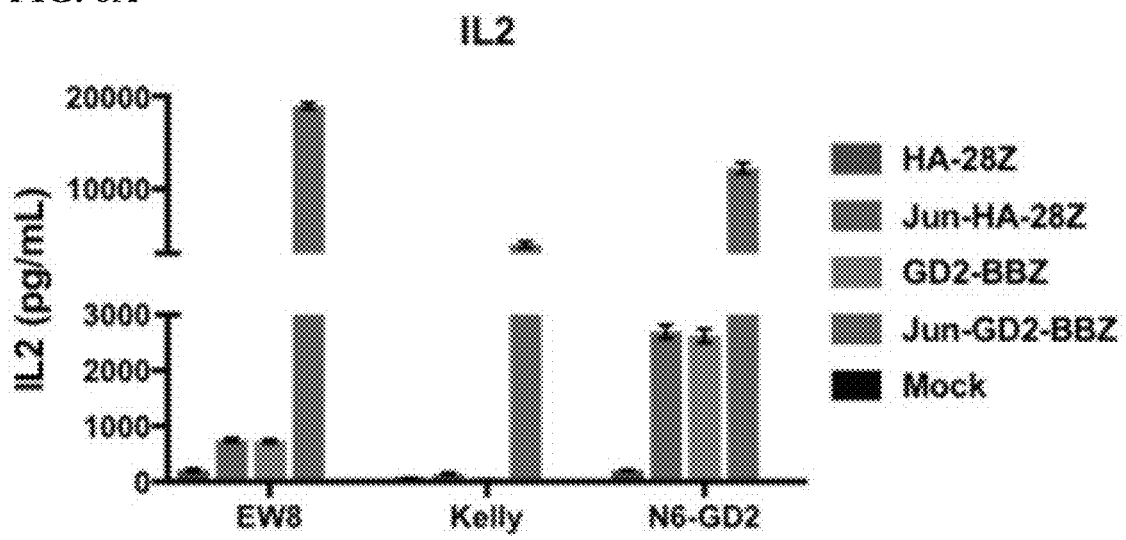
FIG. 6A-F shows that bi-cistronic expression of c-Jun with a CAR enhances CAR T cell proinflammatory cytokine production and decreases IL-10.
Figure 6B:
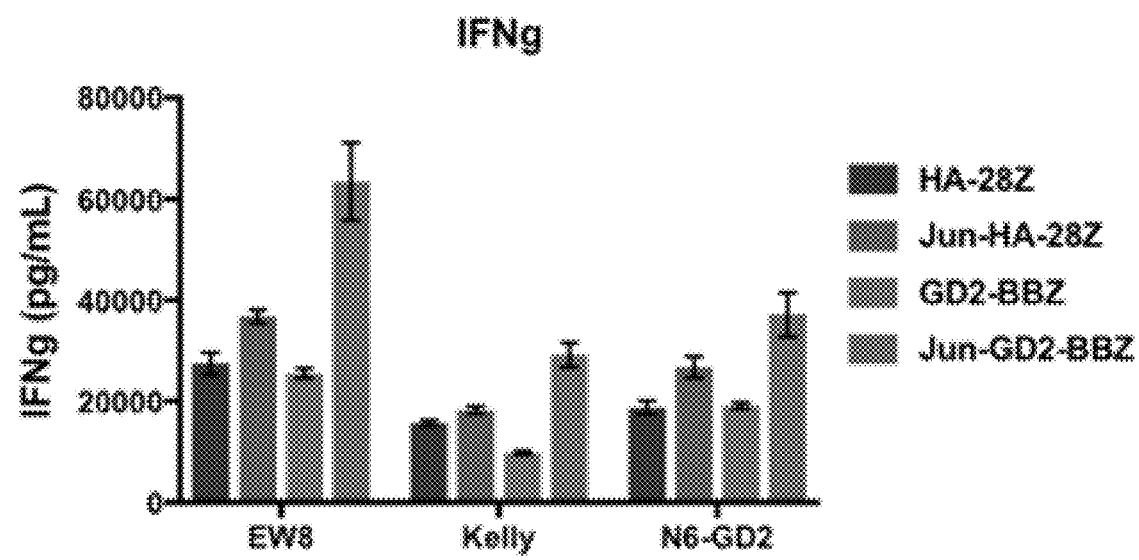
Figure 6C:
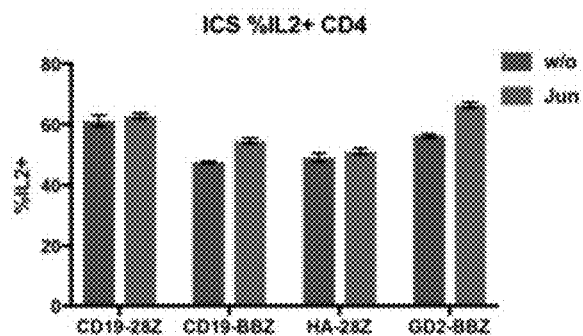
Figure 6C:
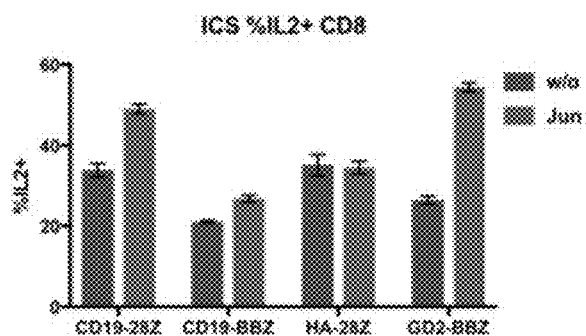
Figure 6D:
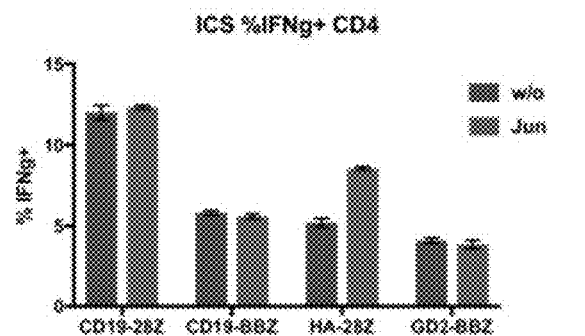
Figure 6D:
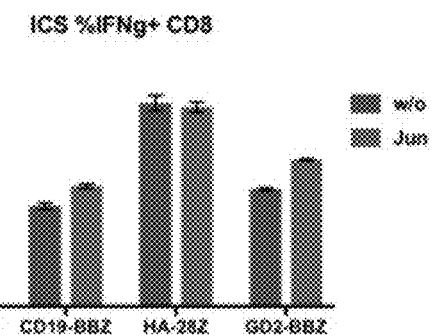
Figure 6E:
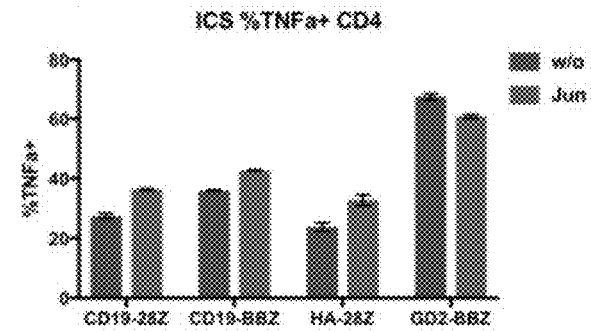
Figure 6E:
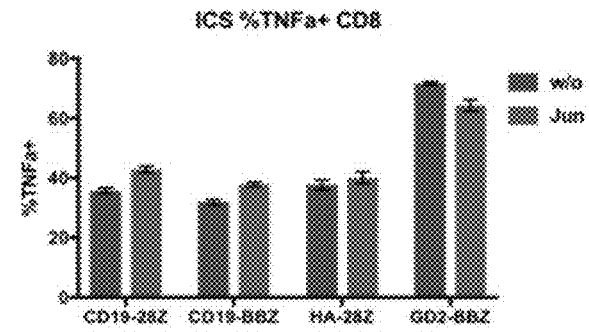
Figure 6F:
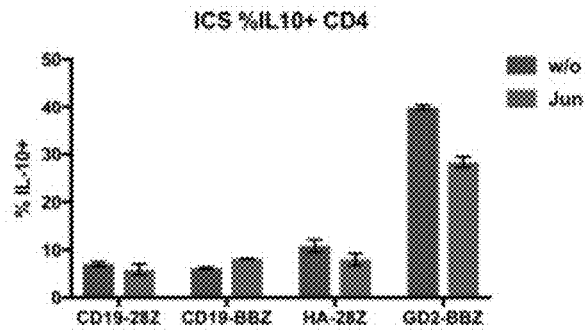
Figure 6F:
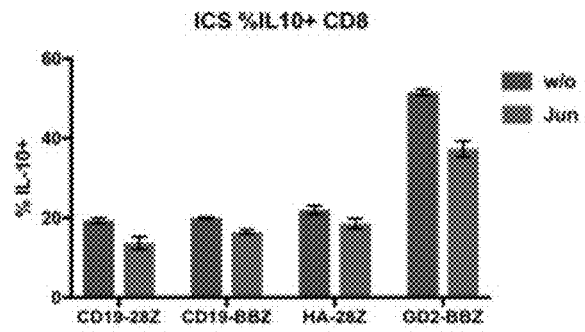
Figure 7A:
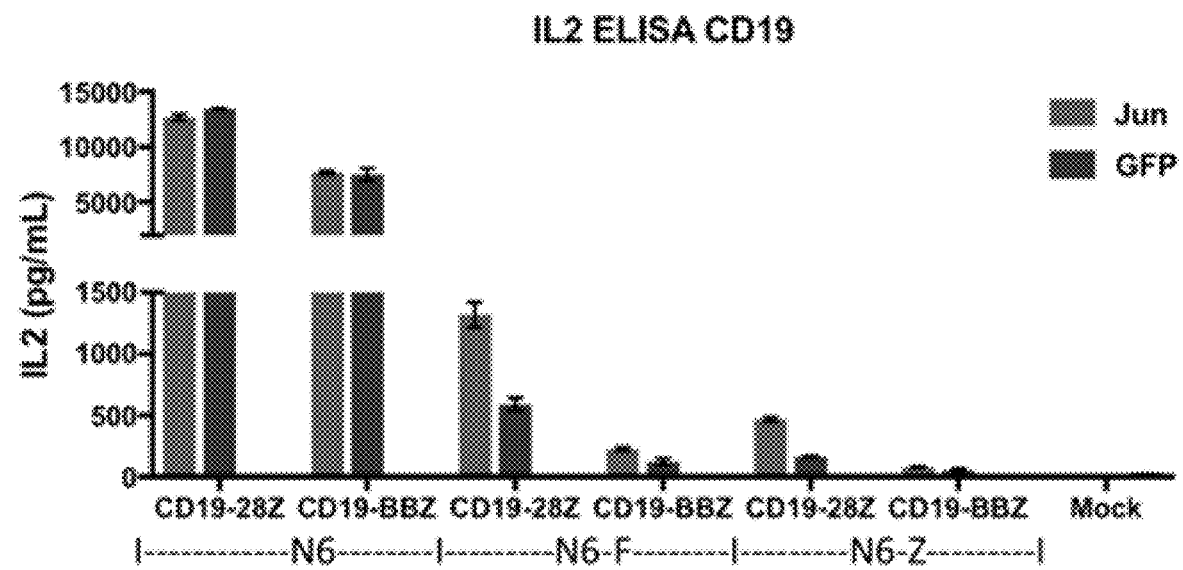
FIG. 7A-E shows that bi-cistronic expression of c-Jun enhances CD19 and CD22 CAR T cell activity in response to tumor cells with low levels of antigen.
Figure 7B:
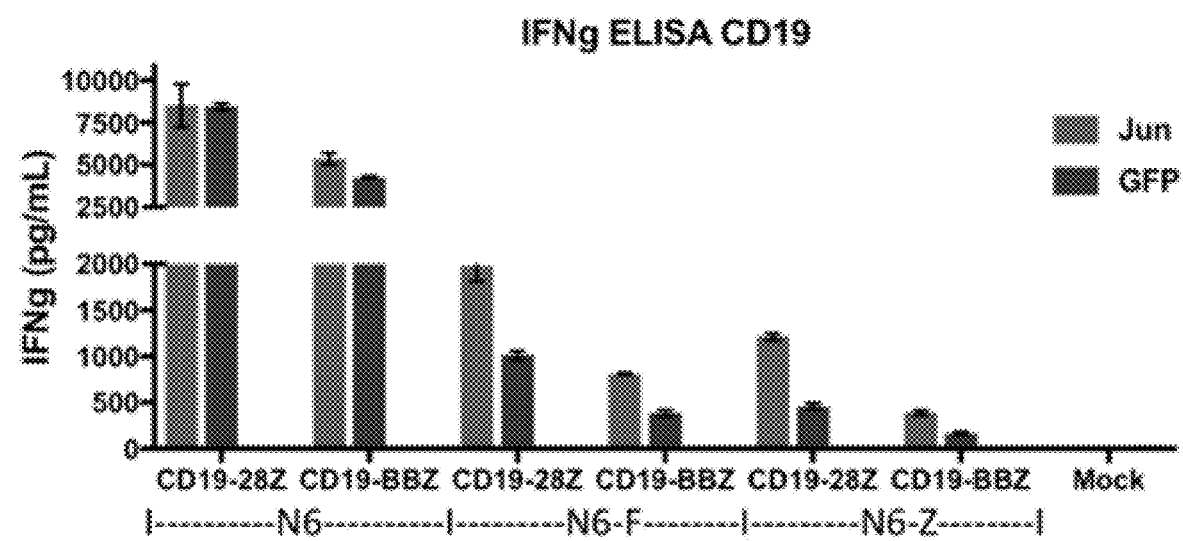
Figure 7C:
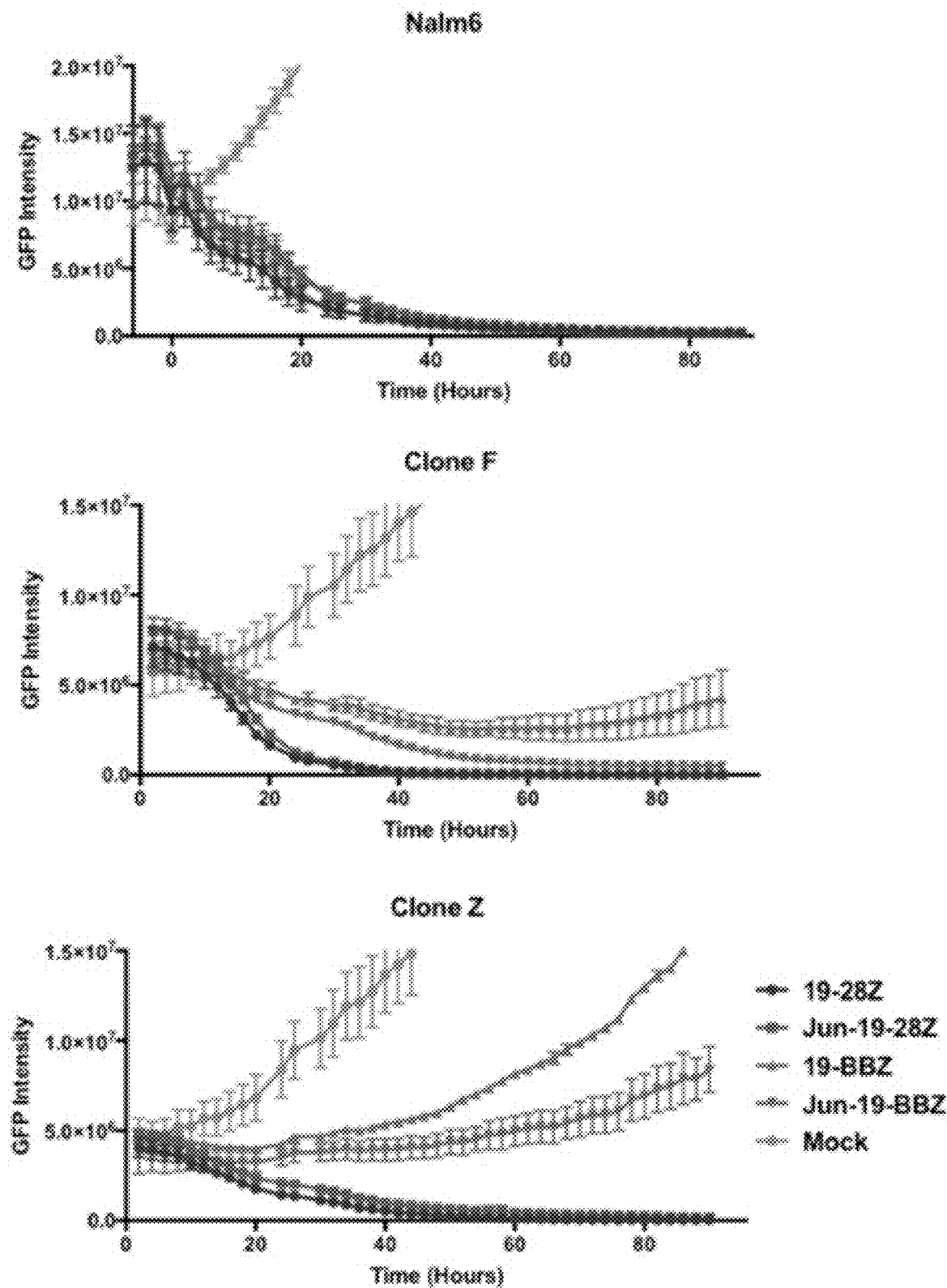
Figure 7D:
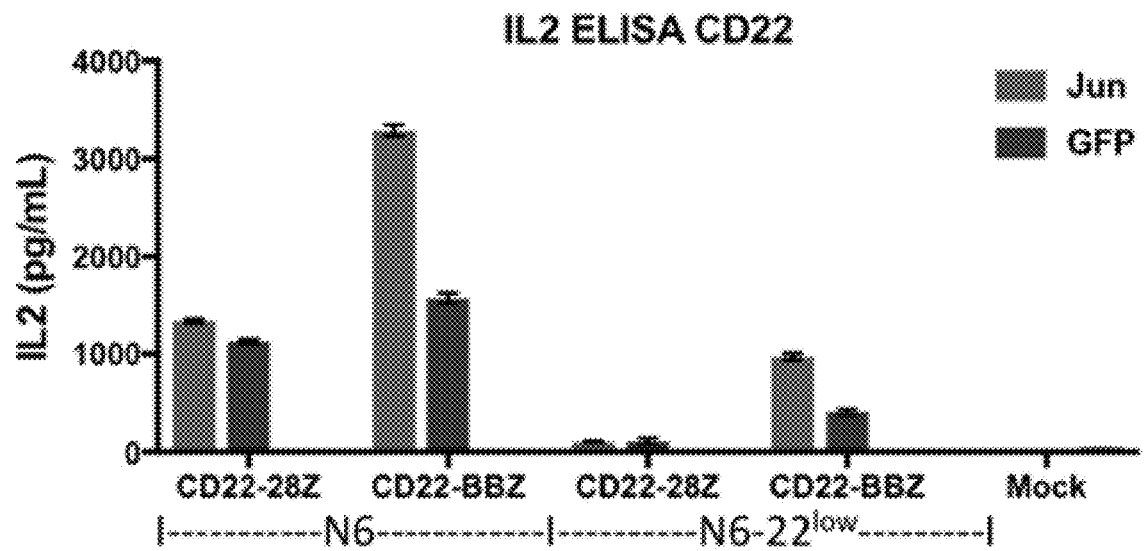
Figure 7E:
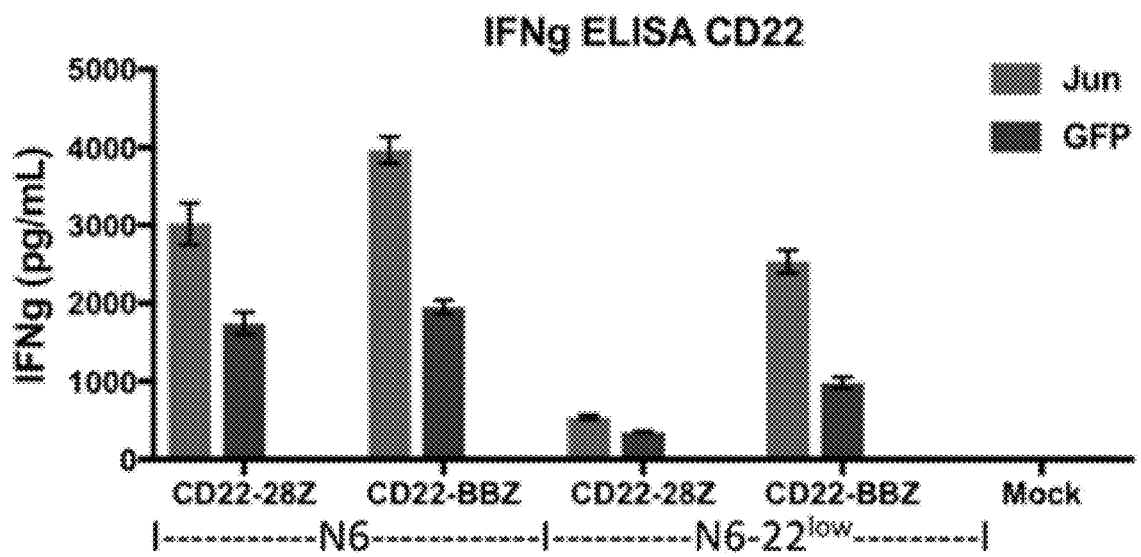
Figure 8A:
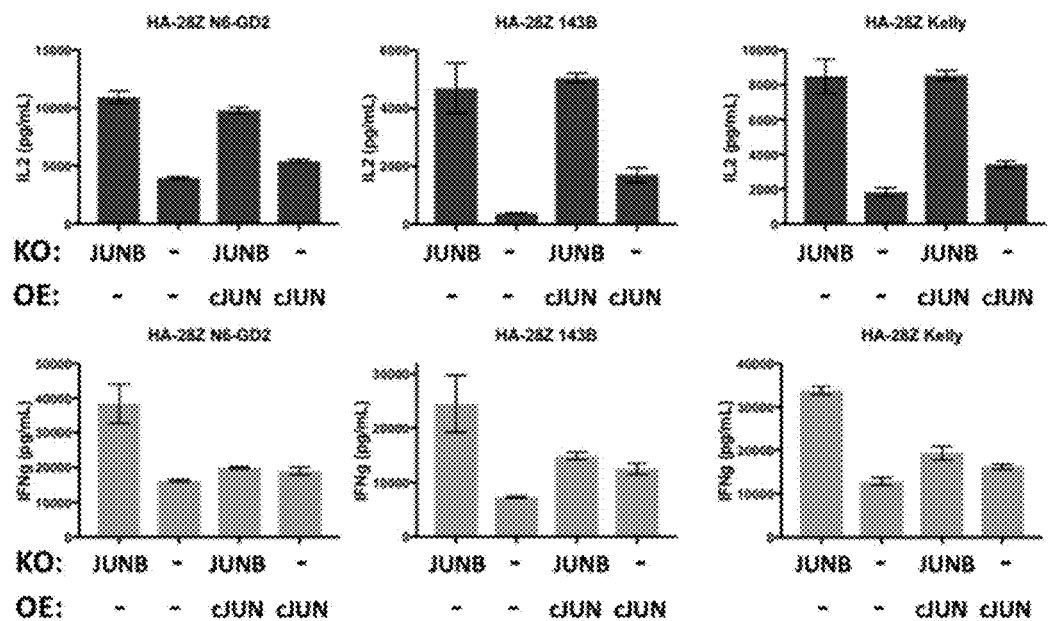
FIG. 8A-D shows that the knockdown of inhibitory AP-1 family members JunB and BATF3 increases IL2 production in exhausted CAR T cells. (A) CRISPR gene knockout (KO) of JunB in HA-28Z exhausted CART cells dramatically increases IL2 (top) and IFNg (bottom) production following exposure to GD2+ cell lines Nalm6-GD2 (left), 143B osteosarcoma (middle), and Kelly neuroblastoma (right). This increase was even greater than for c-Jun overexpression (OE) alone. Dual JUNB-KO and cJUN-OE T cells did not show any benefit compared to JUNB-ko alone. (B) CRISPR gene knockout (KO) of JunB in GD2-BBZ CAR T cells significantly increases IL2 (top) and IFNg (bottom) production following exposure to GD2+ cell lines Nalm6-GD2 (left), 143B osteosarcoma (middle), and Kelly neuroblastoma (right), however, c-Jun overexpressing (OE) GD2-BBZ CAR T cells showed the greatest functional benefit. Dual JUNB-KO and cJUN-OE T cells did not show any benefit compared to cJUN-OE alone. (C) CRISPR gene knockout (KO) of JunB in CD19-28Z (left) or CD19-BBZ (right) CAR T cells did not impact IL2 (top) production following exposure to Nalm6-GD2 leukemia cells, suggesting JunB is a potent inhibitor only in tonically signaling/exhausted GD2 CAR T cells. (D) CRISPR gene knockout (KO) of BATF3 in HA-28Z exhausted CAR T cells increases IL2 (top) production following exposure to Nalm6-GD2 (left) and Kelly neuroblastoma (right) while IFNγ production is unchanged. HA-28Z exhausted CAR T cells edited using three independent gRNAs targeting BATF3 all showed increased IL2 production compared to control or ZB2 edited controls.
Figure 8B:
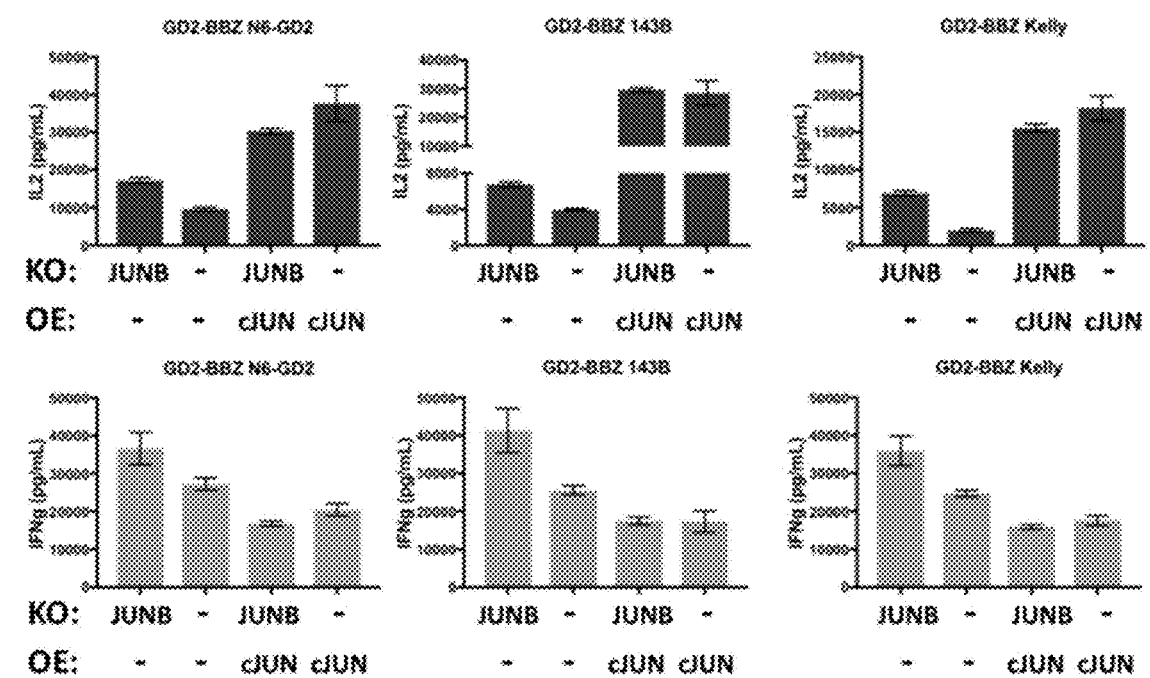
Figure 8C:
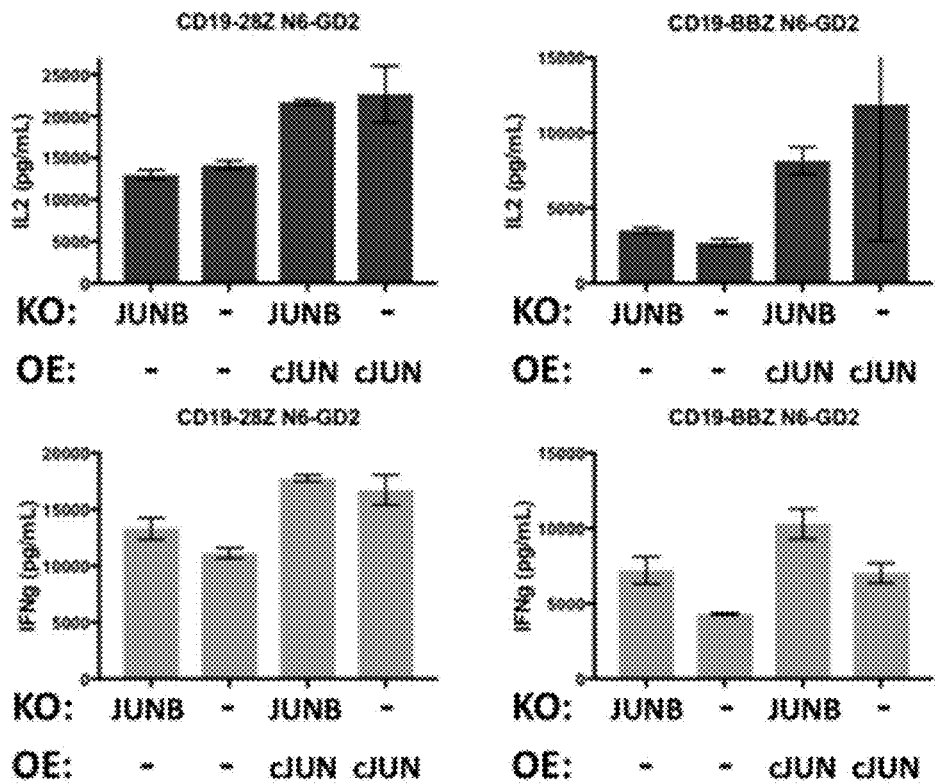
Figure 8D:
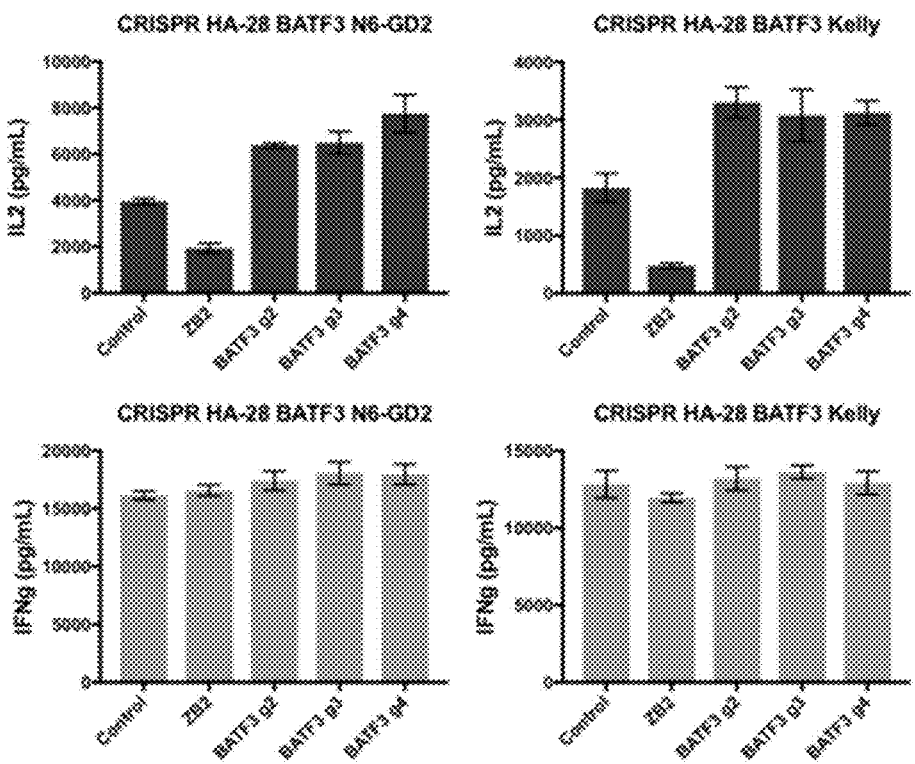

Construction of Bi-Cistronic Vectors Co-Expressing c-Jun and CAR from the Same Vector As c-Jun was shown to be primarily responsible for the increased activity of AP-1 transduced CAR T cells, bi-cistronic retroviral vectors were created that co-express c-Jun and CAR from the same vector, separated by a viral 2A ribosomal skipping peptide sequence (See FIG. 4a). These constructs ensured any CAR+ T cell would also co-express c-Jun and negated the need for co-transduction and sorting to achieve pure double-positive populations. Eight different CAR vectors were separately cloned into the c-Jun backbone: CD19-28Z, CD19-BBZ, CD22-28Z, CD22-BBZ, GD2-28Zshort, GD2-28ZLong, HA(GD2)-28ZLong, and GD2-BBZ, in order to test the functional impact of c-Jun re-expression across multiple antigen specificities and tumor indications.

c-Jun expression in combination with most CARs resulted in decreased expression of surface exhaustion markers (See FIGS. 4b and 5a). Enhanced cytokine secretion was observed in GD2 CAR T cells co-expressing c-Jun compared to control CAR T cell co-expressing GFP (See FIGS. 4d-e, 5c, and 6a-b).

c-Jun mediates increased cytokine secretion in response to both leukemia (Nalm6-GD2) as well as the GD2+ pediatric solid tumors Ewing sarcoma (EW8), osteosarcoma (143B), and neuroblastoma (Kelly) highlighting the broad clinical applicability of c-Jun-enhanced GD2 CAR T cells. Additionally, c-Jun overexpression promotes an increased frequency of central memory CAR T cells (See FIG. 5b). Using intracellular cytokine staining (ICS), increased proinflammatory cytokine production was also observed on an individual cell level (FIGS. 4c and 6c-e) in both CD4+ and CD8+c-Jun-CAR T cells. We also noted a reduction in production of the anti-inflammatory cytokine IL10 in c-Jun CAR T cells compared to controls (See FIG. 6f) was also observed, indicating that enhanced c-Jun expression may contribute to enhanced Th1 cytokine profile.

Example 6 c-Jun Replacement and Functional Activity in Different CAR T Cells

As detailed herein, c-Jun replacement in exhausted CAR T cells (e.g. GD2 CAR T cells) may ameliorate exhaustion in CAR T cells. However, trends for lower exhaustion markers and increased functional activity were also observed in healthy CD19 CART cells. While CD19 CART cells have mediated remarkable clinical responses in B-ALL patients, a growing number of relapses occur in up to 30% of patients with CD19-low or negative disease. CD22 CARs, an alternative strategy to target B-cell malignancies may also be limited by low CD22 antigen density in some patient leukemia cells. Thus, experiments were conducted during development of embodiments of the invention in order to assess and characterize the activity of c-Jun-CD19 and c-Jun-CD22 CART cells against normal (Nalm6) or low antigen expressing tumor cells (Nalm6-F and Z for CD19 or Nalm6-22low) (See FIG. 7).

While c-Jun did not enhance CD19 CAR activity against high antigen levels on Nalm6, there were significant improvements in IL2 (See FIG. 7a) and IFN□ (See FIG. 7b) in response to CD19-low Nalm6 clones Z and F. In an INCUCYTE Immune Cell Killing Assay (See FIG. 7c), the 3 GFP+ Nalm6 cell lines were co-cultured with CAR T cells for 92 hrs. All 4 CD19 CARs kill the original Nalm6 tumor (as measured by loss of GFP intensity over time). Both CD19-28Z and c-Jun-CD19-28Z were able to kill CD19-low tumor cells Clone F and Z, however CD19-BBZ CAR T cells only had a moderate effect. Addition of c-Jun-CD19-BBZ CART cells showed a significant increase in killing CD19 low clones compared to 19-BBZ alone. Enhanced cytokine secretion by CD22 CAR T cells (especially CD22-BBZ) coexpressing c-Jun was also observed in response to both parental Nalm6 and Nalm622low (See FIG. 7d-e).

Example 7

Inhibition of AP-1 Inhibitory Complex Members Reduces T Cell Exhaustion

While enhanced c-Fos and c-Jun expression can increase functionality of modified T cells, there are other inhibitory AP-1 family members expressed in exhausted activated T cells. Accordingly, experiments were conducted during development of embodiments of the invention in order to determine and characterize if inhibition/knockdown of inhibitory AP-1 complex members (e.g., to increase availability of canonical AP-1 factors) could reduce T cell exhaustion (e.g., increase T cell function). CRISPR-Cas9 gRNA systems were designed to target potential inhibitory AP-1 members. Cytokine production was evaluated from JUNB and BATF3 gene edited (knockout, KO) CAR T cells. JUNB knockdown greatly enhanced IL2 and IFNg production from exhausted HA-GD2-28Z and GD2-BBZ CAR T cells while it did not impact CD19 CAR T cells (See FIG. 8A-C). This indicated that JUNB knockdown positively impacted exhausted, but not healthy, T cells. Similarly, BATF3 knockout also increased IL2 (but not IFNg) production from exhausted HA-28Z CAR T cells (See FIG. 8D) compared to control edited T cells.

Example 8

In Vivo Efficacy of c-Jun Modified CAR T Cells

Figure 9A:
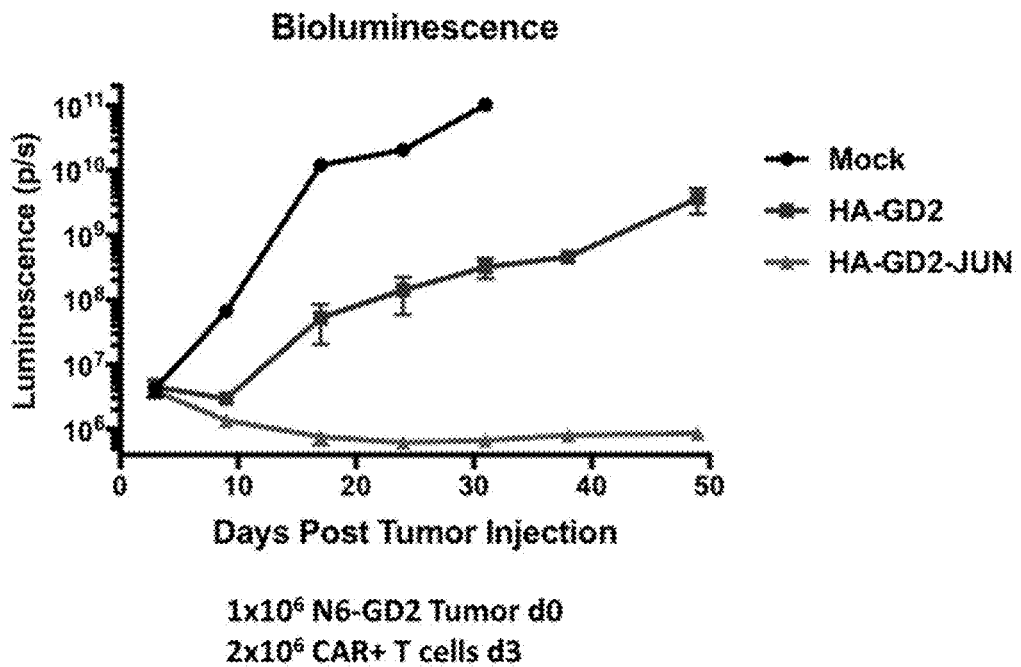
FIG. 9A-B shows that c-Jun-expressing HA-GD2 CAR T cells display superior, curative in vivo activity compared to unmodified HA-GD2 CAR T cells. Growth of Nalm6-GD2 leukemia cells stably expressing firefly luciferase was tracked in vivo using bioluminescent imaging following adoptive transfer of $2\times10^6$ CAR+ or Mock (untransduced) T cells. (A) Quantified bioluminescence over time. (B) Images showing individual mice. n=5 mice per group. (scales are all $1\times10^4$-$1\times10^6$, except Mock d32 scale is adjusted).
Figure 9B:
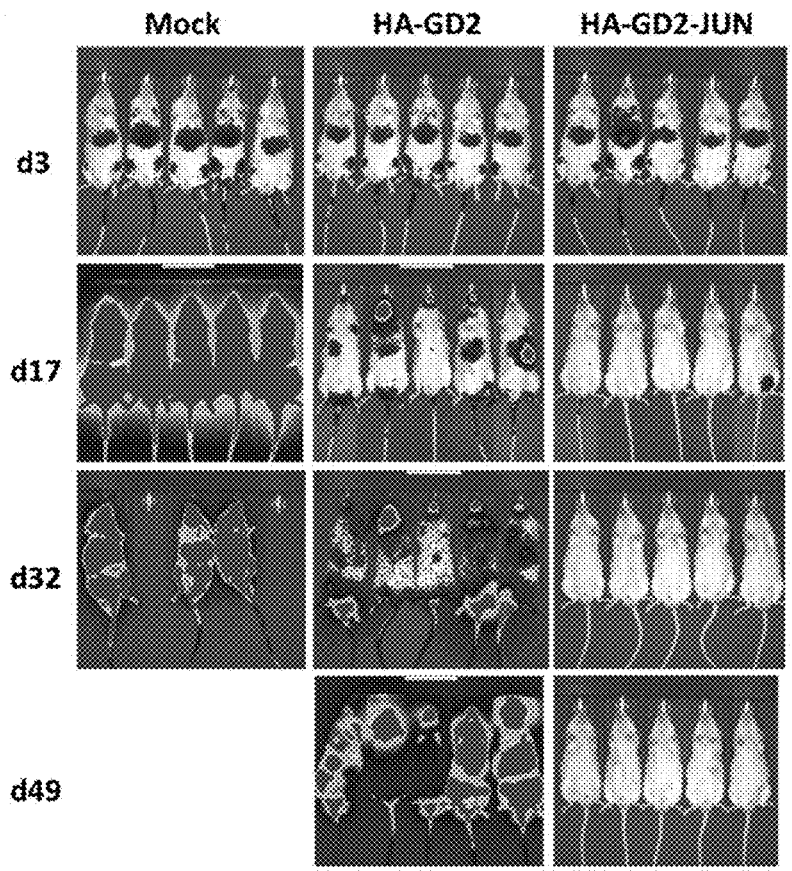
Figure 10:
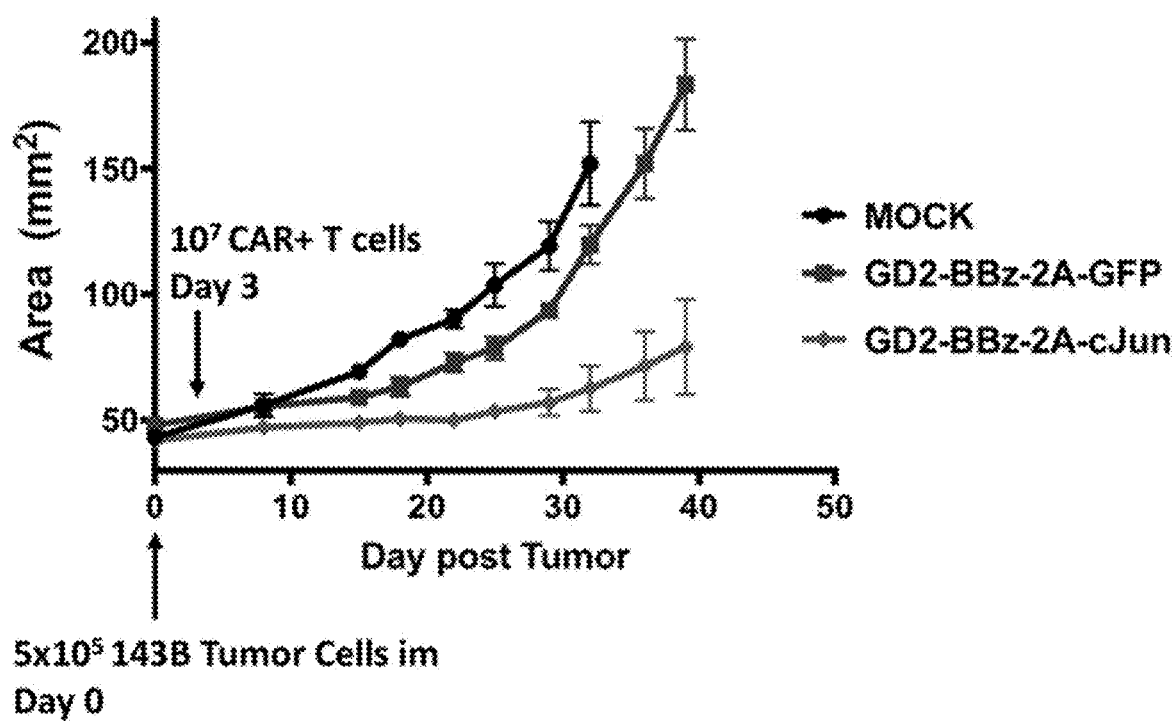
FIG. 10 shows that c-Jun-modified GD2-BBZ CAR T cells display superior in vivo activity in the aggressive 143B osteosarcoma solid tumor model. Growth of intramuscularly implanted 143B osteosarcoma tumor cells was tracked in vivo using caliper measurements following adoptive transfer of $1\times10^7$ CAR+ or Mock (untransduced) T cells. (A) Quantified tumor growth over time for n=5 mice per group.

The in vivo efficacy of c-Jun-modified CAR T cells was assessed in several different tumor models. c-Jun-expressing HA-GD2 exhausted CAR T cells displayed superior, curative in vivo activity compared to unmodified HA-GD2 CAR T cells in a Nalm6 leukemia model engineered to express GD2 (N6-GD2) (See FIG. 9). c-Jun-modified GD2-BBZ CAR T cells display superior in vivo activity in an aggressive osteosarcoma solid tumor model (See FIG. 10). Finally, CD19 CAR T cells with c-Jun expression show enhanced in vivo activity against low antigen density Nalm6-Clone F (See FIG. 11).

Example 9

Expression of the HA-28z CAR in Human T Cells Rapidly Induces Hallmark Features of T Cell Exhaustion GD2-28z CAR is an exhausted phenotype in human T cells following expression of a CAR incorporating the GD2-specific 14g2a scFv, TCR zeta and a CD28 endodomain, as a result of tonic signaling mediated via antigen-independent aggregation (Ref 9; herein incorporated by reference in its entirety). Experiments conducted during development of embodiments herein demonstrate that expression of a CAR containing the 14g2a scFv bearing the E101K point mutation, which renders a higher affinity (HA) interaction with GD219 (HA-28z CAR), similarly induces exhaustion in human T cells albeit with a more severe phenotype (FIGS. 12 and 18a-c). In contrast to CD19-28z CART cells, HA-28z CAR T cells displayed profound phenotypic and functional hallmarks of exhaustion, including reduced expansion in culture (FIG. 12a), increased surface expression of the inhibitory receptors PD-1, TIM-3, LAG-3, and CD39 (FIGS. 12b and 18d), exaggerated effector differentiation and poor memory formation (FIGS. 12c and 18e), and diminished IFN-g and markedly decreased IL-2 production when stimulated with CD19+GD2+ Nalm6 leukemia (FIG. 12d).

Figure 18A:
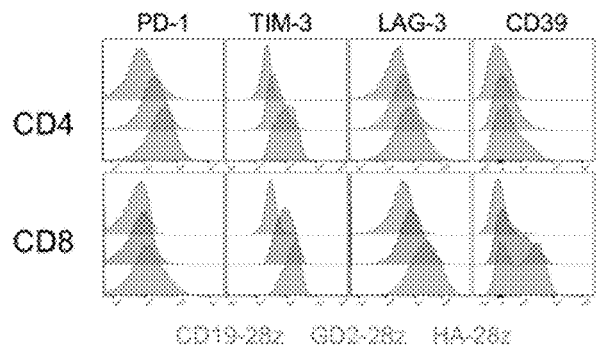
Figure 18B:
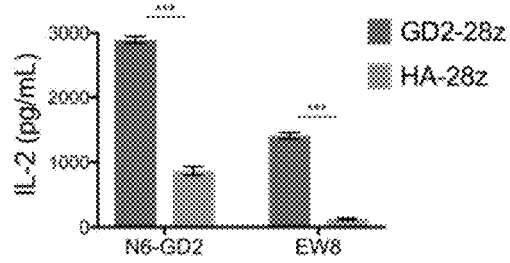
Figure 18C:
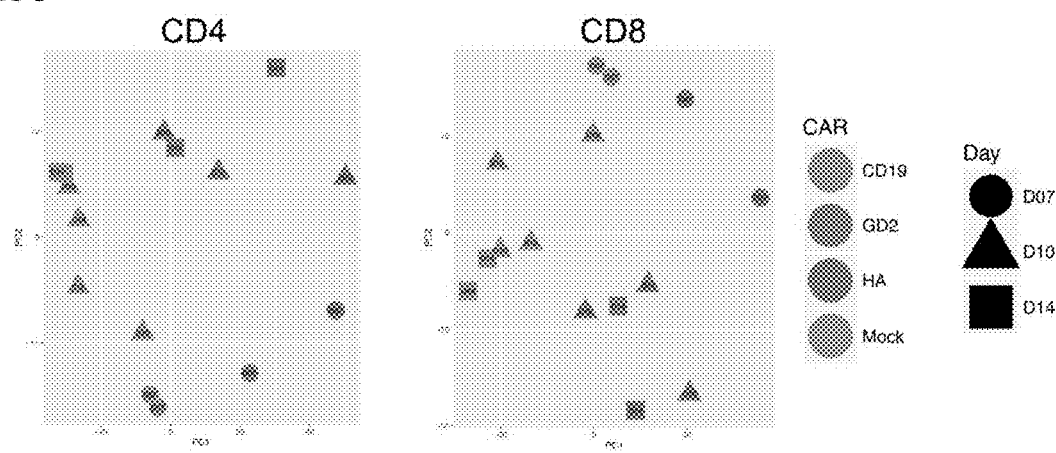
Figure 18D:
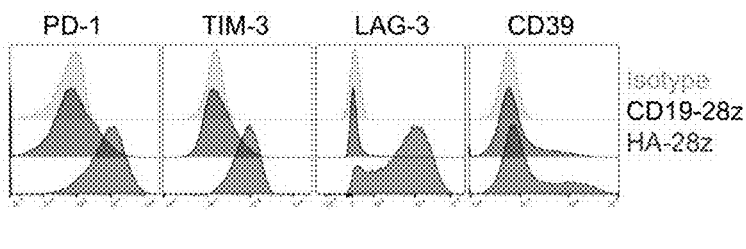
Figure 18E:
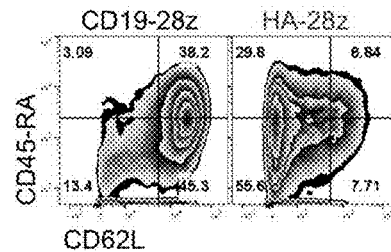
Figure 18F:
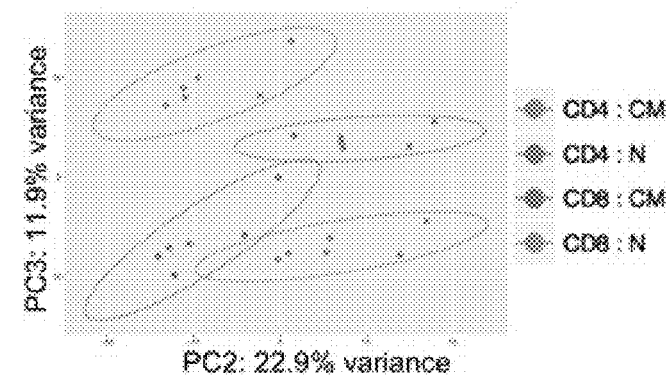

To better elucidate the molecular underpinnings of T cell exhaustion in this system, the transcriptome of HA-28z was compared to CD19-28z CAR T cells. Purified naïve (N) and central memory (CM) T cells were transduced with HA or CD19-28z CAR then isolated RNA on days 7, 10, and 14 of culture. Sorting pre-selected subsets allowed assessing of the impact of T cell differentiation state and the distinction between CD4 and CD8 exhaustion in the development of T cell exhaustion in this model. Principle component analysis (PCA) across all 24 samples revealed that the strongest driver of variance was the presence of the HA- vs CD19-28z CAR (PC1, 39.3% variance, FIG. 12e), consistent with a model wherein tonic signaling in HA-28z CAR T cells drives exhaustion in all T cell subsets studied. Distinctions were, however, observed based upon the starting differentiation state, since N vs CM was reflected in PC2 (22.88% variance) (FIG. 18f) and between CD4 vs CD8 populations, which drove PC3 (11.9% variance) (FIGS. 12e and 18f).

Figure 18G:
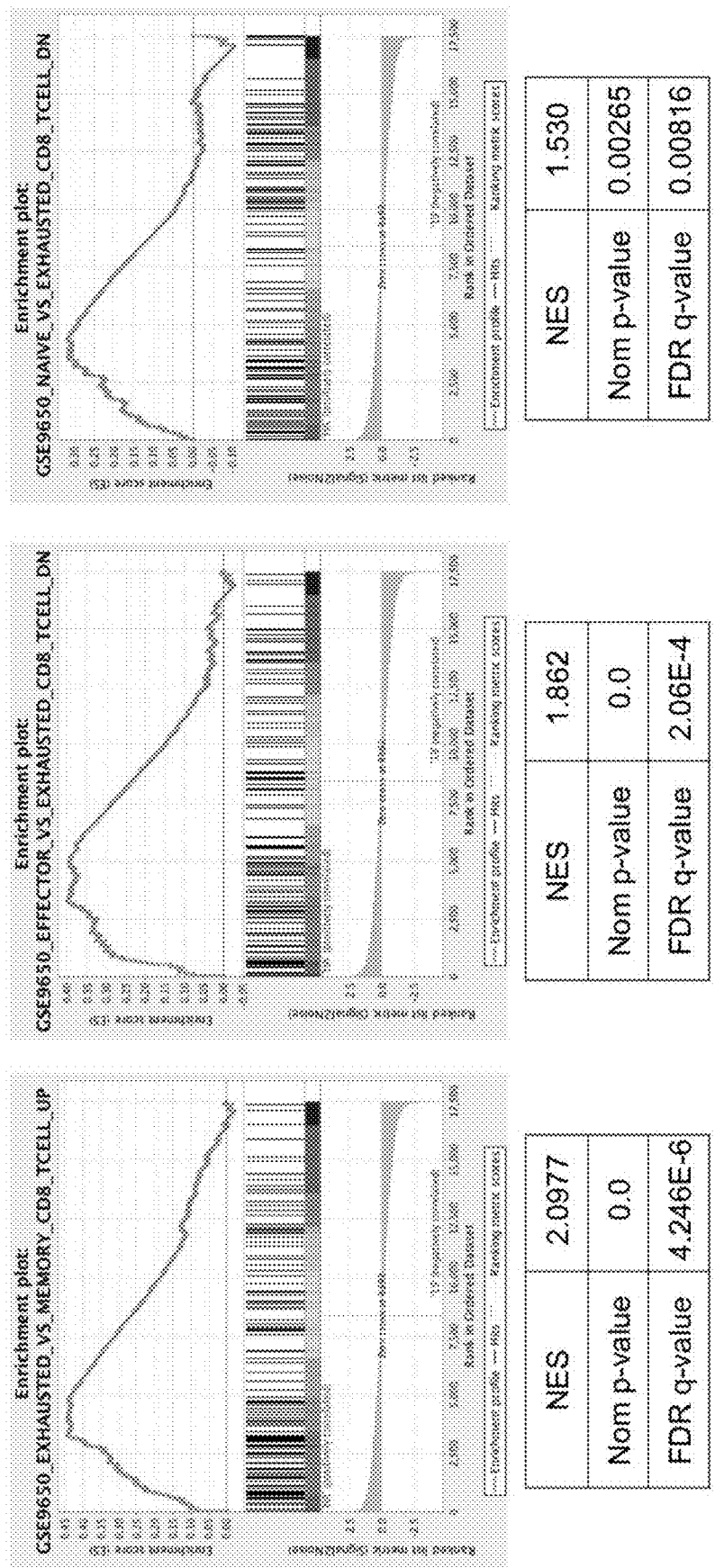

Among the top 200 genes driving PC1 (most differentially expressed in HA- vs CD19-28z CART cells across all subsets) (FIG. 12f) were genes associated with activation (IFNG, GZMB, IL2RA), inhibitory receptors (LAG3, CTLA4) and some inflammatory chemokines/cytokines (CXCL8, IL13, IL1A), whereas genes downregulated in HA-28z CAR T cells include genes associated with naïve and memory T cells (IL7R, TCF7, LEF1, and KLF2). Using GSEA, it was demonstrated that genes upregulated in day 10 HA-28z vs CD19-28z CART cells overlap with exhaustion-associated gene sets previously described in chronic LCMV mouse models13 (FIG. 18g). Although the degree of exhaustion in GD2-28z CAR T cells is less profound, differential gene expression analysis of single cell GD2-28z vs CD19-28z CART cells revealed a similar gene expression profile (FIG. 19). Together, these data credential HA-28z and GD2-28z expressing T cells as models for the study of human T cell exhaustion.

Figure 12I:
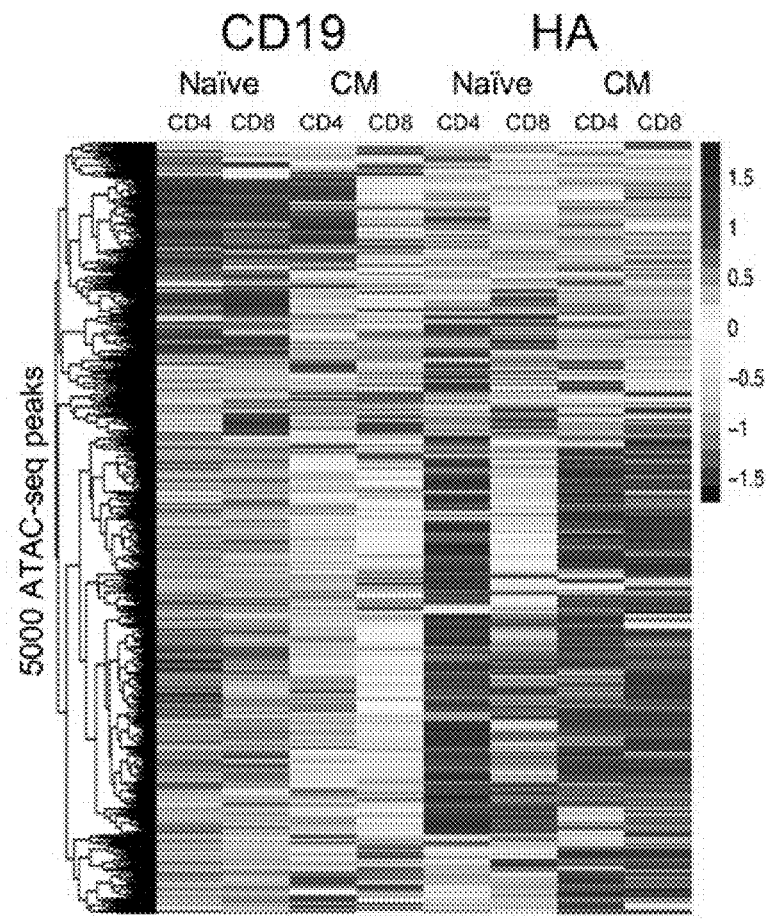
Figure 12J:
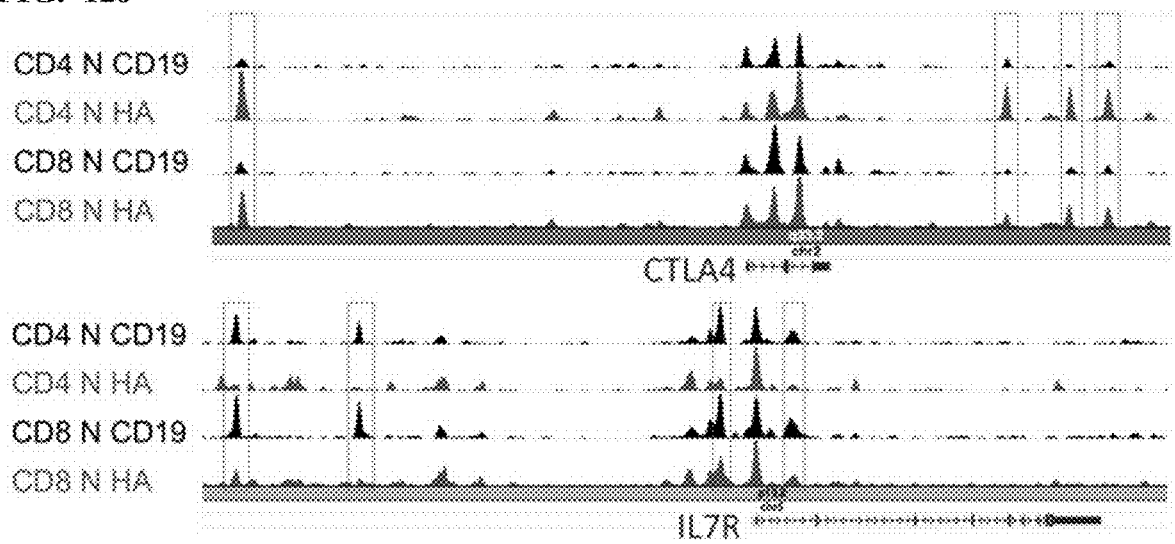
Figure 21A:
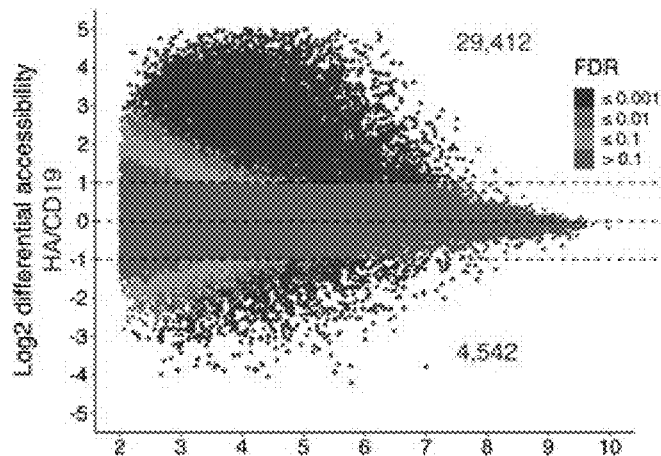
Figure 21B:
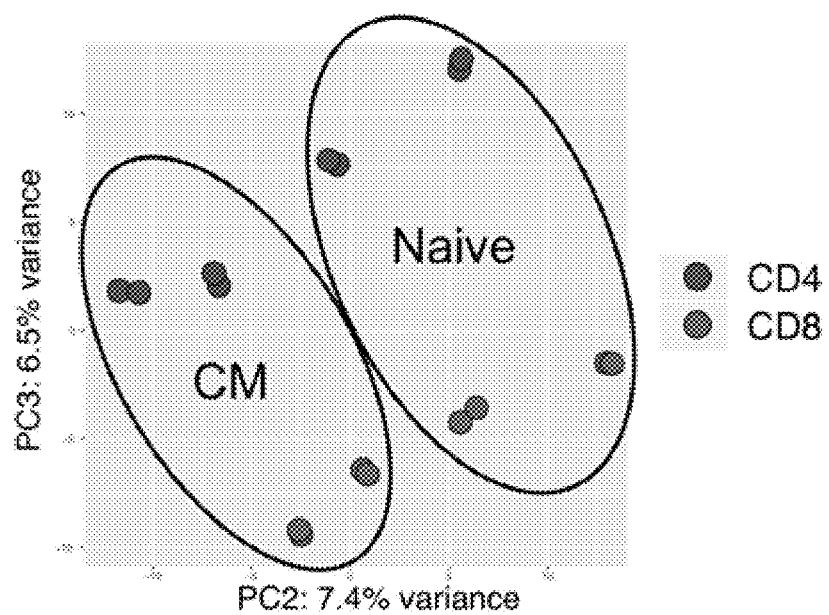

T cell exhaustion is associated with changes in chromatin accessibility in mouse models and human patients with chronic viral infections and cancer (Refs. 12,17; herein incorporated by reference in their entireties). Chromatin accessibility analyses using ATAC-seq20 (FIG. 20) of N or CM derived CD4+ and CD8+ HA-28z vs CD19-28z CAR T cells demonstrated significant changes in the epigenetic signature on day 10 of culture (FIG. 12g) with CD8+ HA-28z CAR T cells displaying >20,000 unique chromatin accessible regions (peaks) compared to <3,000 unique peaks in CD8+ CD19-28z CART cells (FDR<0.1 and log 2FC>1). These patterns of changes in exhaustion-induced chromatin accessibility were similar in CD4+ T cells (FIG. 21a). Similar to the transcriptomic analysis, PCA revealed HA-vs. CD19-CAR as the strongest driver of differential chromatin states (PC1 variance 79.6%, FIG. 12h), with weaker but significant differences observed between N vs CM cells (PC2 variance 7.4%), and between the CD4 vs CD8 subsets (PC3 variance 6.5%) (FIG. 21b). Clustering the top 5000 differentially accessible regions (peaks) revealed globally similar chromatin accessibility in HA-28z CAR T cells regardless of starting subset (FIG. 12i). HA-28z CAR T cells demonstrated increased chromatin accessibility in regulatory sites near exhaustion-associated genes such as CTLA4, and decreased accessibility in regulatory sites near memory associated genes such as IL7R (FIG. 12j).

Example 10

Figure 13A:
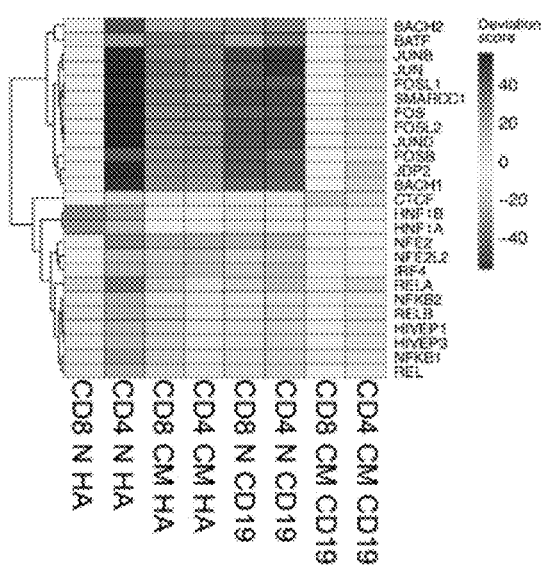
Figure 13B:
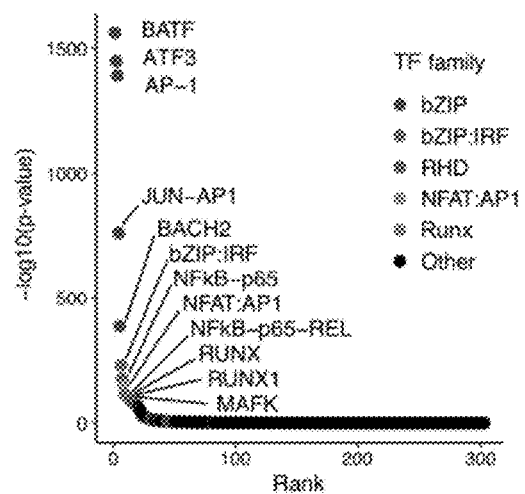
Figure 21C:
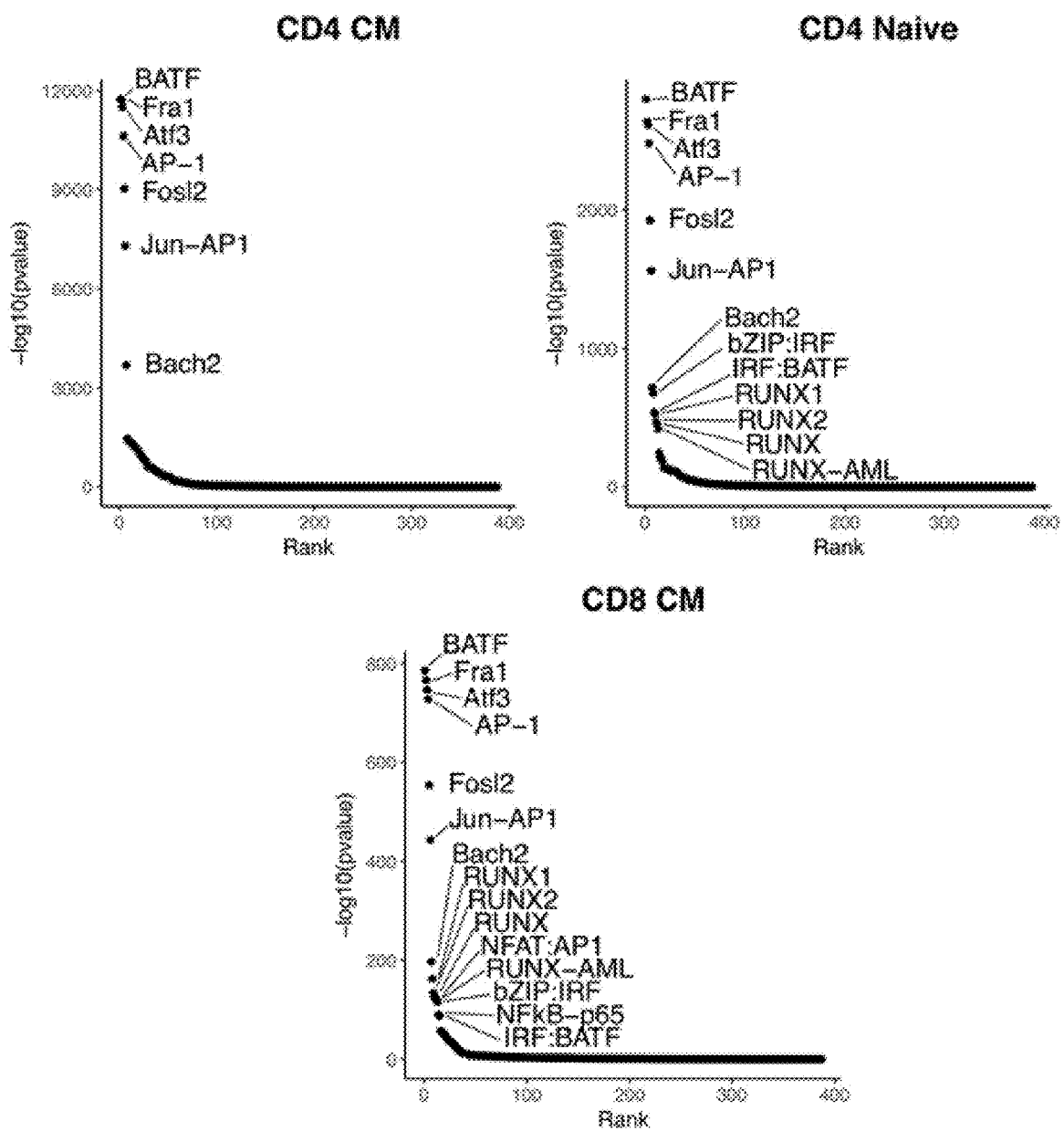

Epigenetic and Transcriptional Analyses Reveal a Strong AP-1 Signature in Exhausted CAR T Cells To identify transcriptional programs predicted to be dysregulated by the epigenetic changes induced in exhausted T cells, transcription factor (TF) motif deviation was compared between exhausted and healthy CAR T cell open chromatin. Using ChromVAR analysis (Ref 21; herein incorporated by reference in its entirety), the 25 most differential motifs across all 8 samples were identified, and it was found that many of these belong to the AP-1 (bZIP) family (FIG. 13a). Similarly, TF motif enrichment analysis revealed AP-1/bZIP and bZIP/IRF binding motifs as among the most significantly enriched in exhausted CAR T cells (FIG. 13b and FIG. 21c).

Figure 21D:
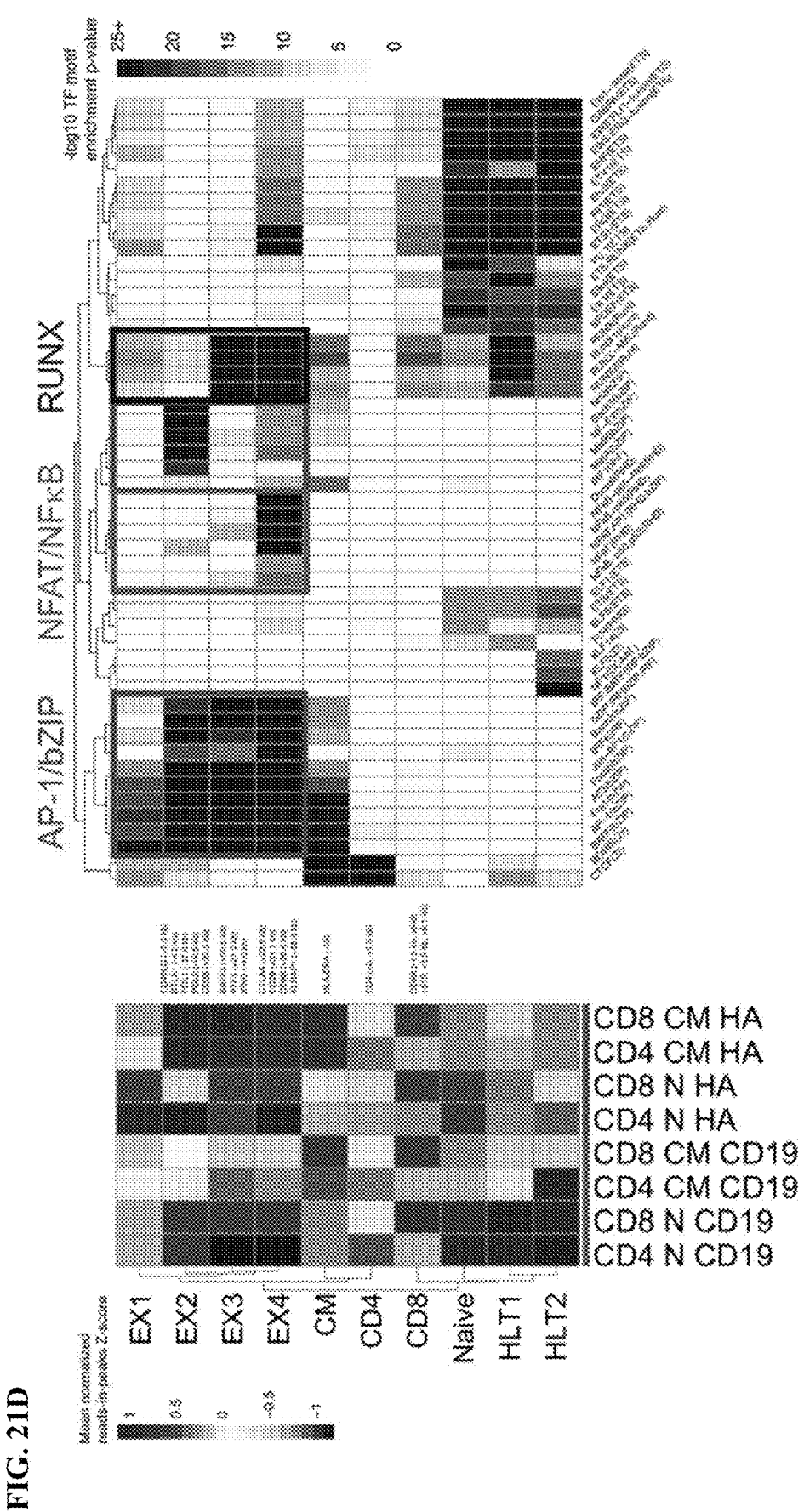

Clustering differentially accessible peaks by shared TF motif enrichment identified 4 clusters associated with exhausted HA-28z CART cells (FIG. 21d, EX1-EX4). Exhaustion-associated clusters contained peaks in the vicinity of genes like BTLA, CD39, IFNG, and CTLA4, suggesting common TF regulation of exhaustion-associated genes. All 4 exhaustion-associated clusters displayed strong enrichment for AP-1 and AP-1-related family TFs, implicating widespread AP-1 TF modulation of exhaustion-associated gene regulation. Strong enrichment for NFkB, NFAT, and RUNX TF family motifs was also observed in some of the exhaustion clusters, indicating that a subset of exhaustion-related genes may be regulated by these transcriptional programs and reproduce epigenetic signatures of exhaustion observed in other models (Refs. 12,17,22; herein incorporated by reference in their entireties). The clusters associated with healthy CD19-28z CART cells (HLT1-2) showed a similar profile to a cluster strongly associated with Naïve starting subset. This observation is consistent with the idea that healthy CAR T cells maintain an epigenetic signature more closely resembling naïve-derived T cells, a subset associated with increased persistence and efficacy in adoptive T cell therapy (Ref 23; herein incorporated by reference in its entirety), whereas chronic antigen stimulation results in broad divergent epigenetic reprogramming.

Figure 13C:
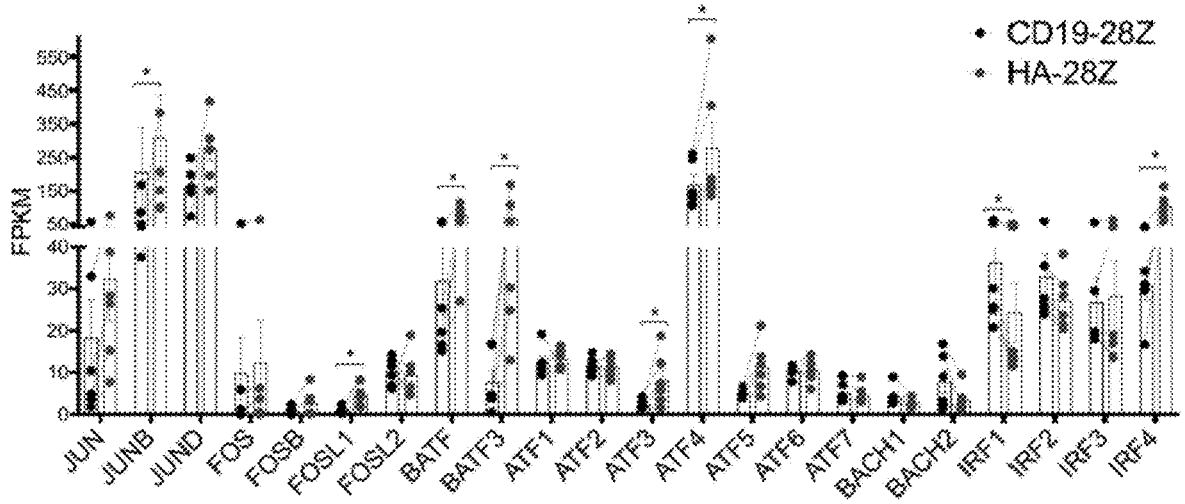
Figure 13D:
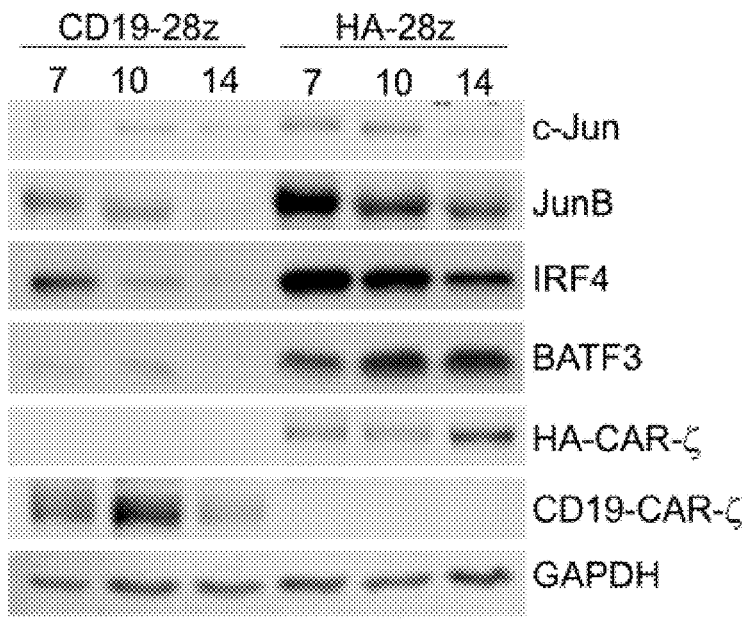
Figure 13E:
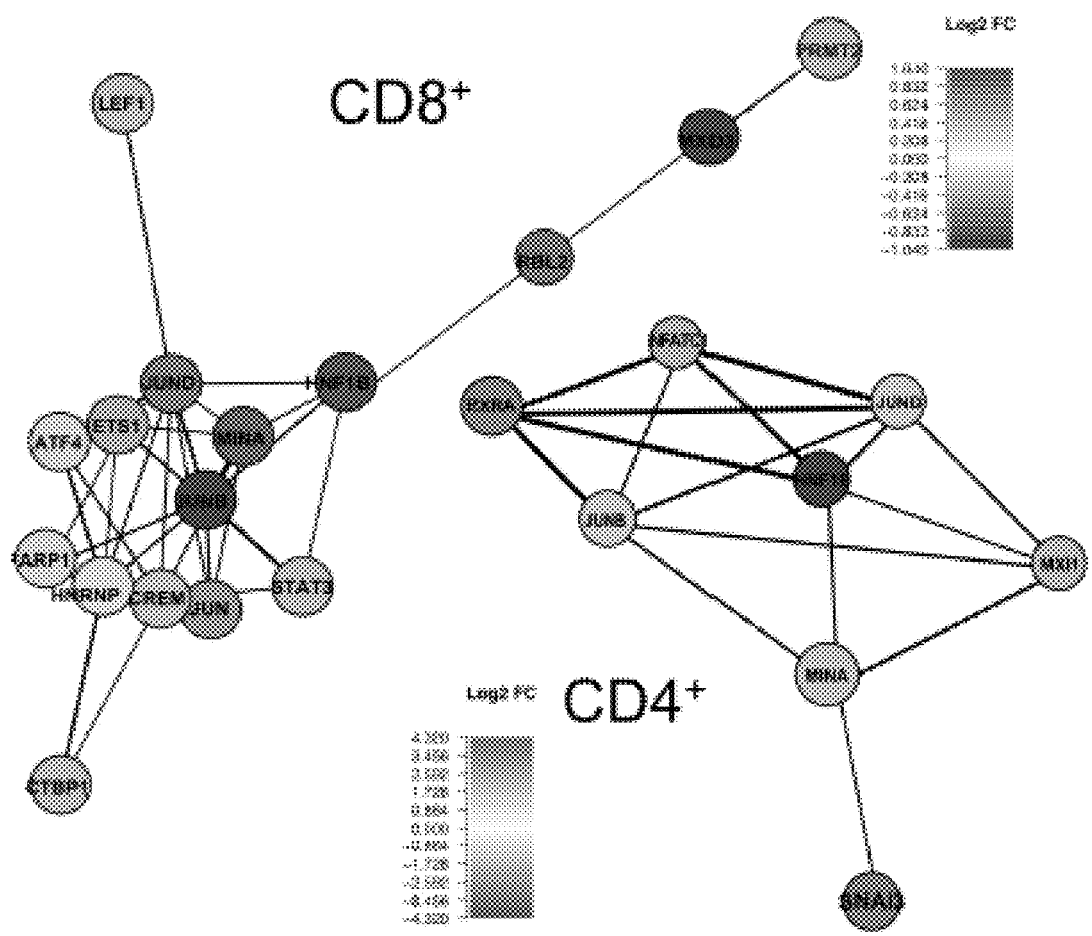

AP-1 related TFs coordinate to form a diverse set of homo and heterodimers through interactions in the common bZIP domain and can dimerize with IRF transcription factors (Refs. 14,24; herein incorporated by reference in their entireties). AP-1 factor complexes compete for binding at DNA elements containing core TGA-G/C-TCA consensus motifs. Activating complexes such as those comprising the classically described AP-1 heterodimer c-Fos and c-Jun drive IL-2 transcription. Conversely, other AP-1 and IRF family members can directly antagonize c-Jun activity and/or drive immunoregulatory gene expression in T cells (Refs. 14,24-29; herein incorporated by reference in their entireties). To assess whether the changes in AP-1 binding chromatin accessibility were associated with increased availability of activating and inhibitory bZIP and IRF TFs, experiments were conducted during development of embodiments herein to compare transcript levels of bZIP and IRF family members using RNA-seq in exhausted HA-28z vs. healthy CD19-28z CAR T cells. Paired RNA-seq analysis across 3 different donors revealed a consistent pattern of bZIP and IRF family member overexpression, which was most significant for JUNB, FOSL1, BATF, BATF3, ATF3, ATF4 and IRF4 (FIG. 13c and FIG. 22a). Western blot analysis confirmed sustained protein overexpression of JunB, IRF4, and BATF3 in HA- vs. CD19 CART cells (FIG. 13d and FIG. 22b), with the immunoregulatory BATF/IRF TFs showing higher levels of expression compared to c-Jun. The biological significance of increased levels of inhibitory bZIP/IRF family members was further indicated by the demonstration that western blotting of Jun immunoprecipitates (IP) revealed that several inhibitory family members are in direct complex with c-Jun and JunB in HA-28z exhausted CAR T cells (FIG. 22c). Comparison of TF profiles by single cell RNA-seq analysis of CD8+ T cells expressing CD19-28z vs. GD2-28z CAR confirmed that the bZIP family members JUN, JUNB, JUND, and ATF4 were among the most differentially expressed and broadly connected in exhausted GD2-28z CAR T cell networks (FIG. 13e and FIG. 19).

Example 11 c-Jun Overexpression (OE) Reduces Functional Exhaustion in CAR T Cells

Based upon the evidence that exhausted CAR T cells manifest very poor IL-2 production (FIG. 12d) and preferentially overexpress bZIP and IRF transcription factors that drive immunoregulatory and exhaustion-associated programs, it was contemplated that T cell dysfunction in exhausted cells might be due to a relative deficiency in c-Jun/c-Fos heterodimers necessary to drive IL-2 transcription. HA-28z and CD19-28z CART cells were co-transduced with a bicistronic lentiviral vector to overexpress c-Jun and c-Fos. HA-28z CAR T cells engineered to overexpress AP-1 demonstrated increased IL-2 production upon antigen stimulation (FIG. 23a-c). However, using single expression vectors enhanced functionality was only observed upon c-Jun OE in HA-28z CAR T cells, whereas transduction with a c-Fos single expression vector yielded no consistent functional improvement (FIG. 23d-e).

Figure 14A:
Figure 14B:
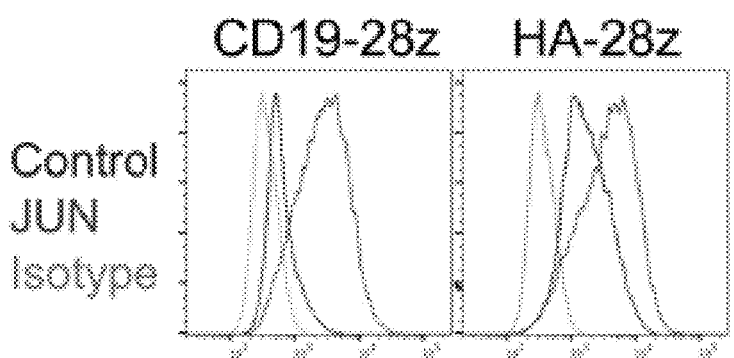
Figure 14C:
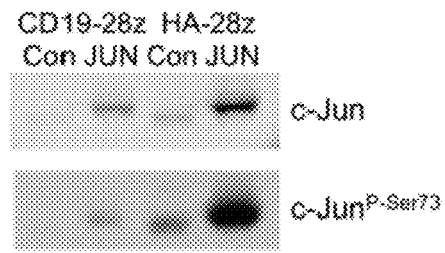
Figure 14D:
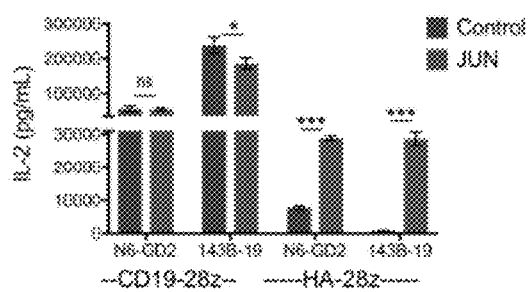
Figure 14E:
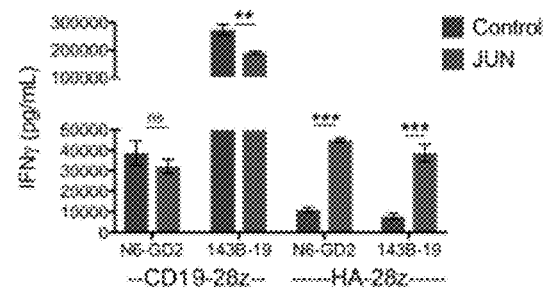
Figure 14F:
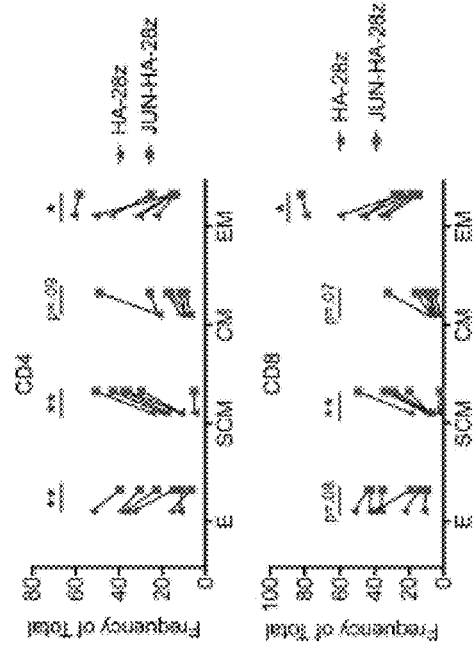
Figure 14F:
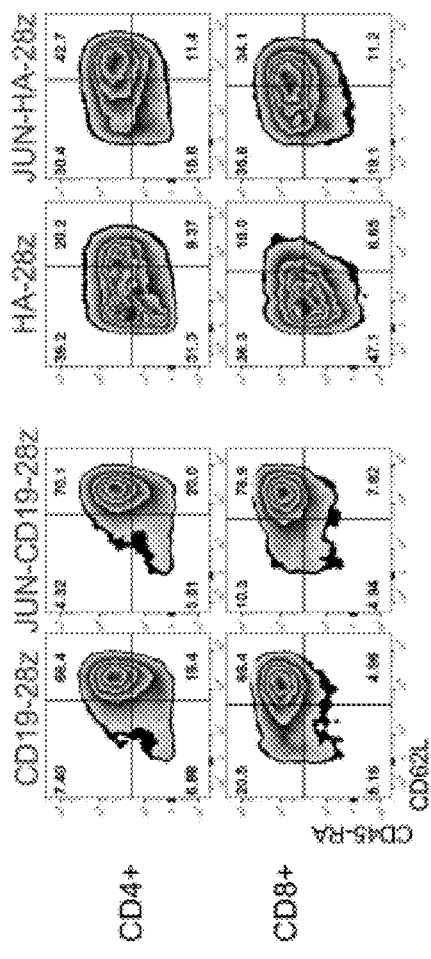

To further investigate the potential for c-Jun to enhance the function of exhausted CAR T cells and to ensure constitutive c-Jun expression in all CAR expressing T cells, bicistronic vectors were created that co-express c-Jun and CAR transgenes separated by the viral P2A skipping peptide (JUN-CARs, FIG. 14a). These expression vectors increased c-Jun expression in both CD19 and HA-28z CART cells (FIG. 14b), although c-Jun was preferentially activated (phosphorylated) in JUN-HA CAR T cells (FIG. 14c), consistent with c-Jun N-terminal phosphorylation (JNP) by JNK proteins activated downstream of the tonic TCR signaling cascade propagated via the HA-28z CAR30. Upon stimulation with GD2+ tumor cell lines, JUN-HA-28z CAR T cells demonstrated a remarkable increase in IL-2 and IFNg production compared to control HA-28z CAR T cells (FIG. 14d-e). The fold increase in cytokine production in the setting of c-Jun OE was substantially greater for JUN-HA CAR compared to JUN-CD19 CAR T cells (FIG. 24a-b). Similarly, JUN-HA CART cells demonstrated increased frequencies of SCM/CM vs E/EM subsets compared to HA-28z CAR T cells (FIG. 14f), whereas no significant difference in subset composition was observed between CD19 and JUN-CD19 CAR T cells at day 10 of culture. Together, the data are consistent with a model wherein c-Jun OE is functionally more significant in exhausted T cells, which overexpress inhibitory bZIP and IRF TFs.

Figure 14G:
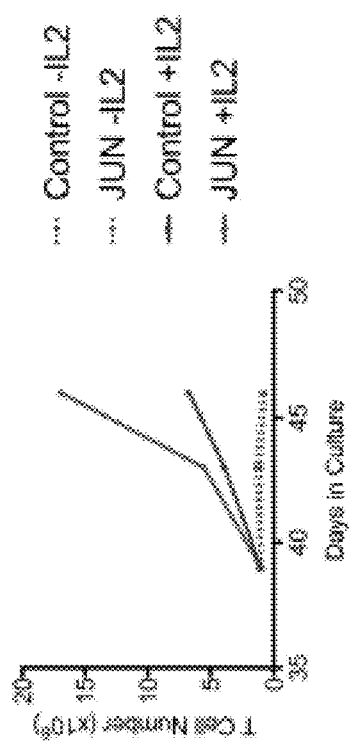
Figure 14G:
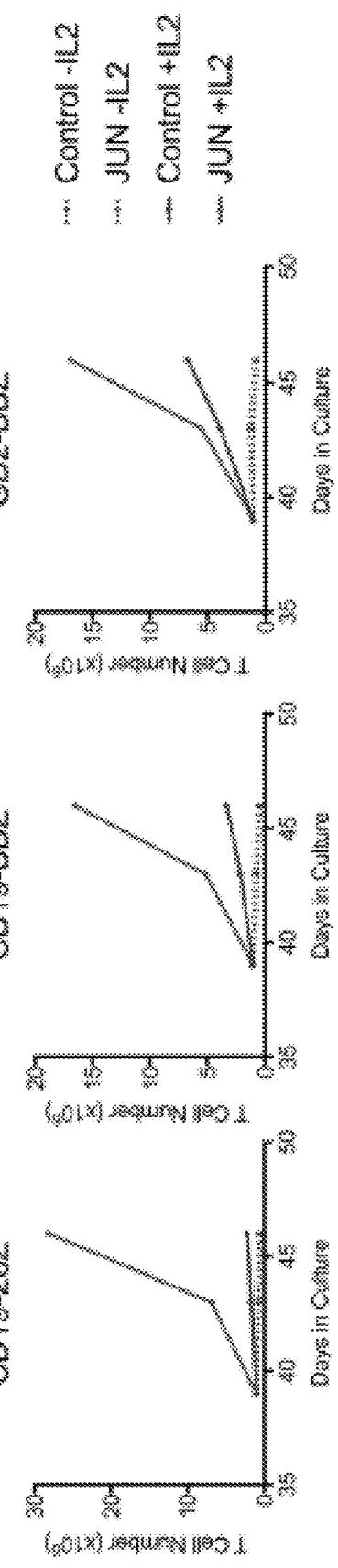

To assess whether c-Jun OE enhances long-term proliferative capacity, which is associated with antitumor effects in solid tumors (Ref 31; herein incorporated by reference in its entirety), and to test whether c-Jun OE could augment function in CAR T cells without tonic signaling (CD19-28z, CD19-BBz) or in those with lesser levels of tonic signaling (GD2-BBz), in vitro expansion of JUN-CAR T cells was measured from 3 different healthy donors over a protracted period (FIG. 24c). A consistent pattern of enhanced long-term proliferative capacity was observed in the presence of c-Jun OE, which remained IL-2-dependent, as these cells immediately ceased expansion in the absence of IL-2 (FIG. 14g). Consistent with c-Jun's capacity to induce resistance to exhaustion, late expanding CD8+ JUN-CD19-28z CAR T cells displayed diminished expression of exhaustion markers and maintained a robust subset of cells bearing a stem cell memory (SCM) phenotype (CD45RA+CD62L+) compared to control CD19-28z CART cells tested at the same timepoint (FIG. 14h-j). Homeostatic expansion of JUN-CART cells adoptively transferred into tumor-free NSG mice was evaluated. Peripheral blood T cell numbers were increased in both JUN-CD19-28z and JUN-CD19-BBz CAR T cell treated mice compared to controls 25 days post infusion (FIG. 14k), which led to accelerated GVHD in the JUN-CD19-BBz CAR T cell-treated mice. Together the data demonstrate that c-Jun OE mitigates T cell exhaustion in numerous CARs tested, including those incorporating CD28 or 4-1BB costimulatory domains, and regardless of whether exhaustion is driven by enforced long-term expansion or tonic signaling.

Example 12

Molecular Requirements for c-Jun-Mediated Rescue of CAR T Cell Exhaustion

Figure 15A:
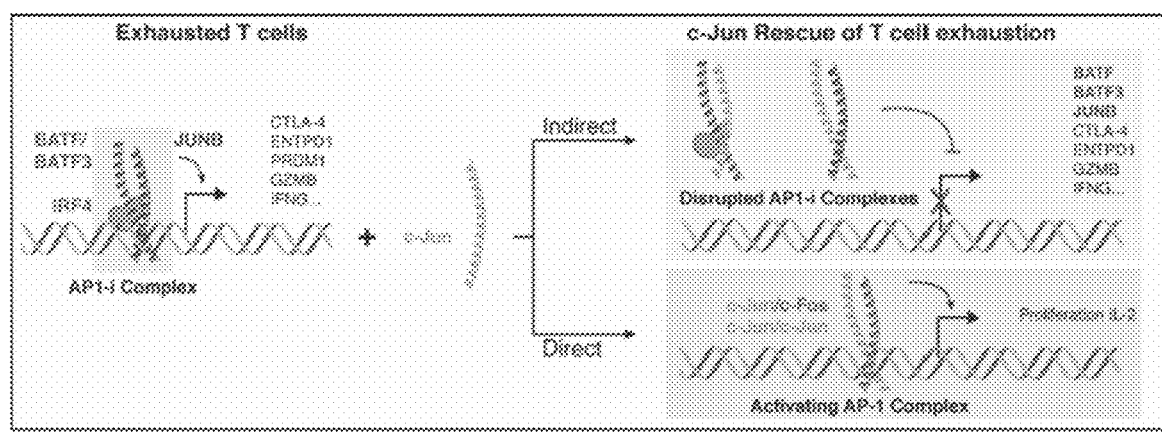
Figure 15A:
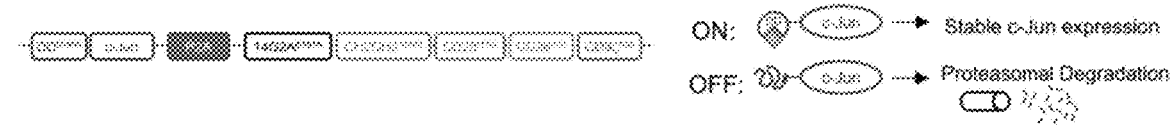
Figure 15D:
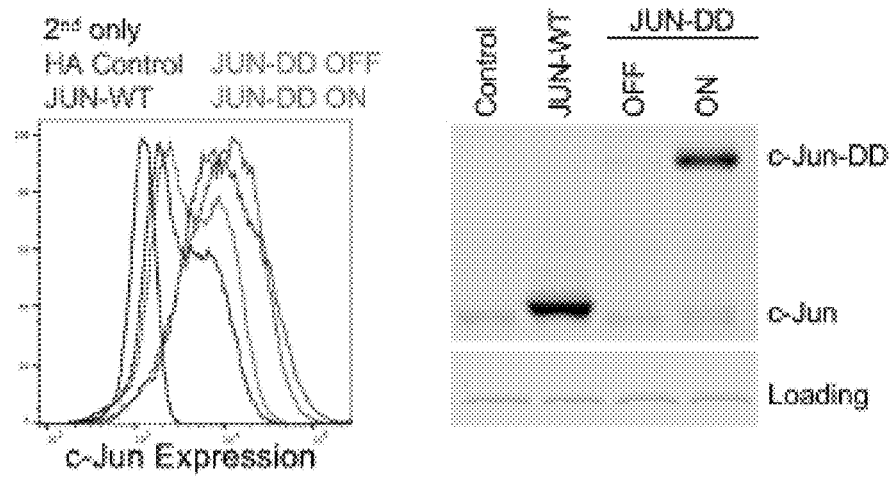
Figure 15E:
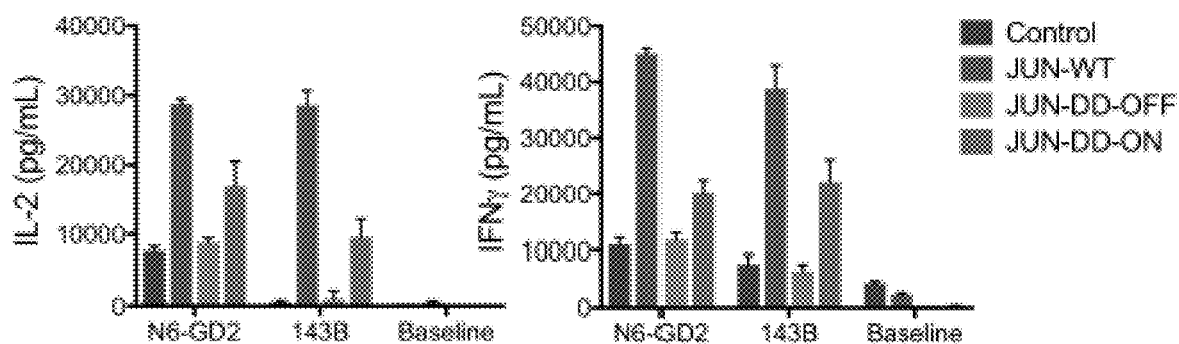
Figure 15F:
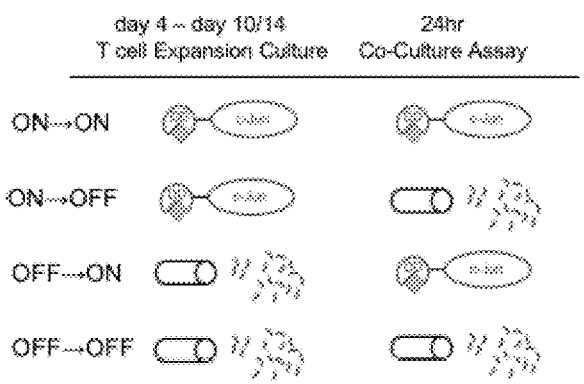
Figure 15G:
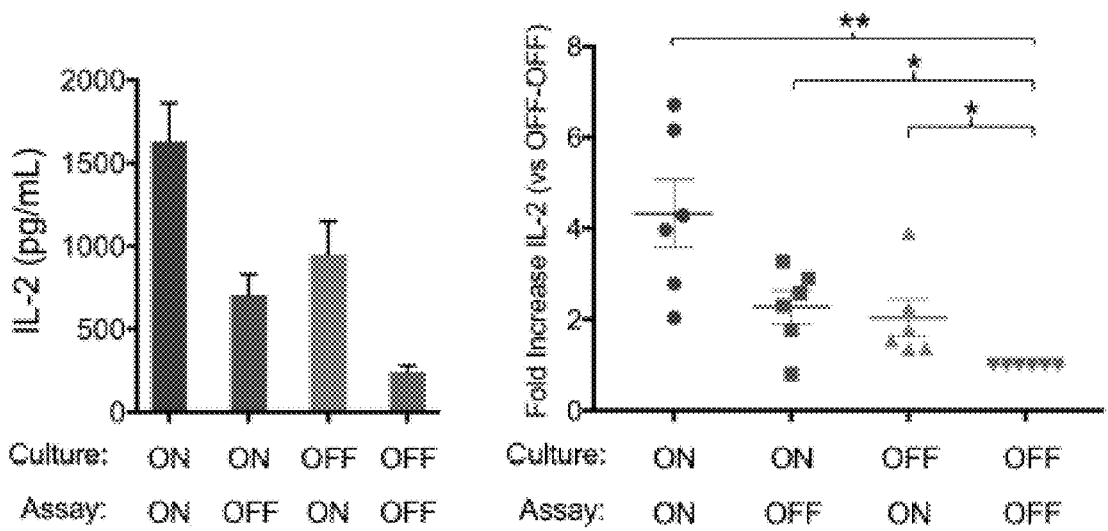
Figure 17F:
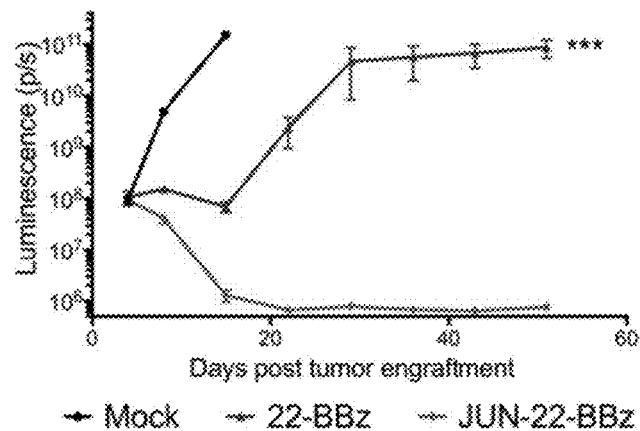
Figure 17G:
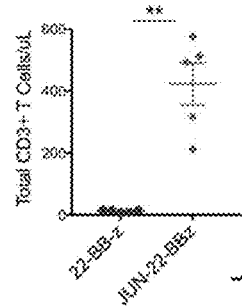
Figure 17H:
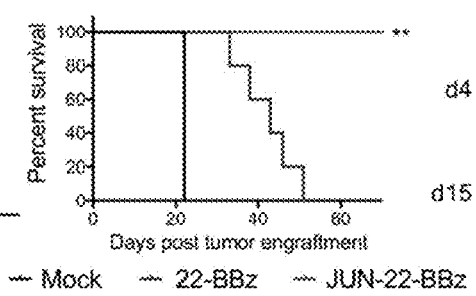
Figure 17I:
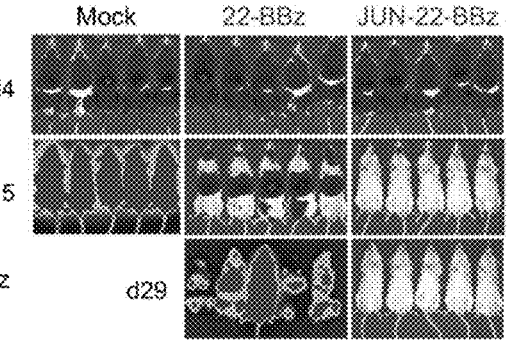

Experiments were conducted during development of embodiments herein to determine whether c-Jun OE could rescue exhausted T cells by two distinct mechanisms that are not mutually exclusive. c-Jun OE could directly enhance AP-1 mediated gene transcription by increasing availability of Fos/Jun or Jun/Jun dimers or could work indirectly by disrupting inhibitory AP-1/IRF transcriptional complexes (AP-1-i)14,24 that drive exhaustion-associated gene expression (FIG. 15a). In order to better understand the mechanisms by which c-Jun OE mitigates T cell exhaustion, the destabilization domain (DD) derived from E. coli dihydrofolate reductase (DHFR) was fused to the N-terminus of c-Jun to temporally regulate c-Jun expression (JUN-DD, FIG. 15b). The DD is stabilized in the presence of the cell permeable small molecule trimethoprim (TMP) and results in stable c-Jun expression, but in absence of TMP, the DD is destabilized, inducing proteasomal degradation of the entire fusion protein (FIG. 15c). JUN-DD CAR T cells rapidly increased c-Jun expression in the presence of TMP (½max at 6.76 hours following drug exposure), whereas JUN-DD rapidly became undetectable in the absence of TMP (t½ of 1.84 hours) (FIG. 15d and FIG. 25a-b). JUN-DD-CAR T cells mediated increases in IL-2 and IFNg production only in the presence of TMP, confirming a critical role for c-Jun levels in modulating CAR T cell functionality (FIG. 15e). It was reasoned that direct effects of c-Jun on transcription could be effected quickly, and therefore tested whether functional rescue would occur when c-Jun OE in HA-28z CAR T cells was restricted to the period of acute antigen stimulation (OFF-ON). In contrast, if c-Jun OE was necessary to compete with inhibitory AP-1 complexes (AP-1i) during induction of exhaustion, a more prolonged exposure during T cell expansion (ON-OFF) may be required (FIG. 15f). Compared to HA-28z CART cells which never experienced c-Jun OE (OFF-OFF), both conditions mediated partial rescue, however, full rescue of IL-2 function required c-Jun OE during both T cell expansion and antigen stimulation (ON-ON) (FIG. 15g). This finding is consistent with a model wherein c-Jun OE both directly enhances gene transcription during acute stimulation downstream of antigen encounter and also indirectly modulates molecular reprogramming during the development of exhaustion. Additionally, reductions in both protein and mRNA expression of JUNB and BATF/BATF3 family members were observed upon c-Jun overexpression (FIG. 25c-d) as well as reduction in the JunB/BATF complexes through IP (FIG. 25e).

The indirect model of c-Jun-mediated disruption of inhibitory AP-1 complexes would be independent of direct c-Jun transcriptional activation. To test whether direct c-Jun-mediated gene activation was necessary for the functional rescue of T cell exhaustion, a JNP-deficient c-Jun was created with alanine substitutions of Ser63 and Ser73 in the c-Jun transactivation domain to prevent phosphorylation at these sites (c-JunAA), which has been demonstrated to be important for c-Jun mediated gene transcription (Refs. 33,34; herein incorporated by reference in their entireties) (FIG. 15h-i). JUNAA-HA-28z CAR T cells demonstrated equivalent increases in IL-2 and IFNg production compared to wildtype JUN-CAR T cells (FIG. 25j). Together, this data is consistent with a model wherein c-Jun mediated rescue of exhausted does not require direct gene activation.

Example 13

JUN-CAR T Cells Mediate Enhanced Antitumor Activity In Vivo

Experiments were conducted during development of embodiments herein to determine whether JUN-CAR T cells would demonstrate enhanced activity in vivo. Nalm6-GD2+ leukemia cells were engrafted into mice and treated with control HA-28z or JUN-HA-28z CAR T cells on day 3. While HA-28z CAR T cells exhibited some anti-tumor activity, the treatment ultimately failed as all mice succumbed to disease (median survival d59). In contrast, JUN-HA-28z CAR T cells mediated complete tumor regression by day 24 and provided long term, tumor-free survival (FIG. 16a-c). To address whether c-Jun OE could enhance the functionality of CARs targeting solid tumors, the effect of JUN-CAR was evaluated using Her2 and GD2 targeting CARs incorporating the 4-1BB costimulatory domain, which has become the preferred signaling domain for imparting long-term persistence (Refs. 35-37; herein incorporated by reference in their entireties). In a protracted ex vivo killing assay of 143b osteosarcoma JUN-Her2-BBz CAR T cells manifested significantly more potent killing activity at a 1:8 effector:target (E:T) ratio, consistent with enhanced potency on a per cell basis (FIG. 16d-e). Similarly, JUN-Her2-BBz CART cells prevented tumor growth in vivo and led to dramatically improved long-term survival, which was associated with increased T cell expansion in vivo (FIG. 16f-h). Similar results were observed when comparing GD2-BBz and JUN-GD2-BBz CAR T cells against 143b osteosarcoma (FIG. 26), confirming the benefit of c-Jun OE in CAR T cells responding to solid tumors and in CAR T cells incorporating 4-1BB signaling domains.

Example 14 c-Jun Overexpression Decreases CAR T Cell Activation Threshold and Permits Recognition of Tumor Cells with Lower Antigen Density The elevated levels of inhibitory AP1 family members in exhausted CART cells raised the prospect that dysfunction in exhausted CAR T cells relates, at least in part, to a higher threshold for activation, which might be normalized by restoring the balance of activating vs inhibitory AP1 family members. To test this, cytokine production of HA-CAR vs. JUN-HA-CART cells was compared in response to serial dilutions of plate-bound 1A7, an anti-idiotype antibody that binds the 14g2a scFv, allowing for control of stimulus strength. c-Jun OE substantially enhanced maximal IL-2 and IFNg produced, and also substantially lowered the amount of 1A7 needed to induce IL-2 secretion, consistent with a reduced activation threshold in JUN-HA-CART cells (FIG. 17a-b).

Limiting target antigen expression levels on tumor cells is increasingly recognized to limit CAR functionality (Refs. 5,6,38; herein incorporated by reference in their entireties). It was recently reported CD22dim relapses in leukemia patients following initial responses to CD22 CAR therapy. Because c-Jun OE lowers the activation threshold in tonically signaling HA-28z CAR T cells, it was assessed whether JUN-CARs would recognize and kill tumor cells with lower antigen density, which may escape recognition by control CAR T cells. When JUN-CD22-BBz CAR (FIG. 17) T cells were challenged with CD22low leukemia (FIG. 17d), JUN-CAR T cells exhibited increased cytokine production in vitro (FIG. 17e) and dramatically increased in vivo anti-tumor activity (FIG. 17f-i). Control CD22-BBz CAR T cells demonstrated initial activity when given at a dose of 3×106 CAR T cells, but this treatment ultimately failed to control tumor growth (mean survival d45). In contrast, JUN-CD22-BBz CAR T cells mediated significant antitumor effects and were completely curative. Thus, c-Jun OE demonstrates significantly improved antitumor control in 4 tumor models, and is associated with improved expansion, resistance to exhaustion, and improved capacity to recognize low antigen targets.

Example 15

Truncated JUN Proteins

Figure 27A:
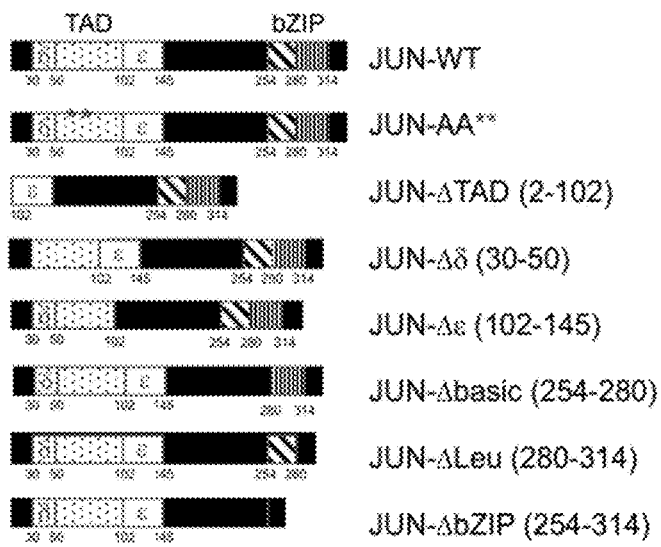
Figure 27B:
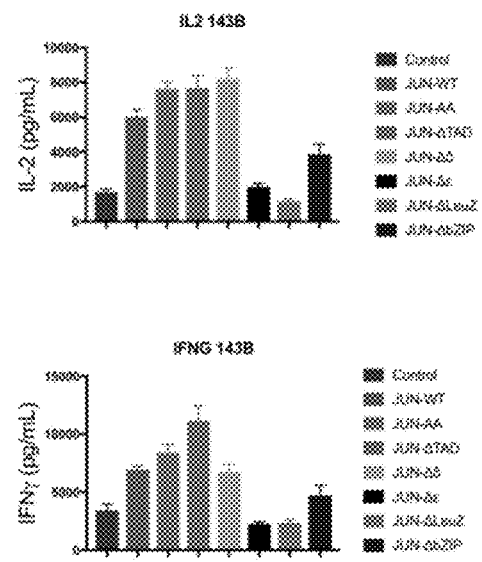
Figure 27C:
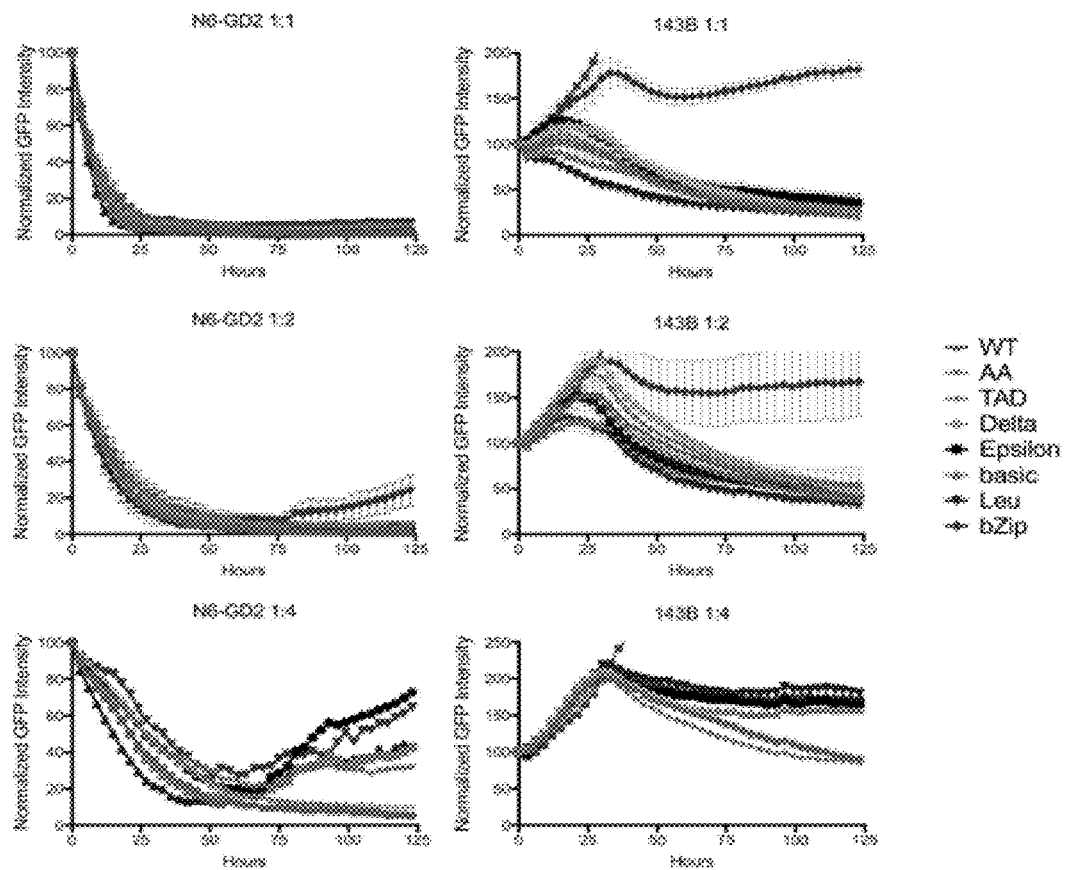
Figure 27D:
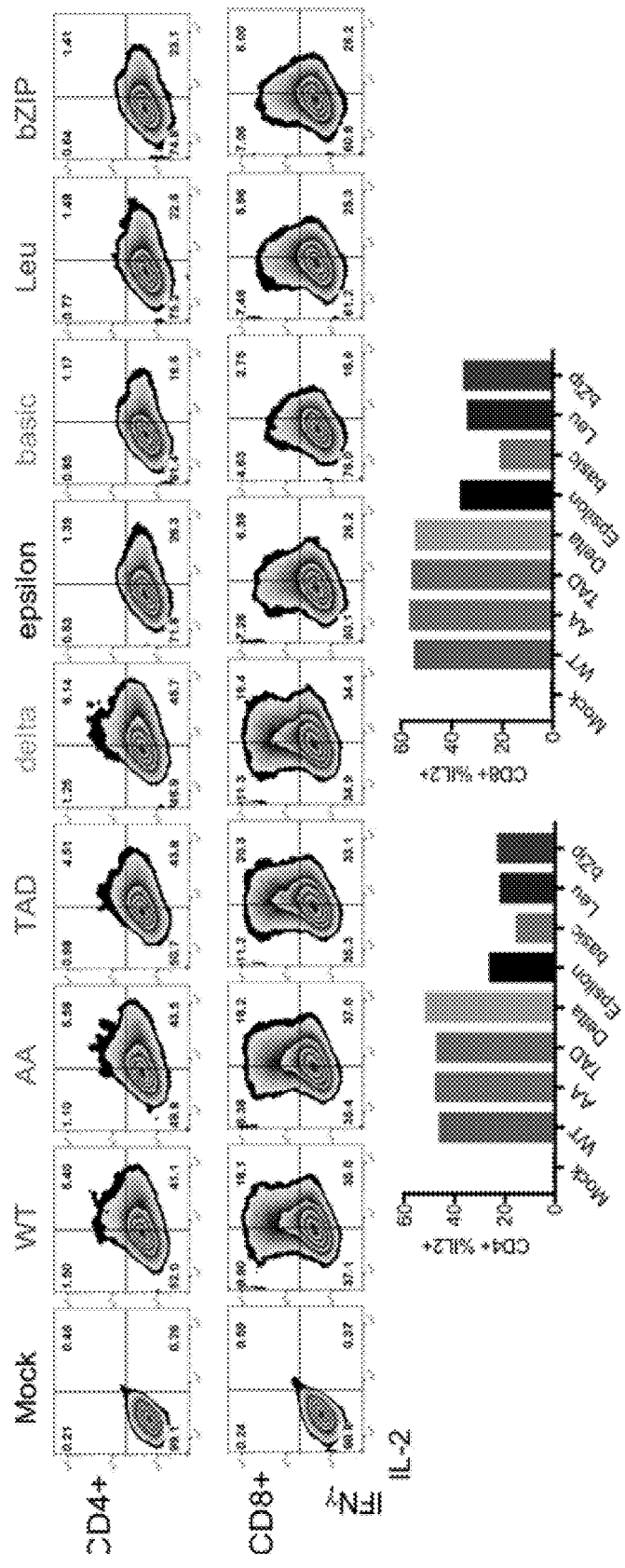
Figure 27E:
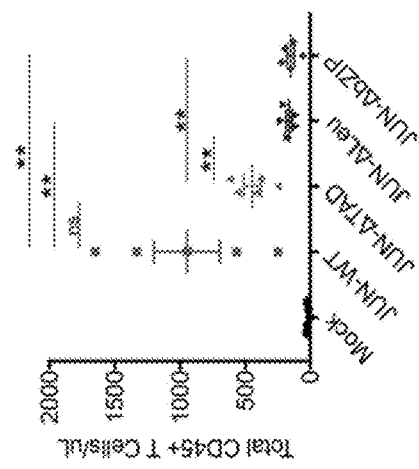

Experiments were conducted during development of embodiments herein to determine the necessary domains of JUN that are responsible for mediating the rescue of dysfunctional T cells. A series of JUN mutants were generated with various domains deleted (FIG. 27a). Mutations of JUN with N-terminal deletions and truncations (JUN-AA, JUN-Dd, and JUN-DTAD) maintain their ability to rescue the function of HA-28z exhausted CAR T cells, whereas C-terminal mutations in the epsilon and bZIP domains are non-functional rescue. The JUN-AA, JUN-Dd, and JUN-DTAD constructs retain equivalent increases in cytokine production compared to JUN-WT (FIG. 27b,d) and improve long term killing at low E:T ratios (FIG. 27c) compared to the JUN-De, JUN-Dbasic, JUN-DLeu, and JUN-DbZIP mutations. Consistent with their improved in vitro functional activity, HA-28z CAR T cells expressing JUN-WT and JUN-DTAD display increased in vivo proliferation compared to JUN-DLeu and JUN-DbZIP when infused into mice bearing N6-GD2 leukemia.

Example 16

Knockdown of IRF4 Dramatically Increases Functional Activity of Exhausted HA-28z CAR T Cells.

Experiments were conducted that optimized CRISPR gRNA for 9 different bZIP/IRF family components and tested the ability of knockdown to rescue the functional activity (cytokine secretion) of exhausted HA-28z CAR T cells. Summary data showing the results of 3-6 independent experiments with healthy donors is provided in FIG. 28. As shown in FIG. 28, while JunB and BATF3 knockout improved functional activity in some donors, IRF4 knockout dramatically improved IL-2 secretion in stimulated HA-28z CAR T cells (left and middle) in all donors tested. IRF4-KO CAR T cells even showed improved baseline secretion of IL-2 from tonic signaling.

Example 17

Transcriptional Mutant (JUN-AA) Also Rescues Functional Activity and Proliferative Capacity in CD19 CAR T Cells.

Experiments were conducted involving the creation of JUN-AA mutations in CD19 CAR T cells. JUN-AA retained the increased reactivity against low antigen density (FIG. 29A) and enhanced long term proliferation in culture (FIG. 29B). In vivo, c-Jun demonstrated improved survival of Nalm6-leukemia mice treated with low dose "stress test" dose of CD19 CAR T cells (FIG. 29C).

Example 18

The Enhanced In Vivo Function of c-Jun Modified HA-28z CAR T Cells can not be Replicated by Ex Vivo Provision of IL-2.

While IL-2 production is an excellent biomarker for an exhaustion-resistant cell, the enhanced function of JUN-CART cells can not be reproduced by IL-2 alone (FIG. 30). 250,000 IU/mouse was given IP on days 7, 9, 11, 13, and 15 post tumor engraftment. $1 \times 10^6$ CAR+ T cells were given IV on day 7. Representative of 3 independent experiments with similar findings is shown in FIG. 30.

Example 19 c-Jun Enhances Her2-BBz CAR T Cell Activity within a Suppressive Solid Tumor Microenvironment.

JUN-CAR T cells demonstrate reduced exhaustion and increased functional activity ex vivo. 143B osteosarcoma xenografts were implanted via intramuscular injection in NSG mice. After solid tumor masses were measurable (day 14 post tumor inoculation), $1 \times 10^7$ Her2-BBz Control (blue) or JUN-Her2-BBz (red) CAR T cells were given IV. FIG. 31A shows that JUN-Her2-BBz CART cells mediated regression of large, established 143B solid tumors while Her2-BBz CAR T cells did not demonstrate any control compared to Mock untransduced T cells. Two weeks post T cell injection (before tumors were completely eradicated in JUN mice), mice were euthanized and solid tumor tissue was extracted and mechanically dissociated (n=6-8 mice per group). FIG. 31B shows that solid tumor digests from JUN treated mice contained a significantly higher percentage of CD8+ T cells (frequency of total viable cells) and retained higher frequency of CAR+CD8+ T cells. FIG. 31C shows that tumor-localized CD8+ T cells showed reduced expression (and co-expression) of exhaustion-associated inhibitory receptors PD-1 and CD39 in JUN-Her2-BBz (n=6 mice per group, left) (representative flow plots on the right).

Figure 31E:
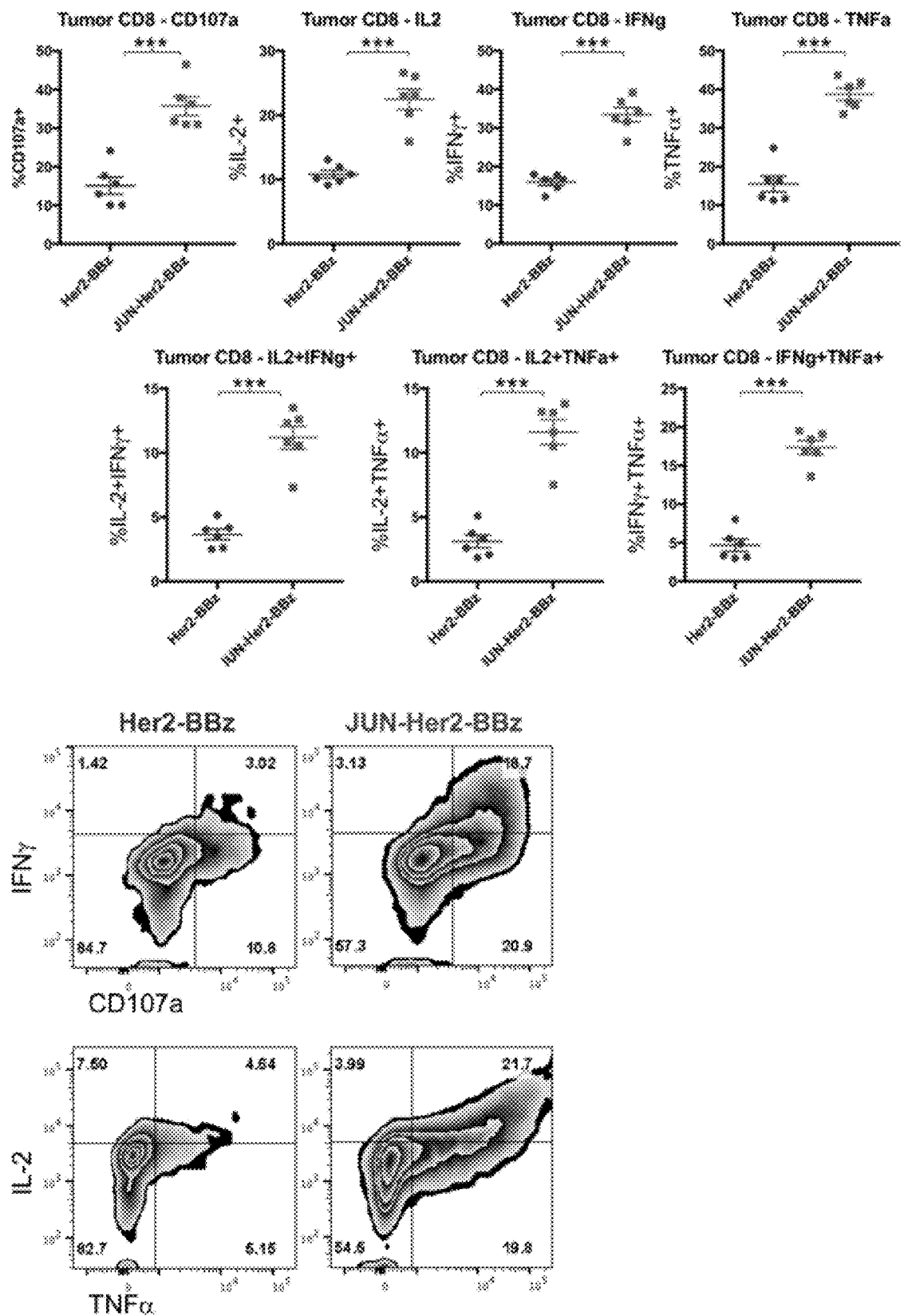

Experiments were next conducted that evaluated the functional capacity of tumor-localized CAR T cells by ex vivo restimulation with Nalm6-Her2+ target cells (FIGS. 31D and E). As shown in FIG. 31D, $5 \times 10^4$ FACS-sorted CD45+ T cells were restimulated with $5 \times 10^4$ target cells and IL-2 secretion was measured following 24 hr by ELISA. As shown in FIG. 31E, $3 \times 10^5$ single cell tumor digests were restimulated with $3 \times 10^5$ Nalm6-Her2+ isolated T cells for 6 hours in the presence of monensin and CD107a antibody. Following 6 hr, single cell production of CD107a, IL-2, IFNγ, and TNFα were assessed by intracellular cytokine staining. Ex vivo stimulated JUN-Her2-BBz CAR T cells displayed a significantly greater frequency of cells producing CD107a, IL-2, IFNγ, TNFα as well as dual-cytokine producing cells compared to Her2-BBz controls.

Example 20 c-Jun Overexpression Increases Resistance to TGFβ-Mediated Suppression of Exhausted HA-28z CAR T Cells.

Control and JUN-WT or JUN-AA modified HA-28z CAR T cells were stimulated with Nalm6-GD2 target cells in the presence or absence of 5 nM TGFβ. As shown in FIG. 32 left, IL-2 secretion was measured by ELISA, one representative donor shown. As shown in FIG. 32 right, fold decrease in IL-2 secretion in TGFβ+ conditions vs without (n=3 independent donors from 3 independent experiments).

Example 21

Transcriptional Changes in c-Jun Modified Cells are Consistent with Reduced Exhaustion and Increased Memory Formation.

Figure 33D:
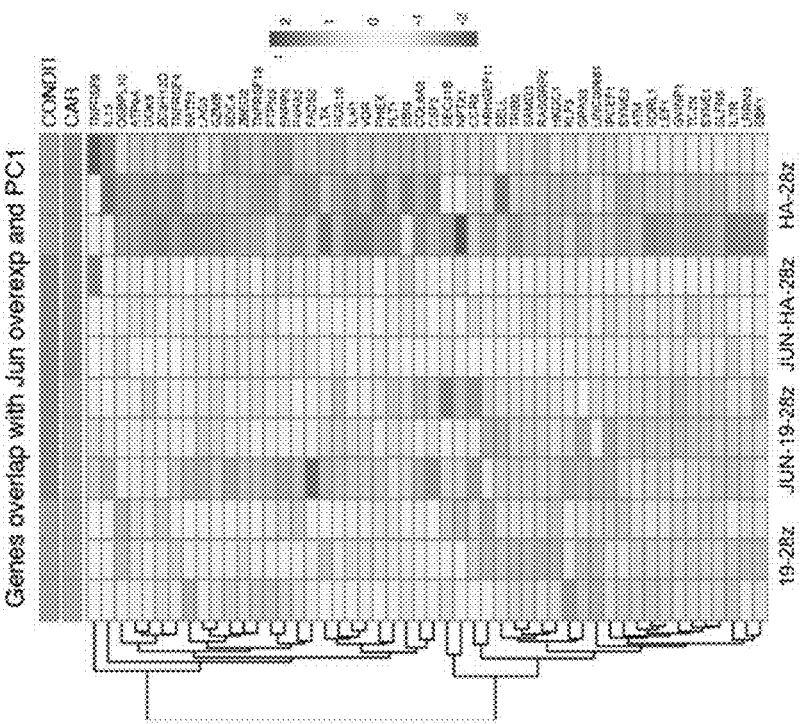
Figures 33B, 33C:
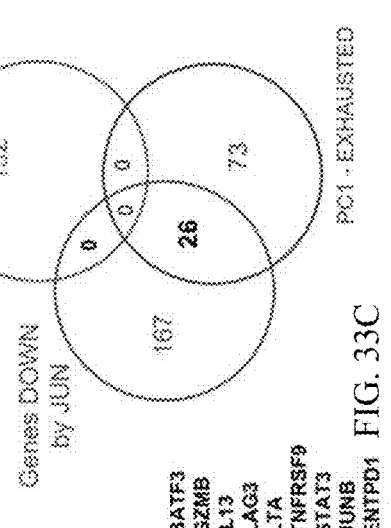
Figure 33A:
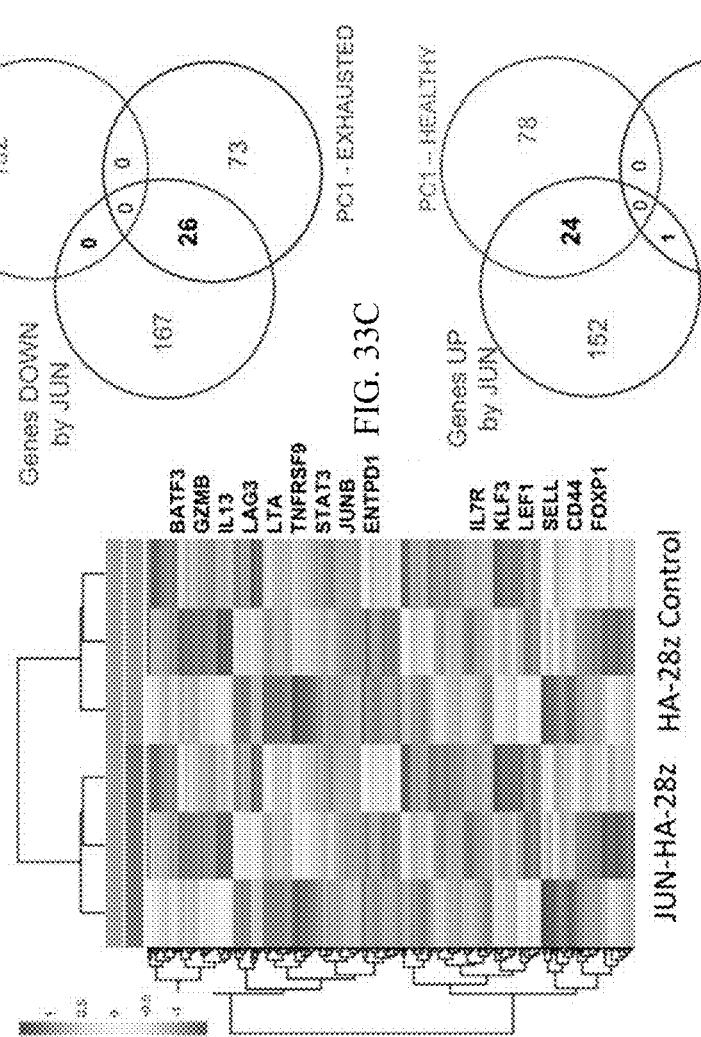

FIG. 33A shows a heat map of genes differentially regulated in exhausted HA-28z CAR upon the addition of c-Jun overexpression (193 genes downregulated by c-Jun, 176 genes upregulated by c-Jun with p(adj)<0.05. n=3 independent donors). Genes of interest are highlighted to the right. Genes downregulated in Jun cells include inhibitory receptors (LAG3, ENTPDJ) and other potentially inhibitory AP-1 family members (BATF3, JUNB) as well as other genes associated with exhaustion (IL13, GZNB, LTA, TNFRSF9). Genes upregulated by c-Jun are associated with Naïve and memory T cells (IL7R, SELL (CD62L), CD44 and transcription factors LEF1 and FOXP1).

FIG. 33B depicts Venn diagrams showing overlap of genes downregulated in c-Jun-HA-28z CART cells and genes driving exhaustion in PC1 whereas FIG. 33C shows genes upregulated in c-Jun show overlap with genes associated with healthy (CD19) CART cells (lower). Approximately 25% of the top genes driving the differences between healthy and exhausted T cells can be modulated by c-Jun overexpression, suggesting the AP-1 family may account for ~25% of the exhausted phenotype in this model.

FIG. 33D shows a heatmap showing gene expression of the 50 genes in the overlap regions from b-c in all 12 samples (n=3 donors per condition).

Table 2 provides a full list of genes changed by c-Jun.

TABLE 2

| DOWNREGULATED in JUN | UPREGULATED IN JUN |
|---|---|
| CSF2 | IGF2 |
| MYH6 | AC132217.1 |
| TNFRSF4 | LIME1 |
| THY1 | SERPINA1 |
| EDARADD | IL7R |
| IL17RB | SYNE2 |
| PDLIM4 | GLIPR1 |
| HLX | MET |
| GZMB | MMP2 |
| PTGS2 | TGM5 |
| RGS16 | TRIB2 |
| CXCL10 | ITGA2 |
| XYLT2 | TRIM9 |
| ATP8B4 | KRT79 |
| AFAP1L2 | NRIP3 |
| COL6A5 | ANXA1 |
| CXCR6 | FOXP1 |
| ATP12A | EVA1A |
| MX1 | FTH1P2 |
| OASL | PHC3 |
| BATF3 | ADIRF-AS1 |
| GZMH | TRIO |
| CCL1 | HHLA2 |
| STAG3 | ENPP6 |

TABLE 2-continued

| DOWNREGULATED in JUN | UPREGULATED IN JUN |
|---|---|
| DOK5 | CD248 |
| TNFRSF18 | SORL1 |
| PTGIR | ABLIM3 |
| PRODH | MPP7 |
| IFI44L | PLS3 |
| LAIR2 | GBP1 |
| BATF | CD44 |
| GRAMD1B | NPTX1 |
| LAMB3 | C16orf74 |
| SLC39A14 | RGL4 |
| FMOD | NRP2 |
| ADAM19 | CAV1 |
| VDR | SVIL |
| HDC | PDP1 |
| KLRC1 | TTLL7 |
| ASS1 | PPP1R14C |
| UNQ6494 | SLC43A3 |
| CD300A | AMIGO3 |
| NINJ1 | NAALADL2 |
| IL13 | PDLIM1 |
| IL4I1 | IGLL1 |
| FAM131C | ARHGEF11 |
| HLA-DRB5 | FAM78B |
| STARD10 | VIM |
| RORC | MAST4 |
| PTPN3 | KAT2B |
| P4HA2 | PLAU |
| TNFSF10 | YPEL2 |
| NCALD | CYP4F22 |
| KLRD1 | NTSR1 |
| CDC42EP1 | CLEC2B |
| PHEX | CDCP1 |
| COL6A3 | RNASE4 |
| HLA-DQB2 | IGF2-AS |
| TNFRSF9 | RBPMS |
| SGPP2 | MYRF |
| G0S2 | PRKACB |
| OAS3 | TNS1 |
| APBB2 | DNMBP |
| CHDH | RAB31 |
| EHBP1L1 | LRRN3 |
| DHRS9 | ALOX5 |
| TSKU | SBK1 |
| CD276 | NINL |
| ZBED2 | RASGRP2 |
| SYNGR2 | LINC00861 |
| DUSP5 | SAMD3 |
| PSD | SLC35F3 |
| HLA-DRB6 | WDFY1 |
| FURIN | FAM110C |
| PLPP1 | ANTXR2 |
| SHROOM1 | KLF3 |
| TMCC2 | OGFRL1 |
| BCL2L1 | C1QTNF3-AMACR |
| ENTPD1 | CHRM3-AS2 |
| NFKBIA | PTPN14 |
| USP18 | CAMSAP2 |
| TP63 | CITED4 |
| ADGRD1 | NDRG1 |
| ENPP2 | AC104958.2 |
| KCNN4 | ZNF69 |
| PCGF2 | MMP25-AS1 |
| CYFIP1 | ARHGEF3 |
| HLA-DQA1 | CREB5 |
| FLT1 | C1orf21 |
| NFKB2 | PITPNM2 |
| GGT1 | SOS1 |
| PIK3AP1 | SNTB1 |
| IGFLR1 | ATM |
| CCL22 | IL1R1 |
| BHLHE40 | ZNF286B |
| CTNNA1 | KIAA1217 |
| TNS3 | CEACAM1 |
| CRTAM | FAM174B |
| MAPK11 | KLF6 |
| IMPDH1P10 | S100A10 |
| CTTN | USP53 |
| FADS2 | CAPN2 |
| SERF1B | KIR3DX1 |
| SDC4 | FAM129A |
| PRF1 | AC022400.3 |
| ARHGAP10 | MIR4435-2HG |
| PDE1B | SMIM11A |
| LAG3 | CDKN2A |
| DHCR24 | TNFSF13B |
| LTA | ABLIM1 |
| ADGRG5 | ANKRD36C |
| MTSS1 | CA2 |
| HSPG2 | GALNT1 |
| GPR137 | SGK1 |
| POMGNT1 | SLFN5 |
| FEZ1 | GVINP1 |
| PLA2G4A | SYNE1 |
| MRPS26 | KLF7 |
| TNIP3 | LIMS2 |
| UBE2SP1 | PARP15 |
| DBNDD2 | MLC1 |
| XAF1 | MAN1A2 |
| EBI3 | SNAI1 |
| WARS | RALGPS2 |
| SQOR | IPCEF1 |
| SOX2 | SEC31B |
| FRY | SGMS1 |
| PROS1 | GPR161 |
| AGFG2 | LPL |
| MAPK8 | EPHA1-AS1 |
| STAT3 | GLI2 |
| CTHRC1 | MTAP |
| MATN4 | ARL10 |
| MAP1S | LGALS3 |
| FUT7 | HACD4 |
| HIVEP3 | LTK |
| MYL9 | GYG1 |
| PSMB3 | CD101 |
| ATP9A | SESTD1 |
| AGFG1 | CYTOR |
| ZNF282 | LEF1 |
| AP000487.1 | AP3S1 |
| PYCR1 | CCR2 |
| JUNB | AL021707.3 |
| HMGB1P17 | DIO1 |
| SETBP1 | GPA33 |
| EPOP | TC2N |
| WSB2 | ITGA4 |
| IRF7 | TMEM200A |
| WIPI1 | ARHGAP33 |
| OSBPL10 | IL11 |
| SLC7A5 | SCRN1 |
| IL21R | RARRES3 |
| SYNGR3 | SH3RF2 |
| ELOVL6 | RNPC3 |
| POU6F1 | PLAG1 |
| VCP | GDF10 |
| RELB | CALCOCO1 |
| SHF | PARD3 |
| MARS | SNX30 |
| TIMD4 | AMOT |
| SH2D2A | MAP4K5 |
| PPP1R9B | CES4A |
| HELZ2 | TRDMT1 |
| CD28 | IL6ST |
| ZC3H12D | SELL |
| AC079329.1 | KCTD12 |
| MAMLD1 | HKDC1 |
| IL23R | FOXP3 |
| PTP4A3 | RETREG1 |
| GGTA1P | PLEKHA5 |
| LINC00877 | TNRC6A |
| DOC2B | CD109 |
| SOX13 | AL121845.2 |
| PIK3R4 | AC097534.2 |
| ADM2 | PCCA |
| BST2 | MXI1 |
| PPP1R16B | |
| PSMD11 | |
| NPDC1 | |

TABLE 2-continued

| DOWNREGULATED in JUN | UPREGULATED IN JUN |
|---|---|
| STAT5A | |
| MRC2 | |
| FAM43A | |
| SLC1A5 | |
| RNF43 | |
| GPT2 | |
| IGLON5 | |
| SLAMF7 | |
| CD247 | |
| ADGRE1 | |
| HNRNPA1P21 | |
| GSTA4 | |
| GPR35 | |

Example 22

Inhibition of IRF4 Reduces T Cell Exhaustion

Control and exhausted T-cells are contacted with effective amounts (0.1-1000 μM) of the IRF4 inhibitors shown in Table 1. Samples are collected and processed for cytokine and interferon production assays. An increase in cytokine IL2 and/or interferon IFNγ production are observed in exhausted T-cells treated with the IRF4 inhibitors as compared to control T-cells.

Example 23

Inhibition of IRF8 Reduces T Cell Exhaustion

Control and exhausted T-cells are contacted with effective amounts (0.1-1000 μM) of the IRF8 inhibitors shown in Table 1. Samples are collected and processed for cytokine and interferon production assays. An increase in cytokine IL2 and/or interferon IFNγ production are observed in exhausted T-cells treated with the IRF8 inhibitors as compared to control T-cells.

Example 24

Inhibition of BATF Reduces T Cell Exhaustion

Control and exhausted T-cells are contacted with effective amounts (0.1-1000 μM) of the BATF inhibitors shown in Table 1. Samples are collected and processed for cytokine and interferon production assays. An increase in cytokine IL2 and/or interferon IFNγ production are observed in exhausted T-cells treated with the BATF inhibitors as compared to control T-cells.

Example 25

Inhibition of BATF3 Reduces T Cell Exhaustion

Control and exhausted T-cells are contacted with effective amounts (0.1-1000 μM) of the BATF3 inhibitors shown in Table 1. Samples are collected and processed for cytokine and interferon production assays. An increase in cytokine IL2 and/or interferon IFNγ production are observed in exhausted T-cells treated with the BATF3 inhibitors as compared to control T-cells.

Example 26

Inhibition of JUNB Reduces T Cell Exhaustion

Control and exhausted T-cells are contacted with effective amounts (0.1-1000 μM) of the JUNB inhibitors shown in Table 1. Samples are collected and processed for cytokine and interferon production assays. An increase in cytokine IL2 and/or interferon IFNγ production are observed in exhausted T-cells treated with the JUNB inhibitors as compared to control T-cells.

Example 27

Inhibition of IRF1 Reduces T Cell Exhaustion

Control and exhausted T-cells are contacted with effective amounts (0.1-1000 μM) of the IRF1 inhibitors shown in Table 1. Samples are collected and processed for cytokine and interferon production assays. An increase in cytokine IL2 and/or interferon IFNγ production are observed in exhausted T-cells treated with the IRF1 inhibitors as compared to control T-cells.

Example 28

Inhibition of IRF2 Reduces T Cell Exhaustion

Control and exhausted T-cells are contacted with effective amounts (0.1-1000 μM) of the IRF2 inhibitors shown in Table 1. Samples are collected and processed for cytokine and interferon production assays. An increase in cytokine IL2 and/or interferon IFNγ production are observed in exhausted T-cells treated with the IRF2 inhibitors as compared to control T-cells.

Example 29

Inhibition of IRF3 Reduces T Cell Exhaustion

Control and exhausted T-cells are contacted with effective amounts (0.1-1000 μM) of the IRF3 inhibitors shown in Table 1. Samples are collected and processed for cytokine and interferon production assays. An increase in cytokine IL2 and/or interferon IFNγ production are observed in exhausted T-cells treated with the IRF3 inhibitors as compared to control T-cells.

Example 30

Inhibition of IRF5 Reduces T Cell Exhaustion

Control and exhausted T-cells are contacted with effective amounts (0.1-1000 μM) of the IRF5 inhibitors shown in Table 1. Samples are collected and processed for cytokine and interferon production assays. An increase in cytokine IL2 and/or interferon IFNγ production are observed in exhausted T-cells treated with the IRF5 inhibitors as compared to control T-cells.

Example 31

Inhibition of IRF6 Reduces T Cell Exhaustion

Control and exhausted T-cells are contacted with effective amounts (0.1-1000 μM) of the IRF6 inhibitors shown in Table 1. Samples are collected and processed for cytokine and interferon production assays. An increase in cytokine IL2 and/or interferon IFNγ production are observed in exhausted T-cells treated with the IRF6 inhibitors as compared to control T-cells.

Example 32

Inhibition of IRF7 Reduces T Cell Exhaustion

Control and exhausted T-cells are contacted with effective amounts (0.1-1000 μM) of the IRF7 inhibitors shown in Table 1. Samples are collected and processed for cytokine and interferon production assays. An increase in cytokine IL2 and/or interferon IFNγ production are observed in exhausted T-cells treated with the IRF7 inhibitors as compared to control T-cells.

Example 33

Inhibition of IRF9 Reduces T Cell Exhaustion

Control and exhausted T-cells are contacted with effective amounts (0.1-1000 μM) of the IRF9 inhibitors shown in Table 1. Samples are collected and processed for cytokine and interferon production assays. An increase in cytokine IL2 and/or interferon IFNγ production are observed in exhausted T-cells treated with the IRF9 inhibitors as compared to control T-cells.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in relevant fields are intended to be within the scope of the following claims.

REFERENCES

The following references, some of which are cited above by number (e.g., Ref. X), are herein incorporated by reference in their entireties.

1. Maude, S. L. et al. Tisagenlecleucel in Children and Young Adults with B-Cell Lymphoblastic Leukemia. N Engl J Med 378, 439-448, doi:10.1056/NEJMoa1709866 (2018).
2. Neelapu, S. S. et al. Axicabtagene Ciloleucel CAR T-Cell Therapy in Refractory Large B-Cell Lymphoma. N Engl J Med 377, 2531-2544, doi:10.1056/NEJMoa1707447 (2017).
3. Fraietta, J. A. et al. Determinants of response and resistance to CD19 chimeric antigen receptor (CAR) T cell therapy of chronic lymphocytic leukemia. Nat Med 24, 563-571, doi:10.1038/s41591-018-0010-1 (2018).
4. June, C. H., O'Connor, R. S., Kawalekar, O. U., Ghassemi, S. & Milone, M. C. CAR T cell immunotherapy for human cancer. Science 359, 1361-1365 (2018).
5. Walker, A. J. et al. Tumor Antigen and Receptor Densities Regulate Efficacy of a Chimeric Antigen Receptor Targeting Anaplastic Lymphoma Kinase. Mol Ther 25, 2189-2201, doi:10.1016/j.ymthe.2017.06.008 (2017).
6. Fry, T. J. et al. CD22-targeted CAR T cells induce remission in B-ALL that is naive or resistant to CD19-targeted CAR immunotherapy. Nat Med 24, 20-28, (2018).
7. Hegde, M., Moll, A. J., Byrd, T. T., Louis, C. U. & Ahmed, N. Cellular immunotherapy for pediatric solid tumors. Cytotherapy 17, 3-17, (2015).
8. Long, A. H. et al. Reduction of MDSCs with All-trans Retinoic Acid Improves CAR Therapy Efficacy for Sarcomas. Cancer Immunol Res 4, 869-880, doi:10.1158/2326-6066.CIR-15-0230 (2016).
9. Long, A. H. et al. 4-1BB costimulation ameliorates T cell exhaustion induced by tonic signaling of chimeric antigen receptors. Nat Med 21, 581-590, doi:10.1038/nm.3838 (2015).
10. Eyquem, J. et al. Targeting a CAR to the TRAC locus with CRISPR/Cas9 enhances tumour rejection. Nature 543, 113-117, doi:10.1038/nature21405 (2017).
11. Fraietta, J. A. et al. Disruption of TET2 promotes the therapeutic efficacy of CD19-targeted T cells. Nature 558, 307-312, doi:10.1038/s41586-018-0178-z (2018).
12. Sen, D. R. et al. The epigenetic landscape of T cell exhaustion. Science 354, 1165-1169, doi:10.1126/science.aae0491 (2016).
13. Wherry, E. J. et al. Molecular signature of CD8+ T cell exhaustion during chronic viral infection. Immunity 27, 670-684, doi:10.1016/j.immuni.2007.09.006 (2007).
14. Man, K. et al. Transcription Factor IRF4 Promotes CD8(+) T Cell Exhaustion and Limits the Development of Memory-like T Cells during Chronic Infection. Immunity 47, 1129-1141 e1125, doi:10.1016/j.immuni.2017.11.021 (2017).
15. Wherry, E. J. & Kurachi, M. Molecular and cellular insights into T cell exhaustion. Nat Rev Immunol 15, 486-499, doi:10.1038/nri3862 (2015).
16. Bengsch, B. et al. Epigenomic-Guided Mass Cytometry Profiling Reveals Disease-Specific Features of Exhausted CD8 T Cells. Immunity 48, 1029-1045 e1025, doi:10.1016/j.immuni.2018.04.026 (2018).
17. Pauken, K. E. et al. Epigenetic stability of exhausted T cells limits durability of reinvigoration by PD-1 blockade. Science 354, 1160-1165, doi:10.1126/science.aaf2807 (2016).
18. Heczey, A. et al. CART Cells Administered in Combination with Lymphodepletion and PD-1 Inhibition to Patients with Neuroblastoma. Mol Ther 25, 2214-2224, doi:10.1016/j.ymthe.2017.05.012 (2017).
19. Horwacik, I. et al. Structural Basis of GD2 Ganglioside and Mimetic Peptide Recognition by 14G2a Antibody. Mol Cell Proteomics 14, 2577-2590, doi:10.1074/mcp.M115.052720 (2015).
20. Buenrostro, J. D., Giresi, P. G., Zaba, L. C., Chang, H. Y. & Greenleaf, W. J. Transposition of native chromatin for fast and sensitive epigenomic profiling of open chromatin, DNA-binding proteins and nucleosome position. Nat Methods 10, 1213-1218, doi:10.1038/nmeth.2688 (2013).
21. Schep, A. N., Wu, B., Buenrostro, J. D. & Greenleaf, W. J. chromVAR: inferring transcription-factor-associated accessibility from single-cell epigenomic data. Nat Methods 14, 975-978, doi:10.1038/nmeth.4401 (2017).
22. Philip, M. et al. Chromatin states define tumour-specific T cell dysfunction and reprogramming. Nature 545, 452-456, doi:10.1038/nature22367 (2017).
23. Singh, N., Perazzelli, J., Grupp, S. A. & Barrett, D. M. Early memory phenotypes drive T cell proliferation in patients with pediatric malignancies. Sci Transl Med 8, 320ra323, doi:10.1126/scitranslmed.aad5222 (2016).
24. Murphy, T. L., Tussiwand, R. & Murphy, K. M. Specificity through cooperation: BATF-IRF interactions control immune-regulatory networks. Nat Rev Immunol 13, 499-509, doi:10.1038/nri3470 (2013).
25. Meixner, A., Karreth, F., Kenner, L. & Wagner, E. F. JunD regulates lymphocyte proliferation and T helper cell cytokine expression. EMBO J 23, 1325-1335, doi:10.1038/sj.emboj.7600133 (2004).
26. Chiu, R., Angel, P. & Karin, M. Jun-B differs in its biological properties from, and is a negative regulator of, c-Jun. Cell 59, 979-986 (1989).
27. Echlin, D. R., Tae, H. J., Mitin, N. & Taparowsky, E. J. B-ATF functions as a negative regulator of AP-1 mediated 27. transcription and blocks cellular transformation by Ras and Fos. Oncogene 19, 1752-1763, doi:10.1038/sj.onc.1203491 (2000).
28. Li, P. et al. BATF-JUN is critical for IRF4-mediated transcription in T cells. Nature 490, 543-546, doi:10.1038/nature11530 (2012).
29. Quigley, M. et al. Transcriptional analysis of HIV-specific CD8+ T cells shows that PD-1 inhibits T cell function by upregulating BATF. Nat Med 16, 1147-1151, doi:10.1038/nm.2232 (2010).
30. Derijard, B. et al. JNK1: a protein kinase stimulated by UV light and Ha-Ras that binds and phosphorylates the c-Jun activation domain. Cell 76, 1025-1037 (1994).
31. S, P. D. A. et al. Antitumor Activity Associated with Prolonged Persistence of Adoptively Transferred NY-ESO-1(c259) T Cells in Synovial Sarcoma. Cancer Discov, doi:10.1158/2159-8290.CD-17-1417 (2018).
32. Iwamoto, M., Bjorklund, T., Lundberg, C., Kirik, D. & Wandless, T. J. A general chemical method to regulate protein stability in the mammalian central nervous system. Chem Biol 17, 981-988, doi:10.1016/j.chembiol.2010.07.009 (2010).
33. Bannister, A. J., Oehler, T., Wilhelm, D., Angel, P. & Kouzarides, T. Stimulation of c-Jun activity by CBP: c-Jun residues Ser63/73 are required for CBP induced stimulation in vivo and CBP binding in vitro. Oncogene 11, 2509-2514 (1995).
34. Weiss, C. et al. JNK phosphorylation relieves HDAC3-dependent suppression of the transcriptional activity of c-Jun. EMBO J 22, 3686-3695, doi:10.1093/emboj/cdg364 (2003).
35. Milone, M. C. et al. Chimeric receptors containing CD137 signal transduction domains mediate enhanced survival of T cells and increased antileukemic efficacy in vivo. Mol Ther 17, 1453-1464, doi:10.1038/mt.2009.83 (2009).
36. Porter, D. L. et al. Chimeric antigen receptor T cells persist and induce sustained remissions in relapsed refractory chronic lymphocytic leukemia. Sci Transl Med 7, 303ra139, doi:10.1126/scitranslmed.aac5415 (2015).
37. Davila, M. L. et al. Efficacy and toxicity management of 19-28z CAR T cell therapy in B cell acute lymphoblastic leukemia. Sci Transl Med 6, 224ra225, doi:10.1126/scitranslmed.3008226 (2014).
38. Majzner, R. G. & Mackall, C. L. Tumor Antigen Escape from CAR T-cell Therapy. Cancer Discov, doi:10.1158/2159-8290.CD-18-0442 (2018).
39. Martinez, G. J. et al. The transcription factor NFAT promotes exhaustion of activated CD8(+) T cells. Immunity 42, 265-278, doi:10.1016/j.immuni.2015.01.006 (2015).
40. Roychoudhuri, R. et al. BACH2 regulates CD8(+) T cell differentiation by controlling access of AP-1 factors to enhancers. Nat Immunol 17, 851-860, doi:10.1038/ni.3441 (2016).
41. Bohmann, D. et al. Human proto-oncogene c-jun encodes a DNA binding protein with structural and functional properties of transcription factor AP-1. Science 238, 1386-1392 (1987).
42. Mariani, O. et al. JUN oncogene amplification and overexpression block adipocytic differentiation in highly aggressive sarcomas. Cancer Cell 11, 361-374, doi:10.1016/j.ccr.2007.02.007 (2007).
43. Shaulian, E. AP-1—The Jun proteins: Oncogenes or tumor suppressors in disguise? Cell Signal 22, 894-899, doi:10.1016/j.cellsig.2009.12.008 (2010).
44. Behrens, A., Jochum, W., Sibilia, M. & Wagner, E. F. Oncogenic transformation by ras and fos is mediated by c-Jun N-terminal phosphorylation. Oncogene 19, 2657-2663, doi:10.1038/sj.onc.1203603 (2000).
45. Di Stasi, A. et al. Inducible apoptosis as a safety switch for adoptive cell therapy. N Engl J Med 365, 1673-1683, doi:10.1056/NEJMoa1106152 (2011).
46. Hudecek, M. et al. The nonsignaling extracellular spacer domain of chimeric antigen receptors is decisive for in vivo antitumor activity. Cancer Immunol Res 3, 125-135, doi:10.1158/2326-6066.CIR-14-0127 (2015).
47. Jena, B. et al. Chimeric antigen receptor (CAR)-specific monoclonal antibody to detect CD19-specific T cells in clinical trials. PLoS One 8, e57838, doi:10.1371/journal.pone.0057838 (2013).
48. Corces, M. R. et al. An improved ATAC-seq protocol reduces background and enables interrogation of frozen tissues. Nat Methods 14, 959-962, doi:10.1038/nmeth.4396 (2017).
49. Wickham, H. Ggplot2: elegant graphics for data analysis. (Springer, 2009).
50. Mootha, V. K. et al. PGC-1alpha-responsive genes involved in oxidative phosphorylation are coordinately downregulated in human diabetes. Nat Genet 34, 267-273, doi:10.1038/ng1180 (2003).
51. Subramanian, A. et al. Gene set enrichment analysis: a knowledge-based approach for interpreting genome-wide expression profiles. Proc Natl Acad Sci USA 102, 15545-15550, doi:10.1073/pnas.0506580102 (2005).
52. Zheng, G. X. et al. Massively parallel digital transcriptional profiling of single cells. Nat Commun 8, 14049, doi:10.1038/ncomms14049 (2017).

What is claimed is:

1. A method of treating cancer in a subject in need thereof, comprising administering to the subject an effective amount of a composition comprising isolated T cells that express a human c-Jun and an engineered receptor, wherein the human c-Jun and the engineered receptor are expressed from separate expression vectors or co-expressed from a single expression vector as separate polypeptides, wherein the engineered receptor is a chimeric antigen receptor (CAR) or an engineered T cell receptor (TCR), and wherein the expressed human c-Jun reduces exhaustion of the isolated T cells in the subject.

2. The method of claim 1, wherein the composition comprises $CD4^+$ T cells and $CD8^+$ T cells.

3. The method of claim 1, wherein the isolated T cells are autologous to the subject.

4. The method of claim 1, wherein the human c-Jun is a wildtype c-Jun.

5. The method of claim 1, wherein the expression vector encoding human c-Jun comprises a viral vector.

6. The method of claim 5, wherein the viral vector is selected from the group consisting of a lentiviral vector, a retroviral vector, an adenoviral vector, and an adeno-associated viral vector.

7. The method of claim 5, wherein the expression vector encoding human c-Jun further encodes the CAR or engineered TCR.

8. The method of claim 1, wherein the cancer is a solid tumor.

9. The method of claim 8, wherein the isolated T cells are autologous to the subject.

10. The method of claim 9, wherein the human c-Jun is a wildtype c-Jun.

11. The method of claim 1, wherein the cancer is a hematopoietic malignancy.

12. A method of enhancing immunity in a subject having cancer, comprising administering to the subject an effective amount of a composition comprising isolated T cells that express a human c-Jun and an engineered receptor, wherein the human c-Jun and the engineered receptor are expressed from separate expression vectors or co-expressed from a single expression vector as separate polypeptides, wherein the engineered receptor is a chimeric antigen receptor (CAR) or an engineered T cell receptor (TCR), and wherein the expressed human c-Jun reduces exhaustion of the isolated T cells in the subject.

\* \* \* \* \*